United States Patent
Zhu et al.

(10) Patent No.: US 11,591,365 B2
(45) Date of Patent: Feb. 28, 2023

(54) BCL9 PEPTIDES AND VARIANTS THEREOF

(71) Applicant: WntRx Pharmaceuticals Inc., Newton, MA (US)

(72) Inventors: David Zhu, Newton, MA (US); Robert Perni, Marlborough, MA (US); Yvonne Angell, San Francisco, CA (US)

(73) Assignee: WntRx Pharmaceuticals Inc., Newton, MA (US)

( * ) Notice: Subject to any disclaimer, the term of this patent is extended or adjusted under 35 U.S.C. 154(b) by 0 days.

(21) Appl. No.: 16/758,888

(22) PCT Filed: Nov. 9, 2018

(86) PCT No.: PCT/US2018/060050
§ 371 (c)(1),
(2) Date: Apr. 24, 2020

(87) PCT Pub. No.: WO2019/094733
PCT Pub. Date: May 16, 2019

(65) Prior Publication Data
US 2020/0262867 A1 Aug. 20, 2020

Related U.S. Application Data

(60) Provisional application No. 62/583,820, filed on Nov. 9, 2017.

(51) Int. Cl.
*C07K 7/04* (2006.01)
*A61P 35/00* (2006.01)
*A61K 38/00* (2006.01)

(52) U.S. Cl.
CPC ............... *C07K 7/04* (2013.01); *A61P 35/00* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 7,192,713 | B1 | 3/2007 | Veidine et al. |
| 9,464,115 | B2 | 10/2016 | Walensky et al. |
| 10,961,290 | B2 * | 3/2021 | Zhu ................... A61K 38/1709 |
| 2014/0113857 | A1 * | 4/2014 | Walensky .............. C07K 14/47 514/6.9 |
| 2016/0108089 | A1 | 4/2016 | Nash et al. |
| 2016/0115204 | A1 | 4/2016 | Nash et al. |

FOREIGN PATENT DOCUMENTS

| | | |
|---|---|---|
| JP | 2017/516072 | 6/2017 |
| WO | WO 2016/131893 * | 8/2016 |
| WO | WO 2017/062518 * | 4/2017 |
| WO | WO2017/062518 | 4/2017 |

OTHER PUBLICATIONS

Venkatraman et al. (Comprehensive Medicinal Chemistry III, 3rd Edition, Jun. 15, 2017) (Year: 2017).*
Dey et al. (Biomaterials. Jul. 2011 ; 32(20): 4647-4658) (Year: 2011).*
Kawamoto (Targeting the BCL9/B9L Binding Interaction with β-catenin as a Potential Anticancer Strategy, Dissertation, 2010) (Year :2010).*
Balkwill et al., "The tumor microenvironment at a glance," J Cell Sci., 2012, 125:5591-5596.
Belenkaya et al., "pygopus encodes a nuclear protein essential for Wingless/Wnt signaling" Development, 2002, 129(17):4089-4101.
Bird et al., "Synthesis and Biophysical Characterization of Stabilized α-Helices of BCL-2 Domains." Methods Enzymol, 2008, Chapter 22, 446, 369-386.
De la Roche et al., "The function of BCL9 in Wnt/β-catenin signaling and colorectal cancer cells," BMC Cancer, 2008, 8(199):13pages.
Grossmann et al. "Inhibition of oncogenic Wnt signaling through direct targeting of β-catenin." PNAS. 2012, 109(44):17942-17947.
International Search Report in International Appln. No. PCT/US2018/060050, dated Apr. 15, 2019, 14 pages.
Kawamoto et al.. "Analysis of the Interaction of BCL9 with β-Catenin and Development of Fluorescence Polarization and Surface Plasmon Resonance Binding Assays for this Interaction," Biochemistiy, 2009, 48(40):9534-9541.
Kim et al., "Synthesis of all-hydrocarbon stapled α-helical peptides by ring-closing olefin metathesis," Nature Protocols, 2011, 6:761-771.
Spranger et al., "Melanoma-intrinsic β-catenin signalling prevents anti-tumour immunity," Nature, 2015, 523:231-235.
Thakur et al., "Pharmacological modulation of beta-catenin and its applications in cancer therapy," J Cell Mol Med., 2013, 17(4):449-456.
PCT International Preliminary Report on Patentability in International Appln. No. PCT/US2018/060050, dated May 22, 2020, 9 pages.
Extended European Search Report in Appln. No. 18876108.4, dated Apr. 19, 2022, 10 pages.
Hill el al., "Constraining cyclic peptides to mimic protein structare motifs," Angewandte Revs., 2014, 53:13020-13041.
Shang et al., "The regulation of B-catenin activity and function in cancer: therapeutic oppostunities," Oncotarget, 2017, 8:20:33972-33989.

* cited by examiner

*Primary Examiner* — Sergio Coffa
(74) *Attorney, Agent, or Firm* — Fish & Richardson P.C.

(57) ABSTRACT

Disclosed here are polypeptides derived from the HD2 domain of human B-cell CLL/lymphoma 9 (BCL9) protein and variants thereof, as well as their use in the diagnosis, prevention, and/or treatment of a disease or disorder. Also disclosed are methods of generating such polypeptides and variants thereof.

11 Claims, 2 Drawing Sheets
Specification includes a Sequence Listing.

BCL9 PEPTIDES AND VARIANTS THEREOF

CLAIM OF PRIORITY

This application claims priority to International Application No. PCT/US2018/060050, filed on Nov. 9, 2018, which claims priority to U.S. Patent Application Ser. No. 62/583,820, filed on Nov. 9, 2017, the entire contents of which are hereby incorporated by reference.

TECHNICAL FIELD

This invention relates to BCL9 peptides, and in particular to variants of HD2 domain within BCL9 peptides.

BACKGROUND

β-catenin is a multifunctional protein of critical importance to cellular homeostasis and processes such as embryogenesis, epithelial cell growth, and organ regeneration. However, aberrant β-catenin signaling can lead to changes in transcriptional activation that can allow tumor growth and development. β-catenin is normally phosphorylated and targeted for degradation by the axin complex, but unphosphorylated β-catenin can accumulate if there is stimulation of the Wnt signaling pathway. Under conditions when the Wnt signaling pathway is activated, β-catenin binds to lymphoid enhancer factor/T cell factor (LEF/TCF) and is translocated into the nucleus to stimulate transcription of Wnt target genes (See, e.g., Clevers and Nusse, Cell 149: 1192-1205 (2012)), such as c-myc and CD44, that play roles in tumorigenesis.

SUMMARY

In one general aspect, the present disclosure provides a polypeptide, or a pharmaceutically acceptable salt thereof, comprising an amino acid sequence

| 368 | 369 | 370 | 371 | 372 | 373 | 374 |
|---|---|---|---|---|---|---|
| $Xaa_3$ | $Xaa_4$ | $Xaa_8$ | $Xaa_5$ | $Xaa_6$ | $Xaa_7$ | (2-Nal) or (2-Dnal), | wherein:

$Xaa_3$ and $Xaa_6$ are each independently an α,α-disubstituted amino acid;

$Xaa_4$ is selected from I, A, Nle, N-MethylI, CBA, and (D-I);

$Xaa_8$ is selected from Q and N-methylQ;

$Xaa_5$ is selected from R, A, Q, E, K, H, N-methylR, homoR, NMeArg, Nar, and Cit; and $Xaa_7$ is selected from CBA, Cha, Cpa, Phe(4-Cl), (D-L), α-MethylL, DCha, N-methylCha, allylGly, AC4C, A6C, Aze, NMeCha, (β-tBu-Ala), Tle, 4-FPh, and 3,4-diClPh; and
wherein the polypeptide has a length of 6-30 amino acids.

In some embodiments, $Xaa_7$ is CBA.

In some embodiments, $Xaa_7$ is selected from Cha and Cpa.

In some embodiments, $Xaa_7$ is selected from α-MethylL, DCha, N-methylCha, and allylGly.

In some embodiments, $Xaa_7$ is selected from AC4C, A6C, Aze, Phe(4-Cl), (β-tBu-Ala), and Tle.

In some embodiments, $Xaa_7$ is selected from Phe(4-Cl), 4-FPh, 3,4-diClPh, and Cha.

In some embodiments, $Xaa_4Xaa_8Xaa_5$ comprise IQR.

In some embodiments, $Xaa_4Xaa_8Xaa_5$ comprise I(N-methylQ)R.

In some embodiments, $Xaa_4Xaa_8Xaa_5$ comprise IQ(N-methylR).

In some embodiments, $Xaa_4Xaa_8Xaa_5$ comprise (CBA)QR.

In some embodiments, $Xaa_4Xaa_8Xaa_5$ comprise IQ(homoR).

In some embodiments, $Xaa_4Xaa_8Xaa_5$ comprise (N-methylI)QR.

In some embodiments, $Xaa_4Xaa_8Xaa_5$ comprise IQQ, IQE, IQ(NMeArg), (Nle)QR, IQ(Nar), or IQC.

In some embodiments, the polypeptide comprises:

| 363 | 364 | 365 | 366 | 367 |
|---|---|---|---|---|
| $Xaa_1$ | $Xaa_9$ | $Xaa_{10}$ | $Xaa_2$ | $Xaa_{11}$ | wherein:

$Xaa_1$ and $Xaa_2$ are each independently selected from L, A, Cha, Cpa, (D-L), CBA, MeL, NMeCha, Dcha, and NptGly;

$Xaa_9$ is selected from Q, E, N-methylQ, N-MeGln, and peptoidQ;

$Xaa_{10}$ is selected from T, N-methylT, and DThr; and $Xaa_{11}$ is selected from R, N-methylR, E, K, homoR, Nar, and Cit.

In some embodiments, $Xaa_1Xaa_9Xaa_{10}Xaa_2Xaa_{11}$ comprise LQTLR.

In some embodiments, $Xaa_1Xaa_9Xaa_{10}Xaa_2Xaa_{11}$ comprise L(N-methylQ)TLR.

In some embodiments, $Xaa_1Xaa_9Xaa_{10}Xaa_2Xaa_{11}$ comprise L(N-methylQ)TL(homoR).

In some embodiments, $Xaa_1Xaa_9Xaa_{10}Xaa_2Xaa_{11}$ comprise L(NMeGln)T(NMeLeu)R.

In some embodiments, wherein $Xaa_1Xaa_9Xaa_{10}Xaa_2Xaa_{11}$ comprise L(N-methylQ)TL(N-methylR).

In some embodiments, $Xaa_1Xaa_9Xaa_{10}Xaa_2Xaa_{11}$ comprise LN-methylQTLR, LETLR, (CBA)QTLR, (CBA)(N-methylQ)TLR, LQT(CBA)R, L(N-methylQ)(N-methylT)LR, L(N-methylQ)T(Cha)R, L(N-methylQ)T(t-methylL)R, or L(N-methylQ)(DThr)LR.

In some embodiments, the polypeptide comprises:

| 358 | 359 | 360 | 361 | 362 |
|---|---|---|---|---|
| $Xaa_{12}$ | $Xaa_{13}$ | $Xaa_{14}$ | $Xaa_{15}$ | S | wherein:

$Xaa_{12}$ is selected from H, N-MeHis, Cys, N-MeCys, homoHis, and NHis;

$Xaa_{13}$ is selected from R, N-methylR, homoArg, Cit, Nar, and Phe(4-guanidino);

$Xaa_{14}$ is selected from E, Q, N-methylE, N-methylQ, N-methylD, and NMeGln; and $Xaa_{15}$ is selected from R, homoR, and N-methylR.

In some embodiments, $Xaa_{12}Xaa_{13}Xaa_{14}Xaa_{15}$ comprise HRER.

In some embodiments, $Xaa_{12}Xaa_{13}Xaa_{14}Xaa_{15}$ comprise HRQR.

In some embodiments, $Xaa_{12}Xaa_{13}Xaa_{14}Xaa_{15}$ comprise HR(N-methylE)R, HR(N-methylE)R, HR(N-methylQ)R, HR(N-methylD)R, H(N-methylR)QR, HRQ(homoR), HRQ(N-methylR), H(homoArg)QR, HRQ(NMeArg), HR(NMeGln)R, (N-MeHis)RQR, (Cys)RQR, (NMeCys)RQR, (homoHis)RQR, (NHis)RQR, H(Cit)(N-methylQ)R, H(Nar)(N-methylQ)R, or H(4-guanidino-Phe)(N-methylQ)R.

In some embodiments, the N-terminus of the polypeptide is modified with a moiety selected from acetyl, propionyl, hexanoyl, 3-phenylpropanoyl, 2-cyclohexylacetyl, diphenylacetyl, 3,5-dihydroxybenzoic acid, 4-(trifluoromethyl)benzoic acid, 5-phenylvaleric acid, 4-biphenyl acetic acid, dimethyl, $HOCH_2CH_2CO-$, and palmitoyl-PEG4.

In some embodiments, the C-terminus of the polypeptide is modified with a moiety selected from $NH_2$, (β-Ala)(β-Ala), (β-Ala)(β-Ala)$NH_2$, GRKKRRQRRRPQK(PEG4-palmitoyl)$NH_2$, K(PEG4-palmitoyl)$NH_2$, GRKKRRQRRRPQ$NH_2$, and 1-(2-aminoethyl)-4-methylpiperazine.

In some embodiments, C-terminus of the polypeptide is modified with $NH_2$.

In some embodiments, C-terminus of the polypeptide is modified with (β-Ala)(β-Ala).

In some embodiments, the N-terminus of the polypeptide is modified with acetyl, and the C-terminus of the polypeptide is modified with $NH_2$.

In some embodiments, the polypeptide is selected from:

SEQ ID NO: 107
LQTLRXaa$_3$IQRXaa$_6$(CBA)(2-Nal)

SEQ ID NO: 108
L(N-methyl Q)TLRXaa$_3$IQRXaa$_6$(CBA)(2-Nal)

SEQ ID NO: 109
LETLRXaa$_3$IQRXaa$_6$(CBA)(2-Nal)

SEQ ID NO: 110
L(N-methylQ)TLRXaa$_3$IQRXaa$_6$(CBA)(2-Nal)(β-Ala)(β-Ala)

SEQ ID NO: 111
L(N-methylQ)TLRXaa$_3$IQRXaa$_6$(CBA)(2-Nal)(β-Ala)(β-Ala)

SEQ ID NO: 112
LQTLRXaa$_3$IQHXaa$_6$(CBA)(2-Nal)

SEQ ID NO: 113
(CBA)QTLRXaa$_3$IQRXaa$_6$(CBA)(2-Nal)

SEQ ID NO: 114
(CBA)(N-methylQ)TLRXaa$_3$IQRXaa$_6$(CBA)(2-Nal)

SEQ ID NO: 115
LQT(CBA)RXaa$_3$IQRXaa$_6$(CBA)(2-Nal)

SEQ ID NO: 116
L(N-methylQ)TLRXaa$_3$I(N-methylQ)RXaa$_6$(CBA)(2-Nal)

SEQ ID NO: 117
LN-MeQTLR(Me)Xaa$_3$IQRXaa$_6$(CBA)(2-Nal)

SEQ ID NO: 118
(Me-L)(N-MeQ)TLRXaa$_3$IQRXaa$_6$(CBA)(2-Nal)

SEQ ID NO: 119
LN(Me-Gln)TLRXaa$_3$IQRXaa$_6$(Cpa)(2-Nal)

SEQ ID NO: 120
L(N-methylQ)TLRXaa$_3$IQRXaa$_6$(CBA)(2-Nal),
wherein N-terminus is modified with $HOCH_2CH_2CO-$.

SEQ ID NO: 121
L(N-methylQ)(N-methylT)LRXaa$_3$IQRXaa$_6$(CBA)(2-Nal)

SEQ ID NO: 122
L(N-methylQ)TLRXaa$_3$IQRXaa$_6$(Cha)(2-Nal)

SEQ ID NO: 123
L(N-methylQ)T(Cha)RXaa$_3$IQRXaa$_6$(CBA)(2-Nal)

SEQ ID NO: 124
L(N-methylQ)TL(N-methylR)Xaa$_3$IQRXaa$_6$(CBA)(2-Nal)

SEQ ID NO: 125
L(N-methylQ)TLRXaa$_3$IQ(N-methylR)Xaa$_6$(CBA)(2-Nal)

SEQ ID NO: 126
L(N-methylQ)T(α-methylL)RXaa$_3$IQRXaa$_6$(CBA)(2-Nal)

SEQ ID NO: 127
LQTLRXaa$_3$IQRXaa$_6$(Cha)(2-Nal)

SEQ ID NO: 128
L(N-methylQ)TL(N-methylR)Xaa$_3$IQ(N-methylR)Xaa$_6$(CBA)(2-Nal)

SEQ ID NO: 129
L(N-methylQ)TLRXaa$_3$(CBA)QRXaa$_6$(CBA)(2-Nal)

SEQ ID NO: 130
L(N-methylQ)(D-Thr)LRXaa$_3$IQRXaa$_6$(CBA)(2-Nal)

SEQ ID NO: 131
L(N-meGln)T(N-MeLeu)RXaa$_3$IQRXaa$_6$(CBA)(2-Nal)

SEQ ID NO: 132
L(N-methylQ)TL(homoR)Xaa$_3$IQRXaa$_6$(CBA)(2-Nal)

SEQ ID NO: 133
L(N-methylQ)TLRXaa$_3$IQ(homoR)Xaa$_6$(CBA)(2-Nal)

SEQ ID NO: 134
L(N-methylQ)TLRXaa$_3$(N-methylI)QRXaa$_6$(CBA)(2-Nal)

SEQ ID NO: 135
L(N-MeGln)TLRXaa$_3$IQRXaa$_6$(CBA)(2-Nal),
wherein N-terminus is modified with propionyl.

SEQ ID NO: 136
L(N-MeGln)TLRXaa$_3$IQRXaa$_6$(CBA)(2-Nal),
wherein N-terminus is modified with hexanoyl.

SEQ ID NO: 137
L(N-MeGln)TLRXaa$_3$IQRXaa$_6$(CBA)(2-Nal),
wherein N-terminus is modified with 3-phenylpropanoyl.

SEQ ID NO: 138
L(N-MeGln)TLRXaa$_3$IQRXaa$_6$(CBA)(2-Nal),
wherein N-terminus is modified with 2-cyclohexylacetyl.

SEQ ID NO: 139
L(N-MeGln)TLRXaa$_3$IQRXaa$_6$(CBA)(2-Nal),
wherein N-terminus is modified with diphenylacetyl.

SEQ ID NO: 140
L(N-methylQ)TLRXaa$_3$IQRXaa$_6$(CBA)(2-Nal),
wherein N-terminus is modified with 3,5-dihydroxybenzoic acid.

-continued

L(N-methylQ)TLRXaa₃IQRXaa₆(CBA)(2-Nal), SEQ ID NO: 141
wherein N-terminus is modified with 4-(trifluoromethyl)benzoic acid.

L(N-methylQ)TLRXaa₃IQRXaa₆(CBA)(2-Nal), SEQ ID NO: 142
wherein N-terminus is modified with 5-phenylvaleric acid.

L(N-methylQ)TLRXaa₃IQRXaa₆(CBA)(2-Nal), SEQ ID NO: 143
wherein N-terminus is modified with 4-biphenyl acetic acid.

L(N-methylQ)TLRXaa₃IQRXaa₆(CBA)(2-Nal), SEQ ID NO: 144
wherein N-terminus is modified with dimethyl.

HRERSLQTLRXaa₃IQQXaa₆(CBA)(2-Nal) SEQ ID NO: 145

HRERSLQTLRXaa₃IQEXaa₆(CBA)(2-Nal), SEQ ID NO: 146
wherein C-terminus is unmodified.

HRQRSLQTLRXaa₃IQRXaa₆(CBA)(2-Nal) SEQ ID NO: 147

HRQRSLQTLRXaa₃IQRXaa₆(CBA)(2-Nal)(β-Ala)(β-Ala) SEQ ID NO: 148

HRQRSLQTLRXaa₃IQRXaa₆(CBA)(2-Nal)(β-Ala)(β-Ala), SEQ ID NO: 149
wherein C-terminus is modified with GRKKRRQRRRPQ-NH2.

HRQRSLQTLRXaa₃IQRXaa₆(CBA)(2-Nal)(β-Ala)(β-Ala), SEQ ID NO: 150
wherein C-terminus is modified with 1-(2-aminoethyl)-4-methylpiperazine.

HR(N-methylE)RSLQTLRXaa₃IQRXaa₆(CBA)(2-Nal) SEQ ID NO: 151

HRERSLQTL(N-methylR)Xaa₃IQRXaa₆(CBA)(2-Nal), SEQ ID NO: 152
wherein C-terminus is unmodified.

HRQRSL(N-methylQ)TLRXaa₃IQRXaa₆(CBA)(2-Nal) SEQ ID NO: 153

HR(N-methylE)RSL(N-methylQ)TLRXaa₃IQRXaa₆(CBA)(2-Nal) SEQ ID NO: 154

HR(N-methylQ)RSL(N-methylQ)TLRXaa₃IQRXaa₆(CBA)(2-Nal) SEQ ID NO: 155

HRQRS(CBA)QTLRXaa₃IQRXaa₆(CBA)(2-Nal) SEQ ID NO: 156

HR(N-methylD)RSLQTLRXaa₃IQRXaa₆(CBA)(2-Nal) SEQ ID NO: 157

H(R-Me)QRSLQTLRXaa₃IQRXaa₆(CBA)(2-Nal) SEQ ID NO: 158

HRQRTLQTLRXaa₃IQRXaa₆(CBA)(2-Nal) SEQ ID NO: 159

HRQRSLQTLRXaa₃IQRXaa₆(CBA)(2-Nal), SEQ ID NO: 160
N-terminus is modified with palmitoyl-PEG4.

HRQRSLQTLRXaa₃IQRXaa₆(CBA)(2-Nal), SEQ ID NO: 161
wherein C-terminus is modified with K(PEG4-palmitoyl)NH₂.

HRQRSLQTLRXaa₃IQRXaa₆(Cpa)(2-Nal) SEQ ID NO: 162

HR(N-methylQ)RSL(N-methylQ)T(Cha)RXaa₃IQRXaa₆(CBA)(2-Nal) SEQ ID NO: 163

HR(N-methylQ)RSL(N-methylQ)TLRXaa₃IQ(N-methylR)Xaa₆(CBA)(2-Nal) SEQ ID NO: 164

HR(N-methylQ)RSL(N-methylQ)(N-methylT)LRXaa₃IQRXaa₆(CBA)(2-Nal) SEQ ID NO: 165

H(N-methylR)QRSLQTLRXaa₃IQRXaa₆(CBA)(2-Nal) SEQ ID NO: 166

HRQ(homoR)SLQTLRXaa₃IQRXaa₆(CBA)(2-Nal) SEQ ID NO: 167

HRQ(N-methylR)SLQTLRXaa₃IQRXaa₆(CBA)(2-Nal) SEQ ID NO: 168

HRQRSL(peptoid-Q)TLRXaa₃IQRXaa₆(CBA)(2-Nal) SEQ ID NO: 169

HRQRSLQTL(homoR)Xaa₃IQRXaa₆(CBA)(2-Nal) SEQ ID NO: 170

HRQRSLQTLRXaa₃IQ(homoR)Xaa₆(CBA)(2-Nal) SEQ ID NO: 171

L(N-methylQ)TLRXaa₃IQRXaa₆(a-methylL)(2-Nal) SEQ ID NO: 172

L(N-methylQ)TLRXaa₃IQRXaa₆D(Cha)(2-Nal) SEQ ID NO: 173

L(N-methylQ)TLRXaa₃IQRXaa₆(N-methylCha)(2-Nal) SEQ ID NO: 174

LQTLRXaa₃IQRXaa₆(allylGly)(2-Nal) SEQ ID NO: 175

HRQRSLQTLRXaa₃IQRXaa₆(AC4C)(2-Nal) SEQ ID NO: 176

HRQRSLQTLRXaa₃IQRXaa₆(A6C)(2-Nal) SEQ ID NO: 177

HRQRSLQTLRXaa₃IQRXaa₆(Aze)(2-Nal) SEQ ID NO: 178

HRQRSLQTLRXaa₃IQRXaa₆(Phe-4-Cl)(2-Nal) SEQ ID NO: 179

HRQRSLQTLRXaa₃IQRXaa₆(Cha)(2-Nal) SEQ ID NO: 180

SEQ ID NO: 181
HR(N-methylQ)RSL(N-methylQ)TLRXaa$_3$IQRXaa$_6$(Cha)(2-Nal)

SEQ ID NO: 182
HRQRSLQTLRXaa$_3$IQRXaa$_6$(N-MeCha)(2-Nal)

SEQ ID NO: 183
H(homoArg)QRSLQTLRXaa$_3$IQRXaa$_6$(Cha)(2-Nal)

SEQ ID NO: 184
HRQ(N-MeArg)SLQTLRXaa$_3$IQRXaa$_6$(Cha)(2-Nal)

SEQ ID NO: 185
HRQRS(Cha)(N-MeGln)TLRXaa$_3$IQRXaa$_6$(Cha)(2-Nal)

SEQ ID NO: 186
HRQRS(N-MeCha)(N-MeGln)TLRXaa$_3$IQRXaa$_6$(Cha)(2-Nal)

SEQ ID NO: 187
HRQRSD(Cha)(N-MeGln)TLRXaa$_3$IQRXaa$_6$(Cha)(2-Nal)

SEQ ID NO: 188
HRQRSLQTLRXaa$_3$IQRXaa$_6$(Cha)(2DNal)

SEQ ID NO: 189
HRQRSLQTL(N-MeArg)Xaa$_3$IQRXaa$_6$(Cha)(2-Nal)

SEQ ID NO: 190
HRQRSLQTLRXaa$_3$IQ(N-MeArg)Xaa$_6$(Cha)(2-Nal)

SEQ ID NO: 191
HRQRSLQTLRXaa$_3$IQRXaa$_6$(β-tBu-Ala)(2-Nal)

SEQ ID NO: 192
HRQRSLQTLRXaa$_3$IQRXaa$_6$(Tle)(2-Nal)

SEQ ID NO: 193
HR(N-MeGln)RSLQTLRXaa$_3$IQRXaa$_6$(β-tBu-Ala)(2-Nal)

SEQ ID NO: 194
HR(N-MeGln)RSLQTLRXaa$_3$IQRXaa$_6$(Tle)(2-Nal)

SEQ ID NO: 195
L(N-methylQ)TLRXaa$_3$IQRXaa$_6$(4-Cl-Ph)(2-Nal)

SEQ ID NO: 196
HRQRSLQTLRXaa$_3$IQRXaa$_6$(4-Cl-Ph)(2-Nal)

SEQ ID NO: 197
HR(N-methylQ)RSL(N-methylQ)TLRXaa$_3$IQRXaa$_6$(4-Cl-Ph)(2-Nal)

SEQ ID NO: 199
HRQRS(Cha)(N-methylQ)TLRXaa$_3$IQRXaa$_6$(4-Cl-Ph)(2-Nal)

SEQ ID NO: 200
HRQRS(Cha)(N-methylQ)TLRXaa$_3$IQRXaa$_6$(4-F-Ph)(2-Nal)

SEQ ID NO: 201
HRQRS(NptGly)(N-methylQ)TLRXaa$_3$IQRXaa$_6$(4-Cl-Ph)(2-Nal)

SEQ ID NO: 202
HR(N-methylQ)RSL(N-methylQ)TLRXaa$_3$IQRXaa$_6$(4-F-Ph)(2-Nal)

SEQ ID NO: 203
HR(N-methylQ)RSL(N-methylQ)TLRXaa$_3$IQRXaa$_6$(3,4-diCl-Ph)(2-Nal)

SEQ ID NO: 204
HR(N-methylQ)RSL(N-methylQ)TLRXaa$_3$(Nle)QRXaa$_6$(Cha)(2-Nal)

SEQ ID NO: 205
HRQRSLQTLRXaa$_3$IQRXaa$_6$(Cha)(2-Nal), wherein N-terminus is modified with palmitoyl-PEG4.

SEQ ID NO: 206
HRQRSLQTLRXaa$_3$IQRXaa$_6$(4-Cl-Ph)(2-Nal), wherein N-terminus is modified with palmitoyl-PEG4.

SEQ ID NO: 207
HR(N-methylQ)RSL(N-methylQ)TLRXaa$_3$IQRXaa$_6$(Cha)(2-Nal), wherein N-terminus is modified with palmitoyl-PEG4.

SEQ ID NO: 208
HR(N-methylQ)RSL(N-methylQ)TLRXaa$_3$IQRXaa$_6$(4-Cl-Ph)(2-Nal), wherein N-terminus is modified with palmitoyl-PEG4.

SEQ ID NO: 209
H(homoArg)QRSLQTLRXaa$_3$IQRXaa$_6$(Cha)(2-Nal), wherein N-terminus is modified with palmitoyl-PEG4.

SEQ ID NO: 210
H(homoArg)QRSLQTLRXaa$_3$IQRXaa$_6$(4-Cl-Ph)(2-Nal), wherein N-terminus is modified with palmitoyl-PEG4.

SEQ ID NO: 211
HRQRS(Cha)(N-methylQ)TLRXaa$_3$IQRXaa$_6$(Cha)(2-Nal), wherein N-terminus is modified with palmitoyl-PEG4.

SEQ ID NO: 212
HRQRS(Cha)(N-methylQ)TLRXaa$_3$IQRXaa$_6$(4-Cl-Ph)(2-Nal), wherein N-terminus is modified with palmitoyl-PEG4.

SEQ ID NO: 213
L(N-methylQ)TLRXaa$_3$IQRXaa$_6$(CBA)(2-Nal), wherein N-terminus is modified with palmitoyl-PEG4.

SEQ ID NO: 214
L(N-methylQ)TLRXaa$_3$IQRXaa$_6$(4-Cl-Ph)(2-Nal), wherein N-terminus is modified with palmitoyl-PEG4.

SEQ ID NO: 215
(N-MeHis)RQRSLQTLRXaa$_3$IQRXaa$_6$(Cha)(2-Nal)

SEQ ID NO: 216
(Cys)RQRSLQTLRXaa$_3$IQRXaa$_6$(Cha)(2-Nal)

-continued

SEQ ID NO: 217
(N-MeCys)RQRSLQTLRXaa₃IQRXaa₆(Cha)(2-Nal)

SEQ ID NO: 218
(homoHis)RQRSLQTLRXaa₃IQRXaa₆(Cha)(2-Nal)

SEQ ID NO: 219
(NHis)RQRSLQTLRXaa₃IQRXaa₆(Cha)(2-Nal)

SEQ ID NO: 220
H(homoArg)QRSLQTL(Nar)Xaa₃IQRXaa₆(Cha)(2-Nal)

SEQ ID NO: 221
H(homoArg)QRSLQTLRXaa₃IQ(Nar)Xaa₆(Cha)(2-Nal)

SEQ ID NO: 222
H(homoArg)QRSLQTLRXaa₃IQ(Cit)Xaa₆(Cha)(2-Nal)

SEQ ID NO: 223
H(homoArg)QRSLQTL(Cit)Xaa₃IQRXaa₆(Cha)(2-Nal)

SEQ ID NO: 224
H(Cit)(N-methylQ)RSL(N-methylQ)TLRXaa₃IQRXaa₆
(Cha)(2-Nal)

SEQ ID NO: 225
H(Nar)(N-methylQ)RSL(N-methylQ)TLRXaa₃IQRXaa₆
(Cha)(2-Nal)

SEQ ID NO: 226
H(4-guanidino-Phe)(N-methylQ)RSL(N-methylQ)
TLRXaa₃IQRXaa₆(Cha)(2-Nal)

In some embodiments, the α,α-disubstituted amino acid is an α-methyl, α-alkenyl amino acid.

In some embodiments, Xaa₃ and Xaa₆ are each independently selected from: (S)-2-(4'-pentenyl)alanine, (R)-2-(4'-pentenyl)alanine, (S)-2-(7'-octenyl)alanine, and (R)-2-(7'-octenyl)alanine.

In some embodiments, Xaa₃ and Xaa₆ are each (S)-2-(4'-pentenyl)alanine.

In some embodiments, one α substituent in the α,α-disubstituted amino acid is methyl, and the other α substituent in the α,α-disubstituted amino acid is a hydrocarbon linker.

In some embodiments, the hydrocarbon linker has formula:

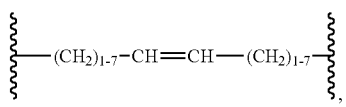

wherein one ⸨ denotes a point of attachment of the hydrocarbon linker to the α carbon atom of Xaa₃, and the other ⸨ denotes a point of attachment of the hydrocarbon linker to the α carbon atom of Xaa₆.

In some embodiments, the hydrocarbon crosslinker has formula:

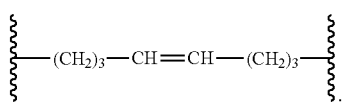

In yet another general aspect, the present disclosure provides a polypeptide, or a pharmaceutically acceptable salt thereof, comprising an amino acid sequence:

| 362 | 363 | 364 | 365 |
|---|---|---|---|
| Xaa₁₆ | Xaa₁ | Xaa₉ | Xaa₁₀ | and an amino acid sequence selected from:

| 368 | 369 | 370 | 371 | 372 |
|---|---|---|---|---|
| Xaa₃ | Xaa₄ | Xaa8 | Xaa₅ | Xaa₆ | wherein:

Xaa₃, Xaa₆, Xaa₁₆ and Xaa₁₀ are each independently an α,α-disubstituted amino acid;

Xaa₁ is selected from L, A, Cha, Cpa, (D-L), CBA, MeL, NMeCha, Dcha, and NptGly;

Xaa₉ is selected from Q, N-methylQ, E, N-MeGln, and peptoidQ;

Xaa₄ is selected from I, A, Nle, N-MethylI, CBA, and (D-I);

Xaa₈ is selected from Q and N-methylQ;

Xaa₅ is selected from R, A, Q, E, K, H, N-MethylR, homoR, NMeArg, Nar, and Cit; and wherein the polypeptide has length of 9-30 amino acids.

In some embodiments, Xaa₁ is selected from L and Cpa.

In some embodiments, Xaa₉ is selected from Q and N-methylQ.

In some embodiments, Xaa₄ is I.

In some embodiments, Xaa₈ is Q.

In some embodiments, Xaa₅ is R.

In some embodiments, Xaa₁Xaa₉ comprise LQ, L(N-methylQ), or (Cpa)(N-methylQ).

In some embodiments, Xaa₄Xaa₈Xaa₅ comprise IQR.

In some embodiments, in addition to the sequences Xaa₁₆Xaa₁Xaa₉Xaa₁₀ and Xaa₃Xaa₄Xaa₈Xaa₅Xaa₆, the polypeptide comprises at least one R.

In some embodiments, in addition to the sequences Xaa₁₆Xaa₁Xaa₉Xaa₁₀ and Xaa₃Xaa₄Xaa₈Xaa₅Xaa₆, the polypeptide comprises at least one L.

In some embodiments, in addition to the sequences Xaa₁₆Xaa₁Xaa₉Xaa₁₀ and Xaa₃Xaa₄Xaa₈Xaa₅Xaa₆, the polypeptide comprises at least one amino acid selected from CBA, Cpa, and Cha.

In some embodiments, in addition to the sequences Xaa₁₆Xaa₁Xaa₉Xaa₁₀ and Xaa₃Xaa₄Xaa₈Xaa₅Xaa₆, the polypeptide comprises at least one (2-Nal).

In some embodiments, in addition to the sequences Xaa₁₆Xaa₁Xaa₉Xaa₁₀ and Xaa₃Xaa₄Xaa₈Xaa₅Xaa₆, the polypeptide comprises at least one (β-Ala).

In some embodiments, in addition to the sequences Xaa₁₆Xaa₁Xaa₉Xaa₁₀ and Xaa₃Xaa₄Xaa₈Xaa₅Xaa₆, the polypeptide comprises HRQR or HRER.

In some embodiments, in addition to the sequences Xaa₁₆Xaa₁Xaa₉Xaa₁₀ and Xaa₃Xaa₄Xaa₈Xaa₅Xaa₆, the polypeptide comprises LR, (Cpa)R or (Cha)R.

In some embodiments, in addition to the sequences Xaa₁₆Xaa₁Xaa₉Xaa₁₀ and Xaa₃Xaa₄Xaa₈Xaa₅Xaa₆, the polypeptide comprises (CBA)(2-Nal), (Cpa)(2-Nal), or (Cha)(2-Nal).

In some embodiments, the polypeptide is selected from:

RXaa₁₆L(N-methylQ)Xaa₁₀LRXaa₃IQRXaa₆(CBA)(2-Nal)(β-Ala)(β-Ala); (SEQ ID NO: 88)

RXaa₁₆(Cpa)(N-methylQ)Xaa₁₀(Cpa)RXaa₃IQRXaa₆(Cpa)(2-Nal)(β-Ala)(β-Ala); (SEQ ID NO: 89)

HRQRXaa₁₆LQXaa₁₀LRXaa₃IQRXaa₆(CBA)(2-Nal); (SEQ ID NO: 90)

HRQRXaa₁₆LQXaa₁₀(Cpa)RXaa₃IQRXaa₆(Cpa)(2-Nal); (SEQ ID NO: 91)

HRQRXaa₁₆LQXaa₁₀(Cha)RXaa₃IQRXaa₆(Cha)(2-Nal); (SEQ ID NO: 92)
and

LEHRERXaa₁₆LQXaa₁₀LRXaa₃IQRXaa₆L. (SEQ ID NO: 93)

In some embodiments, the α,α-disubstituted amino acid is an α-methyl, α-alkenyl amino acid.

In some embodiments, Xaa₃, Xaa₆, Xaa₁₀, and Xaa₁₆ are each independently selected from: (S)-2-(4'-pentenyl)alanine, (R)-2-(4'-pentenyl)alanine, (S)-2-(7'-octenyl)alanine, and (R)-2-(7'-octenyl)alanine.

In some embodiments, Xaa₃, Xaa₆, Xaa₁₀, and Xaa₁₆ are each (S)-2-(4'-pentenyl)alanine.

In some embodiments:
one α substituent in the α,α-disubstituted amino Xaa₃ acid is methyl, and the other α substituent is a first hydrocarbon linker; and in the α,α-disubstituted amino acid Xaa₆ one α substituent is methyl, and the other α substituent is the first hydrocarbon linker; and
one α substituent in the α,α-disubstituted amino Xaa₁₀ acid is methyl, and the other α substituent is a second hydrocarbon linker; and in the α,α-disubstituted amino acid Xaa₁₆ one α substituent is methyl, and the other α substituent is the second hydrocarbon linker.

In some embodiments, the first hydrocarbon linker has formula:

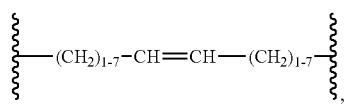

wherein one denotes a point of attachment of the hydrocarbon linker to the α carbon atom of Xaa₃, and the other denotes a point of attachment of the hydrocarbon linker to the α carbon atom of Xaa₆; and
the second hydrocarbon linker has formula:

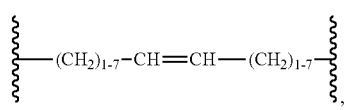

wherein one denotes a point of attachment of the second hydrocarbon linker to the α carbon atom of Xaa₁₀, and the other denotes a point of attachment of the second hydrocarbon linker to the α carbon atom of Xaa₁₆.

In some embodiments, the first hydrocarbon crosslinker has formula:

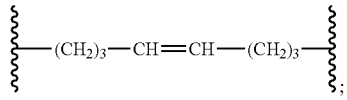

the second hydrocarbon crosslinker has formula:

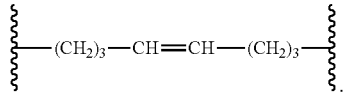

In yet another general aspect, the present disclosure provides a polypeptide, or a pharmaceutically acceptable salt thereof, comprising an amino acid sequence:

| 360 | 361 | 362 | 363 | 364 |
|---|---|---|---|---|
| Xaa₁₄ | Xaa₁₅ | Xaa16 | Xaa₁ | Xaa₉ | and an amino aid sequence selected from:

| 368 | 369 | 370 | 371 | 372 |
|---|---|---|---|---|
| Xaa₃ | Xaa₄ | Xaa₈ | Xaa₅ | Xaa6 | wherein:
Xaa₃, Xaa₆, Xaa₉ and Xaa₁₄ are each independently an α,α-disubstituted amino acid;
Xaa₁₅ is selected from R, homoR, and N-methylR;
Xaa₁₆ is selected from S and T;
Xaa₁ is selected from L, A, Cha, Cpa, (D-L), CBA, MeL, NMeCha, Dcha, and NptGly;
Xaa₄ is selected from I, A, Nle, N-MethylI, CBA, and (D-I);
Xaa₈ is selected from Q and N-methylQ;
Xaa₅ is selected from R, A, Q, E, K, H, N-MethylR, homoR, NMeArg, Nar, and Cit; and
wherein the polypeptide has length of 9-30 amino acids.
In some embodiments, Xaa₁₅ is R.
In some embodiments, Xaa₁₆ is S.
In some embodiments, Xaa₁ is L.
In some embodiments, Xaa₁₅Xaa₁₆Xaa₁ comprise RSL.
In some embodiments, Xaa₄ is I.
In some embodiments, Xaa₈ is Q.
In some embodiments, Xaa₅ is R.
In some embodiments, Xaa₄Xaa₈Xaa₅ comprise IQR.
In some embodiments, in addition to the amino acid sequence Xaa₁₄Xaa₁₅Xaa₁₆Xaa₁Xaa₉ and the amino acid sequence Xaa₃Xaa₄Xaa₈Xaa₅Xaa₆, the polypeptide comprises at least one R.
In some embodiments, in addition to the amino acid sequence Xaa₁₄Xaa₁₅Xaa₁₆Xaa₁Xaa₉ and the amino acid sequence Xaa₃Xaa₄Xaa₈Xaa₅Xaa₆, the polypeptide comprises at least one (2-Nal).
In some embodiments, in addition to the amino acid sequence Xaa₁₄Xaa₁₅Xaa₁₆Xaa₁Xaa₉ and the amino acid sequence Xaa₃Xaa₄Xaa₈Xaa₅Xaa₆, the polypeptide comprises HR.
In some embodiments, in addition to the amino acid sequence Xaa₁₄Xaa₁₅Xaa₁₆Xaa₁Xaa₉ and the amino acid sequence Xaa₃Xaa₄Xaa₈Xaa₅Xaa₆, the polypeptide comprises TLR.

In some embodiments, in addition to the amino acid sequence Xaa$_{14}$Xaa$_{15}$Xaa$_{16}$Xaa$_{1}$Xaa$_{9}$ and the amino acid sequence Xaa$_{3}$Xaa$_{4}$Xaa$_{8}$Xaa$_{5}$Xaa$_{6}$, the polypeptide comprises (CBA)(2-Nal) or (4-ClPh)(2-Nal).

In some embodiments, the polypeptide is selected from:

(SEQ ID NO: 94)
HRXaa$_{14}$RSLXaa$_{9}$TLRXaa$_{3}$IQRXaa$_{6}$(CBA)(2-Nal);

(SEQ ID NO: 95)
HRXaa$_{14}$RSLXaa$_{9}$TLRXaa$_{3}$IQRXaa$_{6}$(CBA)(2-Nal);

(SEQ ID NO: 96)
HRXaa$_{14}$RSLXaa$_{9}$TLRXaa$_{3}$IQRXaa$_{6}$(4-ClPh)(2-Nal);
and (SEQ ID NO: 198
HRXaa$_{14}$RSLXaa$_{9}$TLRXaa$_{3}$IQRXaa$_{6}$(4-Cl-Ph)(2-Nal);

wherein N-terminus of SEQ ID NO: 95 and SEQ ID NO: 96 is modified with palmitoyl-PEG4.

In some embodiments, the α,α-disubstituted amino acid is an α-methyl, α-alkenyl amino acid.

In some embodiments, Xaa$_{3}$, Xaa$_{6}$, Xaa$_{9}$, and Xaa$_{14}$ are each independently selected from: (S)-2-(4'-pentenyl)alanine, (R)-2-(4'-pentenyl)alanine, (S)-2-(7'-octenyl)alanine, and (R)-2-(7'-octenyl)alanine.

In some embodiments, Xaa$_{3}$, Xaa$_{6}$, Xaa$_{9}$, and Xaa$_{14}$ are each (S)-2-(4'-pentenyl)alanine.

In some embodiments:
one α substituent in the α,α-disubstituted amino Xaa$_{3}$ acid is methyl, and the other α substituent is a first hydrocarbon linker; and in the α,α-disubstituted amino acid Xaa$_{6}$ one α substituent is methyl, and the other α substituent is the first hydrocarbon linker; and
one α substituent in the α,α-disubstituted amino Xaa$_{9}$ acid is methyl, and the other α substituent is a second hydrocarbon linker; and in the α,α-disubstituted amino acid Xaa$_{14}$ one α substituent is methyl, and the other α substituent is the second hydrocarbon linker.

In some embodiments, the first hydrocarbon linker has formula:

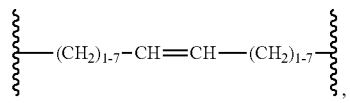

wherein one § denotes a point of attachment of the hydrocarbon linker to the α carbon atom of Xaa$_{3}$, and the other § denotes a point of attachment of the hydrocarbon linker to the α carbon atom of Xaa$_{6}$; and
the second hydrocarbon linker has formula:

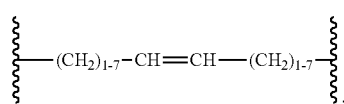

wherein one § denotes a point of attachment of the second hydrocarbon linker to the α carbon atom of Xaa$_{9}$, and the other § denotes a point of attachment of the second hydrocarbon linker to the α carbon atom of Xaa$_{14}$.

In some embodiments, the first hydrocarbon crosslinker has formula:

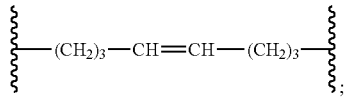

and
the second hydrocarbon crosslinker has formula:

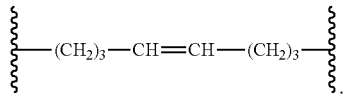

In yet another general aspect, the present disclosure provides a polypeptide, or a pharmaceutically acceptable salt thereof, comprising an amino acid sequence:

| 365 | 366 | 367 | 368 | 369 | 370 | 371 | 372 |
|---|---|---|---|---|---|---|---|
| Xaa$_{10}$ | Xaa$_{2}$ | Xaa$_{11}$ | Xaa$_{3}$ | Xaa$_{4}$ | Xaa$_{8}$ | Xaas$_{5}$ | Xaa$_{6}$ |

Xaa$_{10}$ and Xaa$_{6}$ are each independently an α,α-disubstituted amino acid;
Xaa$_{2}$ is selected from L, A, Cha, Cpa, (D-L), CBA, MeL, NMeCha, Dcha, and NptGly;
Xaa$_{11}$ is selected from R, N-methylR, E, K, homoR, Nar, and Cit;
Xaa$_{3}$ is selected from D and Nle;
Xaa$_{4}$ is selected from I, A, Nle, NMethylI, CBA, and (D-I);
Xaa$_{8}$ is selected from Q and N-methylQ;
Xaa$_{5}$ is selected from R, A, Q, E, K, H, N-methylR, homoR, NMeArg, Nar, and Cit; and
wherein the polypeptide has a length of 8-30 amino acids.
In some embodiments, Xaa$_{2}$ is L.
In some embodiments, Xaa$_{11}$ is R.
In some embodiments, Xaa$_{3}$ is D.
In some embodiments, Xaa$_{4}$ is I.
In some embodiments, Xaa$_{8}$ is Q.
In some embodiments, Xaa$_{5}$ is R.
In some embodiments, Xaa$_{2}$Xaa$_{11}$Xaa$_{3}$Xaa$_{4}$Xaa$_{8}$Xaa$_{5}$ comprises LRDIQR.
In some embodiments, in addition to the amino acid sequence Xaa$_{10}$Xaa$_{2}$Xaa$_{11}$Xaa$_{3}$Xaa$_{4}$Xaa$_{8}$Xaa$_{5}$Xaa$_{6}$, the polypeptide comprises at least one L.
In some embodiments, in addition to the amino acid sequence Xaa$_{10}$Xaa$_{2}$Xaa$_{11}$Xaa$_{3}$Xaa$_{4}$Xaa$_{8}$Xaa$_{5}$Xaa$_{6}$, the polypeptide comprises at least one (2-Nal).
In some embodiments, in addition to the amino acid sequence Xaa$_{10}$Xaa$_{2}$Xaa$_{11}$Xaa$_{3}$Xaa$_{4}$Xaa$_{8}$Xaa$_{5}$Xaa$_{6}$, the polypeptide comprises at least one (β-Ala).
In some embodiments, in addition to the amino acid sequence Xaa$_{10}$Xaa$_{2}$Xaa$_{11}$Xaa$_{3}$Xaa$_{4}$Xaa$_{8}$Xaa$_{5}$Xaa$_{6}$, the polypeptide comprises LQ.
In some embodiments, in addition to the amino acid sequence Xaa$_{10}$Xaa$_{2}$Xaa$_{11}$Xaa$_{3}$Xaa$_{4}$Xaa$_{8}$Xaa$_{5}$Xaa$_{6}$, the polypeptide comprises L(2-Nal).
In some embodiments, in addition to the amino acid sequence Xaa$_{10}$Xaa$_{2}$Xaa$_{11}$Xaa$_{3}$Xaa$_{4}$Xaa$_{8}$Xaa$_{5}$Xaa$_{6}$, the polypeptide comprises at least one (β-Ala).

In some embodiments, in addition to the amino acid sequence $Xaa_{10}Xaa_2Xaa_{11}Xaa_3Xaa_4Xaa_8Xaa_5Xaa_6$, the polypeptide comprises HRERS or HRQRS.

In some embodiments, the polypeptide is:

```
                                       (SEQ ID NO: 97)
LQXaa10LRDIQRXaa6L(2-Nal)(β-Ala)(β-Ala)
```

In some embodiments, the α,α-disubstituted amino acid is an α-methyl, α-alkenyl amino acid.

In some embodiments, $Xaa_6$ and $Xaa_{10}$ are each independently selected from: (S)-2-(4'-pentenyl)alanine, (R)-2-(4'-pentenyl)alanine, (S)-2-(7'-octenyl)alanine, and (R)-2-(7'-octenyl)alanine.

In some embodiments, $Xaa_6$ and $Xaa_{10}$ are each (S)-2-(4'-pentenyl)alanine.

In some embodiments, one α substituent in the α,α-disubstituted amino acid is methyl, and the other α substituent in the α,α-disubstituted amino acid is a hydrocarbon linker.

In some embodiments, the hydrocarbon linker has formula:

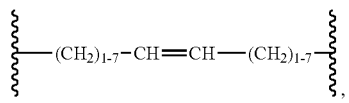

wherein one ⸱ denotes a point of attachment of the hydrocarbon linker to the α carbon atom of $Xaa_6$, and the other ⸱ denotes a point of attachment of the hydrocarbon linker to the α carbon atom of $Xaa_{10}$.

In some embodiments, the hydrocarbon crosslinker has formula:

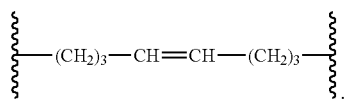

In yet another general aspect, the present disclosure provides a polypeptide, or a pharmaceutically acceptable salt thereof, comprising an amino acid sequence:

```
                                       (SEQ ID NO: 1)
SXaa1QTXaa2RXaa3Xaa4QXaa5Xaa6Xaa7(2-Nal),
``` wherein:

$Xaa_1$ and $Xaa_2$ are each independently selected from L, A, Cha, Cpa, CBA, (D-L), MeL, NMeCha, Dcha, and NptGly;

$Xaa_3$ and $Xaa_6$ are each independently an α,α-disubstituted amino acid;

$Xaa_4$ is selected from I, A, Nle, N-MethylI, CBA, and (D-I);

$Xaa_5$ is selected from R, A, Q, E, K, H, N-MethylR, homoR, NMeArg, Nar, and Cit; and $Xaa_7$ is selected from L, A, CBA, Cha, Cpa, Phe(4-Cl), (D-L), α-MethylL, DCha, N-MethylCha, allylGly, AC4C, A6C, Aze, N-MeCha, (βtBu-Ala), Tle, 4-FPh, and 3,4-diClPh;

wherein the polypeptide has a length of 13-30 amino acids.

In some embodiments:

$Xaa_1$ and $Xaa_2$ are each independently L or A;

$Xaa_4$ is I or A;

$Xaa_5$ is R or A; and $Xaa_7$ is L, A, or CBA.

In some embodiments, $Xaa_1$ and $Xaa_2$ are each L.

In some embodiments, $Xaa_1$ and $Xaa_2$ are each A.

In some embodiments, $Xaa_1$ is L and $Xaa_2$ is A.

In some embodiments, $Xaa_1$ and $Xaa_2$ are each Cha.

In some embodiments, $Xaa_1$ and $Xaa_2$ are each Cpa.

In some embodiments, $Xaa_4$ is I and $Xaa_5$ is R.

In some embodiments, $Xaa_4$ is I and $Xaa_5$ is A.

In some embodiments, $Xaa_4$ is A and $Xaa_5$ is R.

In some embodiments, $Xaa_7$ is selected from Cha, Cpa, Phe(4-Cl), (D-L), α-MethylL, DCha, N-methylCha, allylGly, AC4C, A6C, Aze, N-MeCha, (βtBu-Ala), Tle, 4-FPh, and 3,4-diClPh.

In some embodiments, $Xaa_7$ is L.

In some embodiments, $Xaa_7$ is A.

In some embodiments, $Xaa_7$ is CBA.

In some embodiments, the amino acid sequence SEQ ID NO: 1 is selected from:

```
                                       (SEQ ID NO: 2)
SLQTLRXaa3IQRXaa6L(2-Nal);
and
                                       (SEQ ID NO: 3)
SLQTLRXaa3IQRXaa6(CBA)(2-Nal).
```

In some embodiments, the polypeptide comprises an amino acid sequence RER.

In some embodiments, the polypeptide comprises an amino acid sequence QER.

In some embodiments, the polypeptide has a length of 13-20 amino acids.

In some embodiments, in addition to the amino acid sequence SEQ ID NO: 1, the polypeptide comprises at least one amino acid selected from: Q, L, E, H, and R.

In some embodiments, the polypeptide is selected from any one of the following polypeptides:

```
                                       (SEQ ID NO: 4)
RSLQTLRXaa3IQRXaa6L(2-Nal);

(SEQ ID NO: 5)
RERSLQTLRXaa3IQRXaa6L(2-Nal);

(SEQ ID NO: 6)
HRERSLQTLRXaa3IQRXaa6L(2-Nal);

(SEQ ID NO: 7)
EHRERSLQTLRXaa3IQRXaa6L(2-Nal);

(SEQ ID NO: 8)
QLEHRERSLQTLRXaa3IQRXaa6L(2-Nal);

(SEQ ID NO: 9)
EHRERSLQTLRXaa3IQRXaa6(CBA)(2-Nal);

(SEQ ID NO: 10)
QERSLQTLRXaa3IQRXaa6L(2-Nal);

(SEQ ID NO: 11)
HQERSLQTLRXaa3IQRXaa6L(2-Nal);

(SEQ ID NO: 12)
EHQERSLQTLRXaa3IQRXaa6L(2-Nal);
```

```
                                            (SEQ ID NO: 13)
RERSLQTLRXaa3IQRXaa6(CBA)(2-Nal);
and (SEQ ID NO: 14)
HRERSLQTLRXaa3IQRXaa6(CBA)(2-Nal).
```

In some embodiments, the α,α-disubstituted amino acid is an α-methyl, α-alkenyl amino acid.

In some embodiments, $Xaa_3$ and $Xaa_6$ are each independently selected from: (S)-2-(4'-pentenyl)alanine, (R)-2-(4'-pentenyl)alanine, (S)-2-(7'-octenyl)alanine, and (R)-2-(7'-octenyl)alanine.

In some embodiments, $Xaa_3$ and $Xaa_6$ are each (S)-2-(4'-pentenyl)alanine.

In some embodiments, one α substituent in the α,α-disubstituted amino acid is methyl, and the other α substituent in the α,α-disubstituted amino acid is a hydrocarbon linker.

In some embodiments, the hydrocarbon linker has formula:

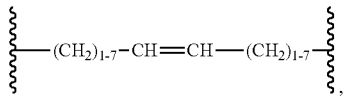

wherein one ⁀ denotes a point of attachment of the hydrocarbon linker to the α carbon atom of $Xaa_3$, and the other ⁀ denotes a point of attachment of the hydrocarbon linker to the α carbon atom of $Xaa_6$.

In some embodiments, the hydrocarbon crosslinker has formula:

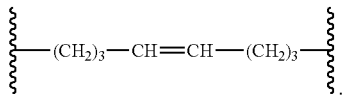

In yet another general aspect, the present disclosure provides a polypeptide, or a pharmaceutically acceptable salt thereof, comprising an amino acid sequence:

```
                                            (SEQ ID NO: 15)
Xaa1QTXaa2RXaa3Xaa4QXaa5Xaa6Xaa7(2-Nal),
``` wherein:

$Xaa_1$ and $Xaa_2$ are each independently L, A, Cha, Cpa, (D-L), CBA, MeL, N-MeCha, Dcha, and NptGly;

$Xaa_3$ and $Xaa_6$ are each independently an α,α-disubstituted amino acid;

$Xaa_4$ is selected from I, A, Nle, N-MethylI, CBA, and (D-I);

$Xaa_5$ is selected from R, A, Q, E, K, H, N-MethylR, homoR, NMeArg, Nar, and Cit; and $Xaa_7$ is selected from L, A, CBA, Cha, Cpa, Phe(4-Cl), (D-L), α-MethylL, DCha, N-MethylCha, allylGly, AC4C, A6C, Aze, N-MeCha, (βtBu-Ala), Tle, 4-FPh, and 3,4-diClPh;

wherein the polypeptide comprises at least one A; and wherein the polypeptide has a length of 12-30 amino acids.

In some embodiments:

$Xaa_1$ and $Xaa_2$ are each independently L or A;

$Xaa_4$ is I or A;

$Xaa_5$ is R or A; and $Xaa_7$ is L, A, or CBA.

In some embodiments, at least one of $Xaa_1$, $Xaa_2$, $Xaa_4$, $Xaa_5$, and $Xaa_7$ is A.

In some embodiments, $Xaa_1$ and $Xaa_2$ are each A.

In some embodiments, $Xaa_1$ is L and $Xaa_2$ is A.

In some embodiments, $Xaa_1$ and $Xaa_2$ are each L.

In some embodiments, $Xaa_2$ and $Xaa_4$ are each A.

In some embodiments, $Xaa_2$ is L and $Xaa_4$ is A.

In some embodiments, $Xaa_2$ is L and $Xaa_4$ is I.

In some embodiments, $Xaa_2$ is A and $Xaa_4$ is I.

In some embodiments, $Xaa_4$ is I and $Xaa_7$ is A.

In some embodiments, $Xaa_5$ is R and $Xaa_7$ is L.

In some embodiments, $Xaa_5$ is R and $Xaa_7$ is A.

In some embodiments, $Xaa_5$ is A and $Xaa_7$ is L.

In some embodiments, $Xaa_5$ is R and $Xaa_7$ is CBA.

In some embodiments, $Xaa_5$ is A and $Xaa_7$ is CBA.

In some embodiments, the amino acid sequence SEQ ID NO: 15 is selected from:

```
                                            (SEQ ID NO: 16)
AQTARXaa3IQRXaa6L(2-Nal);

(SEQ ID NO: 17)
LQTARXaa3AQRXaa6L(2-Nal);

(SEQ ID NO: 18)
LQTLRXaa3AQRXaa6A(2-Nal);

(SEQ ID NO: 19)
LQTLRXaa3IQAXaa6L(2-Nal);
and (SEQ ID NO: 20)
LQTLRXaa3IQAXaa6(CBA)(2-Nal).
```

In some embodiments, the polypeptide comprises an amino acid sequence ERS.

In some embodiments, the polypeptide comprises an amino acid sequence (β-Ala)(β-Ala).

In some embodiments, the polypeptide comprises an amino acid sequence AA.

In some embodiments, the polypeptide has a length of 12-20 amino acids.

In some embodiments, in addition to the amino acid sequence SEQ ID NO: 15, the polypeptide comprises at least one amino acid selected from: Q, L, E, H, R, and S.

In some embodiments, the polypeptide is selected from any one of the following polypeptides:

```
                                            (SEQ ID NO: 21)
AQTARXaa3IQRXaa6L(2-Nal);

(SEQ ID NO: 22)
LQTARXaa3AQRXaa6L(2-Nal);

(SEQ ID NO: 23)
LQTLRXaa3AQRXaa6A(2-Nal);

(SEQ ID NO: 24)
LQTLRXaa3IQAXaa6L(2-Nal);

(SEQ ID NO: 25)
LQTLRXaa3IQAXaa6(CBA)(2-Nal);

(SEQ ID NO: 26)
LQTLRXaa3IQAXaa6L(2-Nal)(β-Ala)(β-Ala);
```

```
                                           (SEQ ID NO: 27)
LQTLRXaa3IQAXaa6L(2-Nal)AA;

(SEQ ID NO: 28)
HRERSLQTLRXaa3IQAXaa6L(2-Nal);

(SEQ ID NO: 29)
HRERSLQTLRXaa3IQAXaa6(CBA)(2-Nal);

(SEQ ID NO: 75)
LQTARXaa3IQRXaa6L(2-Nal);

(SEQ ID NO: 76)
LQTLRXaa3AQRXaa6L(2-Nal);
and (SEQ ID NO: 77)
LQTLRXaa3IQRXaa6A(2-Nal).
```

In some embodiments, the polypeptide is selected from any one of the following polypeptides:

```
                                           (SEQ ID NO: 21)
AQTARXaa3IQRXaa6L(2-Nal);

(SEQ ID NO: 22)
LQTARXaa3AQRXaa6L(2-Nal);

(SEQ ID NO: 23)
LQTLRXaa3AQRXaa6A(2-Nal);

(SEQ ID NO: 24)
LQTLRXaa3IQAXaa6L(2-Nal);

(SEQ ID NO: 25)
LQTLRXaa3IQAXaa6(CBA)(2-Nal);

(SEQ ID NO: 26)
LQTLRXaa3IQAXaa6L(2-Nal)(β-Ala)(β-Ala);

(SEQ ID NO: 27)
LQTLRXaa3IQAXaa6L(2-Nal)AA;

(SEQ ID NO: 28)
HRERSLQTLRXaa3IQAXaa6L(2-Nal);
and (SEQ ID NO: 29)
HRERSLQTLRXaa3IQAXaa6(CBA)(2-Nal).
```

In some embodiments, the α,α-disubstituted amino acid is an α-methyl, α-alkenyl amino acid.

In some embodiments, $Xaa_3$ and $Xaa_6$ are each independently selected from: (S)-2-(4'-pentenyl)alanine, (R)-2-(4'-pentenyl)alanine, (S)-2-(7'-octenyl)alanine, and (R)-2-(7'-octenyl)alanine.

In some embodiments, $Xaa_3$ and $Xaa_6$ are each (S)-2-(4'-pentenyl)alanine.

In some embodiments, one α substituent in the α,α-disubstituted amino acid is methyl, and the other α substituent in the α,α-disubstituted amino acid is a hydrocarbon linker.

In some embodiments, the hydrocarbon linker has formula:

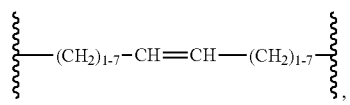

wherein one ⌇ denotes a point of attachment of the hydrocarbon linker to the α carbon atom of $Xaa_3$, and the other ⌇ denotes a point of attachment of the hydrocarbon linker to the α carbon atom of $Xaa_6$.

In some embodiments, the hydrocarbon linker has formula:

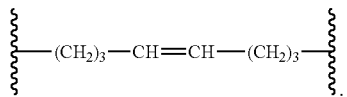

In yet another general aspect, the present disclosure provides a polypeptide, or a pharmaceutically acceptable salt thereof, comprising an amino acid sequence:

```
                                           (SEQ ID NO: 30)
Xaa1QTXaa2RXaa3Xaa4QXaa5Xaa6Xaa7(2-Nal),
``` wherein:

$Xaa_1$ and $Xaa_2$ are each independently L, A, Cha, Cpa, (D-L), CBA, MeL, N-MeCha, Dcha, and NptGly;

$Xaa_3$ and $Xaa_6$ are each independently an α,α-disubstituted amino acid;

$Xaa_4$ is selected from I, A, Nle, N-MethylI, CBA, and (D-I);

$Xaa_5$ is selected from R, A, Q, E, K, H, N-MethylR, homoR, NMeArg, Nar, and Cit; and $Xaa_7$ is selected from L, A, CBA, Cha, Cpa, Phe(4-Cl), (D-L), α-MethylL, DCha, N-MethylCha, allylGly, AC4C, A6C, Aze, N-MeCha, (βtBu-Ala), Tle, 4-FPh, and 3,4-diClPh; and wherein the polypeptide has a length of 13-22 amino acids.

In some embodiments:

$Xaa_1$ and $Xaa_2$ are each independently L or A;

$Xaa_4$ is I or A;

$Xaa_5$ is R or A; and $Xaa_7$ is L, A, or CBA.

In some embodiments, $Xaa_1$ and $Xaa_2$ are each L.

In some embodiments, $Xaa_4$ is I and $Xaa_5$ is R.

In some embodiments, $Xaa_7$ is L.

In some embodiments, the amino acid sequence SEQ ID NO: 30 is

```
                                           (SEQ ID NO: 31)
LQTLRXaa3IQRXaa6L(2-Nal).
```

In some embodiments, in addition to the amino acid sequence SEQ ID NO: 30, the polypeptide comprises at least one amino acid selected from: P, D, and β-Ala.

In some embodiments, in addition to the amino acid sequence SEQ ID NO: 30, the polypeptide comprises at least one amino acid selected from: Q, L, E, H, R, and S.

In some embodiments, the polypeptide is selected from any one of the following polypeptides:

```
                                           (SEQ ID NO: 32)
LQTLRXaa3IQRXaa6L(2-Nal)PD;

(SEQ ID NO: 33)
LQTLRXaa3IQRXaa6L(2-Nal)P;
```

-continued

```
                                          (SEQ ID NO: 34)
LQTLRXaa3IQRXaa6L(2-Nal)(β-Ala)(β-Ala);
and (SEQ ID NO: 34a)
LQTLRXaa3IQRXaa6L(2-Nal)(β-Ala)(β-Ala),
``` wherein C-terminus in SEQ ID NO: 34a is modified with GRKKRRQRRRPQK(PEG4-palmitoyl)NH$_2$.

In some embodiments, the polypeptide is selected from any one of the following polypeptides:

```
                                          (SEQ ID NO: 32)
LQTLRXaa3IQRXaa6L(2-Nal)PD;

(SEQ ID NO: 33)
LQTLRXaa3IQRXaa6L(2-Nal)P;
and (SEQ ID NO: 34)
LQTLRXaa3IQRXaa6L(2-Nal)(β-Ala)(β-Ala).
```

In some embodiments, the α,α-disubstituted amino acid is an α-methyl, α-alkenyl amino acid.

In some embodiments, Xaa$_3$ and Xaa$_6$ are each independently selected from: (S)-2-(4'-pentenyl)alanine, (R)-2-(4'-pentenyl)alanine, (S)-2-(7'-octenyl)alanine, and (R)-2-(7'-octenyl)alanine.

In some embodiments, Xaa$_3$ and Xaa$_6$ are each (S)-2-(4'-pentenyl)alanine.

In some embodiments, one α substituent in the α,α-disubstituted amino acid is methyl, and the other α substituent in the α,α-disubstituted amino acid is a hydrocarbon linker.

In some embodiments, the hydrocarbon linker has formula:

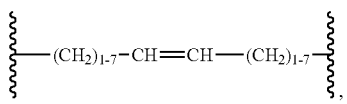

wherein one § denotes a point of attachment of the hydrocarbon linker to the α carbon atom of Xaa$_3$, and the other § denotes a point of attachment of the hydrocarbon linker to the α carbon atom of Xaa$_6$.

In some embodiments, the hydrocarbon crosslinker has formula:

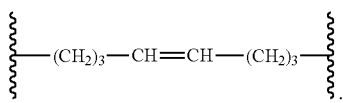

In yet another general aspect, the present disclosure provides a polypeptide, or a pharmaceutically acceptable salt thereof, comprising an amino acid sequence:

```
                                          (SEQ ID NO: 35)
Xaa1TXaa2RXaa3,
``` wherein:
Xaa$_1$ and Xaa$_3$ are each independently an α,α-disubstituted amino acid; and Xaa$_2$ is selected from L, A, Cha, Cpa, (D-L), CBA, MeL, N-MeCha, Dcha, and NptGly;
wherein the polypeptide comprises at least one 2-Nal; and
wherein the polypeptide has a length of 6-30 amino acids.
In some embodiments:
Xaa$_2$ is L or A.
In some embodiments, Xaa$_2$ is L.
In some embodiments, in addition to the amino acid sequence SEQ ID NO: 35, the polypeptide comprises at least one amino acid selected from: Q, L, E, H, I, S, M, and R.
In some embodiments, in addition to the amino acid sequence SEQ ID NO: 35, the polypeptide comprises at least two R.
In some embodiments, in addition to the amino acid sequence SEQ ID NO: 35, the polypeptide comprises three R.
In some embodiments, in addition to the amino acid sequence SEQ ID NO: 35, the polypeptide comprises at least two E.
In some embodiments, in addition to the amino acid sequence SEQ ID NO: 35, the polypeptide comprises at least two L.
In some embodiments, in addition to the amino acid sequence SEQ ID NO: 35, the polypeptide comprises three L.
In some embodiments, in addition to the amino acid sequence SEQ ID NO: 35, the polypeptide comprises at least two Q.
In some embodiments, in addition to the amino acid sequence SEQ ID NO: 35, the polypeptide comprises at least one amino acid selected from H, S, I, and M.
In some embodiments, the polypeptide comprises an amino acid sequence IQR.
In some embodiments, the polypeptide comprises an amino acid sequence ML(2-Nal).
In some embodiments, the polypeptide comprises an amino acid sequence (2-Abu)L(2-Nal)(β-Ala)(β-Ala).
In some embodiments, the polypeptide comprises an amino acid sequence RERSL.
In some embodiments, the polypeptide comprises an amino acid sequence QLEH.
In some embodiments, the polypeptide is selected from:

```
                                          (SEQ ID NO: 36)
QLEHRERSLXaa1TLRXaa3IQRML(2-Nal);
and (SEQ ID NO: 78)
QLEHRERSLXaa1TLRXaa3IQR(2-Abu)L(2-Nal)(β-Ala)
  (β-Ala).
```

In some embodiments, the polypeptide is:

```
                                          (SEQ ID NO: 36)
QLEHRERSLXaa1TLRXaa3IQRML(2-Nal).
```

In some embodiments, the α,α-disubstituted amino acid is an α-methyl, α-alkenyl amino acid.

In some embodiments, Xaa$_1$ and Xaa$_3$ are each independently selected from: (S)-2-(4'-pentenyl)alanine, (R)-2-(4'-pentenyl)alanine, (S)-2-(7'-octenyl)alanine, and (R)-2-(7'-octenyl)alanine.

In some embodiments, Xaa$_1$ and Xaa$_3$ are each (S)-2-(4'-pentenyl)alanine.

In some embodiments, one α substituent in the α,α-disubstituted amino acid is methyl, and the other α substituent in the α,α-disubstituted amino acid is a hydrocarbon linker.

In some embodiments, the hydrocarbon linker has formula:

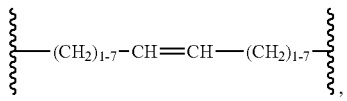

wherein one ⸗ denotes a point of attachment of the hydrocarbon linker to the α carbon atom of Xaa₁, and the other ⸗ denotes a point of attachment of the hydrocarbon linker to the α carbon atom of Xaa₃.

In some embodiments, the hydrocarbon crosslinker has formula:

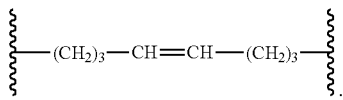

In yet another general aspect, the present disclosure provides a polypeptide, or a pharmaceutically acceptable salt thereof, comprising an amino acid sequence selected from:

```
                                          (SEQ ID NO: 37a)
Xaa₁SLQXaa₂
and (SEQ ID NO: 37b)
Xaa₁S(Cha)(N-methylQ)Xaa₂;
``` and an amino acid sequence selected from:

```
                                          (SEQ ID NO: 38a)
Xaa₃IQRXaa₄
and (SEQ ID NO: 38b)
Xaa₃IQQXaa₄;
``` wherein:

Xaa₁, Xaa₂, Xaa₃ and Xaa₄ are each independently an α,α-disubstituted amino acid; and wherein the polypeptide has length of 10-30 amino acids.

In some embodiments, the polypeptide comprises an amino acid sequence:

```
                                          (SEQ ID NO: 37)
Xaa₁SLQXaa₂,
``` and an amino acid sequence:

```
                                          (SEQ ID NO: 38)
Xaa₃IQRXaa₄.
```

In some embodiments, the polypeptide comprises at least one 2-Nal.

In some embodiments, the polypeptide comprises at least one CBA.

In some embodiments, in addition to the amino acid sequence SEQ ID NO: 37a or the amino acid sequence SEQ ID NO: 37b, and the amino acid sequence SEQ ID NO: 38a or the amino acid sequence SEQ ID NO: 38b, the polypeptide comprises at least one amino acid selected from: L, E, R, H, Q, CBA, N-methylQ, N-methylE, N-methylR, N-methylD, N-methylT, N-methylI, Cpa, Cha, N-MeHis, N-MeCys, homoHis, NHis, homoR, Cit, Nar, Phe(4-guanidino), NMeGln, Nle, 2-Abu, Phe(4-Cl), 3,4-diClPh, 4-FPh, NptGly, NMeCha, Dcha, α-methylL, allylGly, Alg, AC4C, A6C, Aze, (βtBu-Ala), Tle, peptoidQ, DThr, and NMeLeu.

In some embodiments, in addition to the amino acid sequence SEQ ID NO: 37a or the amino acid sequence SEQ ID NO: 37b, and the amino acid sequence SEQ ID NO: 38a or the amino acid sequence SEQ ID NO: 38b, the polypeptide comprises at least one amino acid selected from: L, E, R, H, Q, N-methylE, CBA, N-methylQ, Cha, and N-methylR.

In some embodiments, in addition to the amino acid sequence SEQ ID NO: 37 and the amino acid sequence SEQ ID NO: 38, the polypeptide comprises at least one amino acid selected from: L, E, and R.

In some embodiments, the polypeptide comprises at amino acid sequence RE.

In some embodiments, the polypeptide comprises at amino acid sequence LR.

In some embodiments, the polypeptide comprises at amino acid sequence L(2-Nal).

In some embodiments, the polypeptide comprises at amino acid sequence (CBA)(2-Nal).

In some embodiments, the polypeptide comprises at amino acid sequence selected from HRE, HR(N-methylE), HR(N-MethylQ), HRQ, LR, L(N-methylR), (Cha)R, L(2-Nal), and (CBA)(2-Nal).

In some embodiments, the polypeptide comprises at least one β-Ala.

In some embodiments, the polypeptide has a length of 10-20 amino acids.

In some embodiments, the polypeptide is selected from any one of the following polypeptides:

```
                                          (SEQ ID NO: 39)
REXaa₁SLQXaa₂LRXaa₃IQRXaa₄L(2-Nal);

(SEQ ID NO: 40);
REXaa₁SLQXaa₂LRXaa₃IQRXaa₄L(2-Nal)(β-Ala)(β-Ala);

(SEQ ID NO: 79)
EXaa₁SLQXaa₂LRXaa₃IQRXaa₄L(2-Nal)(β-Ala)(β-Ala);

(SEQ ID NO: 82)
HREXaa₁SLQXaa₂LRXaa₃IQRXaa₄(CBA)(2-Nal);

(SEQ ID NO: 83)
HREXaa₁SLQXaa₂LRXaa₃IQQXaa₄(CBA)(2-Nal);

(SEQ ID NO: 84)
HR(N-methylE)Xaa₁SLQXaa₂LRXaa₃IQRXaa₄(CBA)(2-Nal);

(SEQ ID NO: 85)
HREXaa₁SLQXaa₂L(N-methylR)Xaa₃IQRXaa₄(CBA)(2-Nal);

(SEQ ID NO: 86)
HR(N-methylQ)Xaa₁S(Cha)(N-methylQ)Xaa₂(Cha)RXaa₃IQRXaa₄(Cha)(2-Nal);
and (SEQ ID NO: 87)
HRQXaa₁SLQXaa₂LRXaa₃IQRXaa₄(CBA)(2-Nal).
```

In some embodiments, the polypeptide is selected from any one of the following polypeptides:

REXaa₁SLQXaa₂LRXaa₃IQRXaa₄(2-Nal); (SEQ ID NO: 39)
and

REXaa₁SLQXaa₂LRXaa₃IQRXaa₄(2-Nal)(β-Ala)(β-Ala). (SEQ ID NO: 40)

In some embodiments, the α,α-disubstituted amino acid is an α-methyl, α-alkenyl amino acid.

In some embodiments, Xaa₁ Xaa₂, Xaa₃ and Xaa₄ are each independently selected from: (S)-2-(4'-pentenyl)alanine, (R)-2-(4'-pentenyl)alanine, (S)-2-(7'-octenyl)alanine, and (R)-2-(7'-octenyl)alanine.

In some embodiments, Xaa₁ and Xaa₂ are each (S)-2-(4'-pentenyl)alanine.

In some embodiments, Xaa₃ and Xaa₄ are each (S)-2-(4'-pentenyl)alanine.

In some embodiments, in the α,α-disubstituted amino acid Xaa₁ one α substituent in is methyl, and the other α substituent is a first hydrocarbon linker; and in the α,α-disubstituted amino acid Xaa₂ one α substituent is methyl, and the other α substituent is the first hydrocarbon linker.

In some embodiments, the first hydrocarbon linker has formula:

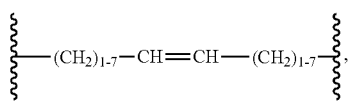

wherein one ⌇ denotes a point of attachment of the first hydrocarbon linker to the α carbon atom of Xaa₁, and the other ⌇ denotes a point of attachment of the first hydrocarbon linker to the α carbon atom of Xaa₂.

In some embodiments, the first hydrocarbon crosslinker has formula:

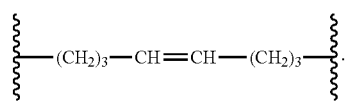

In some embodiments, in the α,α-disubstituted amino acid Xaa₃ one α substituent in is methyl, and the other α substituent is a second hydrocarbon linker; and in the α,α-disubstituted amino acid Xaa₄ one α substituent is methyl, and the other α substituent is the second hydrocarbon linker.

In some embodiments, the second hydrocarbon linker has formula:

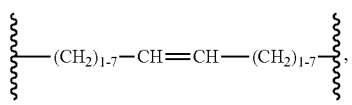 [SMILES: *CC=CC*]

wherein one ⌇ denotes a point of attachment of the second hydrocarbon linker to the α carbon atom of Xaa₃, and the other ⌇ denotes a point of attachment of the second hydrocarbon linker to the α carbon atom of Xaa₄.

In some embodiments, the second hydrocarbon crosslinker has formula:

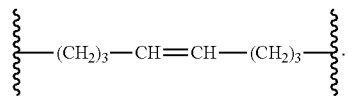

In yet another general aspect, the present disclosure provides a polypeptide, or a pharmaceutically acceptable salt thereof, comprising an amino acid sequence SEQ ID NO: 37:

| 361 | 362 | 363 | 364 | 365 |
|---|---|---|---|---|
| Xaa₁₅ | S | L | Q | Xaa₁₀ | wherein:

Xaa₁₅ and Xaa₁₀ are each independently an α,α-disubstituted amino acid; the polypeptide comprises at least two Nle; and the polypeptide has length of 7-30 amino acids.

In some embodiments, in addition to the amino acid sequence SEQ ID NO: 37, the polypeptide comprises at least one amino acid selected from: L, E, R, H, S, Q, I, CBA, N-methylQ, N-methylE, N-methylR, N-methylD, N-methylT, N-methylI, Cpa, Cha, N-MeHis, N-MeCys, homoHis, NHis, homoR, Cit, Nar, Phe(4-guanidino), NMeGln, Nle, 2-Abu, Phe(4-Cl), 3,4-diClPh, 4-FPh, NptGly, NMeCha, Dcha, α-methylL, allylGly, Alg, AC4C, A6C, Aze, (β-tBu-Ala), Tle, peptoidQ, DThr, and NMeLeu.

In some embodiments, in addition to the amino acid sequence SEQ ID NO: 37, the polypeptide comprises at least one amino acid selected from: H, R, E, S, L, Q, I, CBA, and (2-Nal).

In some embodiments, the polypeptide comprises IQR.

In some embodiments, the polypeptide comprises (Nle)IQR(Nle).

In some embodiments, the polypeptide comprises HRE and LR.

In some embodiments, the polypeptide comprises L(2-Nal).

In some embodiments, the polypeptide comprises (CBA)(2-Nal).

In some embodiments, the polypeptide is selected from:

HREXaa₁₅SLQXaa₁₀LR(Nle)IQR(Nle)L(2-Nal); (SEQ ID NO: 80)
and

HREXaa₁₅SLQXaa₁₀LR(Nle)IQR(Nle)(CBA)(2-Nal). (SEQ ID NO: 81)

In some embodiments, the α,α-disubstituted amino acid is an α-methyl, α-alkenyl amino acid.

In some embodiments, Xaa₁₅ and Xaa₁₀ are each independently selected from: (S)-2-(4'-pentenyl)alanine, (R)-2-(4'-pentenyl)alanine, (S)-2-(7'-octenyl)alanine, and (R)-2-(7'-octenyl)alanine.

In some embodiments, Xaa₁₅ and Xaa₁₀ are each (S)-2-(4'-pentenyl)alanine.

In some embodiments, one α substituent in the α,α-disubstituted amino acid is methyl, and the other α substituent in the α,α-disubstituted amino acid is a hydrocarbon linker.

In some embodiments, the hydrocarbon linker has formula:

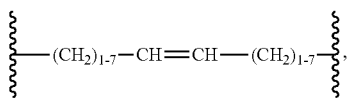

wherein one ⸹ denotes a point of attachment of the hydrocarbon linker to the α carbon atom of Xaa₁₅, and the other ⸹ denotes a point of attachment of the hydrocarbon linker to the α carbon atom of Xaa₁₀.

In some embodiments, the hydrocarbon crosslinker has formula:

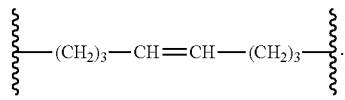

In yet another general aspect, the present disclosure provides a polypeptide, or a pharmaceutically acceptable salt thereof, comprising an amino acid sequence

| 367 | 368 | 369 | 370 | 371 | 372 | 373 | 374 |
|---|---|---|---|---|---|---|---|
| Xaa₁₁ | Xaa₃ | Xaa₄ | Xaa₈ | Xaa₅ | Xaa₆ | Xaa₇ | (2-Nal), | wherein:

Xaa₃ and Xaa₆ are each independently an α,α-disubstituted amino acid;

Xaa₄ is selected from I, A, Nle, N-MethylI, CBA, and (D-I);

Xaa₈ is selected from Q and N-methylQ;

Xaa₅ is selected from R, A, Q, E, K, H, N-methylR, homoR, NMeArg, Nar, and Cit; and Xaa₇ is selected from L, A, CBA, Cha, Cpa, Phe(4-Cl), (D-L), α-MethylL, DCha, N-methylCha, allylGly, AC4C, A6C, Aze, NMeCha, (β-tBu-Ala), Tle, 4-FPh, and 3,4-diClPh;

Xaa₁₁ is selected from R, N-methylR, E, K, homoR, Nar, and Cit; and wherein:
at least one of Xaa₁₁ and Xaa₅ comprises E or K; and
the polypeptide has a length of 8-30 amino acids.

In some embodiments, Xaa₁₁ is E, and Xaa₅ is R.
In some embodiments, Xaa₁₁ is R, and Xaa₅ is E.
In some embodiments, Xaa₁₁ is K and Xaa₅ is R.
In some embodiments, Xaa₁₁ is R and Xaa₅ is K.
In some embodiments, the polypeptide comprises L(2-Nal).
In some embodiments, the polypeptide comprises IQR, IQE, or IQK.
In some embodiments, the polypeptide comprises LQTLE, LQTLR, or LQRLK.
In some embodiments, is selected from:

LQTLEXaa₃IQRXaa₆L(2-Nal);  (SEQ ID NO: 98)

LQTLRXaa₃IQEXaa₆L(2-Nal);  (SEQ ID NO: 99)

LQTLKXaa₃IQRXaa₆L(2-Nal);  (SEQ ID NO: 100)
    and

LQTLRXaa₃IQKXaa₆L(2-Nal).  (SEQ ID NO: 101)

In some embodiments, the α,α-disubstituted amino acid is an α-methyl, α-alkenyl amino acid.

In some embodiments, Xaa₃ and Xaa₆ are each independently selected from: (S)-2-(4'-pentenyl)alanine, (R)-2-(4'-pentenyl)alanine, (S)-2-(7'-octenyl)alanine, and (R)-2-(7'-octenyl)alanine.

In some embodiments, Xaa₃ and Xaa₆ are each (S)-2-(4'-pentenyl)alanine.

In some embodiments, one α substituent in the α,α-disubstituted amino acid is methyl, and the other α substituent in the α,α-disubstituted amino acid is a hydrocarbon linker.

In some embodiments, the hydrocarbon linker has formula:

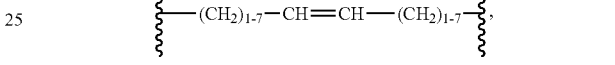

wherein one ⸹ denotes a point of attachment of the hydrocarbon linker to the α carbon atom of Xaa₃, and the other ⸹ denotes a point of attachment of the hydrocarbon linker to the α carbon atom of Xaa₆.

In some embodiments, the hydrocarbon crosslinker has formula:

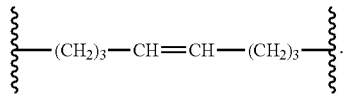

In yet another general aspect, the present disclosure provides a polypeptide, or a pharmaceutically acceptable salt thereof, comprising an amino acid sequence

| 368 | 369 | 370 | 371 | 372 | 373 | 374 |
|---|---|---|---|---|---|---|
| Xaa₃ | Xaa₄ | Xaa₈ | Xaa₅ | Xaa₆ | Xaa₇ | (2-Nal), | wherein:

Xaa₃ and Xaa₆ are each independently an α,α-disubstituted amino acid;

Xaa₄ is selected from I, A, Nle, N-MethylI, CBA, and (D-I);

Xaa₈ is selected from Q and N-methylQ;

Xaa₅ is selected from R, A, Q, E, K, H, N-methylR, homoR, NMeArg, Nar, and Cit; and Xaa₇ is selected from L, A, CBA, Cha, Cpa, Phe(4-Cl), (D-L), α-MethylL, DCha, N-methylCha, allylGly, AC4C, A6C, Aze, NMeCha, (βtBu-Ala), Tle, 4-FPh, and 3,4-diClPh; and wherein:
the polypeptide comprises at least one (D-I) or (D-L); and
the polypeptide has a length of 7-30 amino acids.

In some embodiments, Xaa₄ is (D-I).
In some embodiments, Xaa₇ is (D-L).
In some embodiments, the polypeptide comprises (D-L) QTIR.

In some embodiments, the polypeptide comprises LQT(D-L)R.

In some embodiments, the polypeptide is selected from:

(D-L)QTIRXaa₃IQRXaa₆L(2-Nal); (SEQ ID NO: 102)

LQT(D-L)RXaa₃IQRXaa₆L(2-Nal); (SEQ ID NO: 103)

LQTLRXaa₃(D-I)QRXaa₆L(2-Nal); and (SEQ ID NO: 104)

LQTLRXaa₃IQRXaa₆(D-L)(2-Nal). (SEQ ID NO: 105)

In some embodiments, the α,α-disubstituted amino acid is an α-methyl, α-alkenyl amino acid.

In some embodiments, Xaa₃ and Xaa₆ are each independently selected from: (S)-2-(4'-pentenyl)alanine, (R)-2-(4'-pentenyl)alanine, (S)-2-(7'-octenyl)alanine, and (R)-2-(7'-octenyl)alanine.

In some embodiments, Xaa₃ and Xaa₆ are each (S)-2-(4'-pentenyl)alanine.

In some embodiments, one α substituent in the α,α-disubstituted amino acid is methyl, and the other α substituent in the α,α-disubstituted amino acid is a hydrocarbon linker.

In some embodiments, the hydrocarbon linker has formula:

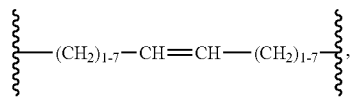

wherein one ⸹ denotes a point of attachment of the hydrocarbon linker to the α carbon atom of Xaa₃, and the other ⸹ denotes a point of attachment of the hydrocarbon linker to the α carbon atom of Xaa₆.

In some embodiments, the hydrocarbon crosslinker has formula:

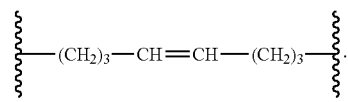

In yet another general aspect, the present disclosure provides a polypeptide, or a pharmaceutically acceptable salt thereof, having a length of 6-30 amino acids, wherein the polypeptide has at least 60% homology to a corresponding fragment of a wild-type HD2 domain of human B-cell CLL/lymphoma 9 (BCL9), and wherein the polypeptide comprises at least one α-monosubstituted non-natural amino acid.

In some embodiments, the fragment of wild-type HD2 domain of human B-cell CLL/lymphoma 9 (BCL9) is any fragment between 355 position and 377 position, inclusive, within the BCL9.

In some embodiments, the α-monosubstituted non-natural amino acid is selected from Nle, β-Ala, 2-Nal, β-L, and CBA.

In some embodiments, the polypeptide comprises at least one 2-Nal.

In some embodiments, the polypeptide comprises at least one CBA.

In some embodiments, the polypeptide comprises at least one Nle.

In some embodiments, the polypeptide comprises two Nle.

In some embodiments, the polypeptide comprises at least one β-L.

In some embodiments, the polypeptide comprises at least one β-Ala.

In some embodiments, the polypeptide comprises two β-Ala.

In some embodiments, the polypeptide comprises at least one amino acid sequence selected from:

DIQRML(2-Nal); (SEQ ID NO: 41)

(Nle)IQR(Nle)L(2-Nal); (SEQ ID NO: 42)

(Nle)IQR(Nle)(CBA)(2-Nal); (SEQ ID NO: 43)

(Nle)IQA(Nle)L(2-Nal); (SEQ ID NO: 44)

(Nle)IQA(Nle)(CBA)(2-Nal); (SEQ ID NO: 45)

(Nle)TLR(Nle); (SEQ ID NO: 46)

QTLR(Nle); and (SEQ ID NO: 47)

QT(β-L)R(Nle). (SEQ ID NO: 48)

In some embodiments, the polypeptide comprises an amino acid sequence RSL.

In some embodiments, the polypeptide comprises an amino acid sequence selected from: HRE and HQE.

In some embodiments, the polypeptide comprises an amino acid sequence QLE.

In some embodiments, the polypeptide is selected from any one of the following polypeptides:

LR(Nle)IQR(Nle)L(2-Nal)(β-Ala)(β-Ala); (SEQ ID NO: 49)

LR(Nle)IQR(Nle)L(2-Nal); (SEQ ID NO: 50)

LQTLRDIQRML(2-Nal); (SEQ ID NO: 51)

LQTLR(Nle)IQR(Nle)L(2-Nal); (SEQ ID NO: 52)

LQTLRDIQRML(2-Nal)PD; (SEQ ID NO: 53)

LQTLR(Nle)IQR(Nle)L(2-Nal)PD; (SEQ ID NO: 54)

LQTLRDIQRML(2-Nal)P; (SEQ ID NO: 55)

```
                                           (SEQ ID NO: 56)
LQTLR(Nle)IQR(Nle)L(2-Nal)P;

(SEQ ID NO: 57)
RSLQTLRDIQRML(2-Nal);

(SEQ ID NO: 58)
RSLQTLR(Nle)IQR(Nle)L(2-Nal);

(SEQ ID NO: 59)
RERSLQTLRDIQRML(2-Nal);

(SEQ ID NO: 60)
RERSLQTLR(Nle)IQR(Nle)L(2-Nal);

(SEQ ID NO: 61)
HRERSLQTLRDIQRML(2-Nal);

(SEQ ID NO: 62)
HRERSLQTLR(Nle)IQR(Nle)L(2-Nal);

(SEQ ID NO: 63)
EHRERSLQTLRDIQRML(2-Nal);

(SEQ ID NO: 64)
EHRERSLQTLR(Nle)IQR(Nle)L(2-Nal);

(SEQ ID NO: 65)
QLEHRERSLQTLRDIQRML(2-Nal);

(SEQ ID NO: 66)
QLEHRERSLQTLR(Nle)IQR(Nle)L(2-Nal);

(SEQ ID NO: 67)
QLEHRERSL(Nle)TLR(Nle)IQRML(2-Nal);

(SEQ ID NO: 68)
RSLQTLR(Nle)IQR(Nle)(CBA)(2-Nal);

(SEQ ID NO: 69)
RSLQTLR(Nle)IQA(Nle)(CBA)(2-Nal);

(SEQ ID NO: 70)
HQERSLQTLR(Nle)IQR(Nle)L(2-Nal);

(SEQ ID NO: 71)
HRERSLQTLR(Nle)IQA(Nle)L(2-Nal);

(SEQ ID NO: 72)
HRERSLQTLR(Nle)IQA(Nle)L(2-Nal)(β-Ala)(β-Ala);

(SEQ ID NO: 73)
HRERSLQT(β-L)R(Nle)IQR(Nle)L(2-Nal);
and (SEQ ID NO: 74)
HQERSLQT(β-L)R(Nle)IQR(Nle)L(2-Nal).
```

In yet another general aspect, the present disclosure provides a pharmaceutically acceptable composition comprising any one of polypeptides disclosed herein, or a pharmaceutically acceptable salt thereof, and a pharmaceutically acceptable carrier.

In yet another general aspect, the present disclosure provides a method of:
inhibiting binding of BCL9 to β-catenin in a subject; and/or
inhibiting canonical Wnt/1-catenin signaling in a subject; and/or
decreasing regulatory T cell survival in a subject; and/or
decreasing expression of VEGF in a tumor in a subject; and/or
increasing CD4+ T cell and CD8+ T cell infiltration into a tumor in a subject; and/or
increasing T helper 17 (Th17) cells into a tumor in a subject; and/or
decreasing dendritic cells in a tumor in a subject; and/or
having a half-life ($T_{1/2}$) greater than at least 2 hours when administrated to a subject; and/or
inducing a tumor microenvironment favoring an immune reaction in a subject; and/or
inhibiting tumor growth in a subject, and/or
inhibiting cancer stem cell proliferation in a subject, and/or
inhibiting tumor metastasis in a subject, and/or
treating cancer in a subject;
the method comprising administering to the subject in need thereof a therapeutically effective amount of any one of polypeptides disclosed herein, or a pharmaceutical composition comprising any one of the polypeptides.

In some embodiments, the cancer is familial adenomatous polyposis (FAP), ocular cancer, rectal cancer, colon cancer, colorectal cancer, cervical cancer, prostate cancer, breast cancer, bladder cancer, oral cancer, benign and malignant tumors, stomach cancer, liver cancer, pancreatic cancer, lung cancer, corpus uteri, ovarian cancer, prostate cancer, testicular cancer, renal cancer, brain/CNS cancer, throat cancer, multiple myeloma, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, gastric cancer, ovarian cancer, hepatocellular carcinoma, or lymphangiogenesis.

In some embodiments, the cancer is colorectal cancer.
In some embodiments, the cancer is gastric cancer.
In some embodiments, the cancer is ovarian cancer.
In some embodiments, the cancer is Hepatocellular carcinoma.
In some embodiments, the cancer is breast cancer.
In some embodiments, the cancer is prostate cancer.
In some embodiments, the cancer is skin melanoma.
In some embodiments, the cancer is lung cancer.

In some embodiments, the method further comprises administering at least one additional agent to the subject.

In some embodiments, the at least one additional agent is selected from the group consisting of: a checkpoint inhibitor, an EGFR inhibitor, a VEGF inhibitor, a chemotherapeutic agent, and a VEGFR inhibitor.

In some embodiments, the checkpoint inhibitor is an anti-PD-1 antibody, an anti-PD-L1 antibody, or an anti-CTLA4 antibody.

In some embodiments, the checkpoint inhibitor targets a stimulatory checkpoint molecule selected from the group consisting of: CD27, CD40, OX40, GITR and CD137.

In some embodiments, the checkpoint inhibitor targets to an inhibitory checkpoint molecule selected from the group consisting of: A2AR, B7-H3, B7-H4, B and T lymphocyte attenuator (BTLA), indoleamine 2,3-dioxygenase (IDO), Killer-cell immunoglobulin-like receptor (KIR), Lymphocyte Activation Gene-3 (LAG3), T-cell Immunoglobulin domain and Mucin domain 3 (TIM-3), VISTA (C10orf54), and V-domain Ig suppressor of T cell activation.

In some embodiments, the EGFR inhibitor is erlotinib, gefitinib, lapatinib, panitumumab, vandetanib, or cetuximab.

In some embodiments, the VEGF inhibitor or VEGFR inhibitor is pazopanib, bevacizumab, sorafenib, sunitinib, axitinib, ponatinib, regorafenib, vandetanib, cabozantinib, ramucirumab, lenvatinib, or ziv-aflibercept.

In some embodiments, the chemotherapeutic agent is cyclophosphamide, methotrexate, 5-fluorouracil (5-FU), doxorubicin, mustine, vincristine, procarbazine, prednisolone, dacarbazine, bleomycin, etoposide, cisplatin, epirubicin, capecitabine, folinic acid, actinomycin, all-trans retinoic acid, azacitidine, azathioprine, bortezomib, carboplatin, chlorambucil, cytarabine, daunorubicin, docetaxel, doxifluridine, fluorouracil, gemcitabine, hydroxyurea, idarubicin, imatinib, irinotecan, mechlorethamine, mercaptopurine, mitoxantrone, paclitaxel, pemetrexed, teniposide, tioguanine, topotecan, valrubicin, vinblastine, vindesine, vinorelbine, or oxaliplatin.

In some embodiments, the method further comprises exposing the subject to radiation therapy and/or chemotherapy.

In some embodiments, the method further comprises measuring at least one biomarker to monitor treatment/inhibition efficacy and/or to select a subject for treatment.

In some embodiments, the biomarker is one or more of BCL9, CD44, Axin2, cMyc, LGR5, VEGFA, Sox2, Oct4, Nanog, and/or active β-catenin.

In some embodiments, a reduced gene expression level and/or protein level of CD44, Axin2, cMyc, LGR5, VEGFA, Sox2, Oct4, Nanog, and/or active β-catenin indicates treatment/inhibition efficacy, and/or wherein a subject is selected for treatment if gene expression levels and/or protein levels of CD44, Axin2, cMyc, LGR5, VEGFA, Sox2, Oct4, Nanog, and/or active β-catenin are elevated.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DETAILED DESCRIPTION

BCL-9, β-Catenin, and Wnt Signaling

Figure 1:
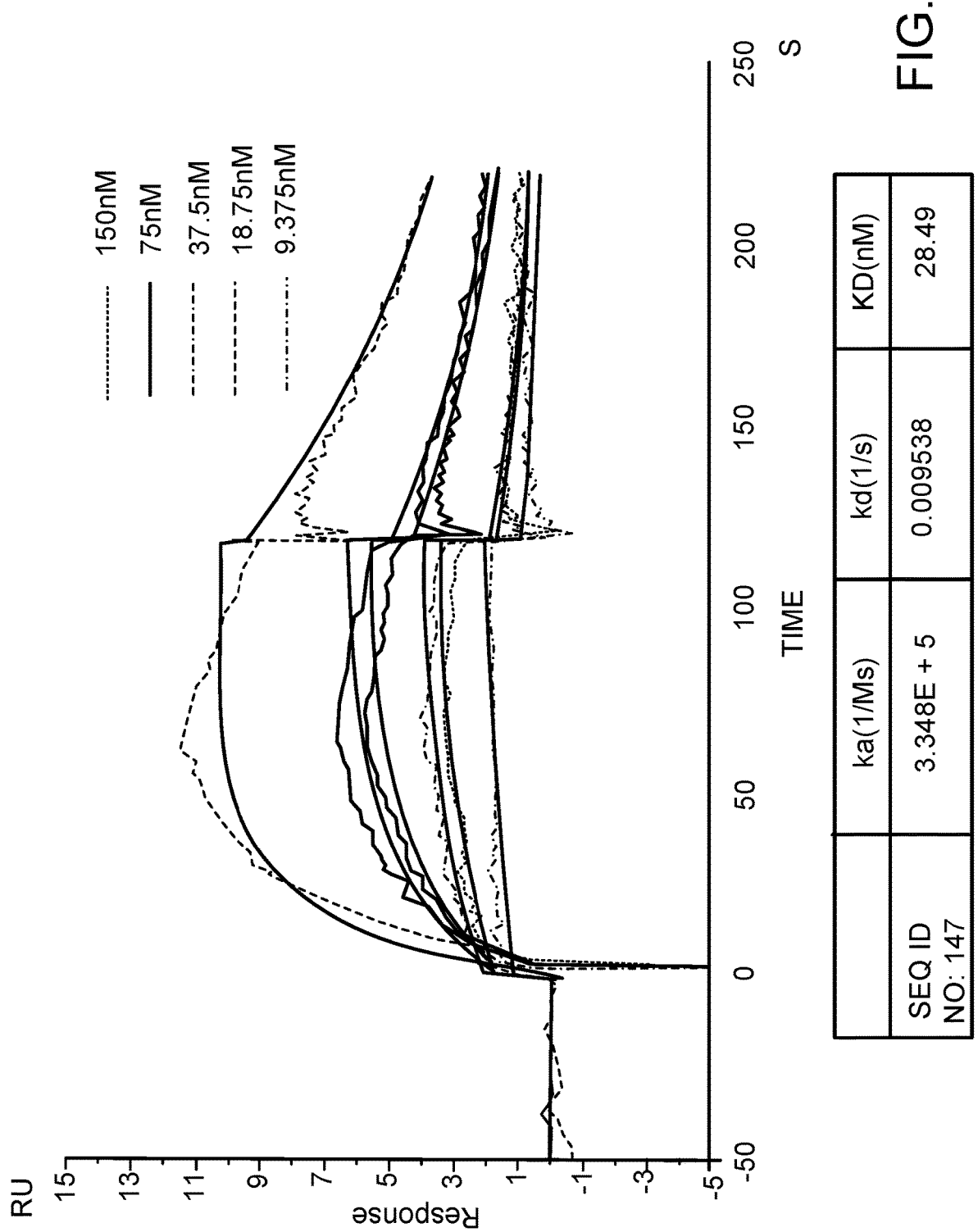
FIG. 1 shows biacore assay to assess β-catenin binding of stapled peptides or SEQ ID NO: 147.
Figure 2:
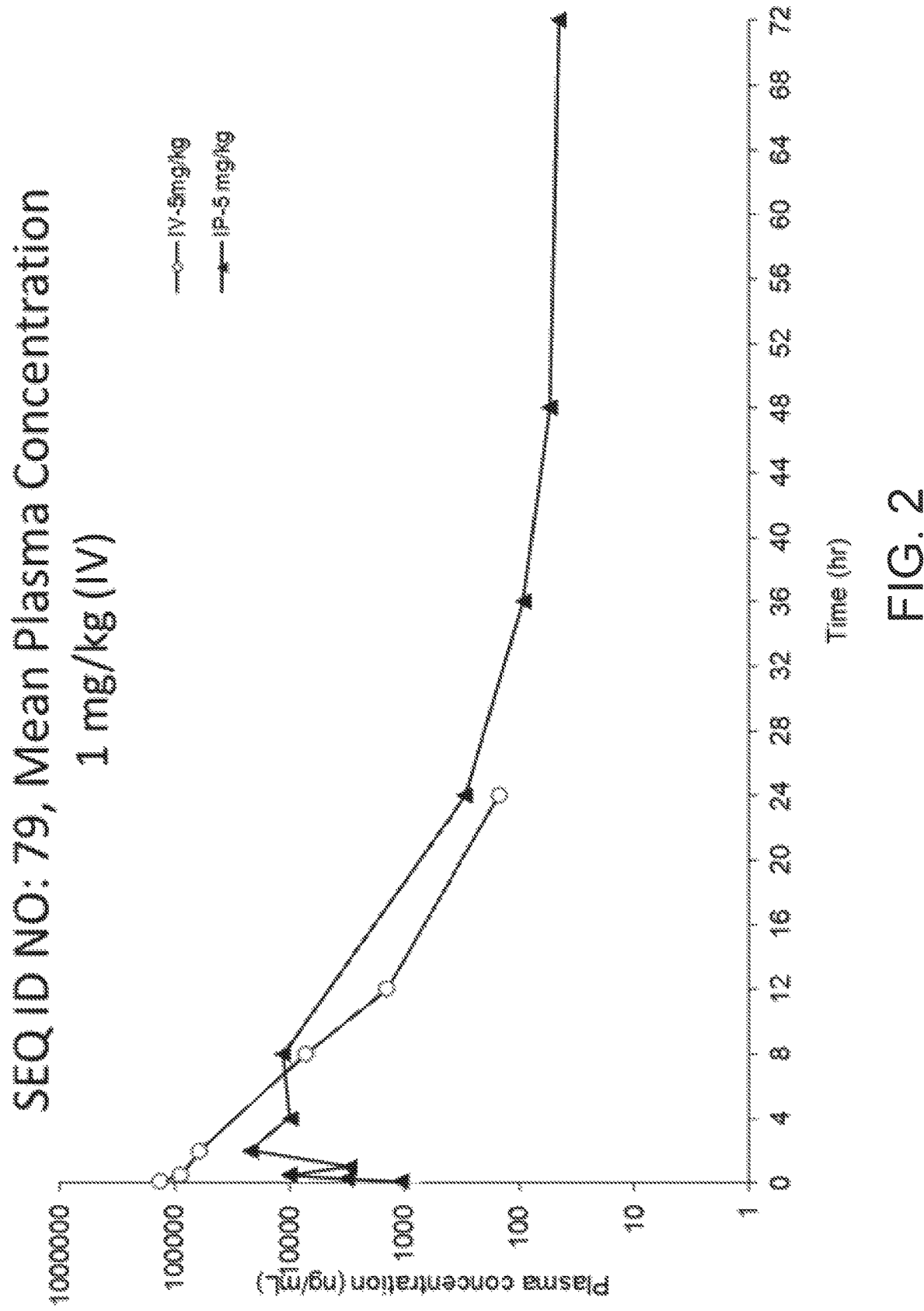
FIG. 2 shows pharmacokinetic profile for stapled peptide SEQ. ID. NO: 79.

Aberrant activation of Wnt signaling is implicated in a variety of cancers, as tumors can become dependent on Wnt signaling for growth and survival (See, e.g., Grossmann et al. PNAS. 109(44):17942-17947 (2012)). Up to 90% of all cases of sporadic colorectal cancers are associated with constitutive activation of Wnt signaling.

β-catenin is a protein that can engage in protein-protein interactions that stimulate Wnt signaling leading to changes in transcriptional activation that can allow tumor growth and development. β-catenin is normally phosphorylated and targeted for degradation by the Axin complex. If there is stimulation of the Wnt signaling pathway, unphosphorylated β-catenin accumulates and binds to lymphoid enhancer factor/T cell factor (LEF/TCF) and is translocated into the nucleus to stimulate transcription of Wnt target genes (See, e.g., Thakur and Mishra, J Cell Mol Med 17(4):449-456 (2013)). Wnt target genes include c-myc and CD44, which are upregulated genes in tumor models. BCL9 is a protein required for efficient β-catenin-mediated transcription in mammalian cells (See, e.g., de la Roche et al., BMC Cancer 8:199 (2008)).

"Canonical" Wnt/β-catenin signaling is a pathway activated by Wnt ligands binding to the Frizzled family of cell-surface receptors, which then regulate expression and intracellular localization of β-catenin. In the absence of Wnt ligands, β-catenin is phosphorylated and ubiquitinated within a destruction complex composed of adenomatous polyposis coli (APC), glycogen synthase kinase-3 (GSK-3), casein kinase-1 (CK1) and Axin, and targeted for degradation in a proteasome-dependent manner. In the presence of Wnt ligands, ubiquitination of β-catenin within the complex is suppressed, leading to saturation of phosphorylated β-catenin, which is then stabilized and translocated to the nucleus. There, phosphorylated β-catenin engages nuclear T-cell factor (TCF) transcription factors, such as Lymphoid Enhancer Factor/3 (LEF/TCF), to induce expression of genes that promote cell proliferation, migration, and survival, including c-Myc28 and Cyclin D.

Several molecules, including BCL9 and its homologue B-cell lymphoma 9-like (B9L), have been shown to be co-activators for Wnt/β-catenin transcription. The formation of a complex consisting of TCF, β-catenin, and BCL9 (or B9L) enhances β-catenin-dependent Wnt transcriptional activity. In normal cells, this transcriptional pathway is turned off when Wnt ligands uncouple from their receptors. However, a variety of loss-of-function mutations in APC and Axin, as well as activating mutations in β-catenin itself, enable β-catenin to escape the destruction complex and accumulate in the nucleus. Such inappropriate persistence of β-catenin promotes oncogenesis in a wide range of common human epithelial cancers, including hepatocellular, breast, colorectal, and hematological malignancies such as multiple myeloma. In addition, active β-catenin signaling results in T-cell exclusion, specifically $CD8^+$ T-cells, which leads to therapy resistance and shorter patient survival times. Thus, blocking Wnt signaling by targeting β-cat may offer a powerful way to treat CRC, potentially preventing both tumor initiation and metastasis. See, e.g., Spranger et al., Nature 523: 231-235 (2015).

Similar to other transcription factors, the development of selective, non-toxic β-catenin inhibitors and their translation to the clinic have proven to be a considerable challenge, as β-catenin interacts with the majority of its protein partners through the same binding surface. Thus, Wnt pathway inhibitors targeting this common binding surface have exhibited significant adverse effects in animal and clinical trials. There are only a few drugs targeting β-catenin in clinical trials, including PRI-724 (Eisai Pharmaceuticals; Phase II), LGK974 (Novartis; Phase I), and OMP-54F28 and OMP-18R5 (OncoMed/Bayer; Phase I). In addition, disruption of LEF/TCF interaction through small molecule and peptide inhibitors of β-cat can have serious side effects, including severe bone marrow hypoplasia, anemia, and generalized wasting of treated mice—likely a result of disrupting homeostatic Wnt signaling in normal hematopoietic and intestinal stem cells. Such therapeutic limitations may derive from disruption of β-catenin-TCF and β-catenin-E-cadherin interactions, which can affect epithelial tissue integrity. Furthermore, biological agents targeting the Frizzled receptor (OMP-54F28 and OMP-18R5) have shown significant bone marrow toxicity during clinical trials. The Wnt ligand is essential for Wnt/β-cat activation, but APC and β-catenin mutations in cancer cells could induce downstream transcription without Wnt ligand activation, so blocking Wnt secretion cannot inhibit endogenous oncogenic Wnt activity due to APC and β-catenin mutations induced downstream gene transcription. LGK974 only targets a small patient population, as identified by certain biomarkers. PRI-724, a small molecule inhibitor, is under phase II trials with daily infusion, but more than once-weekly intravenous (IV) dosing exhibits characteristics undesirable and untenable for clinical development.

Traditionally, Wnt signaling pathways include three different types of signaling: a canonical Wnt signaling pathway where Wnt regulates various transcriptional target genes through a β-catenin dependent manner; a noncanonical Wnt signaling pathway mainly involved in planer cell polarity, where Wnt may function independently of β-catenin; and a noncanonical Wnt/calcium pathway regulating an intracellular calcium level. In the present application, "canonical Wnt signaling" is interchangeably referred as "canonical Wnt/β-catenin signaling" or "Wnt signaling." As described herein, canonical Wnt/1-catenin signaling may refer to pathway components that control the amount of β-catenin in a patient or sample, e.g., by modulating the stability of β-catenin. In some embodiments, canonical Wnt/β-catenin signaling comprises pathway components that transcriptionally modulate one or more genes such as c-myc, ccnd1, cd44, LGR5, VEGFA, AXIN2, and LEF1. In some embodiments, canonical Wnt/β-catenin signaling comprises pathway components that are modulated by the interaction between β-catenin and BCL9. In some embodiments, canonical Wnt/β-catenin signaling comprises one or more genes that are transcriptionally controlled by the interaction between β-catenin and BCL9.

The one or more genes controlled by the interaction between β-catenin and BCL9 may include c-myc, ccnd1, cd44, LGR5, VEGFA, AXIN2, and LEF1. In some embodiments, canonical Wnt/β-catenin signaling comprises one or more proteins, the transcriptional expressions of which are modulated by the interaction between β-catenin and BCL9. Those components may include, for example, c-Myc, Cyclin D1, CD44, LGR5, VEGFA, AXIN2, and LEF1.

Polypeptides Derived from BCL9 HD2 Domain

The HD2 domain of BCL9 protein mediates the binding of BCL9 to β-catenin, and so far, the HD2 domain is the only domain of BLC9 shown to bind to β-catenin in cells (See, e.g., de la Roche 2008). The human BCL9 protein has an amino acid chain of about 1426 amino acids (GeneId 607). In some embodiments, the present application provides a polypeptide containing at least one fragment of the wild-type HD2 domain of the BCL9. The full-length HD2 domain of the BCL9 comprises a sequence of 30 amino acids corresponding to positions 348-377 within BCL9 protein. The sequence of the full-length HD2 domain of human BCL9 protein (SEQ ID NO: X) is shown in Table 1, with numerical reference to the corresponding position of amino acid within the BCL9 protein.

TABLE 1

| 348 | 349 | 350 | 351 | 352 | 353 | 354 | 355 | 356 | 357 | 358 | 359 | 360 | 361 | 362 |
|---|---|---|---|---|---|---|---|---|---|---|---|---|---|---|
| P | D | G | L | S | Q | E | Q | L | E | H | R | E | R | S |
| 363 | 364 | 365 | 366 | 367 | 368 | 369 | 370 | 371 | 372 | 373 | 374 | 375 | 376 | 377 |
| L | Q | T | L | R | D | I | Q | R | M | L | F | P | D | E |

Referring to Table 1, P in position 348 is the N-terminal amino acid, and E in position 377 is the C-terminal amino acid. In some embodiments, the polypeptide described herein comprises the full-length HD2 domain of human BCL9 protein, or a variant thereof. In some embodiments, the polypeptide described herein comprises a fragment of the HD2 domain of human BCL9 protein, or a variant thereof. In some embodiments, the fragment of HD2 domain of human BCL9 protein, or a variant thereof, has a length of 6-30 amino acids. In some embodiments, the polypeptide has a length of 7-14 amino acids, 9-14 amino acids, 7-12 amino acids, 10-14 amino acids, 6-20 amino acids, 7-20 amino acids, 9-20 amino acids, 10-20 amino acids, 11-20 amino acids, 12-20 amino acids, 12-30 amino acids, 13-20 amino acids, 13-22 amino acids, or 14-19 amino acids. For example, the polypeptide has 6, 7, 8, 9, 10, 11, 12, 13, 14, 15, 16, 17, 18, 19, or 20 amino acids. In some embodiments, the polypeptide comprises (or consists of) any fragment of wild-type HD2 domain of BCL9 protein between position 355 and position 377, inclusive, within the BCL9 protein. For example, the polypeptide may contain a sequence of 14 amino acids between positions 363 and 376, or a sequence of 14 amino acids between positions 361 and 374, or a sequence of 16 amino acids between positions 359 and 374, or a sequence of 17 amino acids between positions 358 and 374, or a sequence of 18 amino acids between positions 357 and 374, or a sequence of 20 amino acids between positions 355 and 374 within the BCL9 protein, inclusive, or a variant thereof. In some embodiments, the polypeptide comprises (or consists of) a fragment of HD2 domain corresponding to a sequence of amino acids in positions 355-376 within BCL9 protein, or a variant thereof. In some embodiments, the polypeptide comprises (or consists of) a fragment of HD2 domain corresponding to a sequence of amino acids in positions 366-376, 366-374, 363-374, 363-376, 363-375, 361-374, 359-374, 358-374, 357-374, or 358-376 within BCL9 protein, or a variant thereof.

In certain embodiments, a variant described herein is a polypeptide derived from the HD2 domain of human BCL9 protein and comprises a fragment of the HD2 domain of human BCL9 protein, which is modified by substituting one or more amino acids with other naturally occurring amino acids or non-naturally occurring amino acids. In some embodiments, the variant comprises conservative substitution of one or more amino acids of HD2 domain of BCL9 protein, or a fragment thereof. In some embodiments, at least 1, at least 2, at least 3, at least 4, at least 5, at least 6, or at least 7 amino acids of HD2 domain or a fragment thereof is substituted with a different amino acid. A conservative substitution of an amino acid, i.e., replacing an amino acid with a different amino acid of similar properties (e.g., hydrophilicity, and degree and distribution of charged regions), typically involves a minor change and therefore does not significantly alter the biological activity of the polypeptide. These minor changes may be identified by considering the hydropathic index of amino acids based on a consideration of the hydrophobicity and charge of the amino acid. Amino acids of similar hydropathic indexes and hydrophilicity values can be substituted and still retain protein function. Both the hydrophobicity index and the hydrophilicity value of amino acids are influenced by the particular side chain of that amino acid. Consistent with that observation, amino acid substitutions that are compatible with biological function depend on the relative similarity of the amino acids, and particularly the side chains of those amino acids, as revealed by the hydrophobicity, hydrophilicity, charge, size, and other properties.

In some embodiments, a variant polypeptide described herein has at least 50%, at least 60%, at least 70%, at least 80%, at least 90%, at least 95%, or at least 99% homology to a corresponding fragment of a wild-type HD2 domain of BCL9 protein. In some embodiments, the polypeptide is a variant that has at least 60%, at least 70%, or at least 80% homology to a fragment of HD2 domain corresponding to a sequence of amino acids in positions 363-374, inclusive, within BCL9 protein. In some embodiments, the polypeptide is a variant that has at least 60%, at least 70%, or at least 80% homology to a fragment of HD2 domain corresponding to a sequence of amino acids in positions 363-376, inclusive, within BCL9 protein. In some embodiments, the polypeptide is a variant that has at least 60%, at least 70%, or at least 80% homology to a fragment of HD2 domain corresponding to a sequence of amino acids in positions 363-375, inclusive, within BCL9 protein. In some embodiments, the polypeptide is a variant that has at least 60%, at least 70%, or at least 80% homology to a fragment of HD2 domain corresponding to a sequence of amino acids in positions 361-374, inclusive, within BCL9 protein. In some embodiments, the polypeptide is a variant that has at least 60%, at least 70%, or at least 80% homology to a fragment of HD2 domain corresponding to a sequence of amino acids in positions 359-374, inclusive, within BCL9 protein. In some embodiments, the polypeptide is a variant that has at least 60%, at least 70%, or at least 80% homology to a fragment of HD2 domain corresponding to a sequence of amino acids in positions 358-374, inclusive, within BCL9 protein. In some embodiments, the polypeptide is a variant that has at least 60%, at least 70%, or at least 80% homology to a fragment of HD2 domain corresponding to a sequence of amino acids in positions 357-374, inclusive, within BCL9 protein. In some embodiments, the polypeptide is a variant that has at least 60%, at least 70%, or at least 80% homology to a fragment of HD2 domain corresponding to a sequence of amino acids in positions 355-374, inclusive, within BCL9 protein.

In some embodiments, the variant comprises substitution of L by A (e.g., in corresponding position 373 of BCL9 protein). In some embodiments, the variant comprises substitution of L by A (e.g., in corresponding position 363 or 366 of BCL9 protein). In some embodiments, the variant comprises substitution of I by A (e.g., in corresponding position 369 of BCL9 protein). In some embodiments, the variant comprises substitution of P by A (e.g., in corresponding position 375 of BCL9 protein). In some embodiments, the variant comprises substitution of D by A (e.g., in corresponding position 376 of BCL9 protein). Such subtle change in amino acid hydrocarbon side chain modifies (e.g., reduces) overall lipophilicity of the polypeptide.

In some embodiments, the variant comprises substitution of R by A (e.g., in corresponding position 371 of BCL9 protein). In some embodiments, the variant comprises substitution of R by Q (e.g., in corresponding position 359 of BCL9 protein). Removing at least one R having a charged guanidinium moiety reduces net positive charge of the polypeptide (e.g., the net positive charge may be reduced by −1, −2, or −3, so that the total charge of the polypeptide containing R, H, and/or L is +2 or +3).

Polypeptides Containing α-Monosubstituted Non-Natural Amino Acid

In some embodiments, the variant comprises substitution of one or more amino acids (e.g., 1, 2, 3, or 4 amino acids) of HD2 domain of BCL9 protein or the corresponding fragment thereof by a non-naturally occurring amino acid. In some embodiments, the non-naturally occurring amino acid is α-monosubstituted non-natural amino acid.

In some embodiments, the α-monosubstituted non-natural amino acid is Nle, β-Ala, 2-Nal, β-L, or CBA. In some embodiments, the variant comprises at least one Nle. In some embodiments, the variant comprises at least one 2-Nal. In some embodiments, the variant comprises at least one β-Ala. In some embodiments, the variant comprises at least one β-L. In some embodiments, the variant comprises at least one CBA. In some embodiments, the variant comprises two Nle. In some embodiments, the variant comprises two β-Ala. In some embodiments, the variant comprises two Nle and one 2-Nal. In some embodiments, the variant comprises two Nle, two β-Ala and one 2-Nal. In some embodiments, the variant comprises two Nle, one CBA and one 2-Nal. In some embodiments, the variant comprises two Nle, one β-L and one 2-Nal. In some embodiments, the variant comprises one CBA and one 2-Nal.

In some embodiments, the variant comprises substitution of F by 2-Nal (e.g., in corresponding position 374 of BCL9 protein). In some embodiments, the variant comprises substitution of L by CBA (e.g., in corresponding position 373 of BCL9 protein). In some embodiments, the variant comprises substitution of L by β-L (e.g., in corresponding position 366 of BCL9 protein). In some embodiments, the variant comprises substitution of Q by Nle (e.g., in corresponding position 364 of BCL9 protein). In some embodiments, the variant comprises substitution of D by Nle (e.g., in corresponding position 368 of BCL9 protein). In some embodiments, the variant comprises substitution of M by Nle (e.g., in corresponding position 372 of BCL9 protein).

In some embodiments, the variant comprises one D substituted by Nle, one M substituted by Nle, one L substituted by CBA, and one F substituted by 2-Nal. In some aspects of these embodiments, the variant also comprises one R substituted by A. In some embodiments, the variant comprises one R substituted by Q, one D substituted by Nle, one M substituted by Nle, and one F substituted by 2-Nal. In some embodiments, the variant comprises one R substituted by A, one D substituted by Nle, one M substituted by Nle, and one F substituted by 2-Nal. In some embodiments, the variant comprises one F substituted by 2-Nal, one P substituted by β-Ala, and one D substituted by β-Ala. In some aspects of these embodiments, the variant also comprises one R substituted by A, one D substituted by Nle, and one M substituted by Nle. In some embodiments, the variant comprises one L substituted by β-L, one D substituted by Nle, one M substituted by Nle, and one F substituted by 2-Nal. In some aspects of these embodiments, the variant also comprises one R substituted by Q. In some embodiments, the variant comprises one L substituted by A, and one F substituted by 2-Nal. In some aspects of these embodiments, the variant comprises one I substituted by A. In some embodiments, the variant comprises one I substituted by A, and one F substituted by 2-Nal. In some aspects of these embodiments, the variant comprises one L substituted by A. In some embodiments, the variant comprises two L each substituted by A, and one F substituted by 2-Nal. In some embodiments, the variant comprises one R substituted by A, and one F substituted by 2-Nal. In some aspects of these embodiments, the variant also comprises one P substituted by A, and one D substituted by A. In other aspects of these embodiments, the variant comprises one L substituted by CBA.

In some embodiments, the polypeptide described herein comprises at least one amino acid sequence listed in Table 2.

TABLE 2

| Polypeptide ID | Amino Acid Sequence | Corresponding position within BCL9 protein |
|---|---|---|
| SEQ ID NO: 41 | DIQRML(2-Nal) | 368-374 |
| SEQ ID NO: 42 | (Nle)IQR(Nle)L(2-Nal) | 368-374 |
| SEQ ID NO: 43 | (Nle)IQR(Nle)(CBA)(2-Nal) | 368-374 |
| SEQ ID NO: 44 | (Nle)IQA(Nle)L(2-Nal) | 368-374 |
| SEQ ID NO: 45 | (Nle)IQA(Nle)(CBA)(2-Nal) | 368-374 |
| SEQ ID NO: 46 | (Nle)TLR(Nle) | 364-368 |
| SEQ ID NO: 47 | QTLR(Nle) | 364-368 |
| SEQ ID NO: 48 | QT(β-L)R(Nle) | 364-368 |

In some embodiments, any of the polypeptides disclosed in the present application comprises at least one amino acid sequence listed in Table 3.

TABLE 3

| Amino Acid Sequence | Corresponding position within BCL9 protein |
|---|---|
| (β-Alaa)(β-Ala) | 375-376 |
| AA | 375-376 |
| RSL | 361-363 |
| HRE | 358-360 |
| HQE | 358-360 |
| QLE | 355-357 |
| SLQ | 362-364 |
| IQR | 369-371 |
| IQA | 369-371 |
| RER | 359-361 |
| QER | 359-361 |
| ERS | 360-362 |
| LQTLR | 363-367 |
| RERS | 359-362 |
| HRERS | 358-362 |
| RERSL | 359-363 |
| HQERS | 358-362 |
| RSLQTLR | 361-367 |
| EHRERS | 357-362 |
| QLEH | 355-358 |

In some embodiments, the polypeptide of the present disclosure is selected from any one of polypeptides listed in Table 4.

TABLE 4

| Polypeptide ID | Amino Acid Sequence | Corresponding position within BCL9 protein |
|---|---|---|
| SEQ ID NO: 49 | LR(Nle)IQR(Nle)L(2-Nal)(β-Ala)(β-Ala) | 366-376 |
| SEQ ID NO: 50 | LR(Nle)IQR(Nle)L(2-Nal) | 366-374 |
| SEQ ID NO: 51 | LQTLRDIQRML(2-Nal) | 363-374 |
| SEQ ID NO: 52 | LQTLR(Nle)IQR(Nle)L(2-Nal) | 363-374 |
| SEQ ID NO: 53 | LQTLRDIQRML(2-Nal)PD | 363-376 |
| SEQ ID NO: 54 | LQTLR(Nle)IQR(Nle)L(2-Nal)PD | 363-376 |
| SEQ ID NO: 55 | LQTLRDIQRML(2-Nal)P | 363-375 |
| SEQ ID NO: 56 | LQTLR(Nle)IQR(Nle)L(2-Nal)P | 363-375 |
| SEQ ID NO: 57 | RSLQTLRDIQRML(2-Nal) | 361-374 |
| SEQ ID NO: 58 | RSLQTLR(Nle)IQR(Nle)L(2-Nal) | 361-374 |
| SEQ ID NO: 59 | RERSLQTLRDIQRML(2-Nal) | 359-374 |
| SEQ ID NO: 60 | RERSLQTLR(Nle)IQR(Nle)L(2-Nal) | 359-374 |
| SEQ ID NO: 61 | HRERSLQTLRDIQRML(2-Nal) | 358-374 |
| SEQ ID NO: 62 | HRERSLQTLR(Nle)IQR(Nle)L(2-Nal) | 358-374 |
| SEQ ID NO: 63 | EHRERSLQTLRDIQRML(2-Nal) | 357-374 |
| SEQ ID NO: 64 | EHRERSLQTLR(Nle)IQR(Nle)L(2-Nal) | 357-374 |
| SEQ ID NO: 65 | QLEHRERSLQTLRDIQRML(2-Nal) | 355-374 |
| SEQ ID NO: 66 | QLEHRERSLQTLR(Nle)IQR(Nle)L(2-Nal) | 355-374 |
| SEQ ID NO: 67 | QLEHRERSL(Nle)TLR(Nle)IQRML(2-Nal) | 355-374 |
| SEQ ID NO: 68 | RSLQTLR(Nle)IQR(Nle)(CBA)(2-Nal) | 361-374 |
| SEQ ID NO: 69 | RSLQTLR(Nle)IQA(Nle)(CBA)(2-Nal) | 361-374 |
| SEQ ID NO: 70 | HQERSLQTLR(Nle)IQR(Nle)L(2-Nal) | 358-374 |
| SEQ ID NO: 71 | HRERSLQTLR(Nle)IQA(Nle)L(2-Nal) | 358-374 |
| SEQ ID NO: 72 | HRERSLQTLR(Nle)IQA(Nle)L(2-Nal)(β-Ala)(β-Ala) | 358-376 |
| SEQ ID NO: 73 | HRERSLQT(β-L)R(Nle)IQR(Nle)L(2-Nal) | 358-374 |
| SEQ ID NO: 74 | HQERSLQT(β-L)R(Nle)IQR(Nle)L(2-Nal) | 358-374 |

Unstapled Polypeptides Containing α,α-Disubstituted Amino Acids

In some embodiment, the polypeptide derived from the HD2 domain of human BCL9 protein is capable of undergoing a reaction to form a hydrocarbon linker between two amino acid in the backbone of the polypeptide. As used herein, the polypeptide capable of undergoing a reaction to form one or more hydrocarbon linkers may be referred as an "unstapled polypeptide." In these embodiments, the polypeptide comprises at least two α,α-disubstituted amino acids. In some embodiments, at least one α-substituent within each α,α-disubstituted amino acid in the peptide backbone comprises a double bond. Hence, the polypeptide containing at least two α,α-disubstituted amino acids is capable of undergoing a metatheses reaction to form a hydrocarbon linker between the two α,α-disubstituted amino acids within the peptide backbone.

In some embodiments, the non-naturally occurring α,α-disubstituted amino acid is an α-methyl, α-alkenyl amino acid. In some embodiment, the non-naturally occurring amino acid is a chiral molecule, comprising a chiral center with either S- or R-configuration. In some embodiment, the non-naturally occurring amino acid is selected from:

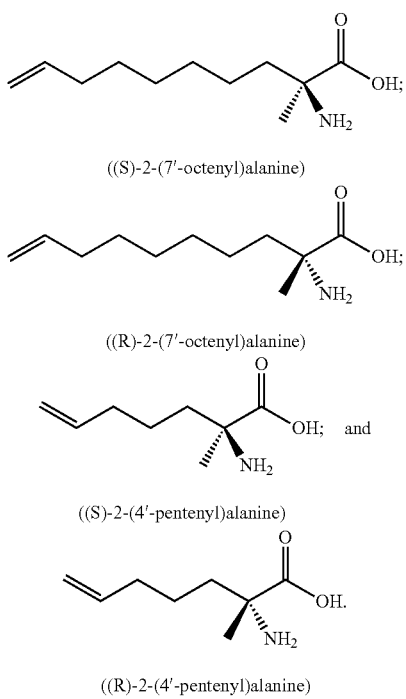

((S)-2-(7'-octenyl)alanine)

((R)-2-(7'-octenyl)alanine)

((S)-2-(4'-pentenyl)alanine)

((R)-2-(4'-pentenyl)alanine)

In some embodiments, the polypeptide of the present disclosure comprises an amino acid sequence as shown below:

| 358 | 359 | 360 | 361 | 362 | 363 | 364 | 365 |
|---|---|---|---|---|---|---|---|
| $Xaa_{12}$ | $Xaa_{13}$ | $Xaa_{14}$ | $Xaa_{15}$ | $Xaa_{16}$ | $Xaa_1$ | $Xaa_9$ | $Xaa_{10}$ |
| 366 | 367 | 368 | 369 | 370 | 371 | 372 | 373 |
| $Xaa_2$ | $Xaa_{11}$ | $Xaa_3$ | $Xaa_4$ | $Xaa_8$ | $Xaa_5$ | $Xaa_6$ | $Xaa_7$ |

In some embodiments, any one of $Xaa_1$-$Xaa_{16}$ may be independently selected from an α,α-disubstituted amino acid (e.g., α-methyl, α-alkenyl amino acid as described here), Q, L, E, H, R, E, R, S, L, Q, T, L, R, D, I, Q, R, M, L, F, P, D, E, 2-Nal. Nle, β-Ala, N-methylQ, N-methylE, N-methylR, N-methylD, N-MethylT, NMethylI, N-MethylL, Cpa, Cha, N-MeHis, N-MeCys, homoHis, NHis, homoR, Cit, Nar, Phe(4-guanidino), NMeGln, Nle, 2-Abu, Phe(4-Cl), 3,4-diClPh, 4-FPh, NptGly, NMeCha, Dcha, α-methylL, allylGly, Alg, AC4C, A6C, Aze, (β-tBu-Ala), Tle, peptoidQ, DThr, NMeLeu, betahomoTrp, homoCha, Lys(Me)2, Narg, Abg, Nar, Hyp, and Ngln.

In some embodiments, any one of $Xaa_1$-$Xaa_{16}$ may be independently selected from an α,α-disubstituted amino acid (e.g., α-methyl, α-alkenyl amino acid as described here), Q, L, E, H, R, E, R, S, L, Q, T, L, R, D, I, Q, R, M, L, F, P, D, E, 2-Nal. Nle, β-Ala, N-methylQ, N-methylE, N-methylR, N-methylD, N-MethylT, NMethylI, N-MethylL, Cpa, Cha, N-MeHis, N-MeCys, homoHis, NHis, homoR, Cit, Nar, Phe(4-guanidino), NMeGln, Nle, 2-Abu, Phe(4-Cl), 3,4-diClPh, 4-FPh, NptGly, NMeCha, Dcha, α-methylL, allylGly, Alg, AC4C, A6C, Aze, (β-tBu-Ala), Tle, peptoidQ, DThr, and NMeLeu.

$Xaa_1$

In some embodiments, $Xaa_1$ is selected from L, MeL, AC4C, A6C, Aze, Cpa, Cha, NMeCha, Dcha, Phe(4-Cl), (βtBu-Ala), Tle, NMeLeu, betahomoTrp, homoCha, 4-ClPh, 4-FPh, 3,4-diClPh, and NptGly.

In some embodiments, $Xaa_1$ is selected from L, A, Cha, Cpa, (D-L), CBA, MeL, NMeCha, Dcha, and NptGly.

In some embodiments, $Xaa_1$ is L. In some embodiments, $Xaa_1$ is A. In some embodiments, $Xaa_1$ is Cha. In some embodiments, $Xaa_1$ is Cpa. In some embodiments, $Xaa_1$ is (D-L). In some embodiments, $Xaa_1$ is CBA. In some embodiments, $Xaa_1$ is MeL. In some embodiments, $Xaa_1$ is NMeCha. In some embodiments, $Xaa_1$ is Dcha. In some embodiments, $Xaa_1$ is NptGly.

$Xaa_2$

In some embodiments, $Xaa_2$ is selected from L, MeL, AC4C, A6C, Aze, Cpa, Cha, NMeCha, Dcha, Phe(4-Cl), (β-tBu-Ala), Tle, NMeLeu, betahomoTrp, homoCha, 4-ClPh, 4-FPh, 3,4-diClPh, and NptGly.

In some embodiments, $Xaa_2$ is selected from L, A, Cha, Cpa, (D-L), CBA, MeL, NMeCha, Dcha, and NptGly.

In some embodiments, $Xaa_2$ is L. In some embodiments, $Xaa_2$ is A. In some embodiments, $Xaa_2$ is Cha. In some embodiments, $Xaa_2$ is Cpa. In some embodiments, $Xaa_2$ is (D-L). In some embodiments, $Xaa_2$ is CBA. In some embodiments, $Xaa_2$ is MeL. In some embodiments, $Xaa_2$ is NMeCha. In some embodiments, $Xaa_2$ is Dcha. In some embodiments, $Xaa_2$ is NptGly.

$Xaa_3$

In some embodiments, $Xaa_3$ is an α,α-disubstituted amino acid.

$Xaa_4$

In some embodiments, $Xaa_4$ is selected from I, Nle, MeL, AC4C, A6C, Aze, Cpa, Cha, NMeCha, Dcha, Phe(4-Cl), (βtBu-Ala), Tle, NMeLeu, betahomoTrp, homoCha, 4-ClPh, 4-FPh, 3,4-diClPh, and NptGly.

In some embodiments, $Xaa_4$ is selected from I, A, Nle, N-methylI, CBA, and (D-I). In some embodiments, $Xaa_4$ is I. In some embodiments, $Xaa_4$ is A. In some embodiments, $Xaa_4$ is Nle. In some embodiments, $Xaa_4$ is N-methylI. In some embodiments, $Xaa_4$ is CBA. In some embodiments, $Xaa_4$ is (D-I).

$Xaa_5$

In some embodiments, $Xaa_5$ is selected from R, R(Me), homoR, NMethylR, NMeArg, Lys(Me)2, Narg, Abg, Cit, Nar, Phe(4-guanidino).

In some embodiments, $Xaa_5$ is selected from R, A, Q, E, K, H, N-methylR, homoR, NMeArg, Nar, and Cit.

In some embodiments, $Xaa_5$ is R. In some embodiments, $Xaa_5$ is A. In some embodiments, $Xaa_5$ is Q. In some embodiments, $Xaa_5$ is E. In some embodiments, $Xaa_5$ is K. In some embodiments, $Xaa_5$ is H. In some embodiments, $Xaa_5$ is N-methylR. In some embodiments, $Xaa_5$ is homoR. In some embodiments, $Xaa_5$ is NMeArg. In some embodiments, $Xaa_5$ is Nar. In some embodiments, $Xaa_5$ is Cit.

$Xaa_6$

In some embodiments, $Xaa_6$ is an α,α-disubstituted amino acid.

$Xaa_7$

In some embodiments, $Xaa_7$ is selected from L, A, CBA, MeL, AC4C, A6C, Aze, Cpa, Cha, NMeCha, Dcha, Phe(4-Cl), (β-tBu-Ala), Tle, NMeLeu, betahomoTrp, homoCha, 4-ClPh, 4-FPh, 3,4-diCiPh, and NptGly.

In some embodiments, $Xaa_7$ is selected from L, A, CBA, Cha, Cpa, Phe(4-Cl), (D-L), α-MethylL, DCha, N-Methyl-Cha, allylGly, AC4C, A6C, Aze, N-MeCha, (β-tBu-Ala), Tle, 4-FPh, and 3,4-diCiPh.

In some embodiments, $Xaa_7$ is L. In some embodiments, $Xaa_7$ is A. In some embodiments, $Xaa_7$ is CBA. In some embodiments, $Xaa_7$ is Cha. In some embodiments, $Xaa_7$ is Cpa. In some embodiments, $Xaa_7$ is Phe(4-Cl). In some embodiments, $Xaa_7$ is (D-L), In some embodiments, $Xaa_7$ is α-MethylL, In some embodiments, $Xaa_7$ is DCha, In some embodiments, $Xaa_7$ is N-methylCha, In some embodiments, $Xaa_7$ is allylGly, In some embodiments, $Xaa_7$ is AC4C, In some embodiments, $Xaa_7$ is A6C, In some embodiments, $Xaa_7$ is Aze, In some embodiments, $Xaa_7$ is N-MeCha, In some embodiments, $Xaa_7$ is (βtBu-Ala), In some embodiments, $Xaa_7$ is Tle, In some embodiments, $Xaa_7$ is 4-FPh, In some embodiments, $Xaa_7$ is 3,4-diCiPh $Xaa_5$ In some embodiments, $Xaa_8$ is selected from Q, N-MethylQ, NMeGln, peptoidQ, and Ngln.

In some embodiments, $Xaa_8$ is selected from Q and N-methylQ.

In some embodiments, $Xaa_8$ is Q. In some embodiments, $Xaa_8$ is N-methylQ.

$Xaa_9$

In some embodiments, $Xaa_9$ is selected from an α,α-disubstituted amino acid, Q, N-MethylQ, NMeGln, peptoidQ, and Ngln.

In some embodiments, $Xaa_9$ is selected from Q, E, N-methylQ, N-MeGln, and peptoidQ.

In some embodiments, $Xaa_9$ is Q. In some embodiments, $Xaa_9$ is E. In some embodiments, $Xaa_9$ is N-methylQ. In some embodiments, $Xaa_9$ is N-MeGln. In some embodiments, $Xaa_9$ is peptoidQ.

$Xaa_{10}$

In some embodiments, $Xaa_{10}$ is selected from an α,α-disubstituted amino acid, T, N-methylT, and DThr.

In some embodiments, $Xaa_{10}$ is selected from T, N-methylT, and DThr. In some embodiments, $Xaa_{10}$ is T. In some embodiments, $Xaa_{10}$ is N-methylT. In some embodiments, $Xaa_{10}$ is DThr.

$Xaa_{11}$

In some embodiments, $Xaa_{11}$ is selected from R, R(Me), homoR, NMethylR, NMeArg, Lys(Me)2, Narg, Abg, Cit, Nar, and Phe(4-guanidino).

In some embodiments, $Xaa_{11}$ is selected from R, N-methylR, E, K, homoR, Nar, and Cit.

In some embodiments, $Xaa_{11}$ is R. In some embodiments, $Xaa_{11}$ is N-methylR.

In some embodiments, $Xaa_{11}$ is E. In some embodiments, $Xaa_{11}$ is K. In some embodiments, $Xaa_{11}$ is homoR. In some embodiments, $Xaa_{11}$ is Nar. In some embodiments, $Xaa_{11}$ is Cit.

$Xaa_{12}$

In some embodiments, $Xaa_{12}$ is selected from H, N-MeHis, Cys, NMeCys, homoHis, and NHis.

In some embodiments, $Xaa_{12}$ is selected from H, N-MeHis, Cys, N-MeCys, homoHis, and NHis.

In some embodiments, $Xaa_{12}$ is H. In some embodiments, $Xaa_{12}$ is N-MeHis.

In some embodiments, $Xaa_{12}$ is Cys. In some embodiments, $Xaa_{12}$ is N-MeCys. In some embodiments, $Xaa_{12}$ is homoHis. In some embodiments, $Xaa_{12}$ is NHis.

$Xaa_{13}$

In some embodiments, $Xaa_{13}$ is selected from R, R(Me), homoR, NMethylR, NMeArg, Lys(Me)2, Narg, Abg, Cit, Nar, and Phe(4-guanidino).

In some embodiments, $Xaa_{13}$ is selected from R, N-methylR, homoArg, Cit, Nar, and Phe(4-guanidino).

In some embodiments, $Xaa_{13}$ is R. In some embodiments, $Xaa_{13}$ is N-methylR.

In some embodiments, $Xaa_{13}$ is homoArg. In some embodiments, $Xaa_{13}$ is Cit. In some embodiments, $Xaa_{13}$ is Nar. In some embodiments, $Xaa_{13}$ is Phe(4-guanidino).

$Xaa_{14}$

In some embodiments, $Xaa_{14}$ is selected from an α,α-disubstituted amino acid, Q, E, N-methylE, N-methylQ, and Ngln.

In some embodiments, $Xaa_{14}$ is selected from E, Q, N-methylE, N-methylQ, N-methylD, and NMeGln.

In some embodiments, $Xaa_{14}$ is Q. In some embodiments, $Xaa_{14}$ is E. In some embodiments, $Xaa_{14}$ is N-methylE. In some embodiments, $Xaa_{14}$ is N-methylQ. In some embodiments, $Xaa_{14}$ is N-methylD. In some embodiments, $Xaa_{14}$ is NMeGln.

$Xaa_{15}$

In some embodiments, $Xaa_{15}$ is selected from an α,α-disubstituted amino acid, R, R(Me), homoR, N-methylR, NMeArg, Lys(Me)2, Narg, Abg, Cit, Nar, and Phe(4-guanidino).

$Xaa_{16}$

In some embodiments, $Xaa_{16}$ is selected from an α,α-disubstituted amino acid, S, T, and Hyp.

In some embodiments, $Xaa_{16}$ is selected from S and T. In some embodiments, $Xaa_{16}$ is S. In some embodiments, $Xaa_{16}$ is T.

In some embodiments, the polypeptide of the present disclosure comprises an amino acid sequence:

| 368 | 369 | 370 | 371 | 372 | 373 | 374 |
|---|---|---|---|---|---|---|
| $Xaa_3$ | $Xaa_4$ | $Xaa_8$ | $Xaa_5$ | $Xaa_6$ | $Xaa_7$ | (2-Nal) | wherein:

$Xaa_3$ and $Xaa_6$ are each independently an α,α-disubstituted amino acid;

$Xaa_4$ is selected from I, A, Nle, N-MethylI, CBA, and (D-I);

$Xaa_8$ is selected from Q and N-methylQ;

$Xaa_5$ is selected from R, A, Q, E, K, H, N-methylR, homoR, NMeArg, Nar, and Cit; and $Xaa_7$ is selected from CBA, Cha, Cpa, Phe(4-Cl), (D-L), α-MethylL, DCha, N-methylCha, allylGly, AC4C, A6C, Aze, NMeCha, (βtBu-Ala), Tle, 4-FPh, and 3,4-diClPh.

In some embodiments, the polypeptide has a length of 6-30 amino acids (e.g., 6-12, 8-24, 10-20, or 10-20 amino acids).

In some embodiments, Xaa$_7$ is CBA.

In some embodiments, Xaa$_7$ is selected from Cha and Cpa. In some embodiments, Xaa$_7$ is selected from α-MethylL, DCha, N-methylCha, and allylGly. In some embodiments, Xaa$_7$ is selected from AC4C, A6C, Aze, Phe(4-Cl), (β-tBu-Ala), and Tle. In some embodiments, Xaa$_7$ is selected from Phe(4-Cl), 4-FPh, 3,4-diClPh, and Cha.

In some embodiments, Xaa$_7$ is Cha. In some embodiments, Xaa$_7$ is Cpa.

In some embodiments, Xaa$_4$Xaa$_8$Xaa$_5$ comprise IQR.

In some embodiments, Xaa$_4$Xaa$_8$Xaa$_5$ comprise I(N-methylQ)R.

In some embodiments, Xaa$_4$Xaa$_8$Xaa$_5$ comprise IQ(N-methylR).

In some embodiments, Xaa$_4$Xaa$_8$Xaa$_5$ comprise (CBA)QR.

In some embodiments, Xaa$_4$Xaa$_8$Xaa$_5$ comprise IQ(homoR).

In some embodiments, Xaa$_4$Xaa$_8$Xaa$_5$ comprise (N-methylI)QR.

In some embodiments, Xaa$_4$Xaa$_8$Xaa$_5$ comprise IQQ.

In some embodiments, Xaa$_4$Xaa$_8$Xaa$_5$ comprise IQE.

In some embodiments, Xaa$_4$Xaa$_8$Xaa$_5$ comprise IQ(N-MeArg).

In some embodiments, Xaa$_4$Xaa$_8$Xaa$_5$ comprise IQ(Nar).

In some embodiments, Xaa$_4$Xaa$_8$Xaa$_5$ comprise IQ(Cit).

In some embodiments, Xaa$_4$Xaa$_8$Xaa$_5$ comprise IQQ, IQE, IQ(NMeArg), (Nle)QR, IQ(Nar), or IQ(Cit).

In some embodiments, the polypeptide comprises:

| 363 | 364 | 365 | 366 | 367 |
|---|---|---|---|---|
| Xaa$_1$ | Xaa$_9$ | Xaa$_{10}$ | Xaa$_2$ | Xaa$_{11}$ | wherein:
Xaa$_1$ and Xaa$_2$ are each independently selected from L, A, Cha, Cpa, (D-L), CBA, MeL, NMeCha, Dcha, and NptGly;
Xaa$_9$ is selected from Q, E, N-methylQ, N-MeGln, and peptoidQ;
Xaa$_{10}$ is selected from T, N-methylT, and DThr; and
Xaa$_{11}$ is selected from R, N-methylR, E, K, homoR, Nar, and Cit.

In some embodiments, Xaa$_1$ is L.
In some embodiments, Xaa$_1$ is CBA.
In some embodiments, Xaa$_2$ is L.
In some embodiments, Xaa$_2$ is CBA.
In some embodiments, Xaa$_1$ and Xaa$_2$ are each L.
In some embodiments, Xaa$_9$ is Q.
In some embodiments, Xaa$_9$ is N-methylQ.
In some embodiments, Xaa$_9$ is N-MeGln.
In some embodiments, Xaa$_1$ and Xaa$_2$ are each L, and Xaa$_9$ is Q.
In some embodiments, Xaa$_1$ and Xaa$_2$ are each L, and Xaa$_9$ is N-methylQ.
In some embodiments, Xaa$_1$ and Xaa$_2$ are each L, and Xaa$_9$ is N-MeGln.
In some embodiments, Xaa$_{10}$ is T.
In some embodiments, Xaa$_{11}$ is selected from R, N-methylR, and homoR.
In some embodiments, Xaa$_{11}$ is R. In some embodiments, Xaa$_{11}$ is N-methylR.
In some embodiments, Xaa$_{11}$ is homoR.
In some embodiments, Xaa$_1$Xaa$_9$Xaa$_{10}$Xaa$_2$Xaa$_{11}$ comprise LQTLR.

In some embodiments, Xaa$_1$Xaa$_9$Xaa$_{10}$Xaa$_2$Xaa$_{11}$ comprise L(N-methylQ)TLR.

In some embodiments, Xaa$_1$Xaa$_9$Xaa$_{10}$Xaa$_2$Xaa$_{11}$ comprise L(N-methylQ)TL(homoR).

In some embodiments, Xaa$_1$Xaa$_9$Xaa$_{10}$Xaa$_2$Xaa$_{11}$ comprise L(NMeGln)T(NMeLeu)R.

In some embodiments, Xaa$_1$Xaa$_9$Xaa$_{10}$Xaa$_2$Xaa$_{11}$ comprise L(N-methylQ)TL(N-methylR).

In some embodiments, Xaa$_1$Xaa$_9$Xaa$_{10}$Xaa$_2$Xaa$_{11}$ comprise LN-methylQTLR.

In some embodiments, Xaa$_1$Xaa$_9$Xaa$_{10}$Xaa$_2$Xaa$_{11}$ comprise LETLR.

In some embodiments, Xaa$_1$Xaa$_9$Xaa$_{10}$Xaa$_2$Xaa$_{11}$ comprise (CBA)QTLR.

In some embodiments, Xaa$_1$Xaa$_9$Xaa$_{10}$Xaa$_2$Xaa$_{11}$ comprise (CBA)(N-methylQ)TLR.

In some embodiments, Xaa$_1$Xaa$_9$Xaa$_{10}$Xaa$_2$Xaa$_{11}$ comprise LQT(CBA)R.

In some embodiments, Xaa$_1$Xaa$_9$Xaa$_{10}$Xaa$_2$Xaa$_{11}$ comprise L(N-methylQ)(N-methylT)LR.

In some embodiments, Xaa$_1$Xaa$_9$Xaa$_{10}$Xaa$_2$Xaa$_{11}$ comprise L(N-methylQ)T(Cha)R. In some embodiments, Xaa$_1$Xaa$_9$Xaa$_{10}$Xaa$_2$Xaa$_{11}$ comprise L(N-methylQ)T(t-methylL)R.

In some embodiments, Xaa$_1$Xaa$_9$Xaa$_{10}$Xaa$_2$Xaa$_{11}$ comprise L(N-methylQ)(DThr)LR.

In some embodiments, the polypeptide comprises:

| 358 | 359 | 360 | 361 | 362 |
|---|---|---|---|---|
| Xaa$_{12}$ | Xaa$_{13}$ | Xaa$_{14}$ | Xaa$_{15}$ | S | wherein:
Xaa$_{12}$ is selected from H, N-MeHis, Cys, N-MeCys, homoHis, and NHis;
Xaa$_{13}$ is selected from R, N-methylR, homoArg, Cit, Nar, and Phe(4-guanidino);
Xaa$_{14}$ is selected from E, Q, N-methylE, N-methylQ, N-methylD, and NMeGln; and
Xaa$_{15}$ is selected from R, homoR, and N-methylR.

In some embodiments, Xaa$_{12}$ is selected from H.
In some embodiments, Xaa$_{13}$ is R.
In some embodiments, Xaa$_{13}$ is N-methylR.
In some embodiments, Xaa$_{14}$ is E.
In some embodiments, Xaa$_{14}$ is Q.
In some embodiments, Xaa$_{14}$ is N-methylE.
In some embodiments, Xaa$_{14}$ is N-methylQ.
In some embodiments, Xaa$_{12}$Xaa$_{13}$Xaa$_{14}$Xaa$_{15}$ comprise HRER.
In some embodiments, Xaa$_{12}$Xaa$_{13}$Xaa$_{14}$Xaa$_{15}$ comprise HRQR.
In some embodiments, Xaa$_{12}$Xaa$_{13}$Xaa$_{14}$Xaa$_{15}$ comprise HR(N-methylE)R.
In some embodiments, Xaa$_{12}$Xaa$_{13}$Xaa$_{14}$Xaa$_{15}$ comprise HR(N-methylE)R.
In some embodiments, Xaa$_{12}$Xaa$_{13}$Xaa$_{14}$Xaa$_{15}$ comprise HR(N-methylQ)R.
In some embodiments, Xaa$_{12}$Xaa$_{13}$Xaa$_{14}$Xaa$_{15}$ comprise HR(N-methylD)R.
In some embodiments, Xaa$_{12}$Xaa$_{13}$Xaa$_{14}$Xaa$_{15}$ comprise H(N-methylR)QR.
In some embodiments, Xaa$_{12}$Xaa$_{13}$Xaa$_{14}$Xaa$_{15}$ comprise HRQ(homoR).
In some embodiments, Xaa$_{12}$Xaa$_{13}$Xaa$_{14}$Xaa$_{15}$ comprise HRQ(N-methylR).
In some embodiments, Xaa$_{12}$Xaa$_{13}$Xaa$_{14}$Xaa$_{15}$ comprise H(homoArg)QR.

In some embodiments, $Xaa_{12}Xaa_{13}Xaa_{14}Xaa_{15}$ comprise HRQ(NMeArg).

In some embodiments, $Xaa_{12}Xaa_{13}Xaa_{14}Xaa_{15}$ comprise HR(NMeGln)R.

In some embodiments, $Xaa_{12}Xaa_{13}Xaa_{14}Xaa_{15}$ comprise (N-MeHis)RQR.

In some embodiments, $Xaa_{12}Xaa_{13}Xaa_{14}Xaa_{15}$ comprise (Cys)RQR.

In some embodiments, $Xaa_{12}Xaa_{13}Xaa_{14}Xaa_{15}$ comprise (NMeCys)RQR.

In some embodiments, $Xaa_{12}Xaa_{13}Xaa_{14}Xaa_{15}$ comprise (homoHis)RQR.

In some embodiments, $Xaa_{12}Xaa_{13}Xaa_{14}Xaa_{15}$ comprise (NHis)RQR.

In some embodiments, $Xaa_{12}Xaa_{13}Xaa_{14}Xaa_{15}$ comprise H(Cit)(N-methylQ)R.

In some embodiments, $Xaa_{12}Xaa_{13}Xaa_{14}Xaa_{15}$ comprise H(Nar)(N-methylQ)R.

In some embodiments, $Xaa_{12}Xaa_{13}Xaa_{14}Xaa_{15}$ comprise H(4-guanidino-Phe)(N-methylQ)R.

In some embodiments, $Xaa_3$ and $Xaa_6$ are the same. In some aspects of these embodiments, $Xaa_3$ and $Xaa_6$ are each (S)-2-(4'-pentenyl)alanine. In other aspects of these embodiments, $Xaa_3$ and $Xaa_6$ are each (R)-2-(4'-pentenyl)alanine. In yet other aspects of these embodiments, $Xaa_3$ and $Xaa_6$ are each (S)-2-(7'-octenyl)alanine. In yet other aspects of these embodiments, $Xaa_3$ and $Xaa_6$ are each (R)-2-(7'-octenyl)alanine.

In some embodiments, $Xaa_3$ and $Xaa_6$ are different α,α-disubstituted amino acids. In some aspects of these embodiments, $Xaa_3$ is (S)-2-(4'-pentenyl)alanine whereas $Xaa_6$ is (R)-2-(4'-pentenyl)alanine. In other aspects of these embodiments, $Xaa_3$ is (R)-2-(4'-pentenyl)alanine whereas $Xaa_6$ is (S)-2-(4'-pentenyl)alanine. In yet other aspects of these embodiments, $Xaa_3$ is (S)-2-(7'-octenyl)alanine whereas $Xaa_6$ is (R)-2-(7'-octenyl)alanine. In yet other aspects of these embodiments, $Xaa_3$ is (R)-2-(7'-octenyl)alanine whereas $Xaa_6$ is (S)-2-(7'-octenyl)alanine. In yet other aspects of these embodiments, $Xaa_3$ is (S)-2-(4'-pentenyl)alanine whereas $Xaa_6$ is (S)-2-(7'-octenyl)alanine. In yet other aspects of these embodiments, $Xaa_3$ is (R)-2-(4'-pentenyl)alanine whereas $Xaa_6$ is (R)-2-(7'-octenyl)alanine. In yet other aspects of these embodiments, $Xaa_3$ is (S)-2-(4'-pentenyl)alanine whereas $Xaa_6$ is (R)-2-(7'-octenyl)alanine. In yet other aspects of these embodiments, $Xaa_3$ is (R)-2-(4'-pentenyl)alanine whereas $Xaa_6$ is (S)-2-(7'-octenyl)alanine. In yet other aspects of these embodiments, $Xaa_3$ is (S)-2-(7'-octenyl)alanine whereas $Xaa_6$ is (S)-2-(4'-pentenyl)alanine. In yet other aspects of these embodiments, $Xaa_3$ is (R)-2-(7'-octenyl)alanine whereas $Xaa_6$ is (R)-2-(4'-pentenyl)alanine. In yet other aspects of these embodiments, $Xaa_3$ is (S)-2-(7'-octenyl)alanine whereas $Xaa_6$ is (R)-2-(4'-pentenyl)alanine. In yet other aspects of these embodiments, $Xaa_3$ is (R)-2-(7'-octenyl)alanine whereas $Xaa_6$ is (S)-2-(4'-pentenyl)alanine.

In some embodiments, the polypeptide is selected from:

```
                                         SEQ ID NO: 107
LQTLRXaa3IQRXaa6(CBA)(2-Nal)

SEQ ID NO: 108
L(N-methylQ)TLRXaa3IQRXaa6(CBA)(2-Nal)

SEQ ID NO: 109
LETLRXaa3IQRXaa6(CBA)(2-Nal)

SEQ ID NO: 110
L(N-methylQ)TLRXaa3IQRXaa6(CBA)(2-Nal)(β-Ala)
(β-Ala)

SEQ ID NO: 111
L(N-methylQ)TLRXaa3IQRXaa6(CBA)(2-Nal)(β-Ala)
(β-Ala)

SEQ ID NO: 112
LQTLRXaa3IQHXaa6(CBA)(2-Nal)

SEQ ID NO: 113
(CBA)QTLRXaa3IQRXaa6(CBA)(2-Nal)

SEQ ID NO: 114
(CBA)(N-methylQ)TLRXaa3IQRXaa6(CBA)(2-Nal)

SEQ ID NO: 115
LQT(CBA)RXaa3IQRXaa6(CBA)(2-Nal)

SEQ ID NO: 116
L(N-methylQ)TLRXaa3I(N-methylQ)RXaa6(CBA)(2-
Nal)

SEQ ID NO: 117
LN-MeQTLR(Me)Xaa3IQRXaa6(CBA)(2-Nal)

SEQ ID NO: 118
(Me-L)(N-MeQ)TLRXaa3IQRXaa6(CBA)(2-Nal)

SEQ ID NO: 119
LN(Me-Gln)TLRXaa3IQRXaa6(Cpa)(2-Nal)

SEQ ID NO: 120
L(N-methylQ)TLRXaa3IQRXaa6(CBA)(2-Nal),
wherein N-terminus is modified with
HOCH2CH2CO—.

SEQ ID NO: 121
L(N-methylQ)(N-methylT)LRXaa3IQRXaa6(CBA)
(2-Nal)

SEQ ID NO: 122
L(N-methylQ)TLRXaa3IQRXaa6(Cha)(2-Nal)

SEQ ID NO: 123
L(N-methylQ)T(Cha)RXaa3IQRXaa6(CBA)(2-Nal)

SEQ ID NO: 124
L(N-methylQ)TL(N-methylR)Xaa3IQRXaa6(CBA)
(2-Nal)

SEQ ID NO: 125
L(N-methylQ)TLRXaa3IQ(N-methylR)Xaa6(CBA)
(2-Nal)

SEQ ID NO: 126
L(N-methylQ)T(α-methylL)RXaa3IQRXaa6(CBA)
(2-Nal)

SEQ ID NO: 127
LQTLRXaa3IQRXaa6(Cha)(2-Nal)

SEQ ID NO: 128
L(N-methylQ)TL(N-methylR)Xaa3IQ(N-
methylR)Xaa6(CBA)(2-Nal)

SEQ ID NO: 129
L(N-methylQ)TLRXaa3(CBA)QRXaa6(CBA)(2-Nal)

SEQ ID NO: 130
L(N-methylQ)(D-Thr)LRXaa3IQRXaa6(CBA)(2-Nal)

SEQ ID NO: 131
L(N-meGln)T(N-MeLeu)RXaa3IQRXaa6(CBA)(2-Nal)

SEQ ID NO: 132
L(N-methylQ)TL(homoR)Xaa3IQRXaa6(CBA)(2-Nal)

SEQ ID NO: 133
L(N-methylQ)TLRXaa3IQ(homoR)Xaa6(CBA)(2-Nal)
```

SEQ ID NO: 134
L(N-methylQ)TLRXaa₃(N-methylI)QRXaa₆(CBA)(2-Nal)

SEQ ID NO: 135
L(N-MeGln)TLRXaa₃IQRXaa6(CBA)(2-Nal),
wherein N-terminus is modified with propionyl.

SEQ ID NO: 136
L(N-MeGln)TLRXaa₃IQRXaa₆(CBA)(2-Nal),
wherein N-terminus is modified with hexanoyl.

SEQ ID NO: 137
L(N-MeGln)TLRXaa₃IQRXaa₆(CBA)(2-Nal),
wherein N-terminus is modified with 3-phenyl-propanoyl.

SEQ ID NO: 138
L(N-MeGln)TLRXaa₃IQRXaa₆(CBA)(2-Nal),
wherein N-terminus is modified with 2-cyclo-hexylacetyl.

SEQ ID NO: 139
L(N-MeGln)TLRXaa₃IQRXaa₆(CBA)(2-Nal),
wherein N-terminus is modified with diphenyl-acetyl.

SEQ ID NO: 140
L(N-methylQ)TLRXaa₃IQRXaa₆(CBA)(2-Nal),
wherein N-terminus is modified with 3,5-dihydroxybenzoic acid.

SEQ ID NO: 141
L(N-methylQ)TLRXaa₃IQRXaa₆(CBA)(2-Nal),
wherein N-terminus is modified with 4-(trifluoromethyl)benzoic acid.

SEQ ID NO: 142
L(N-methylQ)TLRXaa₃IQRXaa₆(CBA)(2-Nal),
wherein N-terminus is modified with 5-phenyl-valeric acid.

SEQ ID NO: 143
L(N-methylQ)TLRXaa₃IQRXaa₆(CBA)(2-Nal),
wherein N-terminus is modified with 4-biphenyl acetic acid.

SEQ ID NO: 144
L(N-methylQ)TLRXaa3IQRXaa₆(CBA)(2-Nal),
wherein N-terminus is modified with dimethyl.

SEQ ID NO: 145
HRERSLQTLRXaa₃IQQXaa₆(CBA)(2-Nal)

SEQ ID NO: 146
HRERSLQTLRXaa₃IQEXaa₆(CBA)(2-Nal),
wherein C-terminus is unmodified.

SEQ ID NO: 147
HRQRSLQTLRXaa₃IQRXaa₆(CBA)(2-Nal)

SEQ ID NO: 148
HRQRSLQTLRXaa₃IQRXaa₆(CBA)(2-Nal)(β-Ala)(β-Ala)

SEQ ID NO: 149
HRQRSLQTLRXaa₃IQRXaa₆(CBA)(2-Nal)(β-Ala)(β-Ala),
wherein C-terminus is modified with GRKKRRQRRRPQ-NH₂.

SEQ ID NO: 150
HRQRSLQTLRXaa₃IQRXaa₆(CBA)(2-Nal)(β-Ala)(β-Ala),
wherein C-terminus is modified with 1-(2-amino-ethyl)-4-methylpiperazine.

SEQ ID NO: 151
HR(N-methylE)RSLQTLRXaa₃IQRXaa₆(CBA)(2-Nal)

SEQ ID NO: 152
HRERSLQTL(N-methylR)Xaa₃IQRXaa₆(CBA)(2-Nal),
wherein C-terminus is unmodified.

SEQ ID NO: 153
HRQRSL(N-methylQ)TLRXaa₃IQRXaa₆(CBA)(2-Nal)

SEQ ID NO: 154
HR(N-methylE)RSL(N-methylQ)TLRXaa₃IQRXaa₆(CBA)(2-Nal)

SEQ ID NO: 155
HR(N-methylQ)RSL(N-methylQ)TLRXaa₃IQRXaa₆(CBA)(2-Nal)

SEQ ID NO: 156
HRQRS(CBA)QTLRXaa₃IQRXaa₆(CBA)(2-Nal)

SEQ ID NO: 157
HR(N-methylD)RSLQTLRXaa₃IQRXaa₆(CBA)(2-Nal)

SEQ ID NO: 158
H(R-Me)QRSLQTLRXaa₃IQRXaa₆(CBA)(2-Nal)

SEQ ID NO: 159
HRQRTLQTLRXaa₃IQRXaa₆(CBA)(2-Nal)

SEQ ID NO: 160
HRQRSLQTLRXaa₃IQRXaa₆(CBA)(2-Nal),
N-terminus is modified with palmitoyl-PEG4.

SEQ ID NO: 161
HRQRSLQTLRXaa₃IQRXaa₆(CBA)(2-Nal),
wherein C-terminus is modified with K(PEG4-palmitoyl)NH₂.

SEQ ID NO: 162
HRQRSLQTLRXaa₃IQRXaa₆(Cpa)(2-Nal)

SEQ ID NO: 163
HR(N-methylQ)RSL(N-methylQ)T(Cha)RXaa₃IQRXaa₆(CBA)(2-Nal)

SEQ ID NO: 164
HR(N-methylQ)RSL(N-methylQ)TLRXaa₃IQ(N-methylR)Xaa₆(CBA)(2-Nal)

SEQ ID NO: 165
HR(N-methylQ)RSL(N-methylQ)(N-methylT)LRXaa₃IQRXaa₆(CBA)(2-Nal)

SEQ ID NO: 166
H(N-methylR)QRSLQTLRXaa₃IQRXaa₆(CBA)(2-Nal)

SEQ ID NO: 167
HRQ(homoR)SLQTLRXaa₃IQRXaa₆(CBA)(2-Nal)

SEQ ID NO: 168
HRQ(N-methylR)SLQTLRXaa₃IQRXaa₆(CBA)(2-Nal)

SEQ ID NO: 169
HRQRSL(peptoid-Q)TLRXaa₃IQRXaa₆(CBA)(2-Nal)

SEQ ID NO: 170
HRQRSLQTL(homoR)Xaa₃IQRXaa₆(CBA)(2-Nal)

SEQ ID NO: 171
HRQRSLQTLRXaa₃IQ(homoR)Xaa₆(CBA)(2-Nal)

SEQ ID NO: 172
L(N-methylQ)TLRXaa₃IQRXaa₆(α-methylL)(2-Nal)

SEQ ID NO: 173
L(N-methylQ)TLRXaa₃IQRXaa₆D(Cha)(2-Nal)

SEQ ID NO: 174
L(N-methylQ)TLRXaa₃IQRXaa₆(N-methylCha)(2-Nal)

-continued

SEQ ID NO: 175
LQTLRXaa$_3$IQRXaa$_6$(allylGly)(2-Nal)

SEQ ID NO: 176
HRQRSLQTLRXaa$_3$IQRXaa$_6$(AC4C)(2-Nal)

SEQ ID NO: 177
HRQRSLQTLRXaa$_3$IQRXaa$_6$(A6C)(2-Nal)

SEQ ID NO: 178
HRQRSLQTLRXaa$_3$IQRXaa$_6$(Aze)(2-Nal)

SEQ ID NO: 179
HRQRSLQTLRXaa$_3$IQRXaa$_6$(Phe-4-Cl)(2-Nal)

SEQ ID NO: 180
HRQRSLQTLRXaa$_3$IQRXaa$_6$(Cha)(2-Nal)

SEQ ID NO: 181
HR(N-methylQ)RSL(N-methylQ)TLRXaa$_3$IQRXaa$_6$(Cha)(2-Nal)

SEQ ID NO: 182
HRQRSLQTLRXaa$_3$IQRXaa$_6$(N-MeCha)(2-Nal)

SEQ ID NO: 183
H(homoArg)QRSLQTLRXaa$_3$IQRXaa$_6$(Cha)(2-Nal)

SEQ ID NO: 184
HRQ(N-MeArg)SLQTLRXaa$_3$IQRXaa$_6$(Cha)(2-Nal)

SEQ ID NO: 185
HRQRS(Cha)(N-MeGln)TLRXaa$_3$IQRXaa$_6$(Cha)(2-Nal)

SEQ ID NO: 186
HRQRS(N-MeCha)(N-MeGln)TLRXaa$_3$IQRXaa$_6$(Cha)(2-Nal)

SEQ ID NO: 187
HRQRSD(Cha)(N-MeGln)TLRXaa$_3$IQRXaa$_6$(Cha)(2-Nal)

SEQ ID NO: 188
HRQRSLQTLRXaa$_3$IQRXaa$_6$(Cha)(2DNal)

SEQ ID NO: 189
HRQRSLQTL(N-MeArg)Xaa$_3$IQRXaa$_6$(Cha)(2-Nal)

SEQ ID NO: 190
HRQRSLQTLRXaa$_3$IQ(N-MeArg)Xaa$_6$(Cha)(2-Nal)

SEQ ID NO: 191
HRQRSLQTLRXaa$_3$IQRXaa$_6$(β-tBu-Ala)(2-Nal)

SEQ ID NO: 192
HRQRSLQTLRXaa$_3$IQRXaa$_6$(Tle)(2-Nal)

SEQ ID NO: 193
HR(N-MeGln)RSLQTLRXaa$_3$IQRXaa$_6$(β-tBu-Ala)(2-Nal)

SEQ ID NO: 194
HR(N-MeGln)RSLQTLRXaa$_3$IQRXaa$_6$(Tle)(2-Nal)

SEQ ID NO: 195
L(N-methylQ)TLRXaa$_3$IQRXaa$_6$(4-Cl-Ph)(2-Nal)

SEQ ID NO: 196
HRQRSLQTLRXaa$_3$IQRXaa$_6$(4-Cl-Ph)(2-Nal)

SEQ ID NO: 197
HR(N-methylQ)RSL(N-methylQ)TLRXaa$_3$IQRXaa$_6$(4-Cl-Ph)(2-Nal)

SEQ ID NO: 199
HRQRS(Cha)(N-methylQ)TLRXaa$_3$IQRXaa$_6$(4-Cl-Ph)(2-Nal)

SEQ ID NO: 200
HRQRS(Cha)(N-methylQ)TLRXaa$_3$IQRXaa$_6$(4-F-Ph)(2-Nal)

SEQ ID NO: 201
HRQRS(NptGly)(N-methylQ)TLRXaa$_3$IQRXaa$_6$(4-Cl-Ph)(2-Nal)

SEQ ID NO: 202
HR(N-methylQ)RSL(N-methylQ)TLRXaa$_3$IQRXaa$_6$(4-F-Ph)(2-Nal)

SEQ ID NO: 203
HR(N-methylQ)RSL(N-methylQ)TLRXaa$_3$IQRXaa$_6$(3,4-diCl-Ph)(2-Nal)

SEQ ID NO: 204
HR(N-methylQ)RSL(N-methylQ)TLRXaa$_3$(Nle)QRXaa$_6$(Cha)(2-Nal)

SEQ ID NO: 205
HRQRSLQTLRXaa$_3$IQRXaa$_6$(Cha)(2-Nal),
wherein N-terminus is modified with palmitoyl-PEG4.

SEQ ID NO: 206
HRQRSLQTLRXaa$_3$IQRXaa$_6$(4-Cl-Ph)(2-Nal),
wherein N-terminus is modified with palmitoyl-PEG4.

SEQ ID NO: 207
HR(N-methylQ)RSL(N-methylQ)TLRXaa$_3$IQRXaa$_6$(Cha)(2-Nal),
wherein N-terminus is modified with palmitoyl-PEG4.

SEQ ID NO: 208
HR(N-methylQ)RSL(N-methylQ)TLRXaa3IQRXaa6(4-Cl-Ph)(2-Nal),
wherein N-terminus is modified with palmitoyl-PEG4.

SEQ ID NO: 209
H(homoArg)QRSLQTLRXaa$_3$IQRXaa$_6$(Cha)(2-Nal),
wherein N-terminus is modified with palmitoyl-PEG4.

SEQ ID NO: 210
H(homoArg)QRSLQTLRXaa$_3$IQRXaa$_6$(4-Cl-Ph)(2-Nal),
wherein N-terminus is modified with palmitoyl-PEG4.

SEQ ID NO: 211
HRQRS(Cha)(N-methylQ)TLRXaa$_3$IQRXaa$_6$(Cha)(2-Nal),
wherein N-terminus is modified with palmitoyl-PEG4.

SEQ ID NO: 212
HRQRS(Cha)(N-methylQ)TLRXaa$_3$IQRXaa$_6$(4-Cl-Ph)(2-Nal),
wherein N-terminus is modified with palmitoyl-PEG4.

SEQ ID NO: 213
L(N-methylQ)TLRXaa$_3$IQRXaa$_6$(CBA)(2-Nal),
wherein N-terminus is modified with palmitoyl-PEG4.

SEQ ID NO: 214
L(N-methylQ)TLRXaa$_3$IQRXaa$_6$(4-Cl-Ph)(2-Nal),
wherein N-terminus is modified with palmitoyl-PEG4.

SEQ ID NO: 215
(N-MeHis)RQRSLQTLRXaa$_3$IQRXaa$_6$(Cha)(2-Nal)

SEQ ID NO: 216
(Cys)RQRSLQTLRXaa$_3$IQRXaa$_6$(Cha)(2-Nal)

-continued

SEQ ID NO: 217
(N-MeCys)RQRSLQTLRXaa₃IQRXaa₆(Cha)(2-Nal)

SEQ ID NO: 218
(homoHis)RQRSLQTLRXaa₃IQRXaa₆(Cha)(2-Nal)

SEQ ID NO: 219
(NHis)RQRSLQTLRXaa₃IQRXaa₆(Cha)(2-Nal)

SEQ ID NO: 220
H(homoArg)QRSLQTL(Nar)Xaa₃IQRXaa₆(Cha)(2-Nal)

SEQ ID NO: 221
H(homoArg)QRSLQTLRXaa₃IQ(Nar)Xaa₆(Cha)(2-Nal)

SEQ ID NO: 222
H(homoArg)QRSLQTLRXaa₃IQ(Cit)Xaa₆(Cha)(2-Nal)

SEQ ID NO: 223
H(homoArg)QRSLQTL(Cit)Xaa₃IQRXaa₆(Cha)(2-Nal)

SEQ ID NO: 224
H(Cit)(N-methylQ)RSL(N-methylQ)TLRXaa₃IQRXaa₆(Cha)(2-Nal)

SEQ ID NO: 225
H(Nar)(N-methylQ)RSL(N-methylQ)TLRXaa₃IQRXaa₆(Cha)(2-Nal)

SEQ ID NO: 226
H(4-guanidino-Phe)(N-methylQ)RSL(N-methylQ)TLRXaa₃IQRXaa₆(Cha)(2-Nal)

wherein $Xaa_3$ and $Xaa_6$ are each (S)-2-(4'-pentenyl)alanine.

In some embodiments, the present application provides a polypeptide comprising an amino acid sequence:

| 362 | 363 | 364 | 365 |
|---|---|---|---|
| $Xaa_{16}$ | $Xaa_1$ | $Xaa_9$ | $Xaa_{10}$ | and an amino acid sequence selected from:

| 368 | 369 | 370 | 371 | 372 |
|---|---|---|---|---|
| $Xaa_3$ | $Xaa_4$ | $Xaa_8$ | $Xaa_5$ | $Xaa_6$ | wherein:

$Xaa_3$, $Xaa_6$, $Xaa_{16}$ and $Xaa_{10}$ are each independently an α,α-disubstituted amino acid;

$Xaa_1$ is selected from L, A, Cha, Cpa, (D-L), CBA, MeL, NMeCha, Dcha, and NptGly;

$Xaa_9$ is selected from Q, N-methylQ, E, N-MeGln, and peptoidQ;

$Xaa_4$ is selected from I, A, Nle, N-MethylI, CBA, and (D-I);

$Xaa_8$ is selected from Q and N-methylQ;

$Xaa_5$ is selected from R, A, Q, E, K, H, N-MethylR, homoR, NMeArg, Nar, and Cit.

In some embodiments, the polypeptide has length of 9-30 amino acids (e.g., 10-30, 10-20, 12-30, or 12-20 amino acids).

In some embodiments, $Xaa_1$ is selected from L and Cpa.
In some embodiments, $Xaa_1$ is L. In some embodiments, $Xaa_1$ is Cpa.
In some embodiments, $Xaa_9$ is selected from Q and N-methylQ.
In some embodiments, $Xaa_9$ is Q.
In some embodiments, $Xaa_4$ is I.
In some embodiments, $Xaa_8$ is Q.
In some embodiments, $Xaa_5$ is R.
In some embodiments, $Xaa_1Xaa_9$ is LQ.
In some embodiments, $Xaa_1Xaa_9$ is L(N-methylQ).
In some embodiments, $Xaa_1Xaa_9$ is (Cpa)(N-methylQ).
In some embodiments, $Xaa_4Xaa_8Xaa_5$ is IQR.

In some embodiments, in addition to the sequences $Xaa_{16}Xaa_1Xaa_9Xaa_{10}$ and $Xaa_3Xaa_4Xaa_8Xaa_5Xaa_6$, the polypeptide comprises at least one R (e.g., one R, two R, or three R).

In some embodiments, in addition to the sequences $Xaa_{16}Xaa_1Xaa_9Xaa_{10}$ and $Xaa_3Xaa_4Xaa_8Xaa_5Xaa_6$, the polypeptide comprises at least one L (e.g., one L, two L, or three L).

In some embodiments, in addition to the sequences $Xaa_{16}Xaa_1Xaa_9Xaa_{10}$ and $Xaa_3Xaa_4Xaa_8Xaa_5Xaa_6$, the polypeptide comprises at least one amino acid selected from CBA, Cpa, and Cha. In some embodiments, the polypeptide comprises CBA. In some embodiments, the polypeptide comprises Cpa. In some embodiments, the polypeptide comprises Cha.

In some embodiments, in addition to the sequences $Xaa_{16}Xaa_1Xaa_9Xaa_{10}$ and $Xaa_3Xaa_4Xaa_8Xaa_5Xaa_6$, the polypeptide comprises at least one (2-Nal) (e.g., one, two, or three 2-Nal).

In some embodiments, in addition to the sequences $Xaa_{16}Xaa_1Xaa_9Xaa_{10}$ and $Xaa_3Xaa_4Xaa_8Xaa_5Xaa_6$, the polypeptide comprises at least one (β-Ala). In some embodiments, the polypeptide comprises (β-Ala)(β-Ala).

In some embodiments, in addition to the sequences $Xaa_{16}Xaa_1Xaa_9Xaa_{10}$ and $Xaa_3Xaa_4Xaa_8Xaa_5Xaa_6$, the polypeptide comprises HRQR. In some embodiments, in addition to the sequences $Xaa_{16}Xaa_1Xaa_9Xaa_{10}$ and $Xaa_3Xaa_4Xaa_8Xaa_5Xaa_6$, the polypeptide comprises HRER.

In some embodiments, in addition to the sequences $Xaa_{16}Xaa_1Xaa_9Xaa_{10}$ and $Xaa_3Xaa_4Xaa_8Xaa_5Xaa_6$, the polypeptide comprises LR.

In some embodiments, in addition to the sequences $Xaa_{16}Xaa_1Xaa_9Xaa_{10}$ and $Xaa_3Xaa_4Xaa_8Xaa_5Xaa_6$, the polypeptide comprises (Cpa)R.

In some embodiments, in addition to the sequences $Xaa_{16}Xaa_1Xaa_9Xaa_{10}$ and $Xaa_3Xaa_4Xaa_8Xaa_5Xaa_6$, the polypeptide comprises (Cha)R.

In some embodiments, in addition to the sequences $Xaa_{16}Xaa_1Xaa_9Xaa_{10}$ and $Xaa_3Xaa_4Xaa_8Xaa_5Xaa_6$, the polypeptide comprises (CBA)(2-Nal).

In some embodiments, in addition to the sequences $Xaa_{16}Xaa_1Xaa_9Xaa_{10}$ and $Xaa_3Xaa_4Xaa_8Xaa_5Xaa_6$, the polypeptide comprises (Cpa)(2-Nal).

In some embodiments, in addition to the sequences $Xaa_{16}Xaa_1Xaa_9Xaa_{10}$ and $Xaa_3Xaa_4Xaa_8Xaa_5Xaa_6$, the polypeptide comprises (Cha)(2-Nal).

In some embodiments, $Xaa_3$ and $Xaa_6$ are the same. In some aspects of these embodiments, $Xaa_3$ and $Xaa_6$ are each (S)-2-(4'-pentenyl)alanine. In other aspects of these embodiments, $Xaa_3$ and $Xaa_6$ are each (R)-2-(4'-pentenyl)alanine. In yet other aspects of these embodiments, $Xaa_3$ and $Xaa_6$ are each (S)-2-(7'-octenyl)alanine. In yet other aspects of these embodiments, $Xaa_3$ and $Xaa_6$ are each (R)-2-(7'-octenyl)alanine.

In some embodiments, $Xaa_3$ and $Xaa_6$ are different α,α-disubstituted amino acids. In some aspects of these embodiments, $Xaa_3$ is (S)-2-(4'-pentenyl)alanine whereas $Xaa_6$ is (R)-2-(4'-pentenyl)alanine. In other aspects of these embodiments, $Xaa_3$ is (R)-2-(4'-pentenyl)alanine whereas $Xaa_6$ is (S)-2-(4'-pentenyl)alanine. In yet other aspects of these embodiments, $Xaa_3$ is (S)-2-(7'-octenyl)alanine whereas $Xaa_6$ is (R)-2-(7'-octenyl)alanine. In yet other aspects of these embodiments, $Xaa_3$ is (R)-2-(7'-octenyl)alanine whereas $Xaa_6$ is (S)-2-(7'-octenyl)alanine. In yet other aspects of these embodiments, Xaa₃ is (S)-2-(4'-pentenyl) alanine whereas Xaa₆ is (S)-2-(7'-octenyl)alanine. In yet other aspects of these embodiments, Xaa₃ is (R)-2-(4'-pentenyl)alanine whereas Xaa₆ is (R)-2-(7'-octenyl)alanine. In yet other aspects of these embodiments, Xaa₃ is (S)-2-(4'-pentenyl)alanine whereas Xaa₆ is (R)-2-(7'-octenyl)alanine. In yet other aspects of these embodiments, Xaa₃ is (R)-2-(4'-pentenyl)alanine whereas Xaa₆ is (S)-2-(7'-octenyl)alanine. In yet other aspects of these embodiments, Xaa₃ is (S)-2-(7'-octenyl)alanine whereas Xaa₆ is (S)-2-(4'-pentenyl)alanine. In yet other aspects of these embodiments, Xaa₃ is (R)-2-(7'-octenyl)alanine whereas Xaa₆ is (R)-2-(4'-pentenyl)alanine. In yet other aspects of these embodiments, Xaa₃ is (S)-2-(7'-octenyl)alanine whereas Xaa₆ is (R)-2-(4'-pentenyl)alanine. In yet other aspects of these embodiments, Xaa₃ is (R)-2-(7'-octenyl)alanine whereas Xaa₆ is (S)-2-(4'-pentenyl)alanine.

In some embodiments, Xaa₁₆ and Xaa₁₀ are the same. In some aspects of these embodiments, Xaa₁₆ and Xaa₁₀ are each (S)-2-(4'-pentenyl)alanine. In other aspects of these embodiments, Xaa₁₆ and Xaa₁₀ are each (R)-2-(4'-pentenyl)alanine. In yet other aspects of these embodiments, Xaa₁₆ and Xaa₁₀ are each (S)-2-(7'-octenyl)alanine. In yet other aspects of these embodiments, Xaa₁₆ and Xaa₁₀ are each (R)-2-(7'-octenyl)alanine.

In some embodiments, Xaa₁₆ and Xaa₁₀ are different α,α-disubstituted amino acids. In some aspects of these embodiments, Xaa₁₆ is (S)-2-(4'-pentenyl)alanine whereas Xaa₁₀ is (R)-2-(4'-pentenyl)alanine. In other aspects of these embodiments, Xaa₁₆ is (R)-2-(4'-pentenyl)alanine whereas Xaa₁₀ is (S)-2-(4'-pentenyl)alanine. In yet other aspects of these embodiments, Xaa₁₆ is (S)-2-(7'-octenyl)alanine whereas Xaa₁₀ is (R)-2-(7'-octenyl)alanine. In yet other aspects of these embodiments, Xaa₁₆ is (R)-2-(7'-octenyl) alanine whereas Xaa₁₀ is (S)-2-(7'-octenyl)alanine. In yet other aspects of these embodiments, Xaa₁₆ is (S)-2-(4'-pentenyl)alanine whereas Xaa₁₀ is (S)-2-(7'-octenyl)alanine. In yet other aspects of these embodiments, Xaa₁₆ is (R)-2-(4'-pentenyl)alanine whereas Xaa₁₀ is (R)-2-(7'-octenyl)alanine. In yet other aspects of these embodiments, Xaa₁₆ is (S)-2-(4'-pentenyl)alanine whereas Xaa₁₀ is (R)-2-(7'-octenyl)alanine. In yet other aspects of these embodiments, Xaa₁₆ is (R)-2-(4'-pentenyl)alanine whereas Xaa₁₀ is (S)-2-(7'-octenyl)alanine. In yet other aspects of these embodiments, Xaa₁₆ is (S)-2-(7'-octenyl)alanine whereas Xaa₁₀ is (S)-2-(4'-pentenyl)alanine. In yet other aspects of these embodiments, Xaa₁₆ is (R)-2-(7'-octenyl)alanine whereas Xaa₁₀ is (R)-2-(4'-pentenyl)alanine. In yet other aspects of these embodiments, Xaa₁₆ is (S)-2-(7'-octenyl)alanine whereas Xaa₁₀ is (R)-2-(4'-pentenyl)alanine. In yet other aspects of these embodiments, Xaa₁₆ is (R)-2-(7'-octenyl)alanine whereas Xaa₁₀ is (S)-2-(4'-pentenyl)alanine.

In some embodiments, Xaa₃, Xaa₆, Xaa₁₆ and Xaa₁₀ are all the same. In some aspects of these embodiments, Xaa₃, Xaa₆, Xaa₁₆ and Xaa₁₀ are each (S)-2-(4'-pentenyl)alanine. In other aspects of these embodiments, Xaa₃, Xaa₆, Xaa₁₆ and Xaa₁₀ are each (R)-2-(4'-pentenyl)alanine. In yet other aspects of these embodiments, Xaa₃, Xaa₆, Xaa₁₆ and Xaa₁₀ are each (S)-2-(7'-octenyl)alanine. In yet other aspects of these embodiments, Xaa₃, Xaa₆, Xaa₁₆ and Xaa₁₀ are each (R)-2-(7'-octenyl)alanine.

In some embodiments, Xaa₃ and Xaa₆ are each (S)-2-(4'-pentenyl)alanine, whereas Xaa₁₆ and Xaa₁₀ are each (R)-2-(4'-pentenyl)alanine. In some embodiments, Xaa₃ and Xaa₆ are each (R)-2-(4'-pentenyl)alanine, whereas Xaa₁₆ and Xaa₁₀ are each (S)-2-(4'-pentenyl)alanine. In some embodiments, Xaa₃ and Xaa₆ are each (S)-2-(7'-octenyl)alanine, whereas Xaa₁₆ and Xaa₁₀ are each (R)-2-(7'-octenyl)alanine. In some embodiments, Xaa₃ and Xaa₆ are each (R)-2-(7'-octenyl)alanine, whereas Xaa₁₆ and Xaa₁₀ are each (S)-2-(7'-octenyl)alanine. In some embodiments, Xaa₃ and Xaa₆ are each (S)-2-(4'-pentenyl)alanine, whereas Xaa₁₆ and Xaa₁₀ are each (S)-2-(7'-octenyl)alanine. In some embodiments, Xaa₃ and Xaa₆ are each (S)-2-(7'-octenyl)alanine, whereas Xaa₁₆ and Xaa₁₀ are each (S)-2-(4'-pentenyl)alanine. In some embodiments, Xaa₃ and Xaa₆ are each (R)-2-(4'-pentenyl)alanine, whereas Xaa₁₆ and Xaa₁₀ are each (R)-2-(7'-octenyl)alanine. In some embodiments, Xaa₃ and Xaa₆ are each (R)-2-(7'-octenyl)alanine, whereas Xaa₁₆ and Xaa₁₀ are each (R)-2-(4'-pentenyl)alanine.

In some embodiments, the polypeptide has amino acid sequence:

```
                                            (SEQ ID NO: 88)
RXaa₁₆L(N-methylQ)Xaa₁₀LRXaa₃IQRXaa₆(CBA)(2-
Nal)(β-Ala)(β-Ala),
``` wherein Xaa₃, Xaa₆, Xaa₁₆, and Xaa₁₀ are each (R)-2-(4'-pentenyl)alanine.

In some embodiments, the polypeptide has amino acid sequence:

```
                                            (SEQ ID NO: 89)
RXaa₁₆(Cpa)(N-methylQ)Xaa₁₀(Cpa)RXaa₃IQRXaa₆

(Cpa)(2-Nal)(β-Ala)(β-Ala),
``` wherein Xaa₃, Xaa₆, Xaa₁₆, and Xaa₁₀ are each (R)-2-(4'-pentenyl)alanine.

In some embodiments, the present application provides a polypeptide having an amino acid sequence:

| 360 | 361 | 362 | 363 | 364 |
|---|---|---|---|---|
| Xaa₁₄ | Xaa₁₅ | Xaa₁₆ | Xaa₁ | Xaa₉ | and an amino acid sequence selected from:

| 368 | 369 | 370 | 371 | 372 |
|---|---|---|---|---|
| Xaa₃ | Xaa₄ | Xaa₈ | Xaa₅ | Xaa₆ | wherein:
Xaa₃, Xaa₆, Xaa₉ and Xaa₁₄ are each independently an α,α-disubstituted amino acid;
Xaa₁₅ is selected from R, homoR, and N-methylR;
Xaa₁₆ is selected from S and T;
Xaa₁ is selected from L, A, Cha, Cpa, (D-L), CBA, MeL, NMeCha, Dcha, and NptGly;
Xaa₄ is selected from I, A, Nle, N-MethylI, CBA, and (D-I);
Xaa₈ is selected from Q and N-methylQ; and
Xaa₅ is selected from R, A, Q, E, K, H, N-MethylR, homoR, NMeArg, Nar, and Cit.

In some embodiments, the polypeptide has length of 9-30 amino acids (e.g., 10-30, 10-20, 12-20, or 12-30 amino acids).

In some embodiments, Xaa₁₅ is R.
In some embodiments, Xaa₁₆ is S.
In some embodiments, Xaa₁ is L.
In some embodiments, Xaa₁₅Xaa₁₆Xaa₁ comprise RSL.
In some embodiments, Xaa₄ is I.
In some embodiments, Xaa₈ is Q.
In some embodiments, Xaa₅ is R.

In some embodiments, $Xaa_4Xaa_8Xaa_5$ comprise IQR.

In some embodiments, in addition to the amino acid sequence $Xaa_{14}Xaa_{15}Xaa_{16}Xaa_1Xaa_9$ and the amino acid sequence $Xaa_3Xaa_4Xaa_8Xaa_5Xaa_6$, the polypeptide comprises at least one R.

In some embodiments, in addition to the amino acid sequence $Xaa_{14}Xaa_{15}Xaa_{16}Xaa_1Xaa_9$ and the amino acid sequence $Xaa_3Xaa_4Xaa_8Xaa_5Xaa_6$, the polypeptide comprises at least one (2-Nal).

In some embodiments, in addition to the amino acid sequence $Xaa_{14}Xaa_{15}Xaa_{16}Xaa_1Xaa_9$ and the amino acid sequence $Xaa_3Xaa_4Xaa_8Xaa_5Xaa_6$, the polypeptide comprises HR.

In some embodiments, in addition to the amino acid sequence $Xaa_{14}Xaa_{15}Xaa_{16}Xaa_1Xaa_9$ and the amino acid sequence $Xaa_3Xaa_4Xaa_8Xaa_5Xaa_6$, the polypeptide comprises TLR.

In some embodiments, in addition to the amino acid sequence $Xaa_{14}Xaa_{15}Xaa_{16}Xaa_1Xaa_9$ and the amino acid sequence $Xaa_3Xaa_4Xaa_8Xaa_5Xaa_6$, the polypeptide comprises (CBA)(2-Nal) or (4-ClPh)(2-Nal).

In some embodiments, $Xaa_3$ and $Xaa_6$ are the same. In some aspects of these embodiments, $Xaa_3$ and $Xaa_6$ are each (S)-2-(4'-pentenyl)alanine. In other aspects of these embodiments, $Xaa_3$ and $Xaa_6$ are each (R)-2-(4'-pentenyl)alanine. In yet other aspects of these embodiments, $Xaa_3$ and $Xaa_6$ are each (S)-2-(7'-octenyl)alanine. In yet other aspects of these embodiments, $Xaa_3$ and $Xaa_6$ are each (R)-2-(7'-octenyl)alanine.

In some embodiments, $Xaa_3$ and $Xaa_6$ are different α,α-disubstituted amino acids. In some aspects of these embodiments, $Xaa_3$ is (S)-2-(4'-pentenyl)alanine whereas $Xaa_6$ is (R)-2-(4'-pentenyl)alanine. In other aspects of these embodiments, $Xaa_3$ is (R)-2-(4'-pentenyl)alanine whereas $Xaa_6$ is (S)-2-(4'-pentenyl)alanine. In yet other aspects of these embodiments, $Xaa_3$ is (S)-2-(7'-octenyl)alanine whereas $Xaa_6$ is (R)-2-(7'-octenyl)alanine. In yet other aspects of these embodiments, $Xaa_3$ is (R)-2-(7'-octenyl)alanine whereas $Xaa_6$ is (S)-2-(7'-octenyl)alanine. In yet other aspects of these embodiments, $Xaa_3$ is (S)-2-(4'-pentenyl)alanine whereas $Xaa_6$ is (S)-2-(7'-octenyl)alanine. In yet other aspects of these embodiments, $Xaa_3$ is (R)-2-(4'-pentenyl)alanine whereas $Xaa_6$ is (R)-2-(7'-octenyl)alanine. In yet other aspects of these embodiments, $Xaa_3$ is (S)-2-(4'-pentenyl)alanine whereas $Xaa_6$ is (R)-2-(7'-octenyl)alanine. In yet other aspects of these embodiments, $Xaa_3$ is (R)-2-(4'-pentenyl)alanine whereas $Xaa_6$ is (S)-2-(7'-octenyl)alanine. In yet other aspects of these embodiments, $Xaa_3$ is (S)-2-(7'-octenyl)alanine whereas $Xaa_6$ is (S)-2-(4'-pentenyl)alanine. In yet other aspects of these embodiments, $Xaa_3$ is (R)-2-(7'-octenyl)alanine whereas $Xaa_6$ is (R)-2-(4'-pentenyl)alanine. In yet other aspects of these embodiments, $Xaa_3$ is (S)-2-(7'-octenyl)alanine whereas $Xaa_6$ is (R)-2-(4'-pentenyl)alanine. In yet other aspects of these embodiments, $Xaa_3$ is (R)-2-(7'-octenyl)alanine whereas $Xaa_6$ is (S)-2-(4'-pentenyl)alanine.

In some embodiments, $Xaa_9$ and $Xaa_{14}$ are the same. In some aspects of these embodiments, $Xaa_9$ and $Xaa_{14}$ are each (S)-2-(4'-pentenyl)alanine. In other aspects of these embodiments, $Xaa_9$ and $Xaa_{14}$ are each (R)-2-(4'-pentenyl)alanine. In yet other aspects of these embodiments, $Xaa_9$ and $Xaa_{14}$ are each (S)-2-(7'-octenyl)alanine. In yet other aspects of these embodiments, $Xaa_9$ and $Xaa_{14}$ are each (R)-2-(7'-octenyl)alanine.

In some embodiments, $Xaa_9$ and $Xaa_{14}$ are different α,α-disubstituted amino acids. In some aspects of these embodiments, $Xaa_{16}$ is (S)-2-(4'-pentenyl)alanine whereas $Xaa_{10}$ is (R)-2-(4'-pentenyl)alanine. In other aspects of these embodiments, $Xaa_9$ is (R)-2-(4'-pentenyl)alanine whereas $Xaa_{14}$ is (S)-2-(4'-pentenyl)alanine. In yet other aspects of these embodiments, $Xaa_9$ is (S)-2-(7'-octenyl)alanine whereas $Xaa_{14}$ is (R)-2-(7'-octenyl)alanine. In yet other aspects of these embodiments, $Xaa_{14}$ is (R)-2-(7'-octenyl)alanine whereas $Xaa_9$ is (S)-2-(7'-octenyl)alanine. In yet other aspects of these embodiments, $Xaa_9$ is (S)-2-(4'-pentenyl)alanine whereas $Xaa_{14}$ is (S)-2-(7'-octenyl)alanine. In yet other aspects of these embodiments, $Xaa_9$ is (R)-2-(4'-pentenyl)alanine whereas $Xaa_{14}$ is (R)-2-(7'-octenyl)alanine. In yet other aspects of these embodiments, $Xaa_9$ is (S)-2-(4'-pentenyl)alanine whereas $Xaa_{14}$ is (R)-2-(7'-octenyl)alanine. In yet other aspects of these embodiments, $Xaa_9$ is (R)-2-(4'-pentenyl)alanine whereas $Xaa_{14}$ is (S)-2-(7'-octenyl)alanine. In yet other aspects of these embodiments, $Xaa_9$ is (S)-2-(7'-octenyl)alanine whereas $Xaa_{14}$ is (S)-2-(4'-pentenyl)alanine. In yet other aspects of these embodiments, $Xaa_9$ is (R)-2-(7'-octenyl)alanine whereas $Xaa_{14}$ is (R)-2-(4'-pentenyl)alanine. In yet other aspects of these embodiments, $Xaa_9$ is (S)-2-(7'-octenyl)alanine whereas $Xaa_{14}$ is (R)-2-(4'-pentenyl)alanine. In yet other aspects of these embodiments, $Xaa_9$ is (R)-2-(7'-octenyl)alanine whereas $Xaa_{14}$ is (S)-2-(4'-pentenyl)alanine.

In some embodiments, $Xaa_3$, $Xaa_6$, $Xaa_9$ and $Xaa_{14}$ are all the same. In some aspects of these embodiments, $Xaa_3$, $Xaa_6$, $Xaa_9$ and $Xaa_{14}$ are each (S)-2-(4'-pentenyl)alanine. In other aspects of these embodiments, $Xaa_3$, $Xaa_6$, $Xaa_9$ and $Xaa_{14}$ are each (R)-2-(4'-pentenyl)alanine. In yet other aspects of these embodiments, $Xaa_3$, $Xaa_6$, $Xaa_9$ and $Xaa_{14}$ are each (S)-2-(7'-octenyl)alanine. In yet other aspects of these embodiments, $Xaa_3$, $Xaa_6$, $Xaa_9$ and $Xaa_{14}$ are each (R)-2-(7'-octenyl)alanine.

In some embodiments, $Xaa_3$ and $Xaa_6$ are each (S)-2-(4'-pentenyl)alanine, whereas $Xaa_9$ and $Xaa_{14}$ are each (R)-2-(4'-pentenyl)alanine. In some embodiments, $Xaa_3$ and $Xaa_6$ are each (R)-2-(4'-pentenyl)alanine, whereas $Xaa_9$ and $Xaa_{14}$ are each (S)-2-(4'-pentenyl)alanine. In some embodiments, $Xaa_3$ and $Xaa_6$ are each (S)-2-(7'-octenyl)alanine, whereas $Xaa_9$ and $Xaa_{14}$ are each (R)-2-(7'-octenyl)alanine. In some embodiments, $Xaa_3$ and $Xaa_6$ are each (R)-2-(7'-octenyl)alanine, whereas $Xaa_9$ and $Xaa_{14}$ are each (S)-2-(7'-octenyl)alanine. In some embodiments, $Xaa_3$ and $Xaa_6$ are each (S)-2-(4'-pentenyl)alanine, whereas $Xaa_9$ and $Xaa_{14}$ are each (S)-2-(7'-octenyl)alanine. In some embodiments, $Xaa_3$ and $Xaa_6$ are each (S)-2-(7'-octenyl)alanine, whereas $Xaa_9$ and $Xaa_{14}$ are each (S)-2-(4'-pentenyl)alanine. In some embodiments, $Xaa_3$ and $Xaa_6$ are each (R)-2-(4'-pentenyl)alanine, whereas $Xaa_9$ and $Xaa_{14}$ are each (R)-2-(7'-octenyl)alanine. In some embodiments, $Xaa_3$ and $Xaa_6$ are each (R)-2-(7'-octenyl)alanine, whereas $Xaa_9$ and $Xaa_{14}$ are each (R)-2-(4'-pentenyl)alanine.

In some embodiments, the polypeptide has amino acid sequence:

(SEQ ID NO: 94)
HRXaa$_{14}$RSLXaa$_9$TLRXaa$_3$IQRXaa$_6$(CBA)(2-Nal), wherein $Xaa_3$, $Xaa_6$, $Xaa_9$, and $Xaa_{14}$ are each (S)-2-(4'-pentenyl)alanine.

In some embodiments, the polypeptide has amino acid sequence:

(SEQ ID NO: 95)
HRXaa$_{14}$RSLXaa$_9$TLRXaa$_3$IQRXaa$_6$(CBA)(2-Nal), wherein Xaa$_3$, Xaa$_6$, Xaa$_9$, and Xaa$_{14}$ are each (S)-2-(4'-pentenyl)alanine, and
wherein N-terminus is modified with palmitoyl-PEG4.

In some embodiments, the polypeptide has amino acid sequence:

(SEQ ID NO: 96)
HRXaa$_{14}$RSLXaa$_9$TLRXaa$_3$IQRXaa$_6$(4-ClPh)(2-Nal), wherein Xaa$_3$, Xaa$_6$, Xaa$_9$, and Xaa$_{14}$ are each (S)-2-(4'-pentenyl)alanine, and
wherein N-terminus is modified with palmitoyl-PEG4.

In some embodiments, the polypeptide has amino acid sequence:

(SEQ ID NO: 198)
HRXaa$_{14}$RSLXaa$_9$TLRXaa$_3$IQRXaa$_6$(4-Cl-Ph)(2-Nal), wherein Xaa$_3$, Xaa$_6$, Xaa$_9$, and Xaa$_{14}$ are each (S)-2-(4'-pentenyl)alanine.

In some embodiments, the present application provides a polypeptide having an amino acid sequence:

| 365 | 366 | 367 | 368 | 369 | 370 | 371 | 372 |
|---|---|---|---|---|---|---|---|
| Xaa$_{10}$ | Xaa$_2$ | Xaa$_{11}$ | Xaa$_3$ | Xaa$_4$ | Xaa$_8$ | Xaa$_5$ | Xaa$_6$ | wherein:
Xaa$_{10}$ and Xaa$_6$ are each independently α,α-disubstituted amino acid;
Xaa$_2$ is selected from L, A, Cha, Cpa, (D-L), CBA, MeL, NMeCha, Dcha, and NptGly;
Xaa$_1$ is selected from R, N-methylR, E, K, homoR, Nar, and Cit;
Xaa$_3$ is selected from D and Nle;
Xaa$_4$ is selected from I, A, Nle, NMethylI, CBA, and (D-I);
Xaa$_8$ is selected from Q and N-methylQ;
Xaa$_5$ is selected from R, A, Q, E, K, H, N-methylR, homoR, NMeArg, Nar, and Cit.

In some embodiments, the polypeptide has a length of 8-30 amino acids (e.g., 10-30, 10-20, 12-30, and 12-20 amino acids).

In some embodiments, Xaa$_2$ is L.
In some embodiments, Xaa$_{11}$ is R.
In some embodiments, Xaa$_3$ is D.
In some embodiments, Xaa$_4$ is I.
In some embodiments, Xaa$_8$ is Q.
In some embodiments, Xaa$_5$ is R.
In some embodiments, Xaa$_2$Xaa$_{11}$Xaa$_3$Xaa$_4$Xaa$_8$Xaa$_5$ comprises LRDIQR.

In some embodiments, in addition to the amino acid sequence Xaa$_{10}$Xaa$_2$Xaa$_{11}$Xaa$_3$Xaa$_4$Xaa$_8$Xaa$_5$Xaa$_6$, the polypeptide comprises at least one L.

In some embodiments, in addition to the amino acid sequence Xaa$_{10}$Xaa$_2$Xaa$_{11}$Xaa$_3$Xaa$_4$Xaa$_8$Xaa$_5$Xaa$_6$, the polypeptide comprises at least one (2-Nal).

In some embodiments, in addition to the amino acid sequence Xaa$_{10}$Xaa$_2$Xaa$_{11}$Xaa$_3$Xaa$_4$Xaa$_8$Xaa$_5$Xaa$_6$, the polypeptide comprises at least one (β-Ala).

In some embodiments, in addition to the amino acid sequence Xaa$_{10}$Xaa$_2$Xaa$_{11}$Xaa$_3$Xaa$_4$Xaa$_8$Xaa$_5$Xaa$_6$, the polypeptide comprises LQ. In some embodiments, in addition to the amino acid sequence Xaa$_{10}$Xaa$_2$Xaa$_{11}$Xaa$_3$Xaa$_4$Xaa$_8$Xaa$_5$Xaa$_6$, the polypeptide comprises L(2-Nal).

In some embodiments, in addition to the amino acid sequence Xaa$_{10}$Xaa$_2$Xaa$_{11}$Xaa$_3$Xaa$_4$Xaa$_8$Xaa$_5$Xaa$_6$, the polypeptide comprises at least one (β-Ala).

In some embodiments, in addition to the amino acid sequence Xaa$_{10}$Xaa$_2$Xaa$_{11}$Xaa$_3$Xaa$_4$Xaa$_8$Xaa$_5$Xaa$_6$, the polypeptide comprises HRERS or HRQRS.

In some embodiments, Xaa$_{10}$ and Xaa$_6$ are the same. In some aspects of these embodiments, Xaa$_{10}$ and Xaa$_6$ are each (S)-2-(4'-pentenyl)alanine. In other aspects of these embodiments, Xaa$_{10}$ and Xaa$_6$ are each (R)-2-(4'-pentenyl)alanine. In yet other aspects of these embodiments, Xaa$_{10}$ and Xaa$_6$ are each (S)-2-(7'-octenyl)alanine. In yet other aspects of these embodiments, Xaa$_{10}$ and Xaa$_6$ are each (R)-2-(7'-octenyl)alanine.

In some embodiments, Xaa$_{10}$ and Xaa$_6$ are different α,α-disubstituted amino acids. In some aspects of these embodiments, Xaa$_{10}$ is (S)-2-(4'-pentenyl)alanine whereas Xaa$_6$ is (R)-2-(4'-pentenyl)alanine. In other aspects of these embodiments, Xaa$_{10}$ is (R)-2-(4'-pentenyl)alanine whereas Xaa$_6$ is (S)-2-(4'-pentenyl)alanine. In yet other aspects of these embodiments, Xaa$_{10}$ is (S)-2-(7'-octenyl)alanine whereas Xaa$_6$ is (R)-2-(7'-octenyl)alanine. In yet other aspects of these embodiments, Xaa$_{10}$ is (R)-2-(7'-octenyl)alanine whereas Xaa$_6$ is (S)-2-(7'-octenyl)alanine. In yet other aspects of these embodiments, Xaa$_{10}$ is (S)-2-(4'-pentenyl)alanine whereas Xaa$_6$ is (S)-2-(7'-octenyl)alanine. In yet other aspects of these embodiments, Xaa$_{10}$ is (R)-2-(4'-pentenyl)alanine whereas Xaa$_6$ is (R)-2-(7'-octenyl)alanine. In yet other aspects of these embodiments, Xaa$_{10}$ is (S)-2-(4'-pentenyl)alanine whereas Xaa$_6$ is (R)-2-(7'-octenyl)alanine. In yet other aspects of these embodiments, Xaa$_{10}$ is (R)-2-(4'-pentenyl)alanine whereas Xaa$_6$ is (S)-2-(7'-octenyl)alanine. In yet other aspects of these embodiments, Xaa$_{10}$ is (S)-2-(7'-octenyl)alanine whereas Xaa$_6$ is (S)-2-(4'-pentenyl)alanine. In yet other aspects of these embodiments, Xaa$_{10}$ is (R)-2-(7'-octenyl)alanine whereas Xaa$_6$ is (R)-2-(4'-pentenyl)alanine. In yet other aspects of these embodiments, Xaa$_{10}$ is (S)-2-(7'-octenyl)alanine whereas Xaa$_6$ is (R)-2-(4'-pentenyl)alanine. In yet other aspects of these embodiments, Xaa$_{10}$ is (R)-2-(7'-octenyl)alanine whereas Xaa$_6$ is (S)-2-(4'-pentenyl)alanine.

In some embodiments, the polypeptide has amino acid sequence:

(SEQ ID NO: 97)
LQXaa$_{10}$LRDIQRXaa$_6$L(2-Nal)(β-Ala)(β-Ala), wherein Xaa$_6$ and Xaa$_{10}$ are each (S)-2-(4'-pentenyl)alanine.

In some embodiments, the polypeptide of the present disclosure comprises an amino acid sequence SEQ ID NO: 1 as shown below:

| Polypeptide ID | Amino Acid Sequence | Corresponding position within BCL9 protein |
|---|---|---|
| SEQ ID NO: 1 | SXaa$_1$QTXaa$_2$RXaa$_3$Xaa$_4$QXaa$_5$Xaa$_6$Xaa$_7$(2-Nal) | 362-374 |

Referring to a polypeptide comprising amino acid sequence SEQ ID NO: 1:

$Xaa_1$ and $Xaa_2$ are each independently selected from L, A, Cha, Cpa, CBA, (D-L), MeL, NMeCha, Dcha, and NptGly;

$Xaa_3$ and $Xaa_6$ are each independently an α,α-disubstituted amino acid;

$Xaa_4$ is selected from I, A, Nle, N-MethylI, CBA, and (D-I);

$Xaa_5$ is selected from R, A, Q, E, K, H, N-MethylR, homoR, NMeArg, Nar, and Cit; and $Xaa_7$ is selected from L, A, CBA, Cha, Cpa, Phe(4-Cl), (D-L), α-MethylL, DCha, N-MethylCha, allylGly, AC4C, A6C, Aze, N-MeCha, (βtBu-Ala), Tle, 4-FPh, and 3,4-diClPh.

In some embodiments:

$Xaa_1$ and $Xaa_2$ are each independently L or A;

$Xaa_3$ and $Xaa_6$ are each independently an α,α-disubstituted amino acid;

$Xaa_4$ is I or A;

$Xaa_5$ is R or A; and $Xaa_7$ is L, A, or CBA.

In some embodiments, the polypeptide comprising amino acid sequence SEQ ID NO: 1 has a length of 13-30 amino acids (e.g., 13-22, 14-30, 16-30, 18-30, 14-22, or 14-20 amino acids).

In some embodiments, the polypeptide of the present disclosure comprises an amino acid sequence SEQ ID NO: 15 as shown below:

| Polypeptide ID | Amino Acid Sequence | Corresponding position within BCL9 protein |
|---|---|---|
| SEQ ID NO: 15 | $Xaa_1QTXaa_2RXaa_3Xaa_4QXaa_5Xaa_6Xaa_7(2-Nal)$ | 363-374 |

Referring to a polypeptide comprising amino acid sequence SEQ ID NO: 15:

$Xaa_1$ and $Xaa_2$ are each independently L, A, Cha, Cpa, (D-L), CBA, MeL, N-MeCha, Dcha, and NptGly;

$Xaa_3$ and $Xaa_6$ are each independently an α,α-disubstituted amino acid;

$Xaa_4$ is selected from I, A, Nle, N-MethylI, CBA, and (D-I);

$Xaa_5$ is selected from R, A, Q, E, K, H, N-MethylR, homoR, NMeArg, Nar, and Cit; and $Xaa_7$ is selected from L, A, CBA, Cha, Cpa, Phe(4-Cl), (D-L), α-MethylL, DCha, N-MethylCha, allylGly, AC4C, A6C, Aze, N-MeCha, (βtBu-Ala), Tle, 4-FPh, and 3,4-diClPh.

In some embodiments:

$Xaa_1$ and $Xaa_2$ are each independently L or A;

$Xaa_3$ and $Xaa_6$ are each independently an α,α-disubstituted amino acid;

$Xaa_4$ is I or A;

$Xaa_5$ is R or A; and $Xaa_7$ is L, A, or CBA.

In some embodiments, the polypeptide comprising an amino acid sequence SEQ ID NO: 15 also comprises at least one A (e.g., two or more A). In some embodiments, the polypeptide comprising an amino acid sequence SEQ ID NO: 15 has a length of 12-30 amino acids (e.g., 12-22, 12-22, 14-22, 12-20, or 12-18 amino acids).

In some embodiments, the polypeptide of the present disclosure comprises an amino acid sequence SEQ ID NO: 30 as shown below:

| Polypeptide ID | Amino Acid Sequence | Corresponding position within BCL9 protein |
|---|---|---|
| SEQ ID NO: 30 | $Xaa_1QTXaa_2RXaa_3Xaa_4QXaa_5Xaa_6Xaa_7(2-Nal)$ | 363-374 |

Referring to a polypeptide comprising amino acid sequence SEQ ID NO: 30:

$Xaa_1$ and $Xaa_2$ are each independently L, A, Cha, Cpa, (D-L), CBA, MeL, N-MeCha, Dcha, and NptGly;

$Xaa_3$ and $Xaa_6$ are each independently an α,α-disubstituted amino acid;

$Xaa_4$ is selected from I, A, Nle, N-MethylI, CBA, and (D-I);

$Xaa_5$ is selected from R, A, Q, E, K, H, N-MethylR, homoR, NMeArg, Nar, and Cit; and $Xaa_7$ is selected from L, A, CBA, Cha, Cpa, Phe(4-Cl), (D-L), α-MethylL, DCha, N-MethylCha, allylGly, AC4C, A6C, Aze, N-MeCha, (βtBu-Ala), Tle, 4-FPh, and 3,4-diClPh.

In some embodiments:

$Xaa_1$ and $Xaa_2$ are each independently L or A;

$Xaa_3$ and $Xaa_6$ are each independently an α,α-disubstituted amino acid;

$Xaa_4$ is I or A;

$Xaa_5$ is R or A; and $Xaa_7$ is L, A, or CBA.

In some embodiments, the polypeptide comprising an amino acid sequence SEQ ID NO: 30 also comprises at least one A. In some embodiments, the polypeptide comprising an amino acid sequence SEQ ID NO: 30 has a length of 12-30 amino acids.

Certain implementations of polypeptides comprising the amino acid sequences SEQ ID NO: 1, SEQ ID NO: 15, and SEQ ID NO: 30 are described below.

In some embodiments, $Xaa_1$ is L. In some embodiments, $Xaa_1$ is A. In some embodiments, $Xaa_2$ is L. In some embodiments, $Xaa_2$ is A. In some embodiments, $Xaa_1$ and $Xaa_2$ are each L. In some embodiments, $Xaa_1$ and $Xaa_2$ are each A. In some embodiments, $Xaa_1$ is L and $Xaa_2$ is A. In some embodiments, $Xaa_1$ is A and $Xaa_2$ is L. In some embodiments, $Xaa_1$ and $Xaa_2$ are each Cha. In some embodiments, $Xaa_1$ and $Xaa_2$ are each Cpa.

In some embodiments, $Xaa_4$ is A. In some embodiments, $Xaa_4$ is I. In some embodiments, $Xaa_2$ and $Xaa_4$ are each A. In some embodiments, $Xaa_2$ is L and $Xaa_4$ is A. In some embodiments, $Xaa_2$ is L and $Xaa_4$ is I. In some embodiments, $Xaa_2$ is A and $Xaa_4$ is I.

In some embodiments, $Xaa_5$ is R. In some embodiments, $Xaa_5$ is A. In some embodiments, $Xaa_4$ is I and $Xaa_5$ is R. In some embodiments, $Xaa_4$ is I and $Xaa_5$ is A.

In some embodiments, $Xaa_4$ is A and $Xaa_5$ is R. In some embodiments, $Xaa_4$ and $Xaa_5$ are both A.

In some embodiments, $Xaa_7$ is L. In some embodiments, $Xaa_7$ is A. In some embodiments, $Xaa_7$ is CBA. In some embodiments, $Xaa_7$ is selected from Cha, Cpa, Phe(4-Cl), (D-L), α-MethylL, DCha, N-methylCha, allylGly, AC4C, A6C, Aze, N-MeCha, (βtBu-Ala), Tle, 4-FPh, and 3,4-diClPh.

In some embodiments, $Xaa_5$ is R and $Xaa_7$ is L. In some embodiments, $Xaa_5$ is R and $Xaa_7$ is A. In some embodiments, $Xaa_5$ is A and $Xaa_7$ is L. In some embodiments, $Xaa_5$ is R and $Xaa_7$ is CBA. In some embodiments, $Xaa_5$ is A and $Xaa_7$ is CBA. In some embodiments, $Xaa_4$ is I and $Xaa_7$ is A.

In some embodiments, at least one of $Xaa_1$, $Xaa_2$, $Xaa_4$, $Xaa_5$, and $Xaa_7$ is A.

In some aspects of these embodiments, at least two of $Xaa_1$, $Xaa_2$, $Xaa_4$, $Xaa_5$, and $Xaa_7$ are A. In other aspects of these embodiments, at least $Xaa_1$ is A. In yet other aspects of these embodiments, at least $Xaa_2$ is A. In yet other aspects of these embodiments, at least $Xaa_4$ is A. In yet other aspects of these embodiments, at least $Xaa_5$ is A. In yet other aspects of these embodiments, at least $Xaa_7$ is A.

In some embodiments, $Xaa_1$ and $Xaa_2$ are each A, $X_4$ is I, $X_5$ is R and $X_7$ is L.

In some embodiments, $Xaa_1$ is L, $Xaa_2$ is A, $X_4$ is A, $X_5$ is R and $X_7$ is L. In some embodiments, $Xaa_1$ and $Xaa_2$ are each L, $X_4$ is I, $X_5$ is R and $X_7$ is L. In some embodiments, $Xaa_1$ and $Xaa_2$ are each L, $X_4$ is I, $X_5$ is A and $X_7$ is L. In some embodiments, $Xaa_1$ and $Xaa_2$ are each L, $X_4$ is I, $X_5$ is R and $X_7$ is CBA. In some embodiments, $Xaa_1$ and $Xaa_2$ are each L, $X_4$ is I, $X_5$ is A and $X_7$ is CBA.

In some embodiments, in addition to amino acid sequence SEQ ID NO: 1, SEQ ID NO: 15, or SEQ ID NO: 30, the polypeptide of the present application comprises at least one amino acid selected from: Q, L, E, H, and R. In some embodiments, in addition to amino acid sequence SEQ ID NO: 1, SEQ ID NO: 15, or SEQ ID NO: 30, the polypeptide of the present application comprises at least one amino acid selected from: Q, L, E, H, R, and S. In some embodiments, in addition to amino acid sequence SEQ ID NO: 1, SEQ ID NO: 15, or SEQ ID NO: 30, the polypeptide of the present application comprises at least one amino acid selected from: P, D, and β-Ala. In some embodiments, the polypeptide comprises at least two Q. In some embodiments, the polypeptide comprises at least three Q. In some embodiments, the polypeptide comprises at least two L. In some embodiments, the polypeptide comprises at least three L. In some embodiments, the polypeptide comprises at least four L. In some embodiments, the polypeptide comprises at least two R. In some embodiments, the polypeptide comprises at least three R. In some embodiments, the polypeptide comprises at least four R. In some embodiments, the polypeptide comprises at least two E. In some embodiments, the polypeptide comprises at least one H and at least one I. In some embodiments, in addition to amino acid sequence SEQ ID NO: 1, SEQ ID NO: 15, or SEQ ID NO: 30, the polypeptide of the present application comprises any of the amino acid sequences listed in Table 3, or combination thereof.

In some embodiments, $Xaa_3$ and $Xaa_6$ are the same. In some aspects of these embodiments, $Xaa_3$ and $Xaa_6$ are each (S)-2-(4'-pentenyl)alanine. In other aspects of these embodiments, $Xaa_3$ and $Xaa_6$ are each (R)-2-(4'-pentenyl)alanine. In yet other aspects of these embodiments, $Xaa_3$ and $Xaa_6$ are each (S)-2-(7'-octenyl)alanine. In yet other aspects of these embodiments, $Xaa_3$ and $Xaa_6$ are each (R)-2-(7'-octenyl)alanine.

In some embodiments, $Xaa_3$ and $Xaa_6$ are different α,α-disubstituted amino acids. In some aspects of these embodiments, $Xaa_3$ is (S)-2-(4'-pentenyl)alanine whereas $Xaa_6$ is (R)-2-(4'-pentenyl)alanine. In other aspects of these embodiments, $Xaa_3$ is (R)-2-(4'-pentenyl)alanine whereas $Xaa_6$ is (S)-2-(4'-pentenyl)alanine. In yet other aspects of these embodiments, $Xaa_3$ is (S)-2-(7'-octenyl)alanine whereas $Xaa_6$ is (R)-2-(7'-octenyl)alanine. In yet other aspects of these embodiments, $Xaa_3$ is (R)-2-(7'-octenyl)alanine whereas $Xaa_6$ is (S)-2-(7'-octenyl)alanine. In yet other aspects of these embodiments, $Xaa_3$ is (S)-2-(4'-pentenyl)alanine whereas $Xaa_6$ is (S)-2-(7'-octenyl)alanine. In yet other aspects of these embodiments, $Xaa_3$ is (R)-2-(4'-pentenyl)alanine whereas $Xaa_6$ is (R)-2-(7'-octenyl)alanine. In yet other aspects of these embodiments, $Xaa_3$ is (S)-2-(4'-pentenyl)alanine whereas $Xaa_6$ is (R)-2-(7'-octenyl)alanine. In yet other aspects of these embodiments, $Xaa_3$ is (R)-2-(4'-pentenyl)alanine whereas $Xaa_6$ is (S)-2-(7'-octenyl)alanine. In yet other aspects of these embodiments, $Xaa_3$ is (S)-2-(7'-octenyl)alanine whereas $Xaa_6$ is (S)-2-(4'-pentenyl)alanine. In yet other aspects of these embodiments, $Xaa_3$ is (R)-2-(7'-octenyl)alanine whereas $Xaa_6$ is (R)-2-(4'-pentenyl)alanine. In yet other aspects of these embodiments, $Xaa_3$ is (S)-2-(7'-octenyl)alanine whereas $Xaa_6$ is (R)-2-(4'-pentenyl)alanine. In yet other aspects of these embodiments, $Xaa_3$ is (R)-2-(7'-octenyl)alanine whereas $Xaa_6$ is (S)-2-(4'-pentenyl)alanine.

In some embodiments, the amino acid sequence SEQ ID NO: 1 is selected from:

```
                                        (SEQ ID NO: 2)
SLQTLRXaa3IQRXaa6L(2-Nal);

and (SEQ ID NO: 3)
SLQTLRXaa3IQRXaa6(CBA)(2-Nal).
```

In some embodiments, the amino acid sequence SEQ ID NO: 15 is selected from:

```
                                        (SEQ ID NO: 16)
AQTARXaa3IQRXaa6L(2-Nal);

(SEQ ID NO: 17)
LQTARXaa3AQRXaa6L(2-Nal);

(SEQ ID NO: 18)
LQTLRXaa3AQRXaa6A(2-Nal);

(SEQ ID NO: 19)
LQTLRXaa3IQAXaa6L(2-Nal);

and (SEQ ID NO: 20)
LQTLRXaa3IQAXaa6(CBA)(2-Nal).
```

In some embodiments, the amino acid sequence SEQ ID NO: 30 is

```
                                        (SEQ ID NO: 31)
LQTLRXaa3IQRXaa6L(2-Nal).
```

In some embodiments, the polypeptide consists of the amino acid sequence:

```
                                        (SEQ ID NO: 4)
RSLQTLRXaa3IQRXaa6L(2-Nal),
``` wherein $Xaa_3$ and $Xaa_6$ are each (S)-2-(4'-pentenyl)alanine.

In some embodiments, the polypeptide consists of the amino acid sequence:

```
                                        (SEQ ID NO: 5)
RERSLQTLRXaa3IQRXaa6L(2-Nal),
``` wherein $Xaa_3$ and $Xaa_6$ are each (S)-2-(4'-pentenyl)alanine.

In some embodiments, the polypeptide consists of the amino acid sequence:

(SEQ ID NO: 6)
HRERSLQTLRXaa$_3$IQRXaa$_6$L(2-Nal), wherein Xaa$_3$ and Xaa$_6$ are each (S)-2-(4'-pentenyl)alanine.
In some embodiments, the polypeptide consists of the amino acid sequence:

(SEQ ID NO: 7)
EHRERSLQTLRXaa$_3$IQRXaa$_6$L(2-Nal), wherein Xaa$_3$ and Xaa$_6$ are each (S)-2-(4'-pentenyl)alanine.
In some embodiments, the polypeptide consists of the amino acid sequence:

(SEQ ID NO: 8)
QLEHRERSLQTLRXaa$_3$IQRXaa$_6$L(2-Nal), wherein Xaa$_3$ and Xaa$_6$ are each (S)-2-(4'-pentenyl)alanine.
In some embodiments, the polypeptide consists of the amino acid sequence:

(SEQ ID NO: 9)
EHRERSLQTLRXaa$_3$IQRXaa$_6$(CBA)(2-Nal), wherein Xaa$_3$ and Xaa$_6$ are each (S)-2-(4'-pentenyl)alanine.
In some embodiments, the polypeptide consists of the amino acid sequence:

(SEQ ID NO: 10)
QERSLQTLRXaa$_3$IQRXaa$_6$L(2-Nal), wherein Xaa$_3$ and Xaa$_6$ are each (S)-2-(4'-pentenyl)alanine.
In some embodiments, the polypeptide consists of the amino acid sequence:

(SEQ ID NO: 11)
HQERSLQTLRXaa$_3$IQRXaa$_6$L(2-Nal), wherein Xaa$_3$ and Xaa$_6$ are each (S)-2-(4'-pentenyl)alanine.
In some embodiments, the polypeptide consists of the amino acid sequence:

(SEQ ID NO: 12)
EHQERSLQTLRXaa$_3$IQRXaa$_6$L(2-Nal), wherein Xaa$_3$ and Xaa$_6$ are each (S)-2-(4'-pentenyl)alanine.
In some embodiments, the polypeptide consists of the amino acid sequence:

(SEQ ID NO: 13)
RERSLQTLRXaa$_3$IQRXaa$_6$ (CBA)(2-Nal), wherein Xaa$_3$ and Xaa$_6$ are each (S)-2-(4'-pentenyl)alanine.

In some embodiments, the polypeptide consists of the amino acid sequence:

(SEQ ID NO: 14)
HRERSLQTLRXaa$_3$IQRXaa$_6$ (CBA)(2-Nal), wherein Xaa$_3$ and Xaa$_6$ are each (S)-2-(4'-pentenyl)alanine.
In some embodiments, the polypeptide consists of the amino acid sequence:

(SEQ ID NO: 21)
AQTARXaa$_3$IQRXaa$_6$L(2-Nal), wherein Xaa$_3$ and Xaa$_6$ are each (S)-2-(4'-pentenyl)alanine.
In some embodiments, the polypeptide consists of the amino acid sequence:

(SEQ ID NO: 22)
LQTARXaa$_3$AQRXaa$_6$L(2-Nal), wherein Xaa$_3$ and Xaa$_6$ are each (S)-2-(4'-pentenyl)alanine.
In some embodiments, the polypeptide consists of the amino acid sequence:

(SEQ ID NO: 23)
LQTLRXaa$_3$AQRXaa$_6$A(2-Nal), wherein Xaa$_3$ and Xaa$_6$ are each (S)-2-(4'-pentenyl)alanine.
In some embodiments, the polypeptide consists of the amino acid sequence:

(SEQ ID NO: 24)
LQTLRXaa$_3$IQAXaa$_6$L(2-Nal), wherein Xaa$_3$ and Xaa$_6$ are each (S)-2-(4'-pentenyl)alanine.
In some embodiments, the polypeptide consists of the amino acid sequence:

(SEQ ID NO: 25)
LQTLRXaa$_3$IQAXaa$_6$(CBA)(2-Nal), wherein Xaa$_3$ and Xaa$_6$ are each (S)-2-(4'-pentenyl)alanine.
In some embodiments, the polypeptide consists of the amino acid sequence:

(SEQ ID NO: 26)
LQTLRXaa$_3$IQAXaa$_6$L(2-Nal)(β-Ala)(β-Ala), wherein Xaa$_3$ and Xaa$_6$ are each (S)-2-(4'-pentenyl)alanine.
In some embodiments, the polypeptide consists of the amino acid sequence:

(SEQ ID NO: 27)
LQTLRXaa$_3$IQAXaa$_6$L(2-Nal)AA, wherein Xaa$_3$ and Xaa$_6$ are each (S)-2-(4'-pentenyl)alanine.

In some embodiments, the polypeptide consists of the amino acid sequence:

HRERSLQTLRXaa₃IQAXaa₆L(2-Nal), (SEQ ID NO: 28)

wherein Xaa₃ and Xaa₆ are each (S)-2-(4'-pentenyl)alanine.

In some embodiments, the polypeptide consists of the amino acid sequence:

HRERSLQTLRXaa₃IQAXaa₆(CBA)(2-Nal), (SEQ ID NO: 29)

wherein Xaa₃ and Xaa₆ are each (S)-2-(4'-pentenyl)alanine.

In some embodiments, the polypeptide consists of the amino acid sequence:

LQTARXaa₃IQRXaa₆L(2-Nal), (SEQ ID NO: 75)

wherein Xaa₃ and Xaa₆ are each (S)-2-(4'-pentenyl)alanine.

In some embodiments, the polypeptide consists of the amino acid sequence:

LQTLRXaa₃AQRXaa₆L(2-Nal), (SEQ ID NO: 76)

wherein Xaa₃ and Xaa₆ are each (S)-2-(4'-pentenyl)alanine.

In some embodiments, the polypeptide consists of the amino acid sequence:

LQTLRXaa₃IQRXaa₆A(2-Nal), (SEQ ID NO: 77)

wherein Xaa₃ and Xaa₆ are each (S)-2-(4'-pentenyl)alanine.

In some embodiments, the polypeptide consists of the amino acid sequence:

LQTLRXaa₃IQRXaa₆L(2-Nal)PD, (SEQ ID NO: 32)

wherein Xaa₃ and Xaa₆ are each (S)-2-(4'-pentenyl)alanine.

In some embodiments, the polypeptide consists of the amino acid sequence:

LQTLRXaa₃IQRXaa₆L(2-Nal)P, (SEQ ID NO: 33)

wherein Xaa₃ and Xaa₆ are each (S)-2-(4'-pentenyl)alanine.

In some embodiments, the polypeptide consists of the amino acid sequence:

LQTLRXaa₃IQRXaa₆L(2-Nal)(β-Ala)(β-Ala), (SEQ ID NO: 34)

wherein Xaa₃ and Xaa₆ are each (S)-2-(4'-pentenyl)alanine.

In some embodiments, the polypeptide consists of the amino acid sequence:

LQTLRXaa₃IQRXaa₆L(2-Nal)(β-Ala)(β-Ala), (SEQ ID NO: 34a)

wherein Xaa₃ and Xaa₆ are each (S)-2-(4'-pentenyl)alanine, and wherein C-terminus in SEQ ID NO: 34a is modified with GRKKRRQRRRPQK(PEG4-palmitoyl)NH₂.

In some embodiments, the polypeptide of the present disclosure comprises an amino acid sequence SEQ ID NO: 35 as shown below:

| Polypeptide ID | Amino Acid Sequence | Corresponding position within BCL9 protein |
|---|---|---|
| SEQ ID NO: 35 | Xaa₁TXaa₂RXaa₃ | 364-368 |

Referring to a polypeptide comprising amino acid sequence SEQ ID NO: 35:

Xaa₁ and Xaa₃ are each independently an α,α-disubstituted amino acid; and

Xaa₂ is selected from L, A, Cha, Cpa, (D-L), CBA, MeL, N-MeCha, Dcha, and NptGly.

In some embodiments:

Xaa₁ and Xaa₃ are each independently an α,α-disubstituted amino acid; and

Xaa₂ is L or A.

In some embodiments, the polypeptide comprising an amino acid sequence SEQ ID NO: 35 also comprises at least one 2-Nal (e.g., two or more 2-NAl). In some embodiments, the polypeptide has a length of 6-30 amino acids (e.g., 6-22, 7-22, 9-22, 12-22, 6-20, 7-20, 9-20, or 12-20 amino acids).

Certain implementations of polypeptides comprising the amino acid sequence SEQ ID NO: 35 are described below.

In some embodiments, Xaa₂ is L. In some embodiments, Xaa₂ is A.

In some embodiments, Xaa₁ and Xaa₃ are the same. In some aspects of these embodiments, Xaa₁ and Xaa₃ are each (S)-2-(4'-pentenyl)alanine. In other aspects of these embodiments, Xaa₁ and Xaa₃ are each (R)-2-(4'-pentenyl)alanine. In yet other aspects of these embodiments, Xaa₁ and Xaa₃ are each (S)-2-(7'-octenyl)alanine. In yet other aspects of these embodiments, Xaa₁ and Xaa₃ are each (R)-2-(7'-octenyl)alanine.

In some embodiments, Xaa₁ and Xaa₃ are different α,α-disubstituted amino acids. In some aspects of these embodiments, Xaa₁ is (S)-2-(4'-pentenyl)alanine whereas Xaa₃ is (R)-2-(4'-pentenyl)alanine. In other aspects of these embodiments, Xaa₁ is (R)-2-(4'-pentenyl)alanine whereas Xaa₃ is (S)-2-(4'-pentenyl)alanine. In yet other aspects of these embodiments, Xaa₁ is (S)-2-(7'-octenyl)alanine whereas Xaa₃ is (R)-2-(7'-octenyl)alanine. In yet other aspects of these embodiments, Xaa₁ is (R)-2-(7'-octenyl)alanine whereas Xaa₃ is (S)-2-(7'-octenyl)alanine. In yet other aspects of these embodiments, Xaa₁ is (S)-2-(4'-pentenyl)alanine whereas Xaa₃ is (S)-2-(7'-octenyl)alanine. In yet other aspects of these embodiments, Xaa₁ is (R)-2-(4'-pentenyl)alanine whereas Xaa₃ is (R)-2-(7'-octenyl)alanine. In yet other aspects of these embodiments, Xaa₁ is (S)-2-(4'-pentenyl)alanine whereas Xaa₃ is (R)-2-(7'-octenyl)alanine. In yet other aspects of these embodiments, Xaa₁ is (R)-2-(4'-pentenyl)alanine whereas Xaa₃ is (S)-2-(7'-octenyl)alanine. In yet other aspects of these embodiments, Xaa₁ is (S)-2-(7'-octenyl)alanine whereas Xaa₃ is (S)-2-(4'-pentenyl)alanine. In yet other aspects of these embodiments, Xaa₁ is (R)-2-(7'-octenyl)alanine whereas Xaa₃ is (R)-2-(4'-pentenyl)alanine. In yet other aspects of these embodiments, Xaa₁ is (S)-2-(7'-octenyl)alanine whereas Xaa₃ is (R)-2-(4'-pentenyl)alanine. In yet other aspects of these embodiments, Xaa₁ is (R)-2-(7'-octenyl)alanine whereas Xaa₃ is (S)-2-(4'-pentenyl)alanine.

In some embodiments, in addition to the amino acid sequence SEQ ID NO: 35, the polypeptide comprises at least one amino acid selected from: Q, L, E, H, I, S, M, and R. In some embodiments, in addition to the amino acid sequence SEQ ID NO: 35, the polypeptide comprises at least one amino acid selected from H, S, I, and M. In some embodiments, the polypeptide comprises at least two Q. In some embodiments, the polypeptide comprises at least two L. In some embodiments, the polypeptide comprises at least three L. In some embodiments, the polypeptide comprises at least four L. In some embodiments, the polypeptide comprises at least two R. In some embodiments, the polypeptide comprises at least three R. In some embodiments, the polypeptide comprises at least four R. In some embodiments, the polypeptide comprises at least two E. In some embodiments, the polypeptide comprises at least one H and at least one I. In some embodiments, in addition to amino acid sequence SEQ ID NO: 35, the polypeptide of the present application comprises any of the amino acid sequences listed in Table 3, or combination thereof. In some embodiments, in addition to amino acid sequence SEQ ID NO: 35, the polypeptide comprises an amino acid sequence ML(2-Nal). In some embodiments, the polypeptide comprising an amino acid sequence SEQ ID NO: 35 also comprises the following amino acid sequences: IQR, RERSL, QLEH, and ML(2-Nal). In some embodiments, the polypeptide comprising an amino acid sequence SEQ ID NO: 35 also comprises the following amino acid sequence: (2-Abu)L(2-Nal)(β-Ala)(β-Ala).

In some embodiments, the polypeptide consists of the amino acid sequence:

QLEHRERSLXaa₁TLRXaa₃IQRML(2-Nal), (SEQ ID NO: 36)

wherein Xaa₁ and Xaa₃ are each (S)-2-(4'-pentenyl)alanine.

In some embodiments, the polypeptide consists of the amino acid sequence:

QLEHRERSLXaa₁TLRXaa₃IQR(2-Abu)L(2-Nal)(β-Ala)(β-Ala), (SEQ ID NO: 78)

wherein Xaa₁ and Xaa₃ are each (S)-2-(4'-pentenyl)alanine.

In some embodiments, the polypeptide of the present disclosure comprises an amino acid sequence selected from:

Xaa₁SLQXaa₂ (SEQ ID NO: 37a)
and

Xaa₁S(Cha)(N-methylQ)Xaa₂; (SEQ ID NO: 37b)

and an amino acid sequence selected from:

Xaa₃IQRXaa₄ (SEQ ID NO: 38a)
and

Xaa₃IQQXaa₄; (SEQ ID NO: 38b)

wherein Xaa₁, Xaa₂, Xaa₃ and Xaa₄ are each independently an α,α-disubstituted amino acid.

In some embodiments, the polypeptide of the present disclosure comprises an amino acid sequences SEQ ID NO: 37 and SEQ ID NO: 38 as shown below:

| Polypeptide ID | Amino Acid Sequence | Corresponding position within BCL9 protein |
|---|---|---|
| SEQ ID NO: 37 | Xaa₁SLQXaa₂ | 361-365 |
| SEQ ID NO: 38 | Xaa₃IQRXaa₄ | 368-372 |

Referring to a polypeptide comprising amino acid sequences SEQ ID NO: 37 and SEQ ID NO: 38:

Xaa₁, Xaa₂, Xaa₃ and Xaa₄ are each independently an α,α-disubstituted amino acid. In some embodiments, the polypeptide has length of 10-30 amino acids (e.g., 10-20, 10-22, 12-22, 12-20, 14-22, or 14-20 amino acids).

Certain implementations of polypeptides comprising amino acid sequences SEQ ID NO: 37 and SEQ ID NO: 38 are described below.

In some embodiments, the polypeptide comprises at least one 2-Nal.

In some embodiments, the polypeptide comprises at least one CBA.

In some embodiments, in addition to amino acid sequences SEQ ID NO: 37 and SEQ ID NO: 38, the polypeptide of the present application comprises any of the amino acid sequences listed in Table 3, or combination thereof. In some embodiments, in addition to the amino acid sequences SEQ ID NO: 37 and SEQ ID NO: 38, the polypeptide comprises at least one amino acid selected from: L, E, and R. In some embodiments, the polypeptide comprises at least two L. In some embodiments, the polypeptide comprises at least three L. In some embodiments, the polypeptide comprises at least two R. In some embodiments, the polypeptide comprises at least three R. In some embodiments, in addition to amino acid sequences SEQ ID NO: 37 and SEQ ID NO: 38, the polypeptide of the present application comprises any of the amino acid sequences listed in Table 3, or combination thereof. In some embodiments, the polypeptide comprising amino acid sequences SEQ ID NO: 37 and SEQ ID NO: 38 also comprises at least one amino acid sequence selected from: RE, LR, and L(2-Nal). In some embodiments, the polypeptide comprises an amino acid sequence: Xaa₂LRXaa₃. In some embodiments, the polypeptide comprises at least one β-Ala. In some embodiments, the polypeptide comprises an amino acid sequence (β-Ala)(β-Ala). In some embodiments, the polypeptide comprises at least one amino acid selected from: L, E, R, H, Q, CBA, N-methylQ, N-methylE, N-methylR, N-methylD, N-methylT, N-methylI, Cpa, Cha, N-MeHis, N-MeCys, homoHis, NHis, homoR, Cit, Nar, Phe(4-guanidino), NMeGln, Nle, 2-Abu, Phe(4-Cl), 3,4-diClPh, 4-FPh, NptGly, NMeCha, Dcha, α-methylL, allylGly, Alg, AC4C, A6C, Aze, (β-tBu-Ala), Tle, peptoidQ, DThr, and NMeLeu. In some embodiments, the polypeptide comprises at least one amino acid selected from: L, E, R, H, Q, N-methylE, CBA, N-methylQ, Cha, and N-methylR.

In some embodiments, the polypeptide comprises at amino acid sequence (CBA)(2-Nal). In some embodiments, the polypeptide comprises at amino acid sequence selected from HRE, HR(N-methylE), HR(N-MethylQ), HRQ, LR, L(N-methylR), (Cha)R, L(2-Nal), and (CBA)(2-Nal).

In some embodiments, $Xaa_1$ and $Xaa_2$ are the same. In some aspects of these embodiments, $Xaa_1$ and $Xaa_2$ are each (S)-2-(4'-pentenyl)alanine. In other aspects of these embodiments, $Xaa_1$ and $Xaa_2$ are each (R)-2-(4'-pentenyl)alanine. In yet other aspects of these embodiments, $Xaa_1$ and $Xaa_2$ are each (S)-2-(7'-octenyl)alanine. In yet other aspects of these embodiments, $Xaa_1$ and $Xaa_2$ are each (R)-2-(7'-octenyl)alanine.

In some embodiments, $Xaa_1$ and $Xaa_2$ are different α,α-disubstituted amino acids. In some aspects of these embodiments, $Xaa_1$ is (S)-2-(4'-pentenyl)alanine whereas $Xaa_2$ is (R)-2-(4'-pentenyl)alanine. In other aspects of these embodiments, $Xaa_1$ is (R)-2-(4'-pentenyl)alanine whereas $Xaa_2$ is (S)-2-(4'-pentenyl)alanine. In yet other aspects of these embodiments, $Xaa_1$ is (S)-2-(7'-octenyl)alanine whereas $Xaa_2$ is (R)-2-(7'-octenyl)alanine. In yet other aspects of these embodiments, $Xaa_1$ is (R)-2-(7'-octenyl)alanine whereas $Xaa_2$ is (S)-2-(7'-octenyl)alanine. In yet other aspects of these embodiments, $Xaa_1$ is (S)-2-(4'-pentenyl)alanine whereas $Xaa_2$ is (S)-2-(7'-octenyl)alanine. In yet other aspects of these embodiments, $Xaa_1$ is (R)-2-(4'-pentenyl)alanine whereas $Xaa_2$ is (R)-2-(7'-octenyl)alanine. In yet other aspects of these embodiments, $Xaa_1$ is (S)-2-(4'-pentenyl)alanine whereas $Xaa_2$ is (R)-2-(7'-octenyl)alanine. In yet other aspects of these embodiments, $Xaa_1$ is (R)-2-(4'-pentenyl)alanine whereas $Xaa_2$ is (S)-2-(7'-octenyl)alanine. In yet other aspects of these embodiments, $Xaa_1$ is (S)-2-(7'-octenyl)alanine whereas $Xaa_2$ is (S)-2-(4'-pentenyl)alanine. In yet other aspects of these embodiments, $Xaa_1$ is (R)-2-(7'-octenyl)alanine whereas $Xaa_2$ is (R)-2-(4'-pentenyl)alanine. In yet other aspects of these embodiments, $Xaa_1$ is (S)-2-(7'-octenyl)alanine whereas $Xaa_2$ is (R)-2-(4'-pentenyl)alanine. In yet other aspects of these embodiments, $Xaa_1$ is (R)-2-(7'-octenyl)alanine whereas $Xaa_2$ is (S)-2-(4'-pentenyl)alanine.

In some embodiments, $Xaa_3$ and $Xaa_4$ are the same. In some aspects of these embodiments, $Xaa_3$ and $Xaa_4$ are each (S)-2-(4'-pentenyl)alanine. In other aspects of these embodiments, $Xaa_3$ and $Xaa_4$ are each (R)-2-(4'-pentenyl)alanine. In yet other aspects of these embodiments, $Xaa_3$ and $Xaa_4$ are each (S)-2-(7'-octenyl)alanine. In yet other aspects of these embodiments, $Xaa_3$ and $Xaa_4$ are each (R)-2-(7'-octenyl)alanine.

In some embodiments, $Xaa_3$ and $Xaa_4$ are different α,α-disubstituted amino acids. In some aspects of these embodiments, $Xaa_3$ is (S)-2-(4'-pentenyl)alanine whereas $Xaa_4$ is (R)-2-(4'-pentenyl)alanine. In other aspects of these embodiments, $Xaa_3$ is (R)-2-(4'-pentenyl)alanine whereas $Xaa_4$ is (S)-2-(4'-pentenyl)alanine. In yet other aspects of these embodiments, $Xaa_3$ is (S)-2-(7'-octenyl)alanine whereas $Xaa_4$ is (R)-2-(7'-octenyl)alanine. In yet other aspects of these embodiments, $Xaa_3$ is (R)-2-(7'-octenyl)alanine whereas $Xaa_4$ is (S)-2-(7'-octenyl)alanine. In yet other aspects of these embodiments, $Xaa_3$ is (S)-2-(4'-pentenyl)alanine whereas $Xaa_4$ is (S)-2-(7'-octenyl)alanine. In yet other aspects of these embodiments, $Xaa_3$ is (R)-2-(4'-pentenyl)alanine whereas $Xaa_4$ is (R)-2-(7'-octenyl)alanine. In yet other aspects of these embodiments, $Xaa_3$ is (S)-2-(4'-pentenyl)alanine whereas $Xaa_4$ is (R)-2-(7'-octenyl)alanine. In yet other aspects of these embodiments, $Xaa_3$ is (R)-2-(4'-pentenyl)alanine whereas $Xaa_4$ is (S)-2-(7'-octenyl)alanine. In yet other aspects of these embodiments, $Xaa_3$ is (S)-2-(7'-octenyl)alanine whereas $Xaa_4$ is (S)-2-(4'-pentenyl)alanine. In yet other aspects of these embodiments, $Xaa_3$ is (R)-2-(7'-octenyl)alanine whereas $Xaa_4$ is (R)-2-(4'-pentenyl)alanine. In yet other aspects of these embodiments, $Xaa_3$ is (S)-2-(7'-octenyl)alanine whereas $Xaa_4$ is (R)-2-(4'-pentenyl)alanine. In yet other aspects of these embodiments, $Xaa_3$ is (R)-2-(7'-octenyl)alanine whereas $Xaa_4$ is (S)-2-(4'-pentenyl)alanine.

In some embodiments, $Xaa_1$, $Xaa_2$, $Xaa_3$ and $Xaa_4$ are all the same. In some aspects of these embodiments, $Xaa_1$, $Xaa_2$, $Xaa_3$ and $Xaa_4$ are each (S)-2-(4'-pentenyl)alanine. In other aspects of these embodiments, $Xaa_1$, $Xaa_2$, $Xaa_3$ and $Xaa_4$ are each (R)-2-(4'-pentenyl)alanine. In yet other aspects of these embodiments, $Xaa_1$, $Xaa_2$, $Xaa_3$ and $Xaa_4$ are each (S)-2-(7'-octenyl)alanine. In yet other aspects of these embodiments, $Xaa_1$, $Xaa_2$, $Xaa_3$ and $Xaa_4$ are each (R)-2-(7'-octenyl)alanine.

In some embodiments, $Xaa_1$ and $Xaa_2$ are each (S)-2-(4'-pentenyl)alanine, whereas $Xaa_3$ and $Xaa_4$ are each (R)-2-(4'-pentenyl)alanine. In some embodiments, $Xaa_1$ and $Xaa_2$ are each (R)-2-(4'-pentenyl)alanine, whereas $Xaa_3$ and $Xaa_4$ are each (S)-2-(4'-pentenyl)alanine. In some embodiments, $Xaa_1$ and $Xaa_2$ are each (S)-2-(7'-octenyl)alanine, whereas $Xaa_3$ and $Xaa_4$ are each (R)-2-(7'-octenyl)alanine. In some embodiments, $Xaa_1$ and $Xaa_2$ are each (R)-2-(7'-octenyl)alanine, whereas $Xaa_3$ and $Xaa_4$ are each (S)-2-(7'-octenyl)alanine. In some embodiments, $Xaa_1$ and $Xaa_2$ are each (S)-2-(4'-pentenyl)alanine, whereas $Xaa_3$ and $Xaa_4$ are each (S)-2-(7'-octenyl)alanine. In some embodiments, $Xaa_1$ and $Xaa_2$ are each (S)-2-(7'-octenyl)alanine, whereas $Xaa_3$ and $Xaa_4$ are each (S)-2-(4'-pentenyl)alanine. In some embodiments, $Xaa_1$ and $Xaa_2$ are each (R)-2-(4'-pentenyl)alanine, whereas $Xaa_3$ and $Xaa_4$ are each (R)-2-(7'-octenyl)alanine. In some embodiments, $Xaa_1$ and $Xaa_2$ are each (R)-2-(7'-octenyl)alanine, whereas $Xaa_3$ and $Xaa_4$ are each (R)-2-(4'-pentenyl)alanine.

In some embodiments, the polypeptide consists of the amino acid sequence:

```
                                    (SEQ ID NO: 39)
REXaa₁SLQXaa₂LRXaa₃IQRXaa₄L(2-Nal),
``` wherein $Xaa_1$, $Xaa_2$, $Xaa_3$ and $Xaa_4$ are each (S)-2-(4'-pentenyl)alanine.

In some embodiments, the polypeptide consists of the amino acid sequence:

```
                                    (SEQ ID NO: 40)
REXaa₁SLQXaa₂LRXaa₃IQRXaa₄L(2-Nal)(β-Ala)(β-Ala),
``` wherein $Xaa_1$, $Xaa_2$, $Xaa_3$ and $Xaa_4$ are each (S)-2-(4'-pentenyl)alanine.

In some embodiments, the polypeptide is selected from any one of the following polypeptides:

```
                                    (SEQ ID NO: 39)
REXaa₁SLQXaa₂LRXaa₃IQRXaa₄(2-Nal);

(SEQ ID NO: 40)
REXaa₁SLQXaa₂LRXaa₃IQRXaa₄L(2-Nal)(β-Ala)(β-Ala);

(SEQ ID NO: 79)
EXaa₁SLQXaa₂LRXaa₃IQRXaa₄(2-Nal)(β-Ala)(β-Ala);
```

-continued (SEQ ID NO: 82)
HREXaa₁SLQXaa₂LRXaa₃IQRXaa₄(CBA)(2-Nal);

(SEQ ID NO: 83)
HREXaa₁SLQXaa₂LRXaa₃IQQXaa₄(CBA)(2-Nal);

(SEQ ID NO: 84)
HR(N-methylE)Xaa₁SLQXaa₂LRXaa₃IQRXaa₄(CBA)(2-Nal);

(SEQ ID NO: 85)
HREXaa₁SLQXaa₂L(N-methylR)Xaa₃IQRXaa₄(CBA)(2-Nal);

(SEQ ID NO: 86)
HR(N-methylQ)Xaa₁S(Cha)(N-methylQ)Xaa₂(Cha)RXaa₃
IQRXaa₄(Cha)(2-Nal);
and (SEQ ID NO: 87)
HRQXaa₁SLQXaa₂LRXaa₃IQRXaa₄(CBA)(2-Nal), wherein Xaa₁, Xaa₂, Xaa₃ and Xaa₄ are each (S)-2-(4'-pentenyl)alanine.

In some embodiments, the present application provides an amino acid sequence SEQ ID NO: 37:

| 361 | 362 | 363 | 364 | 365 |
|---|---|---|---|---|
| Xaa₁₅ | S | L | Q | Xaa₁₀ | wherein:
Xaa₁₅ and Xaa₁₀ are each independently an α,α-disubstituted amino acid.

In some embodiments, the polypeptide comprises at least two Nle.

In some embodiments, the polypeptide has length of 7-30 amino acids (e.g., 7-20, 8-25, 10-30, 12-30, or 9-24 amino acids).

In some embodiments, in addition to the amino acid sequence SEQ ID NO: 37, the polypeptide comprises at least one amino acid selected from: L, E, R, H, S, Q, I, CBA, N-methylQ, N-methylE, N-methylR, N-methylD, N-methylT, N-methylI, Cpa, Cha, N-MeHis, N-MeCys, homoHis, NHis, homoR, Cit, Nar, Phe(4-guanidino), NMeGln, Nle, 2-Abu, Phe(4-Cl), 3,4-diClPh, 4-FPh, NptGly, NMeCha, Dcha, α-methylL, allylGly, Alg, AC4C, A6C, Aze, (βtBu-Ala), Tle, peptoidQ, DThr, and NMeLeu.

In some embodiments, in addition to the amino acid sequence SEQ ID NO: 37, the polypeptide comprises at least one amino acid selected from: H, R, E, S, L, Q, I, CBA, and (2-Nal).

In some embodiments, the polypeptide comprises IQR.
In some embodiments, the polypeptide comprises (Nle)IQR(Nle).
In some embodiments, the polypeptide comprises HRE and LR.
In some embodiments, the polypeptide comprises L(2-Nal).
In some embodiments, the polypeptide comprises (CBA)(2-Nal).

In some embodiments, Xaa₁₅ and Xaa₁₀ are the same. In some aspects of these embodiments, Xaa₁₅ and Xaa₁₀ are each (S)-2-(4'-pentenyl)alanine. In other aspects of these embodiments, Xaa₁₅ and Xaa₁₀ are each (R)-2-(4'-pentenyl)alanine. In yet other aspects of these embodiments, Xaa₁₅ and Xaa₁₀ are each (S)-2-(7'-octenyl)alanine. In yet other aspects of these embodiments, Xaa₁₅ and Xaa₁₀ are each (R)-2-(7'-octenyl)alanine.

In some embodiments, Xaa₁₅ and Xaa₁₀ are different α,α-disubstituted amino acids. In some aspects of these embodiments, Xaa₁₅ is (S)-2-(4'-pentenyl)alanine whereas Xaa₁₀ is (R)-2-(4'-pentenyl)alanine. In other aspects of these embodiments, Xaa₁₅ is (R)-2-(4'-pentenyl)alanine whereas Xaa₁₀ is (S)-2-(4'-pentenyl)alanine. In yet other aspects of these embodiments, Xaa₁₅ is (S)-2-(7'-octenyl)alanine whereas Xaa₁₀ is (R)-2-(7'-octenyl)alanine. In yet other aspects of these embodiments, Xaa₁₅ is (R)-2-(7'-octenyl)alanine whereas Xaa₁₀ is (S)-2-(7'-octenyl)alanine. In yet other aspects of these embodiments, Xaa₁₅ is (S)-2-(4'-pentenyl)alanine whereas Xaa₁₀ is (S)-2-(7'-octenyl)alanine. In yet other aspects of these embodiments, Xaa₁₅ is (R)-2-(4'-pentenyl)alanine whereas Xaa₁₀ is (R)-2-(7'-octenyl)alanine. In yet other aspects of these embodiments, Xaa₁₅ is (S)-2-(4'-pentenyl)alanine whereas Xaa₁₀ is (R)-2-(7'-octenyl)alanine. In yet other aspects of these embodiments, Xaa₁₅ is (R)-2-(4'-pentenyl)alanine whereas Xaa₁₀ is (S)-2-(7'-octenyl)alanine. In yet other aspects of these embodiments, Xaa₁₅ is (S)-2-(7'-octenyl)alanine whereas Xaa₁₀ is (S)-2-(4'-pentenyl)alanine. In yet other aspects of these embodiments, Xaa₁₅ is (R)-2-(7'-octenyl)alanine whereas Xaa₁₀ is (R)-2-(4'-pentenyl)alanine. In yet other aspects of these embodiments, Xaa₁₅ is (S)-2-(7'-octenyl)alanine whereas Xaa₁₀ is (R)-2-(4'-pentenyl)alanine. In yet other aspects of these embodiments, Xaa₁₅ is (R)-2-(7'-octenyl)alanine whereas Xaa₁₀ is (S)-2-(4'-pentenyl)alanine.

In some embodiments, the polypeptide consists of the amino acid sequence:

(SEQ ID NO: 80)
HREXaa₁₅SLQXaa₁₀LR(Nle)IQR(Nle)L(2-Nal), wherein Xaa₁₅ and Xaa₁₀ are each (S)-2-(4'-pentenyl)alanine.

In some embodiments, the polypeptide consists of the amino acid sequence:

(SEQ ID NO: 81)
HREXaa₁₅SLQXaa₁₀LR(Nle)IQR(Nle)(CBA)(2-Nal), wherein Xaa₁₅ and Xaa₁₀ are each (S)-2-(4'-pentenyl)alanine.

In some embodiments, the present disclosure provides a polypeptide having an amino acid sequence:

| 367 | 368 | 369 | 370 | 371 | 372 | 373 | 374 |
|---|---|---|---|---|---|---|---|
| Xaa₁₁ | Xaa₃ | Xaa₄ | Xaa₈ | Xaa₅ | Xaa₆ | Xaa₇ | (2-Nal) | wherein:
Xaa₃ and Xaa₆ are each independently an α,α-disubstituted amino acid;
Xaa₄ is selected from I, A, Nle, N-MethylI, CBA, and (D-I);
Xaa₈ is selected from Q and N-methylQ;
Xaa₅ is selected from R, A, Q, E, K, H, N-methylR, homoR, NMeArg, Nar, and Cit; and
Xaa₇ is selected from L, A, CBA, Cha, Cpa, Phe(4-Cl), (D-L), α-MethylL, DCha, N-methylCha, allylGly, AC4C, A6C, Aze, NMeCha, (β-tBu-Ala), Tle, 4-FPh, and 3,4-diClPh; and
Xaa₁ is selected from R, N-methylR, E, K, homoR, Nar, and Cit.

In some embodiments, at least one of Xaa₁₁ and Xaa₅ comprises E or K.

In some embodiments, the polypeptide has a length of 8-30 amino acids (e.g., 10-25, 12-24, 9-30, 10-30, or 12-30 amino acids).

In some embodiments, $Xaa_{11}$ is E. In some embodiments, $Xaa_{11}$ is R. In some embodiments, $Xaa_{11}$ is K. In some embodiments, $Xaa_5$ is R. In some embodiments, $Xaa_5$ is E. In some embodiments, $Xaa_5$ is K. In some embodiments, $Xaa_{11}$ is E, and $Xaa_5$ is R. In some embodiments, $Xaa_{11}$ is R, and $Xaa_5$ is E. In some embodiments, $Xaa_{11}$ is K and $Xaa_5$ is R. In some embodiments, $Xaa_{11}$ is R and $Xaa_5$ is K.

In some embodiments, the polypeptide comprises L(2-Nal). In some embodiments, the polypeptide comprises IQR, IQE, or IQK. In some embodiments, the polypeptide comprises LQTLE, LQTLR, or LQRLK.

In some embodiments, $Xaa_3$ and $Xaa_6$ are the same. In some aspects of these embodiments, $Xaa_3$ and $Xaa_6$ are each (S)-2-(4'-pentenyl)alanine. In other aspects of these embodiments, $Xaa_3$ and $Xaa_6$ are each (R)-2-(4'-pentenyl)alanine. In yet other aspects of these embodiments, $Xaa_3$ and $Xaa_6$ are each (S)-2-(7'-octenyl)alanine. In yet other aspects of these embodiments, $Xaa_3$ and $Xaa_6$ are each (R)-2-(7'-octenyl)alanine.

In some embodiments, $Xaa_3$ and $Xaa_6$ are different α,α-disubstituted amino acids. In some aspects of these embodiments, $Xaa_3$ is (S)-2-(4'-pentenyl)alanine whereas $Xaa_6$ is (R)-2-(4'-pentenyl)alanine. In other aspects of these embodiments, $Xaa_3$ is (R)-2-(4'-pentenyl)alanine whereas $Xaa_6$ is (S)-2-(4'-pentenyl)alanine. In yet other aspects of these embodiments, $Xaa_3$ is (S)-2-(7'-octenyl)alanine whereas $Xaa_6$ is (R)-2-(7'-octenyl)alanine. In yet other aspects of these embodiments, $Xaa_3$ is (R)-2-(7'-octenyl)alanine whereas $Xaa_6$ is (S)-2-(7'-octenyl)alanine. In yet other aspects of these embodiments, $Xaa_3$ is (S)-2-(4'-pentenyl)alanine whereas $Xaa_6$ is (S)-2-(7'-octenyl)alanine. In yet other aspects of these embodiments, $Xaa_3$ is (R)-2-(4'-pentenyl)alanine whereas $Xaa_6$ is (R)-2-(7'-octenyl)alanine. In yet other aspects of these embodiments, $Xaa_3$ is (S)-2-(4'-pentenyl)alanine whereas $Xaa_6$ is (R)-2-(7'-octenyl)alanine. In yet other aspects of these embodiments, $Xaa_3$ is (R)-2-(4'-pentenyl)alanine whereas $Xaa_6$ is (S)-2-(7'-octenyl)alanine. In yet other aspects of these embodiments, $Xaa_3$ is (S)-2-(7'-octenyl)alanine whereas $Xaa_6$ is (S)-2-(4'-pentenyl)alanine. In yet other aspects of these embodiments, $Xaa_3$ is (R)-2-(7'-octenyl)alanine whereas $Xaa_6$ is (R)-2-(4'-pentenyl)alanine. In yet other aspects of these embodiments, $Xaa_3$ is (S)-2-(7'-octenyl)alanine whereas $Xaa_6$ is (R)-2-(4'-pentenyl)alanine. In yet other aspects of these embodiments, $Xaa_3$ is (R)-2-(7'-octenyl)alanine whereas $Xaa_6$ is (S)-2-(4'-pentenyl)alanine.

In some embodiments, the polypeptide consists of the amino acid sequence:

(SEQ ID NO: 98)
LQTLEXaa$_3$IQRXaa$_6$L(2-Nal), wherein $Xaa_3$ and $Xaa_6$ are each (S)-2-(4'-pentenyl)alanine.

In some embodiments, the polypeptide consists of the amino acid sequence:

(SEQ ID NO: 99)
LQTLRXaa$_3$IQEXaa$_6$L(2-Nal), wherein $Xaa_3$ and $Xaa_6$ are each (S)-2-(4'-pentenyl)alanine.

In some embodiments, the polypeptide consists of the amino acid sequence:

(SEQ ID NO: 100)
LQTLKXaa$_3$IQRXaa$_6$L(2-Nal), wherein $Xaa_3$ and $Xaa_6$ are each (S)-2-(4'-pentenyl)alanine.

In some embodiments, the polypeptide consists of the amino acid sequence:

(SEQ ID NO: 101)
LQTLRXaa$_3$IQKXaa$_6$L(2-Nal), wherein $Xaa_3$ and $Xaa_6$ are each (S)-2-(4'-pentenyl)alanine.

In some embodiments, the present application provides a polypeptide having sequence:

| 368 | 369 | 370 | 371 | 372 | 373 | 374 |
|---|---|---|---|---|---|---|
| $Xaa_3$ | $Xaa_4$ | $Xaa_8$ | $Xaa_5$ | $Xaa_6$ | $Xaa_7$ | (2-Nal) | wherein:

$Xaa_3$ and $Xaa_6$ are each independently an α,α-disubstituted amino acid;

$Xaa_4$ is selected from I, A, Nle, N-MethylI, CBA, and (D-I);

$Xaa_8$ is selected from Q and N-methylQ;

$Xaa_5$ is selected from R, A, Q, E, K, H, N-methylR, homoR, NMeArg, Nar, and Cit; and $Xaa_7$ is selected from L, A, CBA, Cha, Cpa, Phe(4-Cl), (D-L), α-MethylL, DCha, N-methylCha, allylGly, AC4C, A6C, Aze, NMeCha, (βtBu-Ala), Tle, 4-FPh, and 3,4-diClPh.

In some embodiments, the polypeptide comprises at least one (D-I) or (D-L).

In some embodiments, the polypeptide has a length of 7-30 amino acids (e.g., 7-12, 8-30, 8-25, 10-30, 12-24, or 12-20 amino acids).

In some embodiments, $Xaa_4$ is (D-I). In some embodiments, $Xaa_4$ is (D-L).

In some embodiments, $Xaa_7$ is (D-L). In some embodiments, $Xaa_7$ is (D-I).

In some embodiments, the polypeptide comprises (D-L)QTIR.

In some embodiments, the polypeptide comprises LQT(D-L)R.

In some embodiments, $Xaa_3$ and $Xaa_6$ are the same. In some aspects of these embodiments, $Xaa_3$ and $Xaa_6$ are each (S)-2-(4'-pentenyl)alanine. In other aspects of these embodiments, $Xaa_3$ and $Xaa_6$ are each (R)-2-(4'-pentenyl)alanine. In yet other aspects of these embodiments, $Xaa_3$ and $Xaa_6$ are each (S)-2-(7'-octenyl)alanine. In yet other aspects of these embodiments, $Xaa_3$ and $Xaa_6$ are each (R)-2-(7'-octenyl)alanine.

In some embodiments, $Xaa_3$ and $Xaa_6$ are different α,α-disubstituted amino acids. In some aspects of these embodiments, $Xaa_3$ is (S)-2-(4'-pentenyl)alanine whereas $Xaa_6$ is (R)-2-(4'-pentenyl)alanine. In other aspects of these embodiments, $Xaa_3$ is (R)-2-(4'-pentenyl)alanine whereas $Xaa_6$ is (S)-2-(4'-pentenyl)alanine. In yet other aspects of these embodiments, $Xaa_3$ is (S)-2-(7'-octenyl)alanine whereas $Xaa_6$ is (R)-2-(7'-octenyl)alanine. In yet other aspects of these embodiments, $Xaa_3$ is (R)-2-(7'-octenyl)alanine whereas $Xaa_6$ is (S)-2-(7'-octenyl)alanine. In yet other aspects of these embodiments, Xaa₃ is (S)-2-(4'-pentenyl)alanine whereas Xaa₆ is (S)-2-(7'-octenyl)alanine. In yet other aspects of these embodiments, Xaa₃ is (R)-2-(4'-pentenyl)alanine whereas Xaa₆ is (R)-2-(7'-octenyl)alanine. In yet other aspects of these embodiments, Xaa₃ is (S)-2-(4'-pentenyl)alanine whereas Xaa₆ is (R)-2-(7'-octenyl)alanine. In yet other aspects of these embodiments, Xaa₃ is (R)-2-(4'-pentenyl)alanine whereas Xaa₆ is (S)-2-(7'-octenyl)alanine. In yet other aspects of these embodiments, Xaa₃ is (S)-2-(7'-octenyl)alanine whereas Xaa₆ is (S)-2-(4'-pentenyl)alanine. In yet other aspects of these embodiments, Xaa₃ is (R)-2-(7'-octenyl)alanine whereas Xaa₆ is (R)-2-(4'-pentenyl)alanine. In yet other aspects of these embodiments, Xaa₃ is (S)-2-(7'-octenyl)alanine whereas Xaa₆ is (R)-2-(4'-pentenyl)alanine. In yet other aspects of these embodiments, Xaa₃ is (R)-2-(7'-octenyl)alanine whereas Xaa₆ is (S)-2-(4'-pentenyl)alanine.

In some embodiments, the polypeptide consists of the amino acid sequence:

```
                                          (SEQ ID NO: 102)
(D-L)QTIRXaa₃IQRXaa₆L(2-Nal),
``` wherein Xaa₃ and Xaa₆ are each (S)-2-(4'-pentenyl)alanine.

In some embodiments, the polypeptide consists of the amino acid sequence:

```
                                          (SEQ ID NO: 103)
LQT(D-L)RXaa₃IQRXaa₆L(2-Nal),
``` wherein Xaa₃ and Xaa₆ are each (S)-2-(4'-pentenyl)alanine.

In some embodiments, the polypeptide consists of the amino acid sequence:

```
                                          (SEQ ID NO: 104)
LQTLRXaa₃(D-I)QRXaa₆L(2-Nal),
``` wherein Xaa₃ and Xaa₆ are each (S)-2-(4'-pentenyl)alanine.

In some embodiments, the polypeptide consists of the amino acid sequence:

```
                                          (SEQ ID NO: 105)
LQTLRXaa₃IQRXaa₆(D-L)(2-Nal),
``` wherein Xaa₃ and Xaa₆ are each (S)-2-(4'-pentenyl)alanine.

Stapled Polypeptides Derived from BCL9 HD2 Domain

Stabilized peptides have been shown to confer advantages such as increased helical content, proteolytic stability, and increased binding affinity for a target receptor (see Kim 2011). In particular, α-helix domains are known to be amenable to stabilization.

In some embodiments, a polypeptide disclosed herein encompasses a polypeptide that has undergone a reaction (e.g., metathesis reaction) to form one or more hydrocarbon linkers and thus the polypeptide comprises one or more hydrocarbon linkers. The hydrocarbon linker may confer a structural constraint(s) of the α-helix of the polypeptide (e.g., any variant of HD2 domain of BCL9 described herein). In one embodiment, the α-helix of the polypeptide is stabilized by having one or more hydrocarbon linkers between amino acids of the polypeptide.

The hydrocarbon crosslinker may extend across the length of one or more α-helical turns. As it is generally understood that one α-helical turn comprise about 3 to 4 amino acids. Hence, any two amino acids that are chemically connected by a hydrocarbon linker are in positions i and i+4 with respect to each other.

In some embodiments, a hydrocarbon crosslinker disclosed herein is generated by connecting two α,α-disubstituted amino acids incorporated into a single polypeptide. In some embodiments, the hydrocarbon crosslinker is generated by a ring closing metathesis reaction connecting two α,α-disubstituted amino acids. A ring closing metathesis (also referred as a ring closing olefin metathesis) is known in the art (Kim et al., Nature Protocols 6: 761-771 (2011)).

The length of a hydrocarbon crosslinker as described herein may vary depending on the length of the substituents of the α,α-disubstituted amino acid. For instance, by using a suitable α,α-disubstituted amino acid, a hydrocarbon linker generated by a ring closing metathesis reaction may have a length of 1, 2, 3, 4, 5, 6, 7, 8, 9, 10, 11, 12, 13, 14, or 15 carbons. In some embodiments, the hydrocarbon linker has a length of 8-12 carbons. In some embodiments, the hydrocarbon linker has a length of 8 or 11 carbons. In certain embodiments, the hydrocarbon linker is 8-carbons in length. In certain embodiments, the hydrocarbon linker is 11-carbons in length. In some embodiments, the hydrocarbon crosslinker has a length of 2-15 carbons. In some embodiments, the hydrocarbon crosslinker has a length of 5-11 carbons. In some embodiments, the hydrocarbon crosslinker has a length of 7-11 carbons. In some embodiments, the hydrocarbon crosslinker has a length of 7-15 carbons. In some embodiments, the hydrocarbon crosslinker has a length of 8-11 carbons. In some embodiments, the hydrocarbon crosslinker has a length of 7 or 8 or 9 or 10 or 11 carbons, or more. In some embodiments, the hydrocarbon linker contains at least one double bond. In some embodiments, the hydrocarbon linker is an alkenyl crosslinker.

In some embodiments, a stabilized polypeptide may be formed from any of the unstapled polypeptides comprising an α,α-disubstituted amino acid as described herein. In some embodiments, a hydrocarbon linker in the stabilized polypeptide is generated by reacting α-alkenyl groups of at least two α-alkyl, α-alkenyl amino acids within the structure of the polypeptide. That is, the hydrocarbon linker is formed by reacting α-alkenyl group of one amino acid with the α-alkenyl group of the other amino acid to form an alkenyl hydrocarbon linker. In some embodiments, the reaction between the two α-alkenyl groups is a metathesis reaction. In some embodiments, the α-alkenyl group is 4-pentenyl or 7-octenyl group. In some embodiments, in a stabilized polypeptide, one α substituent in an α,α-disubstituted amino acid is methyl, and the other α substituent in the α,α-disubstituted amino acid is a hydrocarbon linker.

In such stabilized polypeptide, there are at least two amino acids in the polypeptide's backbone each having a hydrocarbon linker as an α-substituent.

In some embodiments, the hydrocarbon linker has formula:

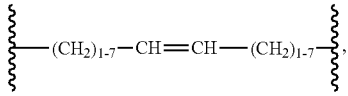

wherein each ⸙ denotes a point of attachment of the hydrocarbon linker to the α carbon atom of an α,α-disubstituted amino acid. In some aspects of these embodiments, the α carbon atom is also substituted by a methyl group (e.g., the α,α-disubstituted amino acid is an α-substituted derivative of alanine). In some embodiments, α carbon of each α,α-disubstituted amino acid connected by the hydrocarbon linker has S-configuration. In some embodiments, α carbon of each α,α-disubstituted amino acid connected by the hydrocarbon linker has R-configuration. In some embodiments, when two α,α-disubstituted amino acids within the polypeptide are connected by a hydrocarbon linker, α carbon of one amino acid has S-configuration, and α carbon of the other amino acid has R-configuration.

In some embodiments, the hydrocarbon crosslinker has formula:

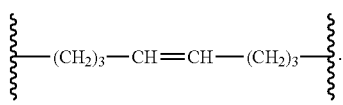

In some embodiments, the hydrocarbon crosslinker has formula:

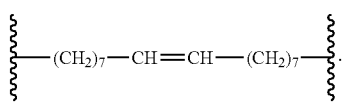

In some embodiments, the hydrocarbon crosslinker has formula:

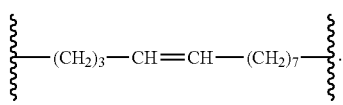

In some embodiments, a stapled polypeptide comprises an amino acid sequence selected from:

```
                                     SEQ ID NO: 107
LQTLRXaa3IQRXaa6(CBA)(2-Nal)

SEQ ID NO: 108
L(N-methylQ)TLRXaa3IQRXaa6(CBA)(2-Nal)

SEQ ID NO: 109
LETLRXaa3IQRXaa6(CBA)(2-Nal)

SEQ ID NO: 110
L(N-methylQ)TLRXaa3IQRXaa6(CBA)(2-Nal)(β-Ala)
(β-Ala)

SEQ ID NO: 111
L(N-methylQ)TLRXaa3IQRXaa6(CBA)(2-Nal)(β-Ala)
(β-Ala)

SEQ ID NO: 112
LQTLRXaa3IQHXaa6(CBA)(2-Nal)

SEQ ID NO: 113
(CBA)QTLRXaa3IQRXaa6(CBA)(2-Nal)

SEQ ID NO: 114
(CBA)(N-methylQ)TLRXaa3IQRXaa6(CBA)(2-Nal)

SEQ ID NO: 115
LQT(CBA)RXaa3IQRXaa6(CBA)(2-Nal)

SEQ ID NO: 116
L(N-methylQ)TLRXaa3I(N-methylQ)RXaa6(CBA)(2-Nal)

SEQ ID NO: 117
LN-MeQTLR(Me)Xaa3IQRXaa6(CBA)(2-Nal)

SEQ ID NO: 118
(Me-L)(N-MeQ)TLRXaa3IQRXaa6(CBA)(2-Nal)

SEQ ID NO: 119
LN(Me-Gln)TLRXaa3IQRXaa6(Cpa)(2-Nal)

SEQ ID NO: 120
L(N-methylQ)TLRXaa3IQRXaa6(CBA)(2-Nal),
wherein N-terminus is modified with HOCH2CH2Co-.

SEQ ID NO: 121
L(N-methylQ)(N-methylT)LRXaa3IQRXaa6(CBA)(2-Nal)

SEQ ID NO: 122
L(N-methylQ)TLRXaa3IQRXaa6(Cha)(2-Nal)

SEQ ID NO: 123
L(N-methylQ)T(Cha)RXaa3IQRXaa6(CBA)(2-Nal)

SEQ ID NO: 124
L(N-methylQ)TL(N-methylR)Xaa3IQRXaa6(CBA)(2-Nal)

SEQ ID NO: 125
L(N-methylQ)TLRXaa3IQ(N-methylR)Xaa6(CBA)(2-Nal)

SEQ ID NO: 126
L(N-methylQ)T(a-methylL)RXaa3IQRXaa6(CBA)(2-Nal)

SEQ ID NO: 127
LQTLRXaa3IQRXaa6(Cha)(2-Nal)

SEQ ID NO: 128
L(N-methylQ)TL(N-methylR)Xaa3IQ(N-methylR)Xaa6
(CBA)(2-Nal)

SEQ ID NO: 129
L(N-methylQ)TLRXaa3(CBA)QRXaa6(CBA)(2-Nal)

SEQ ID NO: 130
L(N-methylQ)(D-Thr)LRXaa3IQRXaa6(CBA)(2-Nal)

SEQ ID NO: 131
L(N-meGln)T(N-MeLeu)RXaa3IQRXaa6(CBA)(2-Nal)

SEQ ID NO: 132
L(N-methylQ)TL(homoR)Xaa3IQRXaa6(CBA)(2-Nal)

SEQ ID NO: 133
L(N-methylQ)TLRXaa3IQ(homoR)Xaa6(CBA)(2-Nal)

SEQ ID NO: 134
L(N-methylQ)TLRXaa3(N-methylI)QRXaa6(CBA)(2-Nal)

SEQ ID NO: 135
L(N-MeGln)TLRXaa3IQRXaa6(CBA)(2-Nal),
wherein N-terminus is modified with propionyl.

SEQ ID NO: 136
L(N-MeGln)TLRXaa3IQRXaa6(CBA)(2-Nal),
wherein N-terminus is modified with hexanoyl.

SEQ ID NO: 137
L(N-MeGln)TLRXaa3IQRXaa6(CBA)(2-Nal),
wherein N-terminus is modified with 3-phenyl-
propanoyl.
```

```
L(N-MeGln)TLRXaa₃IQRXaa₆(CBA)(2-Nal),     SEQ ID NO: 138
wherein N-terminus is modified with 2-cyclohexyl-
acetyl.

SEQ ID NO: 139
L(N-MeGln)TLRXaa₃IQRXaa₆(CBA)(2-Nal),
wherein N-terminus is modified with diphenyl-
acetyl.

SEQ ID NO: 140
L(N-methylQ)TLRXaa₃IQRXaa₆(CBA)(2-Nal),
wherein N-terminus is modified with 3,5-dihydroxy-
benzoic acid.

SEQ ID NO: 141
L(N-methylQ)TLRXaa₃IQRXaa₆(CBA)(2-Nal),
wherein N-terminus is modified with 4-(trifluoro-
methyl)benzoic acid.

SEQ ID NO: 142
L(N-methylQ)TLRXaa₃IQRXaa₆(CBA)(2-Nal),
wherein N-terminus is modified with 5-phenyl-
valeric acid.

SEQ ID NO: 143
L(N-methylQ)TLRXaa₃IQRXaa₆(CBA)(2-Nal),
wherein N-terminus is modified with 4-biphenyl
acetic acid.

SEQ ID NO: 144
L(N-methylQ)TLRXaa₃IQRXaa₆(CBA)(2-Nal),
wherein N-terminus is modified with dimethyl.

SEQ ID NO: 145
HRERSLQTLRXaa₃IQQXaa₆(CBA)(2-Nal)

SEQ ID NO: 146
HRERSLQTLRXaa₃IQEXaa₆(CBA)(2-Nal),
wherein C-terminus is unmodified.

SEQ ID NO: 147
HRQRSLQTLRXaa₃IQRXaa₆(CBA)(2-Nal)

SEQ ID NO: 148
HRQRSLQTLRXaa₃IQRXaa₆(CBA)(2-Nal)(β-Ala)(β-Ala)

SEQ ID NO: 149
HRQRSLQTLRXaa₃IQRXaa₆(CBA)(2-Nal)(β-Ala)(β-Ala),
wherein C-terminus is modified with GRKKRRQRRRPQ-
NH₂.

SEQ ID NO: 150
HRQRSLQTLRXaa₃IQRXaa₆(CBA)(2-Nal)(β-Ala)(β-Ala),
wherein C-terminus is modified with 1-(2-amino-
ethyl)-4-methylpiperazine.

SEQ ID NO: 151
HR(N-methylE)RSLQTLRXaa₃IQRXaa₆(CBA)(2-Nal)

SEQ ID NO: 152
HRERSLQTL(N-methylR)Xaa₃IQRXaa₆(CBA)(2-Nal),
wherein C-terminus is unmodified.

SEQ ID NO: 153
HRQRSL(N-methylQ)TLRXaa₃IQRXaa₆(CBA)(2-Nal)

SEQ ID NO: 154
HR(N-methylE)RSL(N-methylQ)TLRXaa₃IQRXaa₆(CBA)
(2-Nal)

SEQ ID NO: 155
HR(N-methylQ)RSL(N-methylQ)TLRXaa₃IQRXaa₆(CBA)
(2-Nal)

SEQ ID NO: 156
HRQRS(CBA)QTLRXaa₃IQRXaa₆(CBA)(2-Nal)

SEQ ID NO: 157
HR(N-methylD)RSLQTLRXaa₃IQRXaa₆(CBA)(2-Nal)

SEQ ID NO: 158
H(R-Me)QRSLQTLRXaa₃IQRXaa₆(CBA)(2-Nal)

SEQ ID NO: 159
HRQRTLQTLRXaa₃IQRXaa₆(CBA)(2-Nal)

SEQ ID NO: 160
HRQRSLQTLRXaa₃IQRXaa₆(CBA)(2-Nal),
N-terminus is modified with palmitoyl-PEG4.

SEQ ID NO: 161
HRQRSLQTLRXaa₃IQRXaa₆(CBA)(2-Nal),
wherein C-terminus is modified with K(PEG4-
palmitoyl)NH₂.

SEQ ID NO: 162
HRQRSLQTLRXaa₃IQRXaa₆(Cpa)(2-Nal)

SEQ ID NO: 163
HR(N-methylQ)RSL(N-methylQ)T(Cha)RXaa₃IQRXaa₆(CBA)
(2-Nal)

SEQ ID NO: 164
HR(N-methylQ)RSL(N-methylQ)TLRXaa₃IQ(N-methylR)
Xaa₆(CBA)(2-Nal)

SEQ ID NO: 165
HR(N-methylQ)RSL(N-methylQ)(N-methylT)LRXaa₃
IQRXaa₆(CBA)(2-Nal)

SEQ ID NO: 166
H(N-methylR)QRSLQTLRXaa₃IQRXaa₆(CBA)(2-Nal)

SEQ ID NO: 167
HRQ(homoR)SLQTLRXaa₃IQRXaa₆(CBA)(2-Nal)

SEQ ID NO: 168
HRQ(N-methylR)SLQTLRXaa₃IQRXaa₆(CBA)(2-Nal)

SEQ ID NO: 169
HRQRSL(peptoid-Q)TLRXaa₃IQRXaa₆(CBA)(2-Nal)

SEQ ID NO: 170
HRQRSLQTL(homoR)Xaa₃IQRXaa₆(CBA)(2-Nal)

SEQ ID NO: 171
HRQRSLQTLRXaa₃IQ(homoR)Xaa₆(CBA)(2-Nal)

SEQ ID NO: 172
L(N-methylQ)TLRXaa₃IQRXaa₆(a-methylL)(2-Nal)

SEQ ID NO: 173
L(N-methylQ)TLRXaa₃IQRXaa₆D(Cha)(2-Nal)

SEQ ID NO: 174
L(N-methylQ)TLRXaa₃IQRXaa₆(N-methylCha)(2-Nal)

SEQ ID NO: 175
LQTLRXaa₃IQRXaa₆(allylGly)(2-Nal)

SEQ ID NO: 176
HRQRSLQTLRXaa₃IQRXaa₆(AC4C)(2-Nal)

SEQ ID NO: 177
HRQRSLQTLRXaa₃IQRXaa₆(A6C)(2-Nal)

SEQ ID NO: 178
HRQRSLQTLRXaa₃IQRXaa₆(Aze)(2-Nal)

SEQ ID NO: 179
HRQRSLQTLRXaa₃IQRXaa₆(Phe-4-Cl)(2-Nal)

SEQ ID NO: 180
HRQRSLQTLRXaa₃IQRXaa₆(Cha)(2-Nal)

SEQ ID NO: 181
HR(N-methylQ)RSL(N-methylQ)TLRXaa₃IQRXaa₆(Cha)
(2-Nal)
```

-continued

SEQ ID NO: 182
HRQRSLQTLRXaa$_3$IQRXaa$_6$(N-MeCha)(2-Nal)

SEQ ID NO: 183
H(homoArg)QRSLQTLRXaa$_3$IQRXaa$_6$(Cha)(2-Nal)

SEQ ID NO: 184
HRQ(N-MeArg)SLQTLRXaa$_3$IQRXaa$_6$(Cha)(2-Nal)

SEQ ID NO: 185
HRQRS(Cha)(N-MeGln)TLRXaa$_3$IQRXaa$_6$(Cha)(2-Nal)

SEQ ID NO: 186
HRQRS(N-MeCha)(N-MeGln)TLRXaa$_3$IQRXaa$_6$(Cha)(2-Nal)

SEQ ID NO: 187
HRQRSD(Cha)(N-MeGln)TLRXaa$_3$IQRXaa$_6$(Cha)(2-Nal)

SEQ ID NO: 188
HRQRSLQTLRXaa$_3$IQRXaa$_6$(Cha)(2DNal)

SEQ ID NO: 189
HRQRSLQTL(N-MeArg)Xaa$_3$IQRXaa$_6$(Cha)(2-Nal)

SEQ ID NO: 190
HRQRSLQTLRXaa$_3$IQ(N-MeArg)Xaa$_6$(Cha)(2-Nal)

SEQ ID NO: 191
HRQRSLQTLRXaa$_3$IQRXaa$_6$(β-tBu-Ala)(2-Nal)

SEQ ID NO: 192
HRQRSLQTLRXaa$_3$IQRXaa$_6$(Tle)(2-Nal)

SEQ ID NO: 193
HR(N-MeGln)RSLQTLRXaa$_3$IQRXaa$_6$(β-tBu-Ala)(2-Nal)

SEQ ID NO: 194
HR(N-MeGln)RSLQTLRXaa$_3$IQRXaa$_6$(Tle)(2-Nal)

SEQ ID NO: 195
L(N-methylQ)TLRXaa$_3$IQRXaa$_6$(4-Cl-Ph)(2-Nal)

SEQ ID NO: 196
HRQRSLQTLRXaa$_3$IQRXaa$_6$(4-Cl-Ph)(2-Nal)

SEQ ID NO: 197
HR(N-methylQ)RSL(N-methylQ)TLRXaa$_3$IQRXaa$_6$(4-Cl-Ph)(2-Nal)

SEQ ID NO: 199
HRQRS(Cha)(N-methylQ)TLRXaa$_3$IQRXaa$_6$(4-Cl-Ph)(2-Nal)

SEQ ID NO: 200
HRQRS(Cha)(N-methylQ)TLRXaa$_3$IQRXaa$_6$(4-F-Ph)(2-Nal)

SEQ ID NO: 201
HRQRS(NptGly)(N-methylQ)TLRXaa$_3$IQRXaa$_6$(4-Cl-Ph)(2-Nal)

SEQ ID NO: 202
HR(N-methylQ)RSL(N-methylQ)TLRXaa$_3$IQRXaa$_6$(4-F-Ph)(2-Nal)

SEQ ID NO: 203
HR(N-methylQ)RSL(N-methylQ)TLRXaa$_3$IQRXaa$_6$(3,4-diCl-Ph)(2-Nal)

SEQ ID NO: 204
HR(N-methylQ)RSL(N-methylQ)TLRXaa$_3$(Nle)QRXaa$_6$(Cha)(2-Nal)

SEQ ID NO: 205
HRQRSLQTLRXaa$_3$IQRXaa$_6$(Cha)(2-Nal),
wherein N-terminus is modified with palmitoyl-PEG4.

SEQ ID NO: 206
HRQRSLQTLRXaa$_3$IQRXaa$_6$(4-Cl-Ph)(2-Nal),
wherein N-terminus is modified with palmitoyl-PEG4.

SEQ ID NO: 207
HR(N-methylQ)RSL(N-methylQ)TLRXaa$_3$IQRXaa$_6$(Cha)(2-Nal),
wherein N-terminus is modified with palmitoyl-PEG4.

SEQ ID NO: 208
HR(N-methylQ)RSL(N-methylQ)TLRXaa$_3$IQRXaa$_6$(4-Cl-Ph)(2-Nal),
wherein N-terminus is modified with palmitoyl-PEG4.

SEQ ID NO: 209
H(homoArg)QRSLQTLRXaa$_3$IQRXaa$_6$(Cha)(2-Nal),
wherein N-terminus is modified with palmitoyl-PEG4.

SEQ ID NO: 210
H(homoArg)QRSLQTLRXaa$_3$IQRXaa$_6$(4-Cl-Ph)(2-Nal),
wherein N-terminus is modified with palmitoyl-PEG4.

SEQ ID NO: 211
HRQRS(Cha)(N-methylQ)TLRXaa$_3$IQRXaa$_6$(Cha)(2-Nal),
wherein N-terminus is modified with palmitoyl-PEG4.

SEQ ID NO: 212
HRQRS(Cha)(N-methylQ)TLRXaa$_3$IQRXaa$_6$(4-Cl-Ph)(2-Nal),
wherein N-terminus is modified with palmitoyl-PEG4.

SEQ ID NO: 213
L(N-methylQ)TLRXaa$_3$IQRXaa$_6$(CBA)(2-Nal),
wherein N-terminus is modified with palmitoyl-PEG4.

SEQ ID NO: 214
L(N-methylQ)TLRXaa$_3$IQRXaa$_6$(4-Cl-Ph)(2-Nal),
wherein N-terminus is modified with palmitoyl-PEG4.

SEQ ID NO: 215
(N-MeHis)RQRSLQTLRXaa$_3$IQRXaa$_6$(Cha)(2-Nal)

SEQ ID NO: 216
(Cys)RQRSLQTLRXaa$_3$IQRXaa$_6$(Cha)(2-Nal)

SEQ ID NO: 217
(N-MeCys)RQRSLQTLRXaa$_3$IQRXaa$_6$(Cha)(2-Nal)

SEQ ID NO: 218
(homoHis)RQRSLQTLRXaa$_3$IQRXaa$_6$(Cha)(2-Nal)

SEQ ID NO: 219
(NHis)RQRSLQTLRXaa$_3$IQRXaa$_6$(Cha)(2-Nal)

SEQ ID NO: 220
H(homoArg)QRSLQTL(Nar)Xaa$_3$IQRXaa$_6$(Cha)(2-Nal)

SEQ ID NO: 221
H(homoArg)QRSLQTLRXaa$_3$IQ(Nar)Xaa$_6$(Cha)(2-Nal)

SEQ ID NO: 222
H(homoArg)QRSLQTLRXaa$_3$IQ(Cit)Xaa$_6$(Cha)(2-Nal)

```
                                             SEQ ID NO: 223
H(homoArg)QRSLQTL(Cit)Xaa3IQRXaa6(Cha)(2-Nal)

SEQ ID NO: 224
H(Cit)(N-methylQ)RSL(N-methylQ)TLRXaa3IQRXaa6(Cha)

(2-Nal)

SEQ ID NO: 225
H(Nar)(N-methylQ)RSL(N-methylQ)TLRXaa3IQRXaa6(Cha)

(2-Nal)

SEQ ID NO: 226
H(4-guanidino-Phe)(N-methylQ)RSL(N-methylQ)TLRXaa3

IQRXaa6(Cha)(2-Nal)
``` wherein $Xaa_3$ and $Xaa_6$ are each independently an α,α-disubstituted amino acid, wherein one α substituent in the α,α-disubstituted amino acid is methyl, and the other α substituent in the α,α-disubstituted amino acid is a hydrocarbon linker of formula:

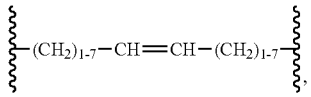

wherein one ⸱ denotes a point of attachment of the hydrocarbon linker to the α carbon atom of $Xaa_3$, and the other ⸱ denotes a point of attachment of the hydrocarbon linker to the α carbon atom of $Xaa_6$. (e.g., $Xaa_3$ and $Xaa_6$ are each an α-substituted derivative of alanine). In some embodiments, α carbon of $Xaa_3$ and α carbon of $Xaa_6$ are in S-configuration.

In some embodiments, the hydrocarbon crosslinker has formula:

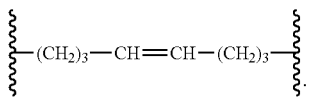

In some embodiments, a stapled polypeptide comprises an amino acid sequence selected from:

```
                                             (SEQ ID NO: 88)
RXaa16L(N-methylQ)Xaa10LRXaa3IQRXaa6(CBA)(2-Nal)

(β-Ala)(β-Ala);

(SEQ ID NO: 89)
RXaa16(Cpa)(N-methylQ)Xaa10(Cpa)RXaa3IQRXaa6(Cpa)

(2-Nal)(β-Ala)(β-Ala);

(SEQ ID NO: 90)
HRQRXaa16LQXaa10LRXaa3IQRXaa6(CBA)(2-Nal);

(SEQ ID NO: 91)
HRQRXaa16LQXaa10(Cpa)RXaa3IQRXaa6(Cpa)(2-Nal);

(SEQ ID NO: 92)
HRQRXaa16LQXaa10(Cha)RXaa3IQRXaa6(Cha)(2-Nal);
and (SEQ ID NO: 93)
LEHRERXaa16LQXaa10LRXaa3IQRXaa6L,
``` wherein $Xaa_{16}$, $Xaa_{10}$, $Xaa_3$ and $Xaa_6$ are each independently an α,α-disubstituted amino acid, wherein one α substituent in the α,α-disubstituted amino acid is methyl, and the other α substituent in the α,α-disubstituted amino acid is a hydrocarbon linker of formula:

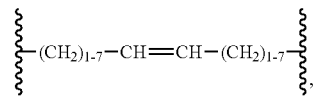

wherein each ⸱ denotes a point of attachment of the hydrocarbon linker to the α carbon atom of $Xaa_{16}$, $Xaa_{10}$, $Xaa_3$ or $Xaa_6$ (one hydrocarbon linker is between $Xaa_{16}$ and $Xaa_{10}$, and another hydrocarbon linker between $Xaa_3$ and $Xaa_6$). In some embodiments, each hydrocarbon crosslinker has formula:

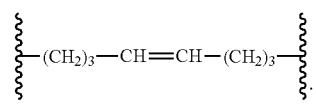

In some embodiments, a stapled polypeptide comprises an amino acid sequence selected from:

```
                                             (SEQ ID NO: 94)
HRXaa14RSLXaa9TLRXaa3IQRXaa6(CBA)(2-Nal);

(SEQ ID NO: 95)
HRXaa14RSLXaa9TLRXaa3IQRXaa6(CBA)(2-Nal);

(SEQ ID NO: 96)
HRXaa14RSLXaa9TLRXaa3IQRXaa6(4-ClPh)(2-Nal);
and (SEQ ID NO: 198)
HRXaa14RSLXaa9TLRXaa3IQRXaa6(4-Cl-Ph)(2-Nal);
``` wherein N-terminus of SEQ ID NO: 95 and SEQ ID NO: 96 is modified with palmitoyl-PEG4, and wherein $Xaa_{14}$, $Xaa_9$, $Xaa_3$ and $Xaa_6$ are each independently an α,α-disubstituted amino acid, wherein one α substituent in the α,α-disubstituted amino acid is methyl, and the other α substituent in the α,α-disubstituted amino acid is a hydrocarbon linker of formula:

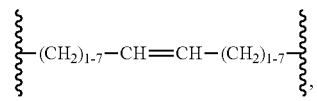

wherein each ⸱ denotes a point of attachment of the hydrocarbon linker to the α carbon atom of $Xaa_{14}$, $Xaa_9$, $Xaa_3$ or $Xaa_6$ (one hydrocarbon linker is between $Xaa_{14}$ and $Xaa_9$, and another hydrocarbon linker between $Xaa_3$ and $Xaa_6$). In some embodiments, each hydrocarbon crosslinker has formula:

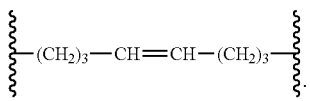

In some embodiments, a stapled polypeptide comprises an amino acid sequence:

(SEQ ID NO: 97)
LQXaa$_{10}$LRDIQRXaa$_6$L(2-Nal)(β-Ala)(β-Ala), wherein Xaa$_{10}$ and Xaa$_6$ are each independently an α,α-disubstituted amino acid, wherein one α substituent in the α,α-disubstituted amino acid is methyl, and the other α substituent in the α,α-disubstituted amino acid is a hydrocarbon linker of formula:

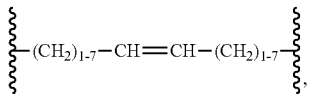

wherein each ⁂ denotes a point of attachment of the hydrocarbon linker to the α carbon atom of Xaa$_{10}$ or Xaa$_6$. In some embodiments, the hydrocarbon crosslinker has formula:

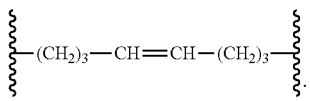

In some embodiments, a stapled polypeptide comprises an amino acid sequence selected from:

(SEQ ID NO: 1)
SXaa$_1$QTXaa$_2$RXaa$_3$Xaa$_4$QXaa$_5$Xaa$_6$Xaa$_7$(2-Nal), (SEQ ID NO: 15)
Xaa$_1$QTXaa$_2$RXaa$_3$Xaa$_4$QXaa$_5$Xaa$_6$Xaa$_7$(2-Nal), (SEQ ID NO: 30)
Xaa$_1$QTXaa$_2$RXaa$_3$Xaa$_4$QXaa$_5$Xaa$_6$Xaa$_7$(2-Nal), (SEQ ID NO: 2)
SLQTLRXaa$_3$IQRXaa$_6$L(2-Nal), (SEQ ID NO: 3)
SLQTLRXaa$_3$IQRXaa$_6$(CBA)(2-Nal), (SEQ ID NO: 16)
AQTARXaa$_3$IQRXaa$_6$L(2-Nal), (SEQ ID NO: 17)
LQTARXaa$_3$AQRXaa$_6$L(2-Nal), (SEQ ID NO: 18)
LQTLRXaa$_3$AQRXaa$_6$A(2-Nal), (SEQ ID NO: 19)
LQTLRXaa$_3$IQAXaa$_6$L(2-Nal), (SEQ ID NO: 20)
LQTLRXaa$_3$IQAXaa$_6$(CBA)(2-Nal),
and (SEQ ID NO: 31)
LQTLRXaa$_3$IQRXaa$_6$L(2-Nal), wherein Xaa$_1$, Xaa$_2$, Xaa$_4$, Xaa$_5$, and Xaa$_7$ are as described herein, and Xaa$_3$ and Xaa$_6$ are each independently an α,α-disubstituted amino acid, wherein one α substituent in the α,α-disubstituted amino acid is methyl, and the other α substituent in the α,α-disubstituted amino acid is a hydrocarbon linker of formula:

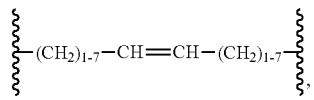

wherein one ⁂ denotes a point of attachment of the hydrocarbon linker to the α carbon atom of Xaa$_3$, and the other ⁂ denotes a point of attachment of the hydrocarbon linker to the α carbon atom of Xaa$_6$. (e.g., Xaa$_3$ and Xaa$_6$ are each an α-substituted derivative of alanine). In some embodiments, α carbon of Xaa$_3$ and α carbon of Xaa$_6$ are in S-configuration. In some embodiments, stapled polypeptide comprising an amino acid sequence SEQ ID NO: 1, SEQ ID NO: 15, SEQ ID NO: 30, SEQ ID NO: 2, SEQ ID NO: 3, SEQ ID NO: 16, SEQ ID NO: 17, SEQ ID NO: 18, SEQ ID NO: 19, SEQ ID NO: 20, or SEQ ID NO: 31, may further comprise any additional amino acids or amino acid sequences, or a combinations thereof, as described herein for an unstapled polypeptide comprising the same SEQ ID NO. For example, the stapled peptide may comprise any of the sequences disclosed in Table 3, or a combination thereof.

In some embodiments, a stapled polypeptide consists of the amino acid sequence:

(SEQ ID NO: 4)
RSLQTLRXaa$_3$IQRXaa$_6$L(2-Nal), wherein the stapled polypeptide contains a hydrocarbon linker of formula:

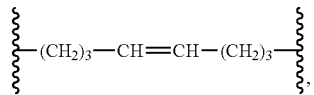

wherein one ⁂ denotes a point of attachment of the hydrocarbon linker to the α carbon atom of Xaa$_3$, and the other ⁂ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in a position), and α carbon of Xaa$_3$ and α carbon of Xaa$_6$ are each in S-configuration.

In some embodiments, a stapled polypeptide consists of the amino acid sequence:

(SEQ ID NO: 5)
RERSLQTLRXaa$_3$IQRXaa$_6$L(2-Nal), wherein the stapled polypeptide contains a hydrocarbon linker of formula:

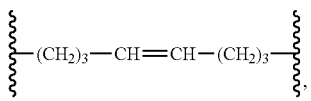

wherein one ξ denotes a point of attachment of the hydrocarbon linker to the α carbon atom of Xaa$_3$, and the other ξ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in α position), and α carbon of Xaa$_3$ and α carbon of Xaa$_6$ are each in S-configuration.

In some embodiments, a stapled polypeptide consists of the amino acid sequence:

(SEQ ID NO: 6)
HRERSLQTLRXaa$_3$IQRXaa$_6$L(2-Nal), wherein the stapled polypeptide contains a hydrocarbon linker of formula:

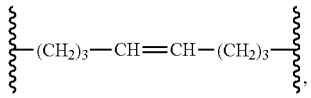

wherein one ξ denotes a point of attachment of the hydrocarbon linker to the α carbon atom of Xaa$_3$, and the other ξ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in α position), and α carbon of Xaa$_3$ and α carbon of Xaa$_6$ are each in S-configuration.

In some embodiments, a stapled polypeptide consists of the amino acid sequence:

(SEQ ID NO: 7)
EHRERSLQTLRXaa$_3$IQRXaa$_6$L(2-Nal), wherein the stapled polypeptide contains a hydrocarbon linker of formula:

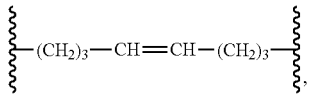

wherein one ξ denotes a point of attachment of the hydrocarbon linker to the α carbon atom of Xaa$_3$, and the other ξ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in α position), and α carbon of Xaa$_3$ and α carbon of Xaa$_6$ are each in S-configuration.

In some embodiments, a stapled polypeptide consists of the amino acid sequence:

(SEQ ID NO: 8)
QLEHRERSLQTLRXaa$_3$IQRXaa$_6$L(2-Nal), wherein the stapled polypeptide contains a hydrocarbon linker of formula:

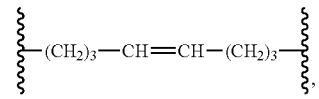

wherein one ξ denotes a point of attachment of the hydrocarbon linker to the α carbon atom of Xaa$_3$, and the other ξ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in α position), and α carbon of Xaa$_3$ and α carbon of Xaa$_6$ are each in S-configuration.

In some embodiments, a stapled polypeptide consists of the amino acid sequence:

(SEQ ID NO: 9)
EHRERSLQTLRXaa$_3$IQRXaa$_6$(CBA)(2-Nal), wherein the stapled polypeptide contains a hydrocarbon linker of formula:

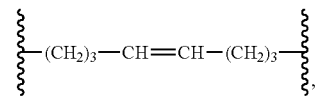

wherein one ξ denotes a point of attachment of the hydrocarbon linker to the α carbon atom of Xaa$_3$, and the other ξ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in α position), and α carbon of Xaa$_3$ and α carbon of Xaa$_6$ are each in S-configuration.

In some embodiments, a stapled polypeptide consists of the amino acid sequence:

(SEQ ID NO: 10)
QERSLQTLRXaa$_3$IQRXaa$_6$L(2-Nal), wherein the stapled polypeptide contains a hydrocarbon linker of formula:

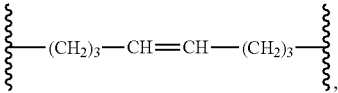

wherein one ξ denotes a point of attachment of the hydrocarbon linker to the α carbon atom of Xaa$_3$, and the other ξ denotes a point of attachment of the hydrocarbon linker to the α carbon atom of Xaa$_6$, one α substituent in Xaa₃ and Xaa₆ is methyl (i.e., Xaa₃ and Xaa₆ are each alanine that is substituted with the hydrocarbon linker in a position), and α carbon of Xaa₃ and α carbon of Xaa₆ are each in S-configuration.

In some embodiments, a stapled polypeptide consists of the amino acid sequence:

HQERSLQTLRXaa₃IQRXaa₆L(2-Nal), (SEQ ID NO: 11)

wherein the stapled polypeptide contains a hydrocarbon linker of formula:

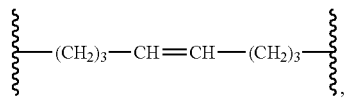

wherein one § denotes a point of attachment of the hydrocarbon linker to the α carbon atom of Xaa₃, and the other § denotes a point of attachment of the hydrocarbon linker to the α carbon atom of Xaa₆, one α substituent in Xaa₃ and Xaa₆ is methyl (i.e., Xaa₃ and Xaa₆ are each alanine that is substituted with the hydrocarbon linker in a position), and α carbon of Xaa₃ and α carbon of Xaa₆ are each in S-configuration.

In some embodiments, a stapled polypeptide consists of the amino acid sequence:

EHQERSLQTLRXaa₃IQRXaa₆L(2-Nal), (SEQ ID NO: 12)

wherein the stapled polypeptide contains a hydrocarbon linker of formula:

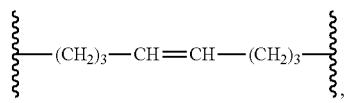

wherein one § denotes a point of attachment of the hydrocarbon linker to the α carbon atom of Xaa₃, and the other § denotes a point of attachment of the hydrocarbon linker to the α carbon atom of Xaa₆, one α substituent in Xaa₃ and Xaa₆ is methyl (i.e., Xaa₃ and Xaa₆ are each alanine that is substituted with the hydrocarbon linker in a position), and α carbon of Xaa₃ and α carbon of Xaa₆ are each in S-configuration.

In some embodiments, a stapled polypeptide consists of the amino acid sequence:

RERSLQTLRXaa₃IQRXaa₆(CBA)(2-Nal), (SEQ ID NO: 13)

wherein the stapled polypeptide contains a hydrocarbon linker of formula:

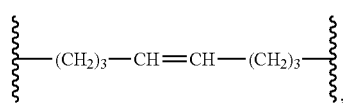

wherein one § denotes a point of attachment of the hydrocarbon linker to the α carbon atom of Xaa₃, and the other § denotes a point of attachment of the hydrocarbon linker to the α carbon atom of Xaa₆, one α substituent in Xaa₃ and Xaa₆ is methyl (i.e., Xaa₃ and Xaa₆ are each alanine that is substituted with the hydrocarbon linker in a position), and α carbon of Xaa₃ and α carbon of Xaa₆ are each in S-configuration.

In some embodiments, a stapled polypeptide consists of the amino acid sequence:

HRERSLQTLRXaa₃IQRXaa₆(CBA)(2-Nal), (SEQ ID NO: 14)

wherein the stapled polypeptide contains a hydrocarbon linker of formula:

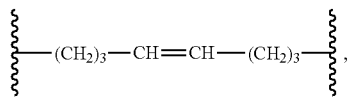

wherein one § denotes a point of attachment of the hydrocarbon linker to the α carbon atom of Xaa₃, and the other § denotes a point of attachment of the hydrocarbon linker to the α carbon atom of Xaa₆, one α substituent in Xaa₃ and Xaa₆ is methyl (i.e., Xaa₃ and Xaa₆ are each alanine that is substituted with the hydrocarbon linker in a position), and α carbon of Xaa₃ and α carbon of Xaa₆ are each in S-configuration.

In some embodiments, a stapled polypeptide consists of the amino acid sequence:

AQTARXaa₃IQRXaa₆L(2-Nal), (SEQ ID NO: 21)

wherein the stapled polypeptide contains a hydrocarbon linker of formula:

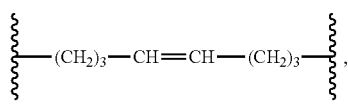

wherein one § denotes a point of attachment of the hydrocarbon linker to the α carbon atom of Xaa₃, and the other § denotes a point of attachment of the hydrocarbon linker to the α carbon atom of Xaa₆, one α substituent in Xaa₃ and Xaa₆ is methyl (i.e., Xaa₃ and Xaa₆ are each alanine that is substituted with the hydrocarbon linker in a position), and α carbon of Xaa₃ and α carbon of Xaa₆ are each in S-configuration.

In some embodiments, a stapled polypeptide consists of the amino acid sequence:

LQTARXaa₃AQRXaa₆L(2-Nal), (SEQ ID NO: 22)

wherein the stapled polypeptide contains a hydrocarbon linker of formula:

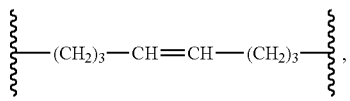

wherein one ⸹ denotes a point of attachment of the hydrocarbon linker to the α carbon atom of Xaa$_3$, and the other ⸹ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in a position), and α carbon of Xaa$_3$ and α carbon of Xaa$_6$ are each in S-configuration.

In some embodiments, a stapled polypeptide consists of the amino acid sequence:

(SEQ ID NO: 23)
LQTLRXaa$_3$AQRXaa$_6$A(2-Nal), wherein the stapled polypeptide contains a hydrocarbon linker of formula:

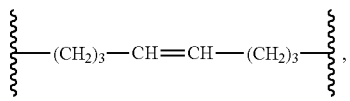

wherein one ⸹ denotes a point of attachment of the hydrocarbon linker to the α carbon atom of Xaa$_3$, and the other ⸹ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in a position), and α carbon of Xaa$_3$ and α carbon of Xaa$_6$ are each in S-configuration.

In some embodiments, a stapled polypeptide consists of the amino acid sequence:

(SEQ ID NO: 24)
LQTLRXaa$_3$IQAXaa$_6$L(2-Nal), wherein the stapled polypeptide contains a hydrocarbon linker of formula:

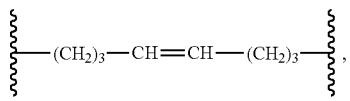

wherein one ⸹ denotes a point of attachment of the hydrocarbon linker to the α carbon atom of Xaa$_3$, and the other ⸹ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in a position), and α carbon of Xaa$_3$ and α carbon of Xaa$_6$ are each in S-configuration.

In some embodiments, a stapled polypeptide consists of the amino acid sequence:

(SEQ ID NO: 25)
LQTLRXaa$_3$IQAXaa$_6$(CBA)(2-Nal), wherein the stapled polypeptide contains a hydrocarbon linker of formula:

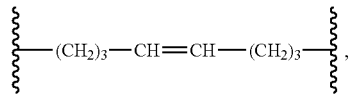

wherein one ⸹ denotes a point of attachment of the hydrocarbon linker to the α carbon atom of Xaa$_3$, and the other ⸹ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in a position), and α carbon of Xaa$_3$ and α carbon of Xaa$_6$ are each in S-configuration.

In some embodiments, a stapled polypeptide consists of the amino acid sequence:

(SEQ ID NO: 26)
LQTLRXaa$_3$IQAXaa$_6$L(2-Nal)(β-Ala)(β-Ala), wherein the stapled polypeptide contains a hydrocarbon linker of formula:

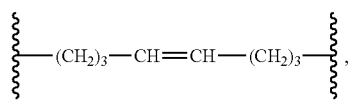

wherein one ⸹ denotes a point of attachment of the hydrocarbon linker to the α carbon atom of Xaa$_3$, and the other ⸹ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in a position), and α carbon of Xaa$_3$ and α carbon of Xaa$_6$ are each in S-configuration.

In some embodiments, a stapled polypeptide consists of the amino acid sequence:

(SEQ ID NO: 27)
LQTLRXaa$_3$IQAXaa$_6$L(2-Nal)AA, wherein the stapled polypeptide contains a hydrocarbon linker of formula:

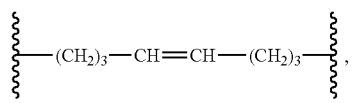

wherein one ⸹ denotes a point of attachment of the hydrocarbon linker to the α carbon atom of Xaa$_3$, and the other ⸹ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in a position), and α carbon of Xaa$_3$ and α carbon of Xaa$_6$ are each in S-configuration.

In some embodiments, a stapled polypeptide consists of the amino acid sequence:

(SEQ ID NO: 28)
HRERSLQTLRXaa$_3$IQAXaa$_6$L(2-Nal), wherein the stapled polypeptide contains a hydrocarbon linker of formula:

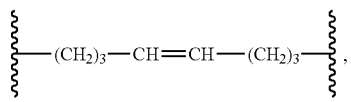

wherein one $\{$ denotes a point of attachment of the hydrocarbon linker to the α carbon atom of Xaa$_3$, and the other $\{$ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in a position), and α carbon of Xaa$_3$ and α carbon of Xaa$_6$ are each in S-configuration.

In some embodiments, a stapled polypeptide consists of the amino acid sequence:

(SEQ ID NO: 29)
HRERSLQTLRXaa$_3$IQAXaa$_6$(CBA)(2-Nal), wherein the stapled polypeptide contains a hydrocarbon linker of formula:

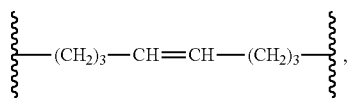

wherein one $\{$ denotes a point of attachment of the hydrocarbon linker to the α carbon atom of Xaa$_3$, and the other $\{$ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in a position), and α carbon of Xaa$_3$ and α carbon of Xaa$_6$ are each in S-configuration.

In some embodiments, a stapled polypeptide consists of the amino acid sequence:

(SEQ ID NO: 75)
LQTARXaa$_3$IQRXaa$_6$L(2-Nal), (SEQ ID NO: 76)
LQTLRXaa$_3$AQRXaa$_6$L(2-Nal),
or (SEQ ID NO: 77)
LQTLRXaa$_3$IQRXaa$_6$A(2-Nal), wherein the stapled polypeptide contains a hydrocarbon linker of formula:

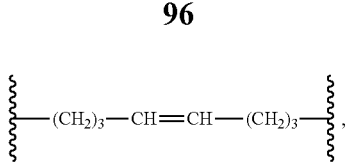

wherein one $\{$ denotes a point of attachment of the hydrocarbon linker to the α carbon atom of Xaa$_3$, and the other $\{$ denotes a point of attachment of the hydrocarbon linker to the α carbon atom of Xaa$_6$.

In some embodiments, a stapled polypeptide consists of the amino acid sequence:

(SEQ ID NO: 32)
LQTLRXaa$_3$IQRXaa$_6$L(2-Nal)PD, wherein the stapled polypeptide contains a hydrocarbon linker of formula:

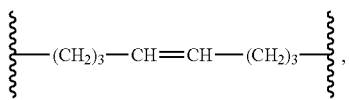

wherein one $\{$ denotes a point of attachment of the hydrocarbon linker to the α carbon atom of Xaa$_3$, and the other $\{$ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in a position), and α carbon of Xaa$_3$ and α carbon of Xaa$_6$ are each in S-configuration.

In some embodiments, a stapled polypeptide consists of the amino acid sequence:

(SEQ ID NO: 33)
LQTLRXaa$_3$IQRXaa$_6$L(2-Nal)P, wherein the stapled polypeptide contains a hydrocarbon linker of formula:

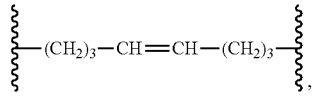

wherein one $\{$ denotes a point of attachment of the hydrocarbon linker to the α carbon atom of Xaa$_3$, and the other $\{$ denotes a point of attachment of the hydrocarbon linker to the α carbon atom of Xaa$_6$, one α substituent in Xaa$_3$ and Xaa$_6$ is methyl (i.e., Xaa$_3$ and Xaa$_6$ are each alanine that is substituted with the hydrocarbon linker in a position), and α carbon of Xaa$_3$ and α carbon of Xaa$_6$ are each in S-configuration.

In some embodiments, a stapled polypeptide consists of the amino acid sequence:

(SEQ ID NO: 34)
LQTLRXaa₃IQRXaa₆L(2-Nal)(β-Ala)(β-Ala), wherein the stapled polypeptide contains a hydrocarbon linker of formula:

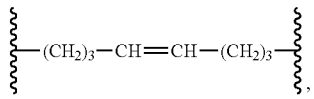

wherein one § denotes a point of attachment of the hydrocarbon linker to the α carbon atom of Xaa₃, and the other § denotes a point of attachment of the hydrocarbon linker to the α carbon atom of Xaa₆, one α substituent in Xaa₃ and Xaa₆ is methyl (i.e., Xaa₃ and Xaa₆ are each alanine that is substituted with the hydrocarbon linker in a position), and α carbon of Xaa₃ and α carbon of Xaa₆ are each in S-configuration.

In some embodiments, a stapled polypeptide consists of the amino acid sequence:

(SEQ ID NO: 34a)
LQTLRXaa₃IQRXaa₆L(2-Nal)(β-Ala)(β-Ala), wherein C-terminus in SEQ ID NO: 34a is modified with GRKKRRQRRRPQK(PEG4-palmitoyl)NH₂, and
wherein the stapled polypeptide contains a hydrocarbon linker of formula:

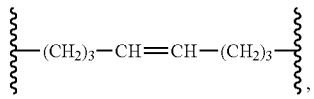

wherein one § denotes a point of attachment of the hydrocarbon linker to the α carbon atom of Xaa₃, and the other § denotes a point of attachment of the hydrocarbon linker to the α carbon atom of Xaa₆.

In some embodiments, a stapled polypeptide consists of the amino acid sequence:

(SEQ ID NO: 36)
QLEHRERSLXaa₁TLRXaa₃IQRML(2-Nal), wherein the stapled polypeptide contains a hydrocarbon linker of formula:

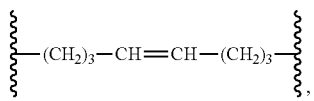

wherein one § denotes a point of attachment of the hydrocarbon linker to the α carbon atom of Xaa₁, and the other § denotes a point of attachment of the hydrocarbon linker to the α carbon atom of Xaa₃, one α substituent in Xaa₁ and Xaa₃ is methyl (i.e., Xaa₁ and Xaa₃ are each alanine that is substituted with the hydrocarbon linker in a position), and α carbon of Xaa₁ and α carbon of Xaa₃ are each in S-configuration.

In some embodiments, a stapled polypeptide consists of the amino acid sequence:

(SEQ ID NO: 78)
QLEHRERSLXaa₁TLRXaa₃IQR(2-Abu)L(2-Nal)(β-Ala)
(β-Ala), wherein the stapled polypeptide contains a hydrocarbon linker of formula:

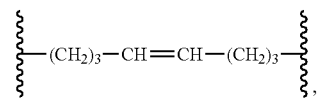

wherein one § denotes a point of attachment of the hydrocarbon linker to the α carbon atom of Xaa₁, and the other § denotes a point of attachment of the hydrocarbon linker to the α carbon atom of Xaa₃.

In some embodiments, a stapled polypeptide consists of the amino acid sequence:

(SEQ ID NO: 39)
REXaa₁SLQXaa₂LRXaa₃IQRXaa₄L(2-Nal), wherein the stapled polypeptide contains a hydrocarbon linker of formula:

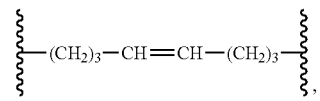

wherein one § denotes a point of attachment of the hydrocarbon linker to the α carbon atom of Xaa₁, and the other § denotes a point of attachment of the hydrocarbon linker to the α carbon atom of Xaa₂, one α substituent in Xaa₁ and Xaa₂ is methyl (i.e., Xaa₁ and Xaa₂ are each alanine that is substituted with the hydrocarbon linker in a position), and α carbon of Xaa₁ and α carbon of Xaa₂ are each in S-configuration; and
a hydrocarbon linker of formula:

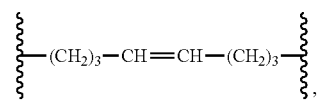

wherein one § denotes a point of attachment of the hydrocarbon linker to the α carbon atom of Xaa₃, and the other § denotes a point of attachment of the hydrocarbon linker to the α carbon atom of Xaa₄, one α substituent in Xaa₃ and Xaa₄ is methyl (i.e., Xaa₃ and Xaa₃ are each alanine that is substituted with the hydrocarbon linker in a position), and α carbon of Xaa₃ and α carbon of Xaa₄ are each in S-configuration.

In some embodiments, a stapled polypeptide consists of the amino acid sequence:

(SEQ ID NO: 40)
REXaa₁SLQXaa₂LRXaa₃IQRXaa₄L(2-Nal)(β-Ala)(β-Ala), wherein the stapled polypeptide contains a hydrocarbon linker of formula:

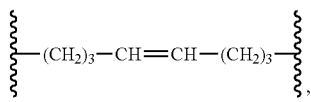

wherein one ⸹ denotes a point of attachment of the hydrocarbon linker to the α carbon atom of Xaa₁, and the other ⸹ denotes a point of attachment of the hydrocarbon linker to the α carbon atom of Xaa₂, one α substituent in Xaa₁ and Xaa₂ is methyl (i.e., Xaa₁ and Xaa₂ are each alanine that is substituted with the hydrocarbon linker in a position), and α carbon of Xaa₁ and α carbon of Xaa₂ are each in S-configuration; and
a hydrocarbon linker of formula:

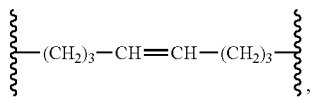

wherein one ⸹ denotes a point of attachment of the hydrocarbon linker to the α carbon atom of Xaa₃, and the other ⸹ denotes a point of attachment of the hydrocarbon linker to the α carbon atom of Xaa₄, one α substituent in Xaa₃ and Xaa₄ is methyl (i.e., Xaa₃ and Xaa₃ are each alanine that is substituted with the hydrocarbon linker in a position), and α carbon of Xaa₃ and α carbon of Xaa₄ are each in S-configuration.

In some embodiments, a stapled polypeptide consists of the amino acid sequence selected from:

(SEQ ID NO: 79)
EXaa₁SLQXaa₂LRXaa₃IQRXaa₄(2-Nal)(β-Ala)(β-Ala);

(SEQ ID NO: 82)
HREXaa₁SLQXaa₂LRXaa₃IQRXaa₄CBA)(2-Nal);

(SEQ ID NO: 83)
HREXaa₁SLQXaa₂LRXaa₃IQQXaa₄(CBA)(2-Nal);

(SEQ ID NO: 84)
HR(N-methylE)Xaa₁SLQXaa₂LRXaa₃IQRXaa₄(CBA)(2-Nal);

(SEQ ID NO: 85)
HREXaa₁SLQXaa₂L(N-methylR)Xaa₃IQRXaa₄(CBA)(2-Nal);

(SEQ ID NO: 86)
HR(N-methylQ)Xaa₁S(Cha)(N-methylQ)Xaa₂(Cha)RXaa₃IQRXaa₄(Cha)(2-Nal);
and (SEQ ID NO: 87)
HRQXaa₁SLQXaa₂LRXaa₃IQRXaa₄(CBA)(2-Nal), wherein one ⸹ denotes a point of attachment of the hydrocarbon linker to the α carbon atom of Xaa₁, and the other ⸹ denotes a point of attachment of the hydrocarbon linker to the α carbon atom of Xaa₂, one α substituent in Xaa₁ and Xaa₂ is methyl (i.e., Xaa₁ and Xaa₂ are each alanine that is substituted with the hydrocarbon linker in a position), and α carbon of Xaa₁ and α carbon of Xaa₂ are each in S-configuration; and
a hydrocarbon linker of formula:

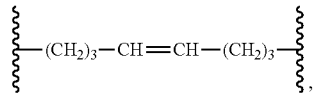

wherein one ⸹ denotes a point of attachment of the hydrocarbon linker to the α carbon atom of Xaa₃, and the other ⸹ denotes a point of attachment of the hydrocarbon linker to the α carbon atom of Xaa₄, one α substituent in Xaa₃ and Xaa₄ is methyl (i.e., Xaa₃ and Xaa₃ are each alanine that is substituted with the hydrocarbon linker in a position), and α carbon of Xaa₃ and α carbon of Xaa₄ are each in S-configuration.

In some embodiments, a stapled polypeptide consists of the amino acid sequence selected from:

(SEQ ID NO: 80)
HREXaa₁₅SLQXaa₁₀LR(Nle)IQR(Nle)L(2-Nal);
and (SEQ ID NO: 81)
HREXaa₁₅SLQXaa₁₀LR(Nle)IQR(Nle)(CBA)(2-Nal), wherein the stapled polypeptide contains a hydrocarbon linker of formula:

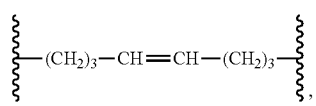

wherein one ⸹ denotes a point of attachment of the hydrocarbon linker to the α carbon atom of Xaa₁₅, and the other ⸹ denotes a point of attachment of the hydrocarbon linker to the α carbon atom of Xaa₁₀.

In some embodiments, a stapled polypeptide consists of the amino acid sequence selected from:

(SEQ ID NO: 98)
LQTLEXaa₃IQRXaa₆L(2-Nal);

(SEQ ID NO: 99)
LQTLRXaa₃IQEXaa₆L(2-Nal);

(SEQ ID NO: 100)
LQTLKXaa₃IQRXaa₆L(2-Nal);
and (SEQ ID NO: 101)
LQTLRXaa₃IQKXaa₆L(2-Nal), wherein the stapled polypeptide contains a hydrocarbon linker of formula:

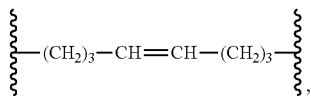

wherein one ⸳ denotes a point of attachment of the hydrocarbon linker to the α carbon atom of Xaa$_3$, and the other ⸳ denotes a point of attachment of the hydrocarbon linker to the α carbon atom of Xaa$_6$.

In some embodiments, a stapled polypeptide consists of the amino acid sequence selected from:

```
                                        (SEQ ID NO: 102)
(D-L)QTIRXaa₃IQRXaa₆L(2-Nal);

(SEQ ID NO: 103)
LQT(D-L)RXaa₃IQRXaa₆L(2-Nal);

(SEQ ID NO: 104)
LQTLRXaa₃(D-I)QRXaa₆L(2-Nal);
and (SEQ ID NO: 105)
LQTLRXaa₃IQRXaa₆(D-L)(2-Nal),
``` wherein the stapled polypeptide contains a hydrocarbon linker of formula:

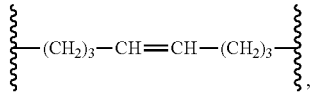

wherein one ⸳ denotes a point of attachment of the hydrocarbon linker to the α carbon atom of Xaa$_3$, and the other ⸳ denotes a point of attachment of the hydrocarbon linker to the α carbon atom of Xaa$_6$.

In some embodiments, any one of the polypeptides described herein may have an N-terminus or C-terminus chemically modified. For example, the N-terminus of the polypeptide may be modified with a moiety selected from acetyl, propionyl, hexanoyl, 3-phenylpropanoyl, 2-cyclohexylacetyl, diphenylacetyl, 3,5-dihydroxybenzoic acid, 4-(trifluoromethyl)benzoic acid, 5-phenylvaleric acid, 4-biphenyl acetic acid, dimethyl, HOCH$_2$CH$_2$CO—, and palmitoyl-PEG4.

In some embodiments, the N-terminus is modified with Ac.

In some embodiments, the N-terminus is modified with palmitoyl-PEG4.

In some embodiments, the C-terminus of the polypeptide may be modified with a moiety selected from NH$_2$, (β-Ala) (β-Ala), (β-Ala)(β-Ala)NH$_2$, GRKKRRQRRRPQK(PEG4-palmitoyl)NH$_2$, GRKKRRQRRRPQNH$_2$, and 1-(2-aminoethyl)-4-methylpiperazine.

In some embodiments, C-terminus of the polypeptide is modified with NH$_2$.

In some embodiments, C-terminus of the polypeptide is modified with (β-Ala)(β-Ala).

In some embodiments, the N-terminus of the polypeptide is modified with acetyl, and the C-terminus of the polypeptide is modified with NH$_2$.

In some embodiments, a salt of any of the polypeptides disclosed herein is formed between an acid and a basic group of the polypeptide, such as an amino functional group, or a base and an acidic group of the polypeptide, such as a carboxyl functional group. According to another embodiment, the polypeptide is a pharmaceutically acceptable acid addition salt.

In some embodiments, acids commonly employed to form pharmaceutically acceptable salts of any of the polypeptides disclosed herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of any of the polypeptides disclosed herein include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C$_1$-C$_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the salt of the polypeptide is trifluoroacetic salt, acetic salt, or hydrochloric salt. In some embodiments, the polypeptide, or a pharmaceutically acceptable salt thereof, is substantially isolated. In some embodiments, the polypeptide, or a pharmaceutically acceptable salt thereof described herein is stable at 2-8° C. for at least one month.

Preparation and Purification of Peptides

The present disclosures also provide methods to manufacture a polypeptide described herein. In some embodiments, a method for manufacturing a polypeptide described herein comprises performing one or more chemical synthesis methods known to the skilled artisan and described herein. See, for example, Fields et al., Chapter 3 in Synthetic Peptides: A User's Guide, ed. Grant, W.H. Freeman & Co., New York, N.Y., 1992, p. 77; and Bird, G. H., et al., Methods Enzymol 446, 369-86 (2008). In some embodiments, a method for manufacturing a polypeptide described herein comprises using solid phase synthesis to generate the polypeptide. For instance, the polypeptide described herein may be manufactured by the automated Merrifield techniques of solid phase synthesis with the alpha-NH$_2$ protected by either t-Boc or Fmoc chemistry using side chain protected amino acids on, for example, an Applied Biosystems Peptide Synthesizer Model 430A or 431 or the AAPPTEC multichannel synthesizer APEX 396.

In some embodiments, the polypeptide described herein may also be manufactured in a high-throughput, combinatorial fashion, e.g., using a high-throughput multichannel combinatorial synthesizer. Other methods of synthesizing peptides are known in the art.

The methods to manufacture the polypeptides described herein may further comprise forming one or more hydrocarbon linkers. The one or more hydrocarbon linkers may be formed by subjecting the polypeptide containing at least two $\alpha,\alpha$-disubstituted amino acids as described herein (e.g., Xaa$_1$, Xaa$_2$, Xaa$_3$, Xaa$_4$, or Xaa$_5$) to metal-mediated ring-closing olefin metathesis. For instance, the synthetic strategy for generating hydrocarbon linkers based on modified Ala residues ($\alpha$-methyl, $\alpha$-alkenyl amino acids) would be known to those of ordinary skill in the art. The hydrocarbon linker connects adjacent turns of the $\alpha$-helix, flanked on each end by an $\alpha$-methyl group. The basis of the chemistry to generate this hydrocarbon linker is incorporation of two $\alpha$-methyl, $\alpha$-alkenyl amino acids during synthesis of a peptide (See Kim 2011). A hydrocarbon linker between these modified amino acids is then generated by use of a ruthenium-mediated ring-closing olefin metathesis. Following the ring closure, the polypeptide may be deprotected and released from such reaction, resulting in a polypeptide comprising one or more hydrocarbon linkers.

The present disclosures also encompass methods of purifying a polypeptide manufactured according to the methods described herein. In some embodiments, the polypeptide is purified by high-performance liquid chromatograph (HPLC). In some embodiments, the purified polypeptide is substantially free of metal. As used herein, the term "substantially free of metal" refers to a composition comprising a polypeptide described herein and a metal at a concentration of less than about 0.5, 1, 2.5, 5, 10, 20, 30, 40, 50, 60, 70, 80, 90, or 100 ppm. In some embodiments, the purified polypeptide is substantially free of metal, comprising less than about 0.5 ppm of metal. In some embodiments, the purified polypeptide comprises less than about 5 ppm of metal. In some embodiments, the purified polypeptide comprises less than about 20 ppm of metal.

Methods of Use

In some embodiments, administration of a polypeptide (e.g., stapled polypeptide) to a subject inhibits Wnt signaling in the subject. In some embodiments, administering of a stabilized BCL9 peptide inhibits binding of BCL9 to $\beta$-catenin. In some embodiments, administration of a stabilized BCL9 peptide inhibits canonical Wnt/$\beta$-catenin signaling. In some embodiments, administering administration of a stabilized BCL9 peptide treat a disease in a subject.

In some embodiments, the polypeptides described herein (e.g., stapled polypeptide) are capable of inhibiting the binding of BCL9 to $\beta$-catenin in vitro and/or in vivo. In some embodiments, a polypeptide derived from the HD2 domain of human BCL9 protein has one or more improved biological functions as compared to an unstapled wild-type HD2 domain of human BCL9 protein or as compared to a fragment of an unstapled wild-type HD2 domain. The one or more biological functions may be selected from one or more of: (1) inhibiting binding of BCL9 to (3-catenin; (2) inhibiting canonical Wnt/$\beta$-catenin signaling; (3) decreasing regulatory T cell survival; (4) decreasing expression of VEGF in a tumor; (5) increasing CD4+ T cell and CD8+ T cell infiltration into a tumor; (6) increasing T helper 17 (Th17) cells in a tumor; (7) decreasing dendritic cells in a tumor; (8) having a half-life (T1/2) greater than at least 2 hours when administrated to a subject; (9) inducing a tumor microenvironment favoring an immune reaction; and (10) inhibiting tumor growth, cancer stem cell proliferation, and/or tumor metastasis.

In some embodiments, a polypeptide described herein exhibits favorable biological functions in some or each of the categories listed above, e.g., potencies in various biochemical and cellular bioassays including a cell-based Wnt and/or $\beta$-catenin transcription assay.

For instance, without being bound to any theory, the polypeptide described herein may have an improved biological function in inhibiting binding of BCL9 to $\beta$-catenin, as assessed in various in vitro assays e.g., Alpha assay or Wnt reporter assay, as compared to a control polypeptide, e.g., an unstapled wild-type human BCL9 HD2 domain. In this context, a polypeptide described herein may have an improved $K_D$ value as compared to that of the control polypeptide or the polypeptide described herein may bind to $\beta$-catenin in presence of the control polypeptide, indicating that the polypeptide described herein has an improved ability to inhibit binding of BCL9 to $\beta$-catenin as compared to the control polypeptide. In some embodiments, the assay used to assess the biological function of the polypeptide described herein provides quantitative readout(s), and the readouts observed with a disclosed polypeptide are at least 30%, 40%, 50%, 60%, 70%, 80%, 90%, 100%, 200%, 300%, or more changed/improved as compared to those observed with a vehicle control polypeptide (e.g., an unstapled wild-type human BCL9 HD2 domain).

Binding of BCL9 to $\beta$-Catenin

In some embodiments, a polypeptide or variant described herein inhibits binding of BCL9 to $\beta$-catenin in vitro and/or in vivo. In some embodiments, the polypeptide or variant disclosed herein inhibits the interaction between Pygo and BCL9 or the formation of a Pygo/BCL9/$\beta$-catenin complex. Pygopus (Pygo) and Legless (Lgs) were discovered in Drosophila as new Wnt signaling components that are essential for Armadillo-mediated transcription during normal development (See e.g., Belenkaya et al., Development (2002) 129(17): 4089-4101). Pygo and BCL9/Legless transduce the Wnt signal by promoting the transcriptional activity of beta-catenin/Armadillo in normal and malignant cells. The ability of a polypeptide to inhibit binding of BCL9 to $\beta$-catenin can be assessed in various assays known in the art. In some embodiments, the polypeptide described herein inhibits binding of BCL9 to $\beta$-catenin when assessed in a Homogeneous Time Resolved Fluorescence (HTRF) binding assay. In this assay, a polypeptide is conjugated to a tag that can recognize another tag attached to its target protein (i.e., $\beta$-catenin). When the polypeptide is bound to the target protein and therefore the two tags are in proximity, a signal is generated and can be quantitatively read to calculate the binding affinity of the polypeptide. In some embodiments, the binding affinity of the polypeptide in this assay is compared against that of a control polypeptide (e.g., an unstapled wild-type HD2 domain human BCL9) to detect improved binding affinity as compared to that of the control polypeptide, indicating that the polypeptide likely would inhibit binding of BCL9 to $\beta$-catenin more efficiently than the control polypeptide. The assay may be conducted in the presence or absence of an untagged control polypeptide. The assay may also be conducted by tagging a control polypeptide (e.g., an unstapled wild-type HD2 domain human BCL9) in the presence or absence of an untagged polypeptide described herein.

In some embodiments, a polypeptide described herein inhibits binding of BCL9 to β-catenin when assessed in an Amplified Luminescence Proximity Homogeneous Assay (ALPHA). In this assay, a polypeptide is conjugated to a donor bead and its target protein (i.e., β-catenin) is attached to an acceptor bead. When the two beads are in proximity due to the binding of the polypeptide to the target protein, a signal is generated and the binding affinity of the polypeptide can be quantitatively calculated. In some embodiments, the binding affinity of the polypeptide in this assay is compared against that of a vehicle or control polypeptide (e.g., an unstapled wild-type HD2 domain human BCL9) to detect improved binding affinity as compared to that of the vehicle or control polypeptide, indicating that the polypeptide likely would inhibit binding of BCL9 to β-catenin more efficiently than the control polypeptide. The assay may be conducted in the presence or absence of an unconjugated control polypeptide. The assay may also be conducted by conjugating the control polypeptide in the presence or absence of an unconjugated polypeptide described herein.

In various embodiments, a polypeptide described herein inhibits binding of BCL9 to β-catenin when assessed in a Wnt transcription assay. In some embodiments, the Wnt transcription assay is a cell-based assay. In some embodiments, the cell-based Wnt transcription assay is a GeneBLAzer® beta-lactamase (bla) reporter assay. Various cell lines, transformed cell lines or primary cells derived from a healthy subject or subject suffering from a disease can be used in this assay. A cell line known to be dependent on canonical Wnt/β-catenin signaling for its survival may also be used. In some embodiments, CellSensor™ LEF/TCF-bla HCT-116 cells are used in this reporter assay. These cells contain a beta-lactamase (BLA) reporter gene under the control of a 0-catenin/LEF/TCF response element stably integrated into HCT-116 cells. As the cells constitutively express beta-lactamase, adding a polypeptide that inhibits binding of BCL9 to β-catenin in this assay leads to reduced production of beta-lactamase. The efficiency of the polypeptide in suppressing Wnt transcription can therefore be quantitatively calculated in this assay. In some embodiments, a polypeptide described herein suppresses the Wnt transcription as measured in a GeneBLAzer® beta-lactamase (bla) reporter assay, which is indicative of the ability of the polypeptide to inhibit binding of BCL9 to β-catenin. In some embodiments, a polypeptide tested in this assay shows an improved $IC_{50}$ in suppressing Wnt transcription as compared to that of a vehicle or control polypeptide (e.g., an unstapled wild-type HD2 domain human BCL9), indicating that the disclosed polypeptide likely inhibits binding of BCL9 to β-catenin more efficiently than the vehicle or control polypeptide.

In some embodiments, a polypeptide described herein inhibits binding of BLC9 to β-catenin when assessed in a cell-viability assay. In some embodiments, the cell-viability assay is a CellTiterGlo luminescent assay, wherein the viability of cells is quantitatively measured. Various cell lines, transformed cell lines or primary cells derived from a healthy subject or subject suffering from a disease can be used in this assay. In some embodiments, a polypeptide described herein suppresses cell growth in this assay more efficiently than a vehicle or control polypeptide (e.g., an unstapled wild-type HD2 domain human BCL9), indicating that the disclosed polypeptide likely inhibits binding of BCL9 to β-catenin more efficiently than the vehicle or control polypeptide.

Canonical Wnt/β-Catenin Signaling

In certain embodiments, the polypeptides described herein can inhibit canonical Wnt/1-catenin signaling. Canonical Wnt/β-catenin signaling can be assessed in various in vitro and/or in vivo assays. In some embodiments, the effect of the polypeptide described herein on canonical Wnt/1-catenin signaling is assessed in a cell-based Wnt transcription assay, e.g., a GeneBLAzer® beta-lactamase (bla) reporter assay. The GeneBLAzer® beta-lactamase (bla) reporter assay measures the strength of canonical Wnt/β-catenin signaling by its ability to control the 0-catenin/LEF/TCF response element and therefore can be used to assess whether a test agent can attenuate or increase the strength of canonical Wnt/1-catenin signaling control of its transcription targets. In some embodiments, a polypeptide described herein suppresses the Wnt transcription as measured in a GeneBLAzer® beta-lactamase (bla) reporter assay, indicating that the polypeptide can inhibit canonical Wnt/1-catenin signaling. In some embodiments, the polypeptide in this assay shows an improved $IC_{50}$ in suppressing Wnt transcription as compared to that of a vehicle or control polypeptide (e.g., an unstapled wild-type HD2 domain human BCL9), indicating that the polypeptide described herein has an improved ability to inhibit canonical Wnt/β-catenin signaling as compared to the vehicle or control polypeptide.

The ability of a polypeptide described herein to inhibit canonical Wnt/β-catenin signaling may also be assessed by measuring the gene expression and/or protein expression of target genes that are transcriptionally controlled by canonical Wnt/0-catenin signaling. The expression of target genes may be assessed in transformed cells contacted with a polypeptide described herein or a subject administered with such polypeptide. The target genes include e.g., c-myc, ccnd1, cd44, LGR5, VEGFA, AXIN2, and LEF1. The expression level of one or more target genes associated with canonical Wnt/1-catenin signaling may be analyzed using known methods in the art, e.g., cell staining, flow cytometry, western-blotting, and/or real-time quantitative PCR (rt-qPCR) analysis. In some embodiments, a polypeptide described herein reduces the expression of one or more target genes in a cell. In some embodiments, the polypeptide described herein reduces the expression of one or more target gene more efficiently than a vehicle or control polypeptide (e.g., an unstapled wild-type HD2 domain human BCL9).

Regulatory T Cell Survival

In some embodiments, a polypeptide described herein decreases regulatory T cell survival. In some embodiments, when administered to a subject, the polypeptide decreases regulatory T cell survival locally (e.g., in a tumor) and/or systemically (e.g., in blood). In some embodiments, when administered to a subject, the polypeptide decreases regulatory T cell survival as compared to a control polypeptide. Various markers, e.g., CD4, FOXP3, and CD25, are known to be expressed on regulatory T cells. The ability of a polypeptide disclosed herein to decrease regulatory T cell survival may be assessed by counting the total number of regulatory T cells present in blood and/or a specific tissue such as a tumor. For instance, samples obtained from a subject contacted with a polypeptide described herein may be stained with antibodies that detect markers associated with regulatory T cells. The samples may also be processed and labeled with antibodies that detect such markers and analyzed by flow cytometry. Gene and/or protein expression of such markers may be determined in a sample and analyzed by e.g., western-blotting and/or rt-qPCR.

In some embodiments, a polypeptide described herein reduces the number of regulatory T cells in blood and/or a tumor when administered to a subject. In some embodiments, the polypeptide reduces the expression of one or more markers associated with regulatory T cells in one or more samples obtained from a subject administered with the polypeptide. In some embodiments, the polypeptide further reduces the expression of the one or more markers as compared to a vehicle or control polypeptide (e.g., an unstapled wild-type HD2 domain human BCL9), when assessed in vivo.

VEGF Expression in a Tumor

In certain embodiments, a polypeptide described herein decreases the expression of VEGF in a tumor when administered to a subject bearing the tumor. Various assays to measure the gene expression and/or protein expression of VEGF in a tumor sample can be employed. For instance, after contacting the subject with the polypeptide, tumor cells may be collected and stained with an anti-VEGF antibody to detect VEGF protein. The cells may also be analyzed by e.g., rt-qPCR to determine the gene expression of VEGF. Other assays that indicate the change of VEGF expression can be employed. For instance, tumor samples from a subject contacted with a polypeptide described herein may be analyzed to detect various angiogenic markers controlled by VEGF. In some embodiments, a polypeptide described herein decreases the expression of VEGF more effectively than a vehicle or control polypeptide (e.g., an unstapled wild-type HD2 domain human BCL9).

CD4+ and/or CD8+ T Cell Infiltration into Tumor

In some embodiments, a polypeptide described herein increases CD4+ T cell and/or CD8+ T cell infiltration into a tumor when administered to a subject bearing the tumor. The infiltration of CD4+ T cells and/or CD8+ T cells into a tumor may be assessed by counting the total number of CD4+ T cells and/or CD8+ T cells present in a tumor or a sample (e.g., a biopsy) from the tumor. In some embodiments, a polypeptide described herein increases CD4+ T cell and/or CD8+ T cell infiltration into a tumor when administered to a subject bearing the tumor more effectively than a vehicle or control polypeptide (e.g., an unstapled wild-type HD2 domain human BCL9). Various markers, e.g., CD4 and CD45, are known to be expressed on CD4+ T cells, also referred as helper T cells. Various markers, e.g., CD8 and CD45, are known to be expressed on CD8+ T cells, also referred as cytotoxic T cells. The ability of the polypeptide to increase CD4+ and/or CD8+ T cell infiltration into a tumor may be assessed in vivo, by administering the polypeptide to a subject having a tumor. A tumor sample can be collected from the subject and stained with antibodies that detect markers associated with CD4+/CD8+ T cells. The samples may also be processed and labeled with, e.g., antibodies that detect such markers and analyzed by, e.g., flow cytometry. Gene and/or protein expression of such markers may also be determined in a sample and analyzed by e.g., western-blotting and/or rt-qPCR. In some embodiments, a polypeptide described herein increases the total amount of CD4+ T cells and/or CD8+ T cells in a tumor as compared to a vehicle or control polypeptide (e.g., an unstapled wild-type HD2 domain human BCL9).

In some embodiments, a polypeptide described herein increases the total number of CD4+ T cells and/or CD8+ T cells in blood when administered to a subject. The systemic increase of CD4+ T cells and/or CD8+ T cells may indicate increased CD4+ T cell and/or CD8+ T cell infiltration into a specific tissue as well, e.g., a tumor. In some embodiments, a polypeptide described herein increases the amount of circulating CD4+ T cells and/or CD8+ T cells in vivo as compared to a vehicle or control polypeptide (e.g., an unstapled wild-type HD2 domain human BCL9).

T Helper 17 Cell Infiltration into Tumor

In some embodiments, a polypeptide described herein increases T helper 17 cell infiltration into a tumor when administered to a subject bearing the tumor. The infiltration of T helper 17 cells into a tumor may be assessed by counting the total number of T helper 17 cells present in the tumor. In some embodiments, a polypeptide described herein increases T helper 17 cell infiltration into a tumor when administered to a subject bearing the tumor as compared to a vehicle or control polypeptide (e.g., an unstapled wild-type HD2 domain human BCL9). Various markers, e.g., IL-17, are known to be expressed on T helper 17 cells. The ability of the polypeptide to increase T helper 17 cell infiltration into a tumor may be assessed in vivo, by administering the polypeptide to a subject having a tumor. A tumor sample can be collected from the subject and stained with, e.g., antibodies that detect markers associated with T helper 17 cells. The samples may also be processed and labeled with antibodies that detect such markers and analyzed by flow cytometry. Gene and/or protein expression of such markers may also be determined in a sample and analyzed by e.g., western-blotting and/or rt-qPCR. The samples may be analyzed to detect the amount of IL-17 present in the samples.

In some embodiments, a polypeptide described herein increases the total amount of T helper 17 cells in blood when administered to a subject. The systemic increase of T helper 17 cells may indicate increased T helper 17 cells infiltration into a specific tissue, e.g., a tumor. The systemic increase of T helper 17 cells may be assessed by measuring the amount of IL-17 present in blood samples collected from a subject. In some embodiments, the polypeptide increases the amount of circulating T helper 17 cells in a subject as compared to a vehicle or control polypeptide (e.g., an unstapled wild-type HD2 domain human BCL9). In some embodiments, a polypeptide described herein increases the amount of circulating IL-17 in a subject as compared to a control polypeptide.

Dendritic Cells in Tumor

In some embodiments, a polypeptide described herein modulate dendritic cells present in a tumor when administered to a subject bearing the tumor. The number of dendritic cells present in a tumor may be assessed, e.g., by staining the tumor with antibodies that recognize one or more markers associated with dendritic cells. In some embodiments, a polypeptide described herein decreases dendritic cells present in a tumor when administered to a subject bearing the tumor more effectively than a vehicle or control polypeptide (e.g., an unstapled wild-type HD2 domain human BCL9). In some embodiments, a polypeptide described herein increases dendritic cells present in a tumor when administered to a subject bearing the tumor more effectively than a vehicle or control polypeptide (e.g., an unstapled wild-type HD2 domain human BCL9). Various markers, e.g., CD11c, are known to be expressed on dendritic cells. The ability of the polypeptide to decrease dendritic cells in a tumor may be assessed in vivo, by administering the polypeptide to a subject. A tumor sample can be collected from the subject and stained with antibodies that detect markers associated with dendritic cells. The samples may also be processed and labeled, e.g., with antibodies that detect such markers and analyzed by, e.g., flow cytometry. Gene and/or protein expression of such markers and analyzed by e.g., western-blotting and rt-qPCR.

In some embodiments, a polypeptide described herein decreases the total amount of dendritic cells in blood when administered to a subject. In some embodiments, a polypeptide described herein increases the total amount of dendritic cells in blood when administered to a subject. The systemic decrease of dendritic cells may indicate that the amount of dendritic cells in a specific tissue, e.g., a tumor, has also decreased. In some embodiments, a polypeptide described herein decreases the amount of circulating dendritic cells in a subject as compared to a vehicle or control polypeptide (e.g., an unstapled wild-type HD2 domain human BCL9). In some embodiments, a polypeptide described herein increases the amount of circulating dendritic cells in a subject as compared to a vehicle or control polypeptide (e.g., an unstapled wild-type HD2 domain human BCL9).

Biomarkers

The present disclosures also encompass methods of measuring at least one biomarker to monitor treatment efficacy of a polypeptide or pharmaceutical composition described herein or to select a subject for treatment with such polypeptide or pharmaceutical composition. In some embodiments, the biomarker is one or more of BCL9, CD44, Axin2, cMyc, LGR5, VEGFA, Sox2, Oct4, Nanog, and/or active β-catenin. As used herein, active β-catenin refers to non-phosphorylated form of β-catenin.

Various known methods can be used to measure the gene expression level and/or protein level of such biomarkers. For instance, a sample from a subject treated with the polypeptide or pharmaceutical composition can be obtained, such as biopsy of a tumor, blood, plasma, serum, urine, amniotic fluid, synovial fluid, endothelial cells, leukocytes, monocytes, other cells, organs, tissues, bone marrow, lymph nodes, or spleen. In some embodiments, the sample is a biopsy of a tumor in a subject. The sample obtained from a subject may be stained with one or more antibodies or other detection agents that detect such biomarkers. The samples may also or alternatively be processed for detecting the present of nucleic acids, such as mRNAs, encoding the biomarkers via e.g., rt-qPCR methods.

In some embodiments, a reduced gene expression level and/or protein level of BCL9, CD44, Axin2, cMyc, LGR5, VEGFA, Sox2, Oct4, Nanog, and/or active β-catenin indicates treatment efficacy of a polypeptide or pharmaceutical composition described herein. The expression level of such biomarker may be measured after e.g., 1 day, 2 days, 3 days, 4 days, 5 days, one week, or two week of administration of the polypeptide or pharmaceutical composition, or any time period in between. In some embodiments, a method is disclosed comprising measuring the level of one or more of the biomarkers after one or more rounds of administration of a polypeptide or pharmaceutical composition described herein. In some embodiments, the method further comprises continuing to administer the polypeptide or pharmaceutical composition if the biomarker levels are reduced. In some embodiments, the method further comprises administering an increased dosage of a polypeptide or pharmaceutical composition described herein if the biomarker levels are not reduced, or increasing the frequency of subsequent administrations. In some embodiments, treatment is discontinued if biomarker levels are not reduced after the initial administration. In various embodiments, biomarker levels are also measured before a first administration of the polypeptide or pharmaceutical composition described herein, and compared to levels after one or more rounds of administration, wherein treatment efficacy and continued treatment steps are determined based on the change in biomarker level(s) from the level(s) prior to administration.

In some embodiments, an increased gene expression level and/or protein level of BCL9, CD44, Axin2, cMyc, LGR5, VEGFA, Sox2, Oct4, Nanog, and/or active β-catenin indicates that a subject would benefit from treatment with a polypeptide or pharmaceutical composition described herein, than a subject who does not have increased gene expression levels and/or protein levels. In some embodiments, methods of treatment are disclosed, comprising selecting patients having increased biomarker levels and administering a polypeptide or pharmaceutical composition described herein.

In certain embodiments, a subject having elevated level of gene and/or protein expression of BCL9, CD44, Axin2, cMyc, LGR5, VEGFA, Sox2, Oct4, Nanog, and/or active β-catenin is selected for treatment with a polypeptide or pharmaceutical composition described herein. In some embodiments, a subject suffering from a tumor is selected for treatment after obtaining a tumor sample from the subject and identifying an elevated gene and/or protein expression of BCL9, CD44, Axin2, cMyc, LGR5, VEGFA, Sox2, Oct4, Nanog, and/or active β-catenin. In some embodiments, a subject suffering from a tumor is selected for treatment after obtaining a tumor sample from the subject and identifying an elevated gene and/or protein level of BCL9. In some embodiments, a subject suffering from a tumor is selected for treatment after obtaining a tumor sample from the subject and identifying an elevated gene and/or protein level of CD44. In some embodiments, a subject suffering from a tumor is selected for treatment after obtaining a tumor sample from the subject and identifying an elevated gene and/or protein level of active β-catenin.

Half-Life in a Subject

In various embodiments, a polypeptide described herein has one or more improved pharmacokinetic parameters as compared to a vehicle or control polypeptide (e.g., an unstapled wild-type HD2 domain human BCL9). Such pharmacokinetic parameters may include e.g., a maximum observed concentration ($C_{max}$), time to reach the maximum concentration ($T_{max}$), terminal half-life ($T_{1/2}$), total body clearance (CL), volume of distribution ($V_z$), area under the curve from the time of dosing to the last measurable concentration ($AUC_{0-t}$), area under the curve from the time of dosing extrapolated to infinity ($AUC_{0-inf}$), and bioavailability.

Methods for assessing pharmacokinetics of an agent are known in the art. For instance, blood samples from a subject administered with a polypeptide described herein may be obtained at 5 min, 1, 2, 4, 6, 8, 12, and 24 hours post-dose. The concentration of the polypeptide in the blood samples can be analyzed by various analytical tools, e.g., LC/MS. Based on the concentration of the polypeptide at each time point, pharmacokinetic parameters are calculated. As used herein, the term "maximum observed concentration ($C_{max}$)" refers to the maximum serum concentration that a polypeptide achieves after administration. Related to the concept of $C_{max}$, the time to reach the maximum concentration ($T_{max}$) is the time that it takes for a polypeptide to reach the maximum serum concentration. The terms "terminal half-life ($T_{1/2}$)" and "half-life ($T_{1/2}$)" are used interchangeably and refer to the time that a polypeptide takes to lose half of its serum concentration. Total body clearance (CL) represents the volume of blood completely cleared of a polypeptide per unit time. The term "volume of distribution ($V_z$)" refers to a theoretically calculated volume that would be required to contain the total amount of a polypeptide administered to a subject at the same concentration observed in the blood. The term "bioavailability" refers to the degree and rate at which a drug is absorbed into a living system or is made available at the site of physiological activity. Bioavailability can be a function of several of the previously described properties, including stability, solubility, immunogenicity and pharmacokinetics, and can be assessed using methods known to one skilled in the art.

In some embodiments, a polypeptide described herein has an improved half-life in a subject as compared to a control polypeptide. In some embodiments, the polypeptide has a half-life greater than at least 0.5, 1, 2, 3, 5, or 8 hours when administered to a subject, or any time period in between. In some embodiments, the polypeptide described herein has a half-life greater than at least 2 hours when administered to a subject. Pharmacokinetic parameters of the polypeptide may be assessed in a mammal including e.g., a mouse, a rat, or a human. The parameters may also be assessed using various administration routes, e.g., intravenous, intraperitoneal, subcutaneous, and intramuscular administration routes. In some embodiments, the pharmacokinetic parameters of the polypeptide described herein are assessed in mice. In some embodiments, the pharmacokinetic parameters of the polypeptide described herein are assessed in mice administered with the polypeptide subcutaneously. In some embodiments, the pharmacokinetic parameters of the polypeptide described herein are assessed in humans. In some embodiments, the pharmacokinetic parameters of the polypeptide described herein are assessed in humans after subcutaneous administration.

Tumor Microenvironment Favoring Immune Reaction

In various embodiments, a polypeptide described herein induces a tumor microenvironment favoring an immune reaction. In various embodiments, a polypeptide described herein induces a tumor microenvironment more favorable to an immune reaction than a vehicle or control polypeptide (e.g., an unstapled wild-type HD2 domain human BCL9).

Various parameters may be used to assess a tumor microenvironment. For instance, an increased ratio between cytotoxic T cells and regulatory T cells in and/or around tumor tissues may indicate that a tumor microenvironment favors an immune reaction. A decreased amount of dendritic cells and/or regulatory T cells in and/or around tumor tissue may also indicate that a tumor microenvironment favors an immune reaction. Other parameters include increased circulating T cells in peripheral blood and an increased ratio between T helper 17 cells and regulatory T cells in and/or around tumor tissues. These parameters may indicate that a tumor microenvironment favors an immune reaction.

In some embodiments, a polypeptide described herein may increase the ratio between the amount of cytotoxic T cells and the amount of regulatory T cells in a tumor microenvironment. In some embodiments, the ratio change caused by the polypeptide is greater than that caused by a vehicle or control polypeptide (e.g., an unstapled wild-type HD2 domain human BCL9).

In some embodiments, a polypeptide described herein may increase the ratio between T helper 17 cells and regulatory T cells in a tumor microenvironment. In some embodiments, the ratio change caused by the polypeptide is greater than that caused by a vehicle or control polypeptide (e.g., an unstapled wild-type HD2 domain human BCL9).

Tumor Growth, Cancer Stem Cell Proliferation, and/or Tumor Metastasis

As Wnt signaling is a regulator of tumor growth, the efficacy of treatments that affect the binding of BCL9 to β-catenin, such as the stabilized peptides of the HD2 domain of the BCL9 peptide described herein, may be assessed in animal models.

The in vivo efficacy of stabilized BCL9 peptides may be assessed in models of human cancers using, e.g., BALB/c nude mice, since xenografts of human cancer cells will grow into tumors in these mice. For example, subcutaneous inoculation with Colo320DM tumor cells, a commercially available cell line derived from human colon cancer tissue, can be used to form a tumor in BALB/c nude mice. Additional in vivo models are also available to assess the in vivo efficacy of a polypeptide disclosed herein. For instance, Human DLD-1 colon cancer cells can be implanted into nude mice to assess tumor growth. The CT26 syngeneic mouse model of colon cancer may also be used, as it allows for assessment of tumor growth in the background of an intact immune system. Other types of cancer cells, e.g., B16 melanoma, 4T1 breast cancer, Renca renal cancer, and Lewis Lung Cell lung cancer cells, may also be used in these known animal models to assess the in vivo efficacy of the polypeptide disclosed herein.

By administering a polypeptide described herein to one or more animal models, the effect of the polypeptide in decreasing tumor growth in vivo may be assessed. In some embodiments, the polypeptide inhibits tumor growth in vivo more effectively than a vehicle or control polypeptide (e.g., an unstapled wild-type HD2 domain human BCL9). In some embodiments, the tumor mass/volume of a subject administered with the polypeptide described herein is at least 10%, 20%, 30%, 40%, 50%, 60%, 70%, 80%, 90%, 95%, or 99% smaller than that of a subject administered with the control polypeptide. From animal data on treatment with stabilized BCL9 peptides, the ability of the peptide to inhibit Wnt signaling can be assessed by e.g., staining of tissue samples with markers of Wnt signaling. These downstream markers of Wnt signaling include e.g., Axin2 and CD44.

Orthotopic mouse models may be used to assess the effects of a polypeptide described herein on tumor metastasis. For instance, an orthotropic animal model may be injected with cells carrying luciferase construct and then administered with its assigned treatment. The presence of the injected cells can be detected by administering luciferin substrate to each treated animal. The intensity of the bioluminescent signal can be quantitatively measured and used as an indicator of cell growth. In some embodiments, a polypeptide described herein suppresses tumor metastasis more effectively than the control polypeptide, when assessed in an orthotopic mouse model. In some embodiments, the polypeptide reduces tumor growth in an orthotopic mouse model at least 10%, 20%, 30%, 40%, 50%, 60%, 70%, 80%, 90%, 95%, or 99% as compared to a vehicle or control polypeptide (e.g., an unstapled wild-type HD2 domain human BCL9).

In some embodiments, the effects of a polypeptide described herein on cancer stem cell proliferation may be assessed by measuring biomarkers of various cancer stem cells. For instance, the expression level of CD44 and/or LGR5 may indicate the amount of cancer stem cells present in a sample. A tumor sample can be collected from a subject and stained with antibodies that detect markers associated with cancer stem cells. The samples may also be processed and labeled, e.g., with antibodies that detect such markers and analyzed by, e.g., flow cytometry. Gene and/or protein expression of such markers can be detected and analyzed by e.g., western-blotting and rt-qPCR. In some embodiments, the polypeptide described herein reduces the expression level of CD44 and/or LGR5 in a tumor when administered to a tumor bearing subject. In some embodiments, a polypeptide described herein more effectively reduces the expression level of CD44 and/or LGR5 than that of a vehicle or control polypeptide (e.g., an unstapled wild-type HD2 domain of human BCL9 protein).

Diseases with Aberrant Wnt/β-Catenin Signaling

Aberrant Wnt/β-catenin signaling has been implicated in the malignant transformation of normal cells into cancerous cells (see Thakur 2013). Activation of Wnt signaling and β-catenin nuclear localization has been linked to a tumor phenotype in multiple models.

The present disclosure encompasses compositions for use and methods of using the stapled polypeptides disclosed herein to inhibit binding of BCL9 to β-catenin in a subject by administering the polypeptide or a pharmaceutical composition comprising the polypeptide to the subject. The present disclosure also encompasses inhibiting canonical Wnt/β-catenin signaling in a subject by administering a polypeptide or pharmaceutical composition disclosed herein. The present disclosures further encompass methods of treating a disease in a subject by administering a polypeptide or pharmaceutical composition described herein to the subject. The disease may be a cancer or other tumorous disease associated with aberrant canonical Wnt/β-catenin signaling.

In some embodiments, the disease, disorder, or condition may be a disease which could benefit from inhibiting canonical Wnt/1-catenin signaling. In some embodiments, such disease, disorder, or condition is a cancer. In some embodiments, the cancer is a cancer where BCL9 and/or β-catenin are highly expressed. In some embodiments, the cancer is a cancer where BCL9 and β-catenin are co-localized in the nucleus of a cancer cell. In some embodiments, the cancer is selected from: familial adenomatous polyposis (FAP), ocular cancer, rectal cancer, colon cancer, colorectal cancer, cervical cancer, prostate cancer, breast cancer, bladder cancer, oral cancer, benign and malignant tumors, stomach cancer, liver cancer, pancreatic cancer, lung cancer, corpus uteri, ovarian cancer, prostate cancer, testicular cancer, renal cancer, brain/CNS cancer, throat cancer, multiple myeloma, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, gastric cancer, ovarian cancer, hepatocellular carcinoma, and lymphangiogenesis. In some embodiments, the cancer is colorectal cancer. In some embodiments, the cancer is gastric cancer. In some embodiments, the cancer is ovarian cancer. In some embodiments, the cancer is Hepatocellular carcinoma. In some embodiments, the cancer is breast cancer. In some embodiments, the cancer is prostate cancer. In some embodiments, the cancer is skin melanoma. In some embodiments, the cancer is lung cancer.

In some embodiments, any of the polypeptide or variant disclosed herein or a pharmaceutical composition comprising such polypeptide can be used to treat a disease, e.g., a cancer listed above.

In some embodiments, a tumor volume in a subject is reduced by more than 10%, 20%, 30%, 40%, or 50% (or any percentage in between) after administration of one or more dosages of a polypeptide described herein or a pharmaceutical composition comprising the polypeptide, as compared to that of a subject treated with a vehicle or an unstapled peptide. In certain embodiments, the reduction is achieved after 1 week, 2 weeks, 3 weeks, or more of administration (or any time period in between). In some embodiments, the tumor volume of a subject is reduced by more than 50%, as compared to that of a subject treated with a vehicle or unstapled peptide, after 2 weeks of administration. A suitable dosage and/or formulation of a pharmaceutical composition for administration to a subject could be determined by one of skill in the art as the materials and techniques necessary for the various methods of administration are available and known in the art. See e.g., Formulation and delivery of peptides and proteins, $1^{st}$ edition, Washington, ACS, pp. 22-45 and Peptide and protein drug delivery, $1^{st}$ edition, New York, Marcel Dekker, Inc., pp. 247-301. In some embodiment, the tumor volume of a subject administered with a polypeptide or a pharmaceutical composition comprising the polypeptide is reduced by more than 50%, as compared to that of a subject treated with a vehicle or wild-type polypeptide, after 2 weeks of administration. In some embodiment, the tumor volume of a subject administered with a polypeptide or a pharmaceutical composition comprising the polypeptide is reduced by more than 10%-50%, as compared to that of a subject treated with a vehicle or wild type polypeptide, after 2 weeks of administration.

Treatment, and the measured parameters of treatment, can be assessed after administration of the polypeptide or pharmaceutical composition alone or in combination with one or more additional therapeutic agents, e.g., as a single bolus or separate sequential administrations. The additional agent may be any of the additional therapeutic agents mentioned herein or known to the skilled artisan. The polypeptide or pharmaceutical composition comprising the polypeptide, and/or the additional agent, may be administered once or multiple times, depending on the chosen regimen.

The present disclosures also encompass a polypeptide or pharmaceutical composition disclosed herein for use in treating a disease in a subject. In some embodiment, the disease may benefit from suppressing canonical Wnt/β-catenin signaling. In some embodiments, the disease is a cancer.

The present disclosures further encompass uses of a polypeptide or pharmaceutical composition disclosed herein in the manufacture of a medicament for treating a disease in a subject. In some embodiment, the disease may benefit from suppressing canonical Wnt/β-catenin signaling. In some an embodiment, the disease is a cancer.

In another embodiment, the disease treated is a disease other than cancer. In certain embodiments, the disease is a bone density defect, vascular defect of the eye, familial exudative vitreoretinopathy, early coronary disease, Alzheimer's disease, autosomal-dominant oligodontia, retinal angiogenesis, osteogenesis imperfecta, Tetra-Amelia syndrome, Mullerian-duct regression and virilization, SERKAL syndrome, Type II diabetes, Fuhrmann syndrome, odonto-onycho-dermal dysplasia, obesity, split hand/foot malformation, caudal duplication, tooth agenesis, skeletal dysplasia, focal dermal hypoplasia, autosomal recessive anonychia, neural tube defects, or sclerosteosis and Van Buchem disease.

Pharmaceutical Compositions, Formulations, Dosages and Routes of Administration

In various embodiments, pharmaceutical compositions comprising one or more of the polypeptides disclosed herein, either alone or in combination with other prophylactic agents, therapeutic agents, and/or pharmaceutically acceptable carriers, are provided. In some embodiments, the pharmaceutical composition may comprise one, two, three, or more polypeptides described herein. The pharmaceutical compositions comprising polypeptides provided herein are for use in, but not limited to, diagnosing, detecting, or monitoring a disorder, in preventing, treating, managing, or ameliorating a disorder or one or more symptoms thereof, and/or in research.

A "pharmaceutically acceptable carrier" refers to e.g., any and all solvents, solids, semisolids, liquid fillers, diluents, encapsulating materials, formulation auxiliaries, media, isotonic and absorption delaying agents, for use with a polypeptide described herein to comprises a "pharmaceutical composition" suitable for administration to a subject. The use of such media and agents for pharmaceutically active substances is well known in the art. Supplementary active compounds can also be incorporated into the compositions. The pharmaceutically acceptable carrier may be selected based on the use and/or administration route of the composition.

The pharmaceutical compositions may be formulated into any of many possible dosage forms, such as, e.g., tablets, capsules, gel capsules, powders, or granules. The pharmaceutical compositions may also be formulated as solutions, suspensions, emulsions, or mixed media. In some embodiments, the pharmaceutical compositions may be formulated as lyophilized formulations or aqueous solutions, that are suitable, for example, for administration by injection or infusion.

In some embodiments, a pharmaceutical composition may be formulated as a solution. For example, the polypeptides described herein may be administered in an unbuffered solution, such as, e.g., in saline, in water, or in dimethyl sulfoxide (DMSO). In some embodiments, the polypeptides may also be administered in a suitable buffer solution. For example, the buffer solution may comprise acetate, citrate, prolamine, carbonate, or phosphate, or any combination thereof. In some embodiments, the buffer solution may be phosphate buffered saline (PBS). The pH and osmolality of the buffer solution containing the polypeptides can be adjusted to be suitable for administering to a subject.

In some embodiments, the pharmaceutical compositions may be formulated as suspensions in aqueous, non-aqueous, or mixed media. In some embodiments, the pharmaceutical composition is formulated in mixed media comprising water and DMSO. Aqueous suspensions may further contain substances which increase the viscosity of the suspension including, for example, sodium carboxymethylcellulose, sorbitol and/or dextran. The suspension may also contain stabilizers.

In some embodiments, the pharmaceutical composition is used for in vivo administration and may be sterile. Sterility may be readily accomplished, e.g., by filtration through sterile filtration membranes.

In various embodiments, a pharmaceutical composition comprising a polypeptide described herein may further comprise at least one additional agent. In some embodiments, the at least one additional agent is selected from one or more of a checkpoint inhibitor, an EGFR inhibitor, a VEGF inhibitor, a VEGFR inhibitor, and an anti-cancer drug.

In some embodiments, the pharmaceutical composition described herein comprises a checkpoint inhibitor. In an embodiment, the checkpoint inhibitor is an anti-PD-1 antibody, an anti-PD-L1 antibody, or an anti-CTLA4 antibody. In an embodiment, the checkpoint inhibitor targets a stimulatory checkpoint molecule such as e.g., CD27, CD40, OX40, GITR, or CD138. In yet another embodiment, the checkpoint inhibitor targets an inhibitory checkpoint molecule such as e.g., A2AR, B7-H3, B7-H4, B and T lymphocyte attenuator (BTLA), indoleamine 2,3-dioxygenase (IDO), Killer-cell immunoglobulin-like receptor (KIR), Lymphocyte Activation Gene-3 (LAG3), T-cell Immunoglobulin domain and Mucin domain 3 (TIM-3), VISTA (C10orf54), or V-domain Ig suppressor of T cell activation.

In some embodiments, a pharmaceutical composition described herein comprises an EGFR inhibitor. In an embodiment, the EGFR inhibitor is erlotinib, gefitinib, lapatinib, panitumumab, vandetanib, or cetuximab.

In some embodiments, a pharmaceutical composition described herein comprises a VEGF or VEGFR inhibitor. In an embodiment, the VEGF or VEGFR inhibitor is pazopanib, bevacizumab, sorafenib, sunitinib, axitinib, ponatinib, regorafenib, vandetanib, cabozantinib, ramucirumab, lenvatinib, or ziv-aflibercept.

In some embodiments, a pharmaceutical composition described herein comprises an anti-cancer drug. The anti-cancer drug may be selected from: cyclophosphamide, methotrexate, 5-fluorouracil (5-FU), doxorubicin, mustine, vincristine, procarbazine, prednisolone, dacarbazine, bleomycin, etoposide, cisplatin, epirubicin, capecitabine, folinic acid, actinomycin, all-trans retinoic acid, azacitidine, azathioprine, bortezomib, carboplatin, chlorambucil, cytarabine, daunorubicin, docetaxel, doxifluridine, fluorouracil, gemcitabine, hydroxyurea, idarubicin, imatinib, irinotecan, mechlorethamine, mercaptopurine, mitoxantrone, paclitaxel, pemetrexed, teniposide, tioguanine, topotecan, valrubicin, vinblastine, vindesine, vinorelbine, and oxaliplatin.

A polypeptide of the present disclosure may be administered to the patient by topical (including ophthalmic and to mucous membranes including vaginal and rectal delivery), pulmonary (e.g., by inhalation or insufflation of powders or aerosols, including by nebulizer, intratracheal, intranasal), epidermal, transdermal, oral, or parenteral route. Parenteral administration includes intravenous, subcutaneous, intraperitoneal, or intramuscular injection or infusion; or intracranial, e.g., intrathecal or intraventricular, administration. In some embodiments, a polypeptide or pharmaceutical composition described herein is administered intravenously. In some embodiments, a polypeptide or pharmaceutical composition described herein is administered intraperitoneally. In some embodiments, a polypeptide or pharmaceutical composition described herein is administered daily, weekly, monthly, or any suitable interval that can be used for treating a disease in a subject.

In the pharmaceutical compositions of the present application, a polypeptide is present in an effective amount (e.g., a therapeutically effective amount). Effective doses may vary, depending on the diseases treated, the severity of the disease, the route of administration, the sex, age and general health condition of the subject, excipient usage, the possibility of co-usage with other therapeutic treatments such as use of other agents and the judgment of the treating physician. In some embodiments, an effective amount of a polypeptide can range, for example, from about 0.001 mg/kg to about 500 mg/kg. Dosage regimens may be adjusted to provide an optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage.

An exemplary, non-limiting range for a therapeutically or prophylactically effective amount of a binding protein provided herein is 0.1-20 mg/kg, for example, 1-10 mg/kg.

Combination Therapies

In certain embodiments, a polypeptide or pharmaceutical composition disclosed herein is administered with at least one additional agent. That is, a polypeptide of the present disclosure and the additional agent may be administered to a patient is separate dosage forms as described herein, either consecutively or simultaneously. In some embodiments, the at least one additional agent is selected from a checkpoint inhibitor, an EGFR inhibitor, a VEGF inhibitor, a VEGFR inhibitor, an anti-cancer drug (e.g., any of the additional therapeutic agents described herein). The stapled peptide and the additional agent may be administered in a therapeutically-effective amount.

In certain embodiments, a subject administered with a polypeptide or pharmaceutical composition disclosed herein is also treated with radiation therapy and/or chemotherapy before, after, or at the same time as the polypeptide or pharmaceutical composition administration.

Kits

The present invention also includes pharmaceutical kits useful, for example, in the treatment of disorders, diseases and conditions referred to herein, which include one or more containers containing a pharmaceutical composition comprising a therapeutically effective amount of a polypeptide of the present disclosure. Such kits can further include, if desired, one or more of various conventional pharmaceutical kit components, such as, for example, containers with one or more pharmaceutically acceptable carriers, additional containers, etc. Instructions, either as inserts or as labels, indicating quantities of the components to be administered, guidelines for administration, and/or guidelines for mixing the components, can also be included in the kit.

Also disclosed herein are kits for performing methods described herein. In various embodiments, a kit for manufacturing a polypeptide described herein is provided. In some embodiments, the kit comprises a polypeptide that is capable of undergoing a reaction to from one or more hydrocarbon linkers. In some embodiments, the kit comprises a metal catalyst for performing metal-mediated ring-closing olefin metathesis.

In some embodiments, the kit comprises agents for detecting the gene and/or protein expression of BCL9, CD44, Axin2, cMyc, LGR5, VEGFA, Sox2, Oct4, Nanog, and/or active β-catenin.

Definitions

To the extent that the term "contain," "include," "have," or grammatical variants of such term are used in either the disclosure or the claims, such term is inclusive in a manner similar to the term "comprising" as "comprising" is interpreted when employed as a transitional word in a claim.

The term "about" means a quantity, level, value, number, frequency, percentage, dimension, size, amount, weight, or length that varies by as much as 30, 25, 20, 15, 10, 9, 8, 7, 6, 5, 4, 3, 2 or 1% to a reference quantity, level, value, number, frequency, percentage, dimension, size, amount, weight or length. When the term "about" is used in conjunction with a numerical range, it modifies that range by extending the boundaries above and below the numerical values set forth. In general, the term "about" is intended to modify a numerical value above and below the stated value by a variance of ≤10%.

As used herein, the term "amino acid" generally refers to organic compounds containing amine (—$NH_2$) and carboxyl (—COOH) functional groups, along with a side chain (R group) specific to each amino acid. The side chain may be hydrophobic or hydrophilic, charged or neutral, as well as aliphatic or aromatic. In natural amino acids, the amine and carboxyl functional groups attached to the same carbon atom, i.e., an amino group is attached to the carbon in α-position relative to carboxyl group.

Any of the amino acids described herein may be in L configuration or in D configuration. In some embodiments, the amino acid is in L configuration. In some embodiments, the amino acid is in D configuration. The 20 natural amino acids are abbreviated herein as shown in Table A:

TABLE A

| Three-letter abbreviation | One-letter abbreviation | Amino acid name |
|---|---|---|
| Ala | A | Alanine |
| Arg | R | Arginine |
| Asn | N | Asparagine |
| Asp | D | Aspartic acid |
| Cys | C | Cysteine |
| Gln | Q | Glutamine |
| Glu | E | Glutamic acid |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Ser | S | Serine |
| Thr | T | Threonine |
| Trp | W | Tryptophan |
| Tyr | Y | Tyrosine |
| Val | V | Valine |

The non-natural amino acids are referred to herein as follows.

Norleucine (abbreviated herein as Nle) is (2S)-2-aminohexanoic acid having the following chemical structure:

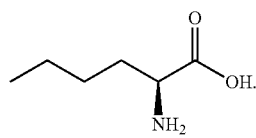

β-Alanine (or beta-alanine, abbreviated herein as β-Ala) is 3-aminopropanoic acid having the following chemical structure:

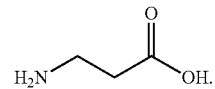

2-Naphthylalanine (abbreviated herein as 2-Nal) is (S)-2-amino-3-(naphthalen-1-yl)propanoic acid having the following chemical structure:

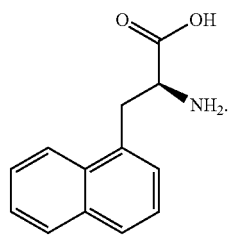 [SMILES: N[C@@H](Cc1cccc2ccccc12)C(=O)O]

D-2-Naphthylalanine (abbreviated herein as 2-Dnal) is (R)-2-amino-3-(naphthalen-1-yl)propanoic acid having the following chemical structure:

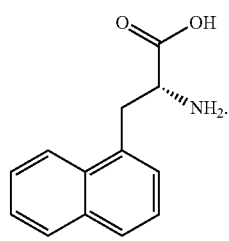 [SMILES: N[C@H](Cc1cccc2ccccc12)C(=O)O]

β-Leucine (abbreviated herein as β-L) is (R)-3-amino-4-methylpentanoic acid having the following chemical structure:

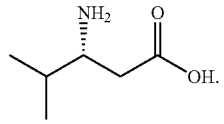

β-cyclobutyl alanine (abbreviated herein as CBA) is (S)-2-amino-3-cyclobutylpropanoic acid having the following chemical structure:

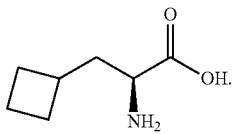

N-Methyl-D-glutamine (abbreviated herein as N-methylQ or NMeGln) is methyl-L-glutamine having the following chemical structure:

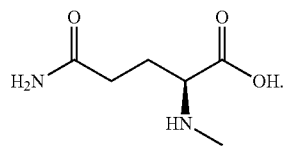

N-methyl arginine (abbreviated herein as N-methylR, NMeArg, or R(Me)) is a compound of the following formula:

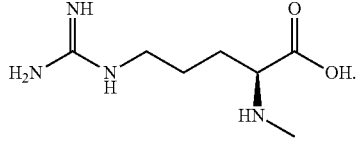

Cyclohexyl L-alanine (abbreviated herein as Cha) is a (S)-2-amino-3-cyclohexylpropanoic acid compound of formula:

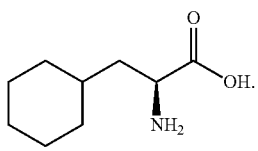 [SMILES: N[C@@H](CC1CCCCC1)C(=O)O]

Cyclohexyl D-alanine (abbreviated herein as Dcha) is a (R)-2-amino-3-cyclohexylpropanoic acid compound of formula:

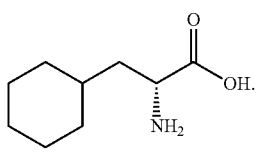 [SMILES: N[C@H](CC1CCCCC1)C(=O)O]

N-methyl cyclohexyl alanine (abbreviated herein as NMeCha) is a (S)-2-amino-3-cyclohexylpropanoic acid compound of formula:

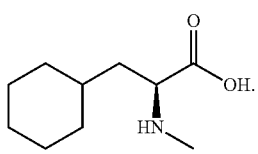

N-methyl leucine (abbreviated herein as MeL, NMeLeu, or N-methylL) is a methyl-L-leucine compound of formula:

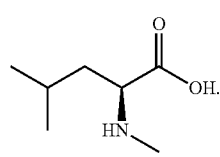

N-methyl histidine (abbreviated herein as N-methylH or N-MeHis) is methyl-L-histidine compound of formula:

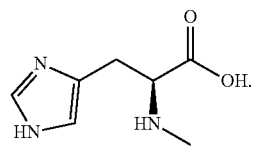

Cyclopropyl-L-alanine (abbreviated herein as Cpa) is (S)-2-amino-3-cyclopropylpropanoic acid compound of formula:

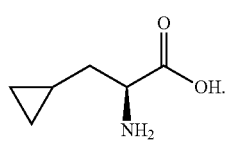

N-methyl L-glutamic acid (abbreviated herein as N-methylE) is methyl-L-glutamic acid compound of formula:

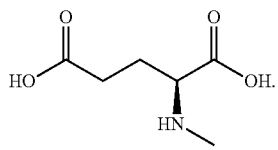

N-methyl aspartic acid (abbreviated herein as N-methylD) is a compound of formula:

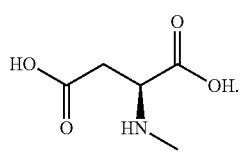

N-methyl L-threonine (abbreviated herein as N-methylT) is a compound of formula:

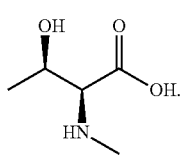

D-threonine (abbreviated herein as DThr) is a compound of formula:

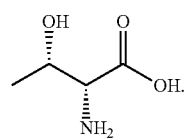

N-methyl-L-isoleucine (abbreviated herein as N-methylI) is a compound of formula:

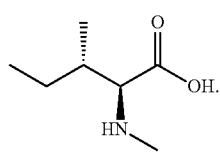

N-methyl-L-cysteine (abbreviated herein as N-MeCys) is a compound of formula:

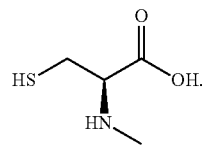

Guanidino-L-phenylalanine (abbreviated herein as Phe(4-guanidino)) is a (S)-2-amino-3-(4-((diaminomethylene)amino)phenyl)propanoic acid compound of formula:

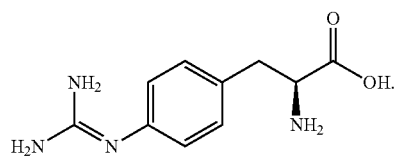 [SMILES: NC(N)=Nc1ccc(C[C@H](N)C(=O)O)cc1]

Homoarginine (abbreviated herein as homoR or homoArg) is a compound of formula:

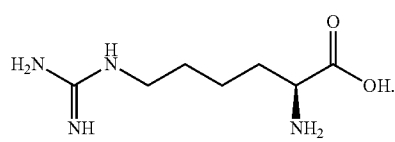 [SMILES: N=C(N)NCCCC[C@H](N)C(=O)O]

Homohistidine (abbreviated herein as homoH or homo-His) is a compound of formula:

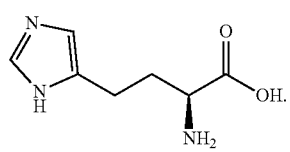 [SMILES: N[C@@H](CCc1cnc[nH]1)C(=O)O]

Citrulline (abbreviated herein as Cit) is an unnatural amino acid of formula:

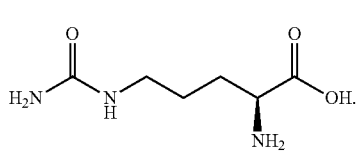

2-aminobutyric acid (abbreviated herein as 2Abu or 2-Abu) is a (S)-2-aminobutanoic acid compound of formula:

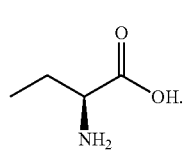

Tertleucine (abbreviated herein as Tle) is a (S)-2-amino-3,3-dimethylbutanoic acid compound of formula:

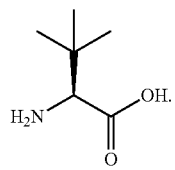

4-Chlorophenyl alanine (abbreviated herein as 4-ClPh or Phe(4-Cl)) is a (S)-2-amino-3-(4-chlorophenyl)propanoic acid compound of formula:

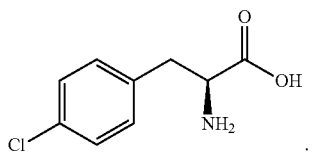 [SMILES: N[C@@H](Cc1ccc(Cl)cc1)C(=O)O]

3,4-Chlorophenyl alanine (abbreviated herein as 3,4-diClPh) is a (S)-2-amino-3-(3,4-dichlorophenyl)propanoic acid compound of formula:

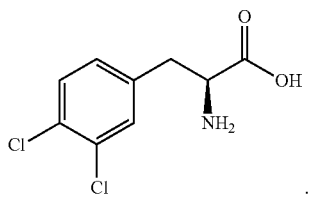 [SMILES: N[C@@H](Cc1ccc(Cl)c(Cl)c1)C(=O)O]

4-fluorophenyl alanine (abbreviated herein as 4-FPh or Phe(4-F)) is a (S)-2-amino-3-(4-fluorophenyl)propanoic acid compound of formula:

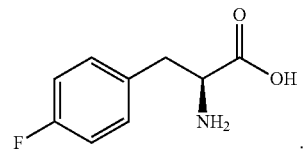

L-alpha-neopentylglycine (abbreviated herein as NptGly), or t-butyl alanine (abbreviated herein as β-tBu-Ala or tBua) is a compound of formula:

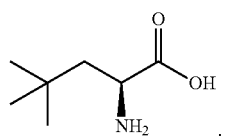

α-Methylleucine (abbreviated herein as α-MethylL) is a (S)-2-amino-2,4-dimethylpentanoic acid compound of formula:

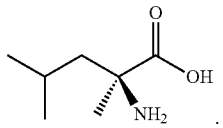

t-Butyl glycine (abbreviated herein as t-Bug) is a compound of formula:

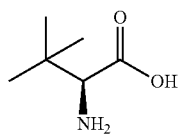

Azetidine-3-carboxylic acid (abbreviated herein as Aze) is a compound of formula:

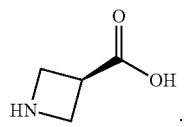

Allyl glycine (abbreviated herein as Alg or allylGly) is a compound of formula:

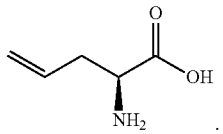

5,5,5-trifluoro leucine (abbreviated herein as Tfl) is a compound of formula:

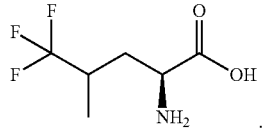

1-aminocyclobutane-1-carboxylic acid (abbreviated herein as AC4C) is a compound of formula:

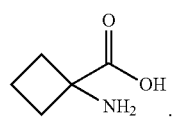

1-aminocyclohexane-1-carboxylic acid (abbreviated herein as A6C) is a compound of formula:

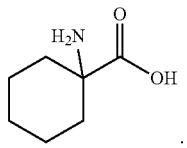

Norarginine (abbreviated herein as Nar) is a compound (S)-2-amino-4-((diaminomethylene)amino)butanoic acid of formula:

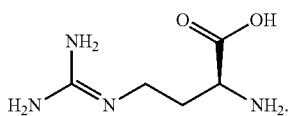

L-β-Homotryptophan (abbreviated herein as betahomoTrp) is a compound of formula:

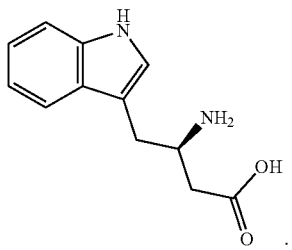 [SMILES: N[C@@H](CC(=O)O)Cc1c[nH]c2ccccc12]

Cyclohexylmethylalanine (abbreviated herein as homo-Cha) is a compound (S)-2-amino-4-cyclohexylbutanoic acid of formula:

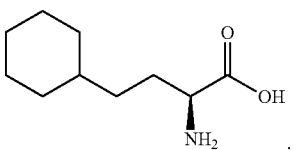 [SMILES: N[C@@H](CCC1CCCCC1)C(=O)O]

Hydroxyproline (abbreviated herein as Hyp) is a compound of formula:

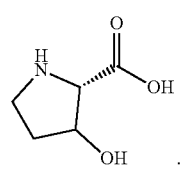

(5-amino-5-oxopentyl)glycine (abbreviated herein as peptoidQ) is a compound having formula:

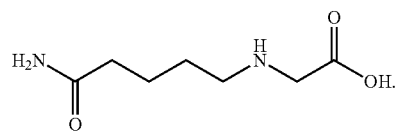 [SMILES: NC(=O)CCCCNCC(=O)O]

His peptoid (abbreviated herein as NHis) is a compound ((1H-imidazol-4-yl)methyl)glycine of formula:

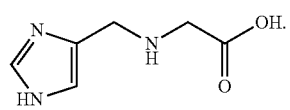 [SMILES: O=C(O)CNCc1c[nH]cn1]

A "variant" as used herein in connection with the polypeptide described herein refers to a polypeptide that differs from a given polypeptide in amino acid sequence and/or chemical structure, but retains one or more biological functions of the given polypeptide (i.e., the polypeptide described herein). For instance, the variant may retain one or more biological functions of a polypeptide derived from the HD2 domain of human BCL9 protein such as e.g., the ability to bind β-catenin, inhibiting canonical Wnt/1-catenin signaling, and/or inhibit binding of BCL9 to β-catenin. The variant polypeptide described herein may have one or more amino acid additions (e.g., insertion), deletions, and/or substitutions from the given polypeptide, as long as it retains the functional properties mentioned above. In some embodiments, the variant polypeptide described herein may have 1-30, 1-20, 1-10, 1-8, 1-5, 1-4, 1-3, or 1-2, or 1, 2, 3, 4, 5, 6, 7, 8, 9, 10, 15, 20, 25, or 30 amino acid additions (e.g., insertion), deletions, and/or substitutions from the wild-type polypeptide, including all integers in between these ranges.

The term "variant" also includes a polypeptide that has a certain percent homology, such as, e.g., at least about 50%, 60%, 70%, 80%, 85%, 90%, 95%, 96%, 97%, 98%, or 99% (or any percentage in between) to a wild-type polypeptide or fragment. As used herein, the term percent (%) homology defines the percentage of residues in the amino acid sequences of the variant and the given polypeptide that are identical after aligning the sequences and other spacing, e.g., using the BLAST alignment software. In some embodiments, the variant comprises a polypeptide that is chemically and/or post-translationally modified in a manner different from the wild-type polypeptide or fragment, but retains one or more biological functions as described above. For instance, the variant may comprise one or more amino acids that are post-transitionally modified by e.g., phosphorylation, acetylation, methylation, ubiquitination, SUMOylation, or other post-translational modifications known in the art. The variant may also comprise one or more chemical modifications, e.g., one or more amino acid side chains that are modified or substituted with a different chemical moiety.

As used herein, the terms "hydrocarbon crosslinker" and "crosslinker" (also known as a hydrocarbon staple, hydrocarbon linker, or a metathesized crosslinker) are used interchangeably and refer to a chemical linker between two amino acids, in which the linker significantly enhances and/or reinforces the secondary structure of a given polypeptide. The hydrocarbon crosslinker as described herein may be based on the incorporation of natural or non-natural amino acids that restrict the structural flexibility of the polypeptide compared to a wildtype (i.e. non-crosslinked) peptide.

The term "polypeptide", as used herein, refers to a sequence amino acids chemically connected by covalent peptide (amide) bonds. That is, and amino group of one amino acids reacted with a carboxyl group of another amino acid to form an amide bond (peptide bond) between the amino acids. Typically, a polypeptide consists of 5-50 amino acid monomers, including an N-terminal amino acid and a C-terminal amino acid. In some embodiments, the terminal amino acid residues are not modified, that is, the polypeptide contains an amino group on one end and a carboxyl group on the other end. In some embodiments, the N-terminus and/or C-terminus of the polypeptide or variant are further modified. In some embodiments, the N-terminus is modified with an acetyl group. In some embodiments, the C-terminus is modified with $NH_2$ group. In some embodiments, the N-terminus and/or C-terminus modification further comprise a fluorenylmethyloxycarbonyl (Fmoc) group.

As used herein, the terms "alkyl" and "$C_{n-m}$ alkyl", employed alone or in combination with other terms, refers to a saturated hydrocarbon group that may be straight-chain (linear) or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the terms "alkylene" and "$C_{n-m}$ alkylene" means a bivalent saturated branched, or straight chain (linear) chemical group containing only carbon and hydrogen atoms, such as methylene, ethylene, n-propylene, iso-propylene, n-butylene, iso-butylene, sec-butylene, tert-butylene, n-pentylene, iso-pentylene, sec-pentylene and neopentylene. Alkylene groups can either be unsubstituted or substituted with one or more substituents. In some embodiments, alkylene groups include 1 to 9 carbon atoms (for example, 1 to 6 carbon atoms, 1 to 4 carbon atoms, or 1 to 2 carbon atoms).

The terms "pharmaceutical" and "pharmaceutically acceptable" are employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" of a disease, condition or disorder refers to decreasing the risk of occurrence of the disease, condition or disorder in a subject or group of subjects (e.g., a subject or group of subjects predisposed to or susceptible to the disease, condition or disorder). In some embodiments, preventing a disease, condition or disorder refers to decreasing the possibility of acquiring the disease, condition or disorder and/or its associated symptoms. In some embodiments, preventing a disease, condition or disorder refers to completely or almost completely stopping the disease, condition or disorder from occurring.

As used herein, the terms "improve," "increase," "enhance," "elevate," "upregulate," and "promote" one or more biological functions are all used interchangeably, and mean that the levels or activities of one or more biological functions or readouts of the functions from in vitro and/or in vivo assays are increased above levels or activities observed in the absence of the polypeptide described herein and/or higher than a vehicle or control polypeptide (e.g., an unstapled wild-type human BCL9 HD2 domain, a polypeptide that does not comprise the core functional domain mediating the interaction between BCL9 and β-catenin, or a control polypeptide comprising a sequence not derived from the HD2 domain of human BCL9 etc.

As used herein, the term "tumor microenvironment" means a cellular microenvironment in and/or around a tumor, including various cells recruited to the tumors, blood vessels, immune cells, signaling molecules, and extracellular matrix. See e.g., Balkwill et al., J Cell Sci (2012) 125: 5591-5596. The polypeptide described herein may alter the composition of immune cells and/or signaling molecules in and/or around a tumor, thereby eliciting an immune reaction in the microenvironment around the tumor.

Examples

Materials and Methods

Each polypeptide (including stabled polypeptides) used in the following examples was generated by a one on-resin synthesis method. Peptide elongation was performed on resin to generate each polypeptide. In case of stapled polypeptides, the peptide backbone synthesis was followed by a ring closing metathesis reaction to generate a hydrocarbon linker.

Methods of synthesizing hydrocarbon linkers using modified Ala residues (α,α-disubstituted amino acids such as α-methyl, α-alkenyl amino acids) are known in the art. See e.g., US20140113857 and Kim 2011.

Hydrocarbon linkers with different lengths, such as an 8-carbon crosslinker and an 11-carbon crosslinker, can be generated using an α-methyl, α-alkenyl amino acid with an alkenyl chain of suitable length. For instance, (S)2-(4'-pentenyl)Ala was incorporated into a polypeptide to construct a stabilized polypeptide having an 8-carbon crosslinker with an S-configuration on both ends. (R)2-(4'-pentenyl)Ala was incorporated into a polypeptide to construct a stabilized polypeptide having an 8-carbon crosslinker with an R-configuration on both ends. For a stabilized polypeptide having an 8-carbon crosslinker with an S-configuration on one end and an R-configuration on the other end, (S)2-(4'-pentenyl)Ala and (R)2-(4'-pentenyl)Ala were used, respectively. To construct a stabilized polypeptide having an 11-carbon crosslinker with an S-configuration on one end and an R-configuration on the other end, (R)2-(7'-octenyl)Ala and (S)2-(4'-pentenyl)Ala were used, respectively.

Each polypeptide was purified using standard high-performance liquid chromatography (HPLC) protocols. A Zorbax C18 reverse-phase column, 9.4×250 mm (Agilent, pore size 80 Å, particle size 3.5 μm) was used. The solvents used were A: water, 0.1% (vol/vol) TFA; B: acetonitrile, 0.1% (vol/vol) TFA. The flow rate was 4 ml/min. The gradient was 10-100% (vol/vol) B over 30 min; 100% B over 5 min; 100-10% (vol/vol) B over 4 min; 10% (vol/vol) B over 1 min. The injection volume was 100-400 μl. The wavelength (nm) was 280 (for Fmoc-, Trp- or Tyr-containing peptides), or 220 (for others).

Example 1—Unstapled Polypeptides Containing α-Monosubstituted Non-Natural Amino Acid The following peptides were prepared according to the methods and procedures similar to those described in the "Materials and methods section".

| Polypeptide ID | Amino Acid Sequence |
| --- | --- |
| SEQ ID NO: 49 | LR(Nle)IQR(Nle)L(2-Nal)(β-Ala)(β-Ala) |
| SEQ ID NO: 50 | LR(Nle)IQR(Nle)L(2-Nal) |
| SEQ ID NO: 51 | LQTLRDIQRML(2-Nal) |
| SEQ ID NO: 52 | LQTLR(Nle)IQR(Nle)L(2-Nal) |
| SEQ ID NO: 53 | LQTLRDIQRML(2-Nal)PD |
| SEQ ID NO: 54 | LQTLR(Nle)IQR(Nle)L(2-Nal)PD |
| SEQ ID NO: 55 | LQTLRDIQRML(2-Nal)P |
| SEQ ID NO: 56 | LQTLR(Nle)IQR(Nle)L(2-Nal)P |
| SEQ ID NO: 57 | RSLQTLRDIQRML(2-Nal) |
| SEQ ID NO: 58 | RSLQTLR(Nle)IQR(Nle)L(2-Nal) |
| SEQ ID NO: 59 | RERSLQTLRDIQRML(2-Nal) |
| SEQ ID NO: 60 | RERSLQTLR(Nle)IQR(Nle)L(2-Nal) |
| SEQ ID NO: 61 | HRERSLQTLRDIQRML(2-Nal) |
| SEQ ID NO: 62 | HRERSLQTLR(Nle)IQR(Nle)L(2-Nal) |
| SEQ ID NO: 63 | EHRERSLQTLRDIQRML(2-Nal) |
| SEQ ID NO: 64 | EHRERSLQTLR(Nle)IQR(Nle)L(2-Nal) |
| SEQ ID NO: 65 | QLEHRERSLQTLRDIQRML(2-Nal) |
| SEQ ID NO: 66 | QLEHRERSLQTLR(Nle)IQR(Nle)L(2-Nal) |
| SEQ ID NO: 67 | QLEHRERSL(Nle)TLR(Nle)IQRML(2-Nal) |
| SEQ ID NO: 68 | RSLQTLR(Nle)IQR(Nle)(CBA)(2-Nal) |
| SEQ ID NO: 69 | RSLQTLR(Nle)IQA(Nle)(CBA)(2-Nal) |
| SEQ ID NO: 70 | HQERSLQTLR(Nle)IQR(Nle)L(2-Nal) |
| SEQ ID NO: 71 | HRERSLQTLR(Nle)IQA(Nle)L(2-Nal) |
| SEQ ID NO: 72 | HRERSLQTLR(Nle)IQA(Nle)L(2-Nal)(β-Ala)(β-Ala) |
| SEQ ID NO: 73 | HRERSLQT(β-L)R(Nle)IQR(Nle)L(2-Nal) |
| SEQ ID NO: 74 | HQERSLQT(β-L)R(Nle)IQR(Nle)L(2-Nal) |

Example 2—Unstapled Polypeptides Containing α,α-Disubstituted Amino Acids

The following peptides were prepared according to the methods and procedures similar to those described in the "Materials and methods section", using (S)-2-(4'-pentenyl)alanine is place of each X and Z.

| Polypeptide ID | Amino Acid Sequence |
| --- | --- |
| SEQ ID NO: 4 | RSLQTLRXIQRXL(2-Nal) |
| SEQ ID NO: 5 | RERSLQTLRXIQRXL(2-Nal) |
| SEQ ID NO: 6 | HRERSLQTLRXIQRXL(2-Nal) |
| SEQ ID NO: 7 | EHRERSLQTLRXIQRXL(2-Nal) |
| SEQ ID NO: 8 | QLEHRERSLQTLRXIQRXL(2-Nal) |
| SEQ ID NO: 9 | EHRERSLQTLRXIQRX(CBA)(2-Nal) |
| SEQ ID NO: 10 | QERSLQTLRXIQRXL(2-Nal) |
| SEQ ID NO: 11 | HQERSLQTLRXIQRXL(2-Nal) |
| SEQ ID NO: 12 | EHQERSLQTLRXIQRXL(2-Nal) |
| SEQ ID NO: 13 | RERSLQTLRXIQRX(CBA)(2-Nal) |
| SEQ ID NO: 14 | HRERSLQTLRXIQRX(CBA)(2-Nal) |
| SEQ ID NO: 21 | AQTARXIQRXL(2-Nal) |
| SEQ ID NO: 22 | LQTARXAQRXL(2-Nal) |
| SEQ ID NO: 23 | LQTLRXAQRXA(2-Nal) |
| SEQ ID NO: 24 | LQTLRXIQAXL(2-Nal) |
| SEQ ID NO: 26 | LQTLRXIQAXL(2-Nal)(β-Ala)(β-Ala) |
| EQ ID NO: 27 | LQTLRXIQAXL(2-Nal)AA |
| SEQ ID NO: 28 | HRERSLQTLRXIQAXL(2-Nal) |
| SEQ ID NO: 29 | HRERSLQTLRXIQAX(CBA)(2-Nal) |
| SEQ ID NO: 32 | LQTLRXIQRXL(2-Nal)PD |
| SEQ ID NO: 33 | LQTLRXIQRXL(2-Nal)P |
| SEQ ID NO: 34 | LQTLRXIQRXL(2-Nal)(β-Ala) |

| Polypeptide ID | Amino Acid Sequence |
|---|---|
| SEQ ID NO: 36 | QLEHRERSLXTLRXIQRML(2-Nal) |
| SEQ ID NO: 39 | REXSLQXLRZIQRZL(2-Nal) |
| SEQ ID NO: 40 | REXSLQXLRZIQRZL(2-Nal)(β-Ala)(β-Ala) |

Example 3—Stapled Polypeptides

The following peptides were prepared according to the methods and procedures similar to those described in the "Materials and methods section" by a metathesis reaction forming a hydrocarbon linker of formula:

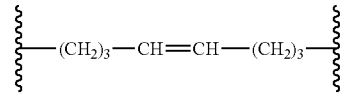

between each pair of X and Z, where each ⸘ denotes a point of attachment of the hydrocarbon linker to the α carbon atom of X or Z, and α carbon of each X and Z is in S-configuration.

| Polypeptide ID | Amino Acid Sequence[1] |
|---|---|
| SEQ ID NO: 4 | RSLQTLRXIQRXL(2-Nal) |
| SEQ ID NO: 5 | RERSLQTLRXIQRXL(2-Nal) |
| SEQ ID NO: 6 | HRERSLQTLRXIQRXL(2-Nal) |
| SEQ ID NO: 7 | EHRERSLQTLRXIQRXL(2-Nal) |
| SEQ ID NO: 8 | QLEHRERSLQTLRXIQRXL(2-Nal) |
| SEQ ID NO: 9 | EHRERSLQTLRXIQRX(CBA)(2-Nal) |
| SEQ ID NO: 10 | QERSLQTLRXIQRXL(2-Nal) |
| SEQ ID NO: 11 | HQERSLQTLRXIQRXL(2-Nal) |
| SEQ ID NO: 12 | EHQERSLQTLRXIQRXL(2-Nal) |
| SEQ ID NO: 13 | RERSLQTLRXIQRX(CBA)(2-Nal) |
| SEQ ID NO: 14 | HRERSLQTLRXIQRX(CBA)(2-Nal) |
| SEQ ID NO: 21 | AQTARXIQRXL(2-Nal) |
| SEQ ID NO: 22 | LQTARXAQRXL(2-Nal) |
| SEQ ID NO: 23 | LQTLRXAQRXA(2-Nal) |
| SEQ ID NO: 24 | LQTLRXIQAXL(2-Nal) |
| SEQ ID NO: 26 | LQTLRXIQAXL(2-Nal)(β-Ala)(β-Ala) |
| SEQ ID NO: 27 | LQTLRXIQAXL(2-Nal)AA |
| SEQ ID NO: 28 | HRERSLQTLRXIQAXL(2-Nal) |
| SEQ ID NO: 29 | HRERSLQTLRXIQAX(CBA)(2-Nal) |
| SEQ ID NO: 32 | LQTLRXIQRXL(2-Nal)PD |
| SEQ ID NO: 33 | LQTLRXIQRXL(2-Nal)P |
| SEQ ID NO: 34 | LQTLRXIQRXL(2-Nal)(β-Ala)(β-Ala) |
| SEQ ID NO: 34a | LQTLRXIQRXL(2-Nal)(β-Ala)(β-Ala)[2] |
| SEQ ID NO: 36 | QLEHRERSLXTLRXIQRML(2-Nal) |
| SEQ ID NO: 39 | REXSLQXLRZIQRZL(2-Nal) |
| SEQ ID NO: 40 | REXSLQXLRZIQRZL(2-Nal)(β-Ala)(β-Ala) |
| SEQ ID NO: 75 | LQTARXIQRXL(2-Nal) |
| SEQ ID NO: 76 | LQTLRXAQRXL(2-Nal) |

| Polypeptide ID | Amino Acid Sequence[1] |
|---|---|
| SEQ ID NO: 77 | LQTLRXIQRXA(2-Nal) |
| SEQ ID NO: 78 | QLEHRERSLXTLRXIQR(2-Abu)L(2-Nal)β-Alaβ-Ala |
| SEQ ID NO: 79 | EXSLQXLRXIQRXL(2-Nal)(β-Ala)(β-Ala) |
| SEQ ID NO: 80 | HREXSLQXLR(Nle)IQR(Nle)L(2-Nal)[15] |
| SEQ ID NO: 81 | HREXSLQXLR(Nle)IQR(Nle)(CBA)(2-Nal)[15] |
| SEQ ID NO: 82 | HREXSLQXLRZIQRZ(CBA)(2-Nal)[14] |
| SEQ ID NO: 83 | HREXSLQXLRXIQQX(CBA)(2-Nal)[15] |
| SEQ ID NO: 84 | HR(N-methylE)XSLQXLRZIQRZ(CBA)(2-Nal)[15] |
| SEQ ID NO: 85 | HREXSLQXL(N-methylR)ZIQRZ(CBA)(2-Nal)[15] |
| SEQ ID NO: 86 | HR(N-Methyl)QXS(Cha)(N-MethylQ)X(Cha)RZIQRZ(Cha)(2-Nal) |
| SEQ ID NO: 87 | HRQXSLQXLRZIQRZ(CBA)(2-Nal) |
| SEQ ID NO: 88 | RXL(N-methylQ)XLRZIQRZ(CBA)(2-Nal)(β-Ala)(β-Ala) |
| SEQ ID NO: 89 | RX(Cpa)(N-methylQ)X(Cpa)RXIQRX(Cpa)(2-Nal)(β-Ala)(β-Ala) |
| SEQ ID NO: 90 | HRQRXLQXLRZIQRZ(CBA)(2-Nal) |
| SEQ ID NO: 91 | HRQRXLQX(Cpa)RZIQRZ(Cpa)(2-Nal) |
| SEQ ID NO: 92 | HRQRXLQX(Cha)RZIQRZ(Cha)(2-Nal) |
| SEQ ID NO: 93 | LEHRERXLQXLRZIQRZL |
| SEQ ID NO: 94 | HRXRSLXTLRZIQRZ(CBA)(2-Nal) |
| SEQ ID NO: 95 | HRXRSLXTLRZIQRZ(CBA)(2-Nal)[16] |
| SEQ ID NO: 96 | HRXRSLXTLRZIQRZ(4-ClPh)(2-Nal)[16] |
| SEQ ID NO: 97 | LQXLRDIQRXL(2-Nal)(β-Ala)(β-Ala) |
| SEQ ID NO: 98 | LQTLEXIQRXL(2-Nal) |
| SEQ ID NO: 99 | LQTLRXIQEXL(2-Nal) |
| SEQ ID NO: 100 | LQTLKXIQRXL(2-Nal) |
| SEQ ID NO: 101 | LQTLRXIQKXL(2-Nal) |
| SEQ ID NO: 102 | (D-L)QTIRXIQRXL(2-Nal) |
| SEQ ID NO: 103 | LQT(D-L)RXIQRXL(2-Nal) |
| SEQ ID NO: 104 | LQTLRX(D-I)QRXL(2-Nal) |
| SEQ ID NO: 105 | LQTLRXIQRX(D-L)(2-Nal) |
| SEQ ID NO: 107 | LQTLRXIQRX(CBA)(2-Nal) |
| SEQ ID NO: 108 | L(N-methylQ)TLRXIQRX(CBA)(2-Nal) |
| SEQ ID NO: 109 | LETLRXIQRX(CBA)(2-Nal) |
| SEQ ID NO: 110 | L(N-methylQ)TLRXIQRX(CBA)(2-Nal)(β-Ala)(β-Ala) |
| SEQ ID NO: 111 | L(N-methylQ)TLRXIQRX(CBA)(2-Nal)(β-Ala)(β-Ala) |
| SEQ ID NO: 112 | LQTLRXIQHX(CBA)(2-Nal) |

-continued

| Polypeptide ID | Amino Acid Sequence[1] |
|---|---|
| SEQ ID NO: 113 | (CBA)QTLRXIQRX(CBA)(2-Nal) |
| SEQ ID NO: 114 | (CBA)(N-methylQ)TLRXIQRX(CBA)(2-Nal) |
| SEQ ID NO: 115 | LQT(CBA)RXIQRX(CBA)(2-Nal) |
| SEQ ID NO: 116 | L(N-methylQ)TLRXI(N-methylQ)RX(CBA)(2-Nal) |
| SEQ ID NO: 117 | LN-MeQTLR(Me)XIQRX(CBA)(2-Nal) |
| SEQ ID NO: 118 | (Me-L)(N-MeQ)TLRXIQRX(CBA)(2-Nal) |
| SEQ ID NO: 119 | LN(Me-Gln)TLRXIQRX(Cpa)(2-Nal) |
| SEQ ID NO: 120 | L(N-methylQ)TLRXIQRX(CBA)(2-Nal)[3] |
| SEQ ID NO: 121 | L(N-methylQ)(N-methylT)LRXIQRX(CBA)(2-Nal) |
| SEQ ID NO: 122 | L(N-methylQ)TLRXIQRX(Cha)(2-Nal) |
| SEQ ID NO: 123 | L(N-methylQ)T(Cha)RXIQRX(CBA)(2-Nal) |
| SEQ ID NO: 124 | L(N-methylQ)TL(N-methylR)XIQRX(CBA)(2-Nal) |
| SEQ ID NO: 125 | L(N-methylQ)TLRXIQ(N-methylR)X(CBA)(2-Nal) |
| SEQ ID NO: 126 | L(N-methylQ)T($\alpha$-methylL)RXIQRX(CBA)(2-Nal) |
| SEQ ID NO: 127 | LQTLRXIQRX(Cha)(2-Nal) |
| SEQ ID NO: 128 | L(N-methylQ)TL(N-methylR)XIQ(N-methylR)X(CBA)(2-Nal) |
| SEQ ID NO: 129 | L(N-methylQ)TLRX(CBA)QRX(CBA)(2-Nal) |
| SEQ ID NO: 130 | L(N-methylQ)(D-Thr)LRXIQRX(CBA)(2-Nal) |
| SEQ ID NO: 131 | L(N-meGln)T(N-MeLeu)RXIQRX(CBA)(2-Nal) |
| SEQ ID NO: 132 | L(N-methylQ)TL(homoR)XIQRX(CBA)(2-Nal) |
| SEQ ID NO: 133 | L(N-methylQ)TLRXIQ(homoR)X(CBA)(2-Nal) |
| SEQ ID NO: 134 | L(N-methylQ)TLRX(N-methylI)QRX(CBA)(2-Nal) |
| SEQ ID NO: 135 | L(N-MeGln)TLRXIQRX(CBA)(2-Nal)[4] |
| SEQ ID NO: 136 | L(N-MeGln)TLRXIQRX(CBA)(2-Nal)[5] |
| SEQ ID NO: 137 | L(N-MeGln)TLRXIQRX(CBA)(2-Nal)[6] |
| SEQ ID NO: 138 | L(N-MeGln)TLRXIQRX(CBA)(2-Nal)7 |
| SEQ ID NO: 139 | L(N-MeGln)TLRXIQRX(CBA)(2-Nal)[8] |
| SEQ ID NO: 140 | L(N-methylQ)TLRXIQRX(CBA)(2-Nal)9 |
| SEQ ID NO: 141 | L(N-methylQ)TLRXIQRX(CBA)(2-Nal)[19] |
| SEQ ID NO: 142 | L(N-methylQ)TLRXIQRX(CBA)(2-Nal)[11] |
| SEQ ID NO: 143 | L(N-methylQ)TLRXIQRX(CBA)(2-Nal)[12] |
| SEQ ID NO: 144 | L(N-methylQ)TLRXIQRX(CBA)(2-Nal)[13] |
| SEQ ID NO: 145 | HRERSLQTLRXIQQX(CBA)(2-Nal) |
| SEQ ID NO: 146 | HRERSLQTLRXIQEX(CBA)(2-Nal)[15] |
| SEQ ID NO: 147 | HRQRSLQTLRXIQRX(CBA)(2-Nal) |
| SEQ ID NO: 148 | HRQRSLQTLRXIQRX(CBA)(2-Nal)($\beta$-Ala)($\beta$-Ala) |
| SEQ ID NO: 149 | HRQRSLQTLRXIQRX(CBA)(2-Nal)($\beta$-Ala)($\beta$-Ala)[17] |

-continued

| Polypeptide ID | Amino Acid Sequence[1] |
|---|---|
| SEQ ID NO: 150 | HRQRSLQTLRXIQRX(CBA)(2-Nal)(β-Ala)(β-Ala)[18] |
| SEQ ID NO: 151 | HR(N-methylE)RSLQTLRXIQRX(CBA)(2-Nal) |
| SEQ ID NO: 152 | HRERSLQTL(N-methylR)XIQRX(CBA)(2-Nal)[15] |
| SEQ ID NO: 153 | HRQRSL(N-methylQ)TLRXIQRX(CBA)(2-Nal) |
| SEQ ID NO: 154 | HR(N-methylE)RSL(N-methylQ)TLRXIQRX(CBA)(2-Nal) |
| SEQ ID NO: 155 | HR(N-methylQ)RSL(N-methylQ)TLRXIQRX(CBA)(2-Nal) |
| SEQ ID NO: 156 | HRQRS(CBA)QTLRXIQRX(CBA)(2-Nal) |
| SEQ ID NO: 157 | HR(N-methylD)RSLQTLRXIQRX(CBA)(2-Nal) |
| SEQ ID NO: 158 | H(R-Me)QRSLQTLRXIQRX(CBA)(2-Nal) |
| SEQ ID NO: 159 | HRQRTLQTLRXIQRX(CBA)(2-Nal) |
| SEQ ID NO: 160 | HRQRSLQTLRXIQRX(CBA)(2-Nal)[16] |
| SEQ ID NO: 161 | HRQRSLQTLRXIQRX(CBA)(2-Nal)[19] |
| SEQ ID NO: 162 | HRQRSLQTLRXIQRX(Cpa)(2-Nal) |
| SEQ ID NO: 163 | HR(N-methylQ)RSL(N-methylQ)T(Cha)RXIQRX(CBA)(2-Nal) |
| SEQ ID NO: 164 | HR(N-methylQ)RSL(N-methylQ)TLRXIQ(N-methylR)X(CBA)(2-Nal) |
| SEQ ID NO: 165 | HR(N-methylQ)RSL(N-methylQ)(N-methylT)LRXIQRX(CBA)(2-Nal) |
| SEQ ID NO: 166 | H(N-methylR)QRSLQTLRXIQRX(CBA)(2-Nal) |
| SEQ ID NO: 167 | HRQ(homoR)SLQTLRXIQRX(CBA)(2-Nal) |
| SEQ ID NO: 168 | HRQ(N-methylR)SLQTLRXIQRX(CBA)(2-Nal) |
| SEQ ID NO: 169 | HRQRSL(peptoid-Q)TLRXIQRX(CBA)(2-Nal) |
| SEQ ID NO: 170 | HRQRSLQTL(homoR)XIQRX(CBA)(2-Nal) |
| SEQ ID NO: 171 | HRQRSLQTLRXIQ(homoR)X(CBA)(2-Nal) |
| SEQ ID NO: 172 | L(N-methylQ)TLRXIQRX(α-methylL)(2-Nal) |
| SEQ ID NO: 173 | L(N-methylQ)TLRXIQRXD(Cha)(2-Nal) |
| SEQ ID NO: 174 | L(N-methylQ)TLRXIQRX(N-methylCha)(2-Nal) |
| SEQ ID NO: 175 | LQTLRXIQRX(allylGly)(2-Nal) |
| SEQ ID NO: 176 | HRQRSLQTLRXIQRX(AC4C)(2-Nal) |
| SEQ ID NO: 177 | HRQRSLQTLRXIQRX(A6C)(2-Nal) |
| SEQ ID NO: 178 | HRQRSLQTLRXIQRX(Aze)(2-Nal) |
| SEQ ID NO: 179 | HRQRSLQTLRXIQRX(Phe-4-Cl)(2-Nal) |
| SEQ ID NO: 180 | HRQRSLQTLRXIQRX(Cha)(2-Nal) |
| SEQ ID NO: 181 | HR(N-methylQ)RSL(N-methylQ)TLRXIQRX(Cha)(2-Nal) |
| SEQ ID NO: 182 | HRQRSLQTLRXIQRX(N-MeCha)(2-Nal) |
| SEQ ID NO: 183 | H(homoArg)QRSLQTLRXIQRX(Cha)(2-Nal) |
| SEQ ID NO: 184 | HRQ(N-MeArg)SLQTLRXIQRX(Cha)(2-Nal) |

-continued

| Polypeptide ID | Amino Acid Sequence[1] |
|---|---|
| SEQ ID NO: 185 | HRQRS(Cha)(N-MeGln)TLRXIQRX(Cha)(2-Nal) |
| SEQ ID NO: 186 | HRQRS(N-MeCha)(N-MeGln)TLRXIQRX(Cha)(2-Nal) |
| SEQ ID NO: 187 | HRQRSD(Cha)(N-MeGln)TLRXIQRX(Cha)(2-Nal) |
| SEQ ID NO: 188 | HRQRSLQTLRXIQRX(Cha)(2DNal) |
| SEQ ID NO: 189 | HRQRSLQTL(N-MeArg)XIQRX(Cha)(2-Nal) |
| SEQ ID NO: 190 | HRQRSLQTLRXIQ(N-MeArg)X(Cha)(2-Nal) |
| SEQ ID NO: 191 | HRQRSLQTLRXIQRX(β-tBu-Ala)(2-Nal) |
| SEQ ID NO: 192 | HRQRSLQTLRXIQRX(Tle)(2-Nal) |
| SEQ ID NO: 193 | HR(N-MeGln)RSLQTLRXIQRX(β-tBu-Ala)(2-Nal) |
| SEQ ID NO: 194 | HR(N-MeGln)RSLQTLRXIQRX(Tle)(2-Nal) |
| SEQ ID NO: 195 | L(N-methylQ)TLRXIQRX(4-Cl-Ph)(2-Nal) |
| SEQ ID NO: 196 | HRQRSLQTLRXIQRX(4-Cl-Ph)(2-Nal) |
| SEQ ID NO: 197 | HR(N-methylQ)RSL(N-methylQ)TLRXIQRX(4-Cl-Ph)(2-Nal) |
| SEQ ID NO: 198 | HRXRSLXTLRXIQRX(4-Cl-Ph)(2-Nal) |
| SEQ ID NO: 199 | HRQRS(Cha)(N-methylQ)TLRXIQRX(4-Cl-Ph)(2-Nal) |
| SEQ ID NO: 200 | HRQRS(Cha)(N-methylQ)TLRXIQRX(4-F-Ph)(2-Nal) |
| SEQ ID NO: 201 | HRQRS(NptGly)(N-methylQ)TLRXIQRX(4-Cl-Ph)(2-Nal) |
| SEQ ID NO: 202 | HR(N-methylQ)RSL(N-methylQ)TLRXIQRX(4-F-Ph)(2-Nal) |
| SEQ ID NO: 203 | HR(N-methylQ)RSL(N-methylQ)TLRXIQRX(3,4-diCl-Ph)(2-Nal) |
| SEQ ID NO: 204 | HR(N-methylQ)RSL(N-methylQ)TLRX(Nle)QRX(Cha)(2-Nal) |
| SEQ ID NO: 205 | HRQRSLQTLRXIQRX(Cha)(2-Nal)[16] |
| SEQ ID NO: 206 | HRQRSLQTLRXIQRX(4-Cl-Ph)(2-Nal)[16] |
| SEQ ID NO: 207 | HR(N-methylQ)RSL(N-methylQ)TLRXIQRX(Cha)(2-Nal)[16] |
| SEQ ID NO: 208 | HR(N-methylQ)RSL(N-methylQ)TLRXIQRX(4-Cl-Ph)(2-Nal)[16] |
| SEQ ID NO: 209 | H(homoArg)QRSLQTLRXIQRX(Cha)(2-Nal)[16] |
| SEQ ID NO: 210 | H(homoArg)QRSLQTLRXIQRX(4-Cl-Ph)(2-Nal)[16] |
| SEQ ID NO: 211 | HRQRS(Cha)(N-methylQ)TLRXIQRX(Cha)(2-Nal)[16] |
| SEQ ID NO: 212 | HRQRS(Cha)(N-methylQ)TLRXIQRX(4-Cl-Ph)(2-Nal)[16] |
| SEQ ID NO: 213 | L(N-methylQ)TLRXIQRX(CBA)(2-Nal)[16] |
| SEQ ID NO: 214 | L(N-methylQ)TLRXIQRX(4-Cl-Ph)(2-Nal)[16] |
| SEQ ID NO: 215 | (N-MeHis)RQRSLQTLRXIQRX(Cha)(2-Nal) |
| SEQ ID NO: 216 | (Cys)RQRSLQTLRXIQRX(Cha)(2-Nal) |

| Polypeptide ID | Amino Acid Sequence[1] |
|---|---|
| SEQ ID NO: 217 | (N-MeCys)RQRSLQTLRXIQRX(Cha)(2-Nal) |
| SEQ ID NO: 218 | (homoHis)RQRSLQTLRXIQRX(Cha)(2-Nal) |
| SEQ ID NO: 219 | (NHis)RQRSLQTLRXIQRX(Cha)(2-Nal) |
| SEQ ID NO: 220 | H(homoArg)QRSLQTL(Nar)XIQRX(Cha)(2-Nal) |
| SEQ ID NO: 221 | H(homoArg)QRSLQTLRXIQ(Nar)X(Cha)(2-Nal) |
| SEQ ID NO: 222 | H(homoArg)QRSLQTLRXIQ(Cit)X(Cha)(2-Nal) |
| SEQ ID NO: 223 | H(homoArg)QRSLQTL(Cit)XIQRX(Cha)(2-Nal) |
| SEQ ID NO: 224 | H(Cit)(N-methylQ)RSL(N-methylQ)TLRXIQRX(Cha)(2-Nal) |
| SEQ ID NO: 225 | H(Nar)(N-methylQ)RSL(N-methylQ)TLRXIQRX(Cha)(2-Nal) |
| SEQ ID NO: 226 | H(4-guanidino-Phe)(N-methylQ)RSL(N-methylQ)TLRXIQRX(Cha)(2-Nal) |

[1] unless specified otherwise, N-terminus of the peptide is modified with an Ac group, and C-terminus is modified with $NH_2$.
[2] C-terminus is modified with GRKKRRQRRRPQK(PEG4-palmitoyl)$NH_2$
[3] N-terminus is modified with $HOCH_2CH_2CO-$.
[4] N-terminus is modified with propionyl.
[5] N-terminus is modified with hexanoyl.
[6] N-terminus is modified with 3-phenylpropanoyl.
[7] N-terminus is modified with 2-cyclohexylacetyl.
[8] N-terminus is modified with diphenylacetyl.
[9] N-terminus is modified with 3,5-dihydroxybenzoic acid.
[10] N-terminus is modified with 4-(trifluoromethyl)benzoic acid.
[11] N-terminus is modified with 5-phenylvaleric acid.
[12] N-terminus is modified with 4-biphenyl acetic acid.
[13] N-terminus is modified with dimethyl.
[14] N-terminus and C-terminus are not modified.
[15] C-terminus is unmodified.
[16] N-terminus is modified with palmitoyl-PEG4.
[17] C-terminus is modified with GRKKRRQRRRPQ-$NH_2$.
[18] C-terminus is modified with 1-(2-aminoethyl)-4-methylpiperazine.
[19] C-terminus is modified with K(PEG4-palmitoyl)$NH_2$.

Example 4—Alpha Assay

Inhibition of binding of BCL9 to β-catenin was assessed in an Amplified Luminescence Proximity Homogeneous Assay (ALPHA). In this assay, a polypeptide is conjugated to a donor bead and its target protein (i.e., β-catenin) is attached to an acceptor bead. When the two beads are in proximity due to the binding of the polypeptide to the target protein, a signal is generated and the binding affinity of the polypeptide can be quantitatively calculated. The assay may be conducted in the presence or absence of an unconjugated control polypeptide. Results of the Alpha assay are presented in Table 4a.

TABLE 4a

| Entry No. | $IC_{50}$, $mM^1$ | $IC_{50}$, $mM^2$ | Entry No. | $IC_{50}$, $mM^1$ | $IC_{50}$, $mM^2$ |
|---|---|---|---|---|---|
| SEQ ID NO: 49 | n/a | 6.71 | SEQ ID NO: 33 | n/a | 11.77 |
| SEQ ID NO: 50 | n/a | 2.54 | SEQ ID NO: 34 | n/a | 9.62 |
| SEQ ID NO: 51 | n/a | 5.78 | SEQ ID NO: 34a | 0.02 | 1.38 |
| SEQ ID NO: 52 | n/a | 4.70 | SEQ ID NO: 4 | n/a | 1.91 |
| SEQ ID NO: 53 | n/a | 27.89 | SEQ ID NO: 5 | 6.8 | 1.45 |
| SEQ ID NO: 54 | n/a | 14.65 | SEQ ID NO: 6 | 5.3 | 0.67 |
| SEQ ID NO: 55 | n/a | 30.30 | SEQ ID NO: 7 | 9.1 | 0.81 |
| SEQ ID NO: 56 | n/a | 10.12 | SEQ ID NO: 8 | 6.3 | 0.77 |
| SEQ ID NO: 57 | n/a | 13.59 | SEQ ID NO: 36 | 50.7 | 0.94 |
| SEQ ID NO: 58 | n/a | 2.84 | SEQ ID NO: 24 | n/a | n/a |
| SEQ ID NO: 59 | n/a | 5.95 | SEQ ID NO: 26 | n/a | n/a |
| SEQ ID NO: 60 | n/a | 2.42 | SEQ ID NO: 27 | n/a | 6.117 |
| SEQ ID NO: 61 | n/a | 1.38 | SEQ ID NO: 39 | 0.56 | 2.195 |
| SEQ ID NO: 62 | n/a | 0.84 | SEQ ID NO: 40 | 0.83 | 2.385 |
| SEQ ID NO: 63 | n/a | 2.50 | SEQ ID NO: 28 | 3.24 | 1.998 |
| SEQ ID NO: 64 | n/a | 1.73 | SEQ ID NO: 9 | 1.90 | 1.503 |
| SEQ ID NO: 65 | n/a | 1.64 | SEQ ID NO: 10 | n/a | 4.198 |
| SEQ ID NO: 66 | n/a | 0.73 | SEQ ID NO: 11 | 1.51 | 2.113 |
| SEQ ID NO: 67 | n/a | 1.08 | SEQ ID NO: 12 | n/a | 4.156 |
| SEQ ID NO: 68 | n/a | n/a | SEQ ID NO: 13 | 1.61 | 0.844 |
| SEQ ID NO: 69 | n/a | n/a | SEQ ID NO: 14 | 1.49 | 0.457 |
| SEQ ID NO: 70 | n/a | n/a | SEQ ID NO: 29 | 2.68 | 1.349 |
| SEQ ID NO: 71 | n/a | n/a | SEQ ID NO: 75 | n/a | 6.29 |
| SEQ ID NO: 72 | n/a | n/a | SEQ ID NO: 76 | n/a | 8.99 |
| SEQ ID NO: 73 | n/a | n/a | SEQ ID NO: 77 | n/a | 7.68 |
| SEQ ID NO: 74 | n/a | n/a | SEQ ID NO: 78 | n/a | 0.09 |
| SEQ ID NO: 21 | n/a | 7.61 | SEQ ID NO: 79 | n/a | n/a |
| SEQ ID NO: 22 | n/a | 11.42 | SEQ ID NO: 80 | n/a | 5.334 |
| SEQ ID NO: 23 | n/a | 29.98 | SEQ ID NO: 81 | n/a | 45.518 |
| SEQ ID NO: 32 | n/a | 12.16 | SEQ ID NO: 82 | >5 | 1.008 |
| SEQ ID NO: 83 | n/a | 50.000 | SEQ ID NO: 90 | 1.83 | 0.857 |
| SEQ ID NO: 84 | n/a | n/a | SEQ ID NO: 91 | n/a | n/a |
| SEQ ID NO: 85 | n/a | n/a | SEQ ID NO: 92 | 2.54 | 0.497 |
| SEQ ID NO: 86 | n/a | n/a | SEQ ID NO: 93 | n/a | n/a |
| SEQ ID NO: 87 | n/a | 2.664 | SEQ ID NO: 94 | 3.34 | 0.175 |
| SEQ ID NO: 88 | n/a | n/a | SEQ ID NO: 95 | n/a | n/a |
| SEQ ID NO: 89 | n/a | 2.46 | SEQ ID NO: 96 | n/a | n/a |
| SEQ ID NO: 97 | n/a | n/a | SEQ ID NO: 117 | n/a | 4.23 |

TABLE 4a-continued

| Entry No. | IC$_{50}$, mM[1] | IC$_{50}$, mM[2] | Entry No. | IC$_{50}$, mM[1] | IC$_{50}$, mM[2] |
|---|---|---|---|---|---|
| SEQ ID NO: 98 | n/a | 47.10 | SEQ ID NO: 118 | n/a | 6.33 |
| SEQ ID NO: 99 | n/a | 50.00 | SEQ ID NO: 119 | n/a | 15.84 |
| SEQ ID NO: 100 | n/a | 14.38 | SEQ ID NO: 120 | n/a | 5.44 |
| SEQ ID NO: 101 | n/a | 10.61 | SEQ ID NO: 121 | n/a | 5.01 |
| SEQ ID NO: 102 | n/a | 6.84 | SEQ ID NO: 122 | n/a | 7.17 |
| SEQ ID NO: 103 | n/a | 2.86 | SEQ ID NO: 123 | n/a | 3.62 |
| SEQ ID NO: 104 | n/a | n/a | SEQ ID NO: 124 | n/a | 2.74 |
| SEQ ID NO: 105 | n/a | 10.65 | SEQ ID NO: 125 | n/a | 10.64 |
| SEQ ID NO: 107 | >5 | 0.316 | SEQ ID NO: 126 | n/a | 7.43 |
| SEQ ID NO: 108 | 3.1 | 0.408 | SEQ ID NO: 127 | n/a | 10.08 |
| SEQ ID NO: 109 | >5 | 0.913 | SEQ ID NO: 128 | n/a | 29.54 |
| SEQ ID NO: 110 | n/a | 12.87 | SEQ ID NO: 129 | n/a | 2.06 |
| SEQ ID NO: 111 | 3.07 | 0.005 | SEQ ID NO: 130 | n/a | n/a |
| SEQ ID NO: 112 | n/a | 5.65 | SEQ ID NO: 131 | n/a | n/a |
| SEQ ID NO: 113 | n/a | 6.99 | SEQ ID NO: 132 | n/a | 11.23 |
| SEQ ID NO: 114 | n/a | 4.90 | SEQ ID NO: 133 | n/a | 9.20 |
| SEQ ID NO: 115 | n/a | 4.53 | SEQ ID NO: 134 | n/a | n/a |
| SEQ ID NO: 116 | n/a | 26.90 | SEQ ID NO: 135 | n/a | 8.54 |
| SEQ ID NO: 136 | n/a | 3.52 | SEQ ID NO: 166 | 4.17 | 0.403 |
| SEQ ID NO: 137 | n/a | 8.36 | SEQ ID NO: 167 | 4.76 | 0.356 |
| SEQ ID NO: 138 | n/a | 3.82 | SEQ ID NO: 168 | 4.14 | 0.434 |
| SEQ ID NO: 139 | n/a | 4.58 | SEQ ID NO: 169 | 4.98 | 0.328 |
| SEQ ID NO: 140 | n/a | 8.16 | SEQ ID NO: 170 | 5.17 | 0.430 |
| SEQ ID NO: 141 | n/a | 2.25 | SEQ ID NO: 171 | 4.76 | 0.340 |
| SEQ ID NO: 142 | n/a | 6.07 | SEQ ID NO: 172 | n/a | 8.00 |
| SEQ ID NO: 143 | n/a | 6.66 | SEQ ID NO: 173 | n/a | 14.73 |
| SEQ ID NO: 144 | n/a | 2.13 | SEQ ID NO: 174 | n/a | 6.88 |
| SEQ ID NO: 145 | >5 | 0.154 | SEQ ID NO: 175 | n/a | 9.71 |
| SEQ ID NO: 146 | n/a | 0.493 | SEQ ID NO: 176 | >5 | 0.236 |
| SEQ ID NO: 147 | 2.53 | 0.186 | SEQ ID NO: 177 | 2.67 | 0.211 |
| SEQ ID NO: 148 | 2.60 | 0.359 | SEQ ID NO: 178 | >5 | 0.563 |
| SEQ ID NO: 149 | 3.44 | 0.004 | SEQ ID NO: 179 | 4.68 | 0.059 |
| SEQ ID NO: 150 | n/a | n/a | SEQ ID NO: 180 | 1.88 | 0.138 |
| SEQ ID NO: 151 | 3.10 | 0.261 | SEQ ID NO: 181 | 1.82 | 0.186 |
| SEQ ID NO: 152 | >5 | 0.794 | SEQ ID NO: 182 | n/a | n/a |
| SEQ ID NO: 153 | 2.56 | 0.261 | SEQ ID NO: 183 | 2.53 | 0.119 |
| SEQ ID NO: 154 | 1.91 | 0.661 | SEQ ID NO: 184 | 2.43 | 0.195 |
| SEQ ID NO: 155 | 2.15 | 0.281 | SEQ ID NO: 185 | 1.90 | 0.223 |
| SEQ ID NO: 156 | 2.63 | 0.253 | SEQ ID NO: 186 | 2.23 | 0.232 |
| SEQ ID NO: 157 | 3.17 | 0.525 | SEQ ID NO: 187 | 2.18 | 0.201 |
| SEQ ID NO: 158 | 3.32 | 0.383 | SEQ ID NO: 188 | 3.28 | 0.387 |
| SEQ ID NO: 159 | 2.48 | 0.291 | SEQ ID NO: 189 | 3.25 | 0.247 |
| SEQ ID NO: 160 | 0.83 | 0.361 | SEQ ID NO: 190 | 5.89 | 0.271 |
| SEQ ID NO: 161 | 3.35 | 0.791 | SEQ ID NO: 191 | 2.87 | 0.322 |
| SEQ ID NO: 162 | 4.19 | 0.322 | SEQ ID NO: 192 | 2.59 | 0.329 |
| SEQ ID NO: 163 | 2.39 | 0.195 | SEQ ID NO: 193 | 2.67 | 0.323 |
| SEQ ID NO: 164 | n/a | 1.475 | SEQ ID NO: 194 | 3.75 | 0.398 |
| SEQ ID NO: 165 | n/a | n/a | SEQ ID NO: 195 | n/a | 13.004 |
| SEQ ID NO: 196 | n/a | 0.063 | SEQ ID NO: 212 | n/a | n/a |
| SEQ ID NO: 197 | n/a | n/a | SEQ ID NO: 213 | n/a | 0.466 |
| SEQ ID NO: 198 | n/a | n/a | SEQ ID NO: 214 | n/a | n/a |
| SEQ ID NO: 199 | n/a | n/a | SEQ ID NO: 215 | n/a | 9.522 |
| SEQ ID NO: 200 | n/a | 0.324 | SEQ ID NO: 216 | n/a | 0.155 |
| SEQ ID NO: 201 | n/a | n/a | SEQ ID NO: 217 | n/a | 0.384 |
| SEQ ID NO: 202 | n/a | 0.294 | SEQ ID NO: 218 | n/a | n/a |
| SEQ ID NO: 203 | n/a | 0.312 | SEQ ID NO: 219 | n/a | n/a |
| SEQ ID NO: 204 | n/a | 0.463 | SEQ ID NO: 220 | n/a | n/a |
| SEQ ID NO: 205 | n/a | n/a | SEQ ID NO: 221 | n/a | n/a |
| SEQ ID NO: 206 | n/a | n/a | SEQ ID NO: 222 | n/a | 0.742 |
| SEQ ID NO: 207 | n/a | 0.354 | SEQ ID NO: 223 | n/a | 0.573 |
| SEQ ID NO: 208 | n/a | n/a | SEQ ID NO: 224 | n/a | n/a |
| SEQ ID NO: 209 | n/a | 0.253 | SEQ ID NO: 225 | n/a | n/a |
| SEQ ID NO: 210 | n/a | n/a | SEQ ID NO: 226 | n/a | n/a |
| SEQ ID NO: 211 | n/a | 0.305 | | | |

[1]Colo320DM cell viability
[2]ALPHA Screen

Example 5—Wnt Reporter Assay

Wnt/Beta-Catenin-LEF-TCF-bla HCT116-Inhibitor Screen, Constitutively Activated. LEF-TCF-bla HCT116 cells are thawed and prepared as described above for the Activator Screen. 32 µL of cell suspension is added to each well of a 384-well Poly-D-Lysine assay plate. Cells in Assay Media are incubated for 16-24 hours in the plate at 37° C./5% $CO_2$ in a humidified incubator. 4 µL of a 10× serial dilution of ICG-001 (control inhibitor starting concentration, 25,000 nM) or compounds are added to appropriate wells of the plate. 4 µL of Assay Media is added to all wells to bring the final assay volume to 40 µL. The plate is incubated for 5 hours at 37° C./5% $CO_2$ in a humidified incubator. 8 µL of 1 µM Substrate Loading Solution is added to each well and the plate is incubated for 2 hours at room temperature. The plate is read on a fluorescence plate reader.

| Entry No. | IC$_{50}$ (nM) |
|---|---|
| SEQ ID NO: 147 | 1540 |
| SEQ ID NO: 108 | 3160 |
| SEQ ID NO: 154 | 2260 |
| SEQ ID NO: 177 | 4450 |
| SEQ ID NO: 162 | 7050 |
| SEQ ID NO: 180 | 2210 |
| SEQ ID NO: 181 | 4460 |
| SEQ ID NO: 163 | 4430 |

Other Embodiments

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

The invention claimed is:
1. A polypeptide selected from:

| | |
|---|---|
| LQTLRXaa$_3$IQRXaa$_6$(CBA)(2-Nal) | SEQ ID NO: 107 |
| L(N-methylQ)TLRXaa$_3$IQRXaa$_6$(CBA)(2-Nal) | SEQ ID NO: 108 |
| LETLRXaa$_3$IQRXaa$_6$(CBA)(2-Nal) | SEQ ID NO: 109 |
| L(N-methylQ)TLRXaa$_3$IQRXaa$_6$(CBA)(2-Nal)(β-Ala)(β-Ala) | SEQ ID NO: 110 |

-continued

| | |
|---|---|
| L(N-methylQ)TLRXaa₃IQRXaa₆(CBA)(2-Nal)(β-Ala)(β-Ala) | SEQ ID NO: 111 |
| LQTLRXaa₃IQHXaa₆(CBA)(2-Nal) | SEQ ID NO: 112 |
| (CBA)QTLRXaa₃IQRXaa₆(CBA)(2-Nal) | SEQ ID NO: 113 |
| (CBA)(N-methylQ)TLRXaa₃IQRXaa₆(CBA)(2-Nal) | SEQ ID NO: 114 |
| LQT(CBA)RXaa₃IQRXaa₆(CBA)(2-Nal) | SEQ ID NO: 115 |
| L(N-methylQ)TLRXaa₃I(N-methylQ)RXaa₆(CBA)(2-Nal) | SEQ ID NO: 116 |
| LN-MeQTLR(Me)Xaa₃IQRXaa₆(CBA)(2-Nal) | SEQ ID NO: 117 |
| (Me-L)(N-MeQ)TLRXaa₃IQRXaa₆(CBA)(2-Nal) | SEQ ID NO: 118 |
| LN(Me-Gln)TLRXaa₃IQRXaa₆(Cpa)(2-Nal) | SEQ ID NO: 119 |
| L(N-methylQ)TLRXaa₃IQRXaa₆(CBA)(2-Nal),<br>wherein N-terminus is modified with HOCH₂CH₂CO-. | SEQ ID NO: 120 |
| L(N-methylQ)(N-methylT)LRXaa₃IQRXaa₆(CBA)(2-Nal) | SEQ ID NO: 121 |
| L(N-methylQ)TLRXaa₃IQRXaa₆(Cha)(2-Nal) | SEQ ID NO: 122 |
| L(N-methylQ)T(Cha)RXaa₃IQRXaa₆(CBA)(2-Nal) | SEQ ID NO: 123 |
| L(N-methylQ)TL(N-methylR)Xaa₃IQRXaa₆(CBA)(2-Nal) | SEQ ID NO: 124 |
| L(N-methylQ)TLRXaa₃IQ(N-methylR)Xaa₆(CBA)(2-Nal) | SEQ ID NO: 125 |
| L(N-methylQ)T(α-methylL)RXaa₃IQRXaa₆(CBA)(2-Nal) | SEQ ID NO: 126 |
| LQTLRXaa₃IQRXaa₆(Cha)(2-Nal) | SEQ ID NO: 127 |
| L(N-methylQ)TL(N-methylR)Xaa₃IQ(N-methylR)Xaa₆(CBA)(2-Nal) | SEQ ID NO: 128 |
| L(N-methylQ)TLRXaa₃(CBA)QRXaa₆(CBA)(2-Nal) | SEQ ID NO: 129 |
| L(N-methylQ)(D-Thr)LRXaa₃IQRXaa₆(CBA)(2-Nal) | SEQ ID NO: 130 |
| L(N-meGln)T(N-MeLeu)RXaa₃IQRXaa₆(CBA)(2-Nal) | SEQ ID NO: 131 |
| L(N-methylQ)TL(homoR)Xaa₃IQRXaa₆(CBA)(2-Nal) | SEQ ID NO: 132 |
| L(N-methylQ)TLRXaa₃IQ(homoR)Xaa₆(CBA)(2-Nal) | SEQ ID NO: 133 |
| L(N-methylQ)TLRXaa₃(N-methylI)QRXaa₆(CBA)(2-Nal) | SEQ ID NO: 134 |
| L(N-MeGln)TLRXaa₃IQRXaa₆(CBA)(2-Nal),<br>wherein N-terminus is modified with propionyl. | SEQ ID NO: 135 |
| L(N-MeGln)TLRXaa₃IQRXaa₆(CBA)(2-Nal),<br>wherein N-terminus is modified with hexanoyl. | SEQ ID NO: 136 |
| L(N-MeGln)TLRXaa₃IQRXaa₆(CBA)(2-Nal),<br>wherein N-terminus is modified with 3-phenylpropanoyl. | SEQ ID NO: 137 |
| L(N-MeGln)TLRXaa₃IQRXaa₆(CBA)(2-Nal),<br>wherein N-terminus is modified with 2-cyclohexylacetyl. | SEQ ID NO: 138 |
| L(N-MeGln)TLRXaa₃IQRXaa₆(CBA)(2-Nal),<br>wherein N-terminus is modified with diphenylacetyl. | SEQ ID NO: 139 |
| L(N-methylQ)TLRXaa₃IQRXaa₆(CBA)(2-Nal),<br>wherein N-terminus is modified with 3,5-dihydroxybenzoicacid. | SEQ ID NO: 140 |
| L(N-methylQ)TLRXaa₃IQRXaa₆(CBA)(2-Nal),<br>wherein N-terminus is modified with 4-(trifluoromethyl)benzoicacid. | SEQ ID NO: 141 |
| L(N-methylQ)TLRXaa₃IQRXaa₆(CBA)(2-Nal),<br>wherein N-terminus is modified with 5-phenylvalericacid. | SEQ ID NO: 142 |
| L(N-methylQ)TLRXaa₃IQRXaa₆(CBA)(2-Nal),<br>wherein N-terminus is modified with 4-biphenylaceticacid. | SEQ ID NO: 143 |
| L(N-methylQ)TLRXaa₃IQRXaa₆(CBA)(2-Nal),<br>wherein N-terminus is modified with dimethyl. | SEQ ID NO: 144 |

-continued

| | |
|---|---|
| HRERSLQTLRXaa₃IQQXaa₆(CBA)(2-Nal) | SEQ ID NO: 145 |
| HRERSLQTLRXaa₃IQEXaa₆(CBA)(2-Nal), wherein C-terminus is unmodified. | SEQ ID NO: 146 |
| HRQRSLQTLRXaa₃IQRXaa₆(CBA)(2-Nal) | SEQ ID NO: 147 |
| HRQRSLQTLRXaa₃IQRXaa₆(CBA)(2-Nal)(β-Ala)(β-Ala) | SEQ ID NO: 148 |
| HRQRSLQTLRXaa₃IQRXaa₆(CBA)(2-Nal)(β-Ala)(β-Ala), wherein C-terminus is modified with GRKKRRQRRRPQ-NH₂. | SEQ ID NO: 149 |
| HRQRSLQTLRXaa₃IQRXaa₆(CBA)(2-Nal)(β-Ala)(β-Ala), wherein C-terminus is modified with 1-(2-aminoethyl)-4-methylpiperazine. | SEQ ID NO: 150 |
| HR(N-methylE)RSLQTLRXaa₃IQRXaa₆(CBA)(2-Nal) | SEQ ID NO: 151 |
| HRERSLQTL(N-methylR)Xaa₃IQRXaa₆(CBA)(2-Nal), wherein C-terminus is unmodified. | SEQ ID NO: 152 |
| HRQRSL(N-methylQ)TLRXaa₃IQRXaa₆(CBA)(2-Nal) | SEQ ID NO: 153 |
| HR(N-methylE)RSL(N-methylQ)TLRXaa₃IQRXaa₆(CBA)(2-Nal) | SEQ ID NO: 154 |
| HR(N-methylQ)RSL(N-methylQ)TLRXaa₃IQRXaa₆(CBA)(2-Nal) | SEQ ID NO: 155 |
| HRQRS(CBA)QTLRXaa₃IQRXaa₆(CBA)(2-Nal) | SEQ ID NO: 156 |
| HR(N-methylD)RSLQTLRXaa₃IQRXaa₆(CBA)(2-Nal) | SEQ ID NO: 157 |
| H(R-Me)QRSLQTLRXaa₃IQRXaa₆(CBA)(2-Nal) | SEQ ID NO: 158 |
| HRQRTLQTLRXaa₃IQRXaa₆(CBA)(2-Nal) | SEQ ID NO: 159 |
| HRQRSLQTLRXaa₃IQRXaa₆(CBA)(2-Nal), N-terminus is modified with palmitoyl-PEG4. | SEQ ID NO: 160 |
| HRQRSLQTLRXaa₃IQRXaa₆(CBA)(2-Nal), wherein the C-terminus is modified with K(PEG4-palmitoyl)NH₂. | SEQ ID NO: 161 |
| HRQRSLQTLRXaa₃IQRXaa₆(Cpa)(2-Nal) | SEQ ID NO: 162 |
| HR(N-methylQ)RSL(N-methylQ)T(Cha)RXaa₃IQRXaa₆(CBA)(2-Nal) | SEQ ID NO: 163 |
| HR(N-methylQ)RSL(N-methylQ)TLRXaa₃IQ(N-methylR)Xaa₆(CBA)(2-Nal) | SEQ ID NO: 164 |
| HR(N-methylQ)RSL(N-methylQ)(N-methylT)LRXaa₃IQRXaa₆(CBA)(2-Nal) | SEQ ID NO: 165 |
| H(N-methylR)QRSLQTLRXaa₃IQRXaa₆(CBA)(2-Nal) | SEQ ID NO: 166 |
| HRQ(homoR)SLQTLRXaa₃IQRXaa₆(CBA)(2-Nal) | SEQ ID NO: 167 |
| HRQ(N-methylR)SLQTLRXaa₃IQRXaa₆(CBA)(2-Nal) | SEQ ID NO: 168 |
| HRQRSL(peptoid-Q)TLRXaa₃IQRXaa₆(CBA)(2-Nal) | SEQ ID NO: 169 |
| HRQRSLQTL(homoR)Xaa₃IQRXaa₆(CBA)(2-Nal) | SEQ ID NO: 170 |
| HRQRSLQTLRXaa₃IQ(homoR)Xaa₆(CBA)(2-Nal) | SEQ ID NO: 171 |
| L(N-methylQ)TLRXaa₃IQRXaa₆(α-methylL)(2-Nal) | SEQ ID NO: 172 |
| L(N-methylQ)TLRXaa₃IQRXaa₆D(Cha)(2-Nal) | SEQ ID NO: 173 |
| L(N-methylQ)TLRXaa₃IQRXaa₆(N-methylCha)(2-Nal) | SEQ ID NO: 174 |
| LQTLRXaa₃IQRXaa₆(allylGly)(2-Nal) | SEQ ID NO: 175 |
| HRQRSLQTLRXaa₃IQRXaa₆(AC4C)(2-Nal) | SEQ ID NO: 176 |
| HRQRSLQTLRXaa₃IQRXaa₆(A6C)(2-Nal) | SEQ ID NO: 177 |
| HRQRSLQTLRXaa₃IQRXaa₆(Aze)(2-Nal) | SEQ ID NO: 178 |
| HRQRSLQTLRXaa₃IQRXaa₆(Phe-4-Cl)(2-Nal) | SEQ ID NO: 179 |

| | |
|---|---|
| HRQRSLQTLRXaa₃IQRXaa₆(Cha)(2-Nal) | SEQ ID NO: 180 |
| HR(N-methylQ)RSL(N-methylQ)TLRXaa₃IQRXaa₆(Cha)(2-Nal) | SEQ ID NO: 181 |
| HRQRSLQTLRXaa₃IQRXaa₆(N-MeCha)(2-Nal) | SEQ ID NO: 182 |
| H(homoArg)QRSLQTLRXaa₃IQRXaa₆(Cha)(2-Nal) | SEQ ID NO: 183 |
| HRQ(N-MeArg)SLQTLRXaa₃IQRXaa₆(Cha)(2-Nal) | SEQ ID NO: 184 |
| HRQRS(Cha)(N-MeGln)TLRXaa₃IQRXaa₆(Cha)(2-Nal) | SEQ ID NO: 185 |
| HRQRS(N-MeCha)(N-MeGln)TLRXaa₃IQRXaa₆(Cha)(2-Nal) | SEQ ID NO: 186 |
| HRQRSD(Cha)(N-MeGln)TLRXaa₃IQRXaa₆(Cha)(2-Nal) | SEQ ID NO: 187 |
| HRQRSLQTLRXaa₃IQRXaa₆(Cha)(2DNal) | SEQ ID NO: 188 |
| HRQRSLQTL(N-MeArg)Xaa₃IQRXaa₆(Cha)(2-Nal) | SEQ ID NO: 189 |
| HRQRSLQTLRXaa₃IQ(N-MeArg)Xaa₆(Cha)(2-Nal) | SEQ ID NO: 190 |
| HRQRSLQTLRXaa₃IQRXaa₆(β-tBu-Ala)(2-Nal) | SEQ ID NO: 191 |
| HRQRSLQTLRXaa₃IQRXaa₆(Tle)(2-Nal) | SEQ ID NO: 192 |
| HR(N-MeGln)RSLQTLRXaa₃IQRXaa₆(β-tBu-Ala)(2-Nal) | SEQ ID NO: 193 |
| HR(N-MeGln)RSLQTLRXaa₃IQRXaa₆(Tle)(2-Nal) | SEQ ID NO: 194 |
| L(N-methylQ)TLRXaa₃IQRXaa₆(4-Cl-Ph)(2-Nal) | SEQ ID NO: 195 |
| HRQRSLQTLRXaa₃IQRXaa₆(4-Cl-Ph)(2-Nal) | SEQ ID NO: 196 |
| HR(N-methylQ)RSL(N-methylQ)TLRXaa₃IQRXaa₆(4-Cl-Ph)(2-Nal) | SEQ ID NO: 197 |
| HRQRS(Cha)(N-methylQ)TLRXaa₃IQRXaa₆(4-Cl-Ph)(2-Nal) | SEQ ID NO: 199 |
| HRQRS(Cha)(N-methylQ)TLRXaa₃IQRXaa₆(4-F-Ph)(2-Nal) | SEQ ID NO: 200 |
| HRQRS(NptGly)(N-methylQ)TLRXaa₃IQRXaa₆(4-Cl-Ph)(2-Nal) | SEQ ID NO: 201 |
| HR(N-methylQ)RSL(N-methylQ)TLRXaa₃IQRXaa₆(4-F-Ph)(2-Nal) | SEQ ID NO: 202 |
| HR(N-methylQ)RSL(N-methylQ)TLRXaa₃IQRXaa₆(3,4-diCl-Ph)(2-Nal) | SEQ ID NO: 203 |
| HR(N-methylQ)RSL(N-methylQ)TLRXaa₃(Nle)QRXaa₆(Cha)(2-Nal) | SEQ ID NO: 204 |
| HRQRSLQTLRXaa₃IQRXaa₆(Cha)(2-Nal),<br>wherein N-terminus is modified with palmitoyl-PEG4. | SEQ ID NO: 205 |
| HRQRSLQTLRXaa₃IQRXaa₆(4-Cl-Ph)(2-Nal),<br>wherein N-terminus is modified with palmitoyl-PEG4. | SEQ ID NO: 206 |
| HR(N-methylQ)RSL(N-methylQ)TLRXaa₃IQRXaa₆(Cha)(2-Nal),<br>wherein N-terminus is modified with palmitoyl-PEG4. | SEQ ID NO: 207 |
| HR(N-methylQ)RSL(N-methylQ)TLRXaa₃IQRXaa₆(4-Cl-Ph)(2-Nal),<br>wherein N-terminus is modified with palmitoyl-PEG4. | SEQ ID NO: 208 |
| H(homoArg)QRSLQTLRXaa₃IQRXaa₆(Cha)(2-Nal),<br>wherein N-terminus is modified with palmitoyl-PEG4. | SEQ ID NO: 209 |
| H(homoArg)QRSLQTLRXaa₃IQRXaa₆(4-Cl-Ph)(2-Nal),<br>wherein N-terminus is modified with palmitoyl-PEG4. | SEQ ID NO: 210 |
| HRQRS(Cha)(N-methylQ)TLRXaa₃IQRXaa₆(Cha)(2-Nal),<br>wherein N-terminus is modified with palmitoyl-PEG4. | SEQ ID NO: 211 |
| HRQRS(Cha)(N-methylQ)TLRXaa₃IQRXaa₆(4-Cl-Ph)(2-Nal),<br>wherein N-terminus is modified with palmitoyl-PEG4. | SEQ ID NO: 212 |
| L(N-methylQ)TLRXaa₃IQRXaa₆(CBA)(2-Nal),<br>wherein N-terminus is modified with palmitoyl-PEG4. | SEQ ID NO: 213 |
| L(N-methylQ)TLRXaa₃IQRXaa₆(4-Cl-Ph)(2-Nal),<br>wherein N-terminus is modified with palmitoyl-PEG4. | SEQ ID NO: 214 |

| | |
|---|---|
| (N-MeHis)RQRSLQTLRXaa₃IQRXaa₆(Cha)(2-Nal) | SEQ ID NO: 215 |
| (Cys)RQRSLQTLRXaa₃IQRXaa₆(Cha)(2-Nal) | SEQ ID NO: 216 |
| (N-MeCys)RQRSLQTLRXaa₃IQRXaa₆(Cha)(2-Nal) | SEQ ID NO: 217 |
| (homoHis)RQRSLQTLRXaa₃IQRXaa₆(Cha)(2-Nal) | SEQ ID NO: 218 |
| (NHis)RQRSLQTLRXaa₃IQRXaa₆(Cha)(2-Nal) | SEQ ID NO: 219 |
| H(homoArg)QRSLQTL(Nar)Xaa₃IQRXaa₆(Cha)(2-Nal) | SEQ ID NO: 220 |
| H(homoArg)QRSLQTLRXaa₃IQ(Nar)Xaa₆(Cha)(2-Nal) | SEQ ID NO: 221 |
| H(homoArg)QRSLQTLRXaa₃IQ(Cit)Xaa₆(Cha)(2-Nal) | SEQ ID NO: 222 |
| H(homoArg)QRSLQTL(Cit)Xaa₃IQRXaa₆(Cha)(2-Nal) | SEQ ID NO: 223 |
| H(Cit)(N-methylQ)RSL(N-methylQ)TLRXaa₃IQRXaa₆(Cha)(2-Nal) | SEQ ID NO: 224 |
| H(Nar)(N-methylQ)RSL(N-methylQ)TLRXaa₃IQRXaa₆(Cha)(2-Nal) | SEQ ID NO: 225 |
| H(4-guanidino-Phe)(N-methylQ)RSL(N-methylQ)TLRXaa₃IQRXaa₆(Cha)(2-Nal) | SEQ ID NO: 226 | or a pharmaceutically acceptable salt thereof.

2. The polypeptide of claim 1, wherein the α,α-disubstituted amino acid is an α-methyl, α-alkenyl amino acid.

3. The polypeptide of claim 2, wherein Xaa₃ and Xaa₆ are each independently selected from: (S)-2-(4'-pentenyl)alanine, (R)-2-(4'-pentenyl)alanine, (S)-2-(7'-octenyl)alanine, and (R)-2-(7'-octenyl)alanine.

4. The polypeptide of claim 1, wherein one α substituent in the α,α-disubstituted amino acid is methyl, and the other α substituent in the α,α-disubstituted amino acid is a hydrocarbon linker.

5. The polypeptide of claim 4, wherein the hydrocarbon linker has formula:

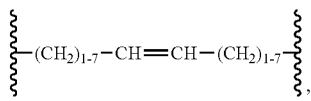

wherein one ⸹ denotes a point of attachment of the hydrocarbon linker to the α carbon atom of Xaa₃, and the other ⸹ denotes a point of attachment of the hydrocarbon linker to the α carbon atom of Xaa₆.

6. The polypeptide of claim 5, wherein the hydrocarbon crosslinker has formula:

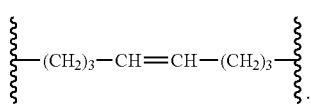

7. A pharmaceutical composition comprising a polypeptide of claim 1, or a pharmaceutically acceptable salt thereof, and a pharmaceutically acceptable carrier.

8. A polypeptide selected from any one of the following polypeptides:

```
                                          (SEQ ID NO: 32)
LQTLRXaa₃IQRXaa₆L(2-Nal)PD;

(SEQ ID NO: 33)
LQTLRXaa₃IQRXaa₆L(2-Nal)P;

(SEQ ID NO: 34)
LQTLRXaa₃IQRXaa₆L(2-Nal)(β-Ala)(β-Ala);
and (SEQ ID NO: 34a)
LQTLRXaa₃IQRXaa₆L(2-Nal)(β-Ala)(β-Ala),
``` wherein C-terminus in SEQ ID NO: 34a is modified with GRKKRRQRRRPQK(PEG4-palmitoyl)NH₂.

9. The polypeptide of claim 8, wherein the α,α-disubstituted amino acid is an α-methyl, α-alkenyl amino acid.

10. The polypeptide of claim 8, wherein one α substituent in the α,α-disubstituted amino acid is methyl, and the other α substituent in the α,α-disubstituted amino acid is a hydrocarbon linker.

11. The polypeptide of claim 10, wherein the hydrocarbon linker has formula:

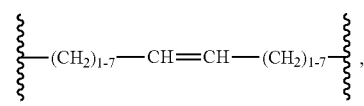

wherein one ⸹ denotes a point of attachment of the hydrocarbon linker to the α carbon atom of Xaa₃, and the other ⸹ denotes a point of attachment of the hydrocarbon linker to the α carbon atom of Xaa₆.

* * * * *

SEQUENCE LISTING

<160> NUMBER OF SEQ ID NOS: 279

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Leu, Ala, Cyclohexyl L-alanine, Cyclopropyl-L-

```
        alanine, Beta-cyclobutyl alanine, D-Leucine, N-methyl leucine,
        N-methyl cyclohexyl alanine, Cyclohexyl D-alanine or
        L-alpha-neopentylglycine
<220> FEATURE:
<221> NAME/KEY: MOD_RES
<222> LOCATION: (5)..(5)
<223> OTHER INFORMATION: Leu, Ala, Cyclohexyl L-alanine, Cyclopropyl-L-
        alanine, Beta-cyclobutyl alanine, D-Leucine, N-methyl leucine,
        N-methyl cyclohexyl alanine, Cyclohexyl D-alanine or L-alpha-
        neopentylglycine
<220> FEATURE:
<221> NAME/KEY: MOD_RES
<222> LOCATION: (7)..(7)
<223> OTHER INFORMATION: Any alpha, alpha-disubstituted amino acid
<220> FEATURE:
<221> NAME/KEY: MOD_RES
<222> LOCATION: (8)..(8)
<223> OTHER INFORMATION: Ile, Ala, Norleucine, N-methyl-L-isoleucine,
        Beta-cyclobutylalanine or D-Isoleucine
<220> FEATURE:
<221> NAME/KEY: MOD_RES
<222> LOCATION: (10)..(10)
<223> OTHER INFORMATION: Arg, Ala, Gln, Glu, Lys, His, N-methylarginine,
        Homoarginine, N-methylarginine, Norarginine or Citrulline
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: Leu, Ala, Beta-cyclobutyl alanine, Cyclohexyl
        L-alanine, Cyclopropyl-L-alanine, 4-Chlorophenyl alanine,
        D-Leucine, Alpha methylleucine, Cyclohexyl D-alanine, N-methyl
        cyclohexyl alanine, Allyl glycine, 1-aminocyclobutane-1
<220> FEATURE:
<221> NAME/KEY: MOD_RES
<222> LOCATION: (12)..(12)
<223> OTHER INFORMATION: CONT. FROM ABOVE: -carboxylic acid,
        1-aminocyclohexane-1-carboxylic acid, Azetidine-3-carboxylic acid,
        N-methyl cyclohexyl alanine, Beta-tBu-Ala, Tertleucine,
        4-fluorophenyl alanine, or 3,4-Chlorophenyl alanine
<220> FEATURE:
<221> NAME/KEY: MOD_RES
<222> LOCATION: (13)..(13)
<223> OTHER INFORMATION: 2-Naphthylalanine

<400> SEQUENCE: 1

Ser Xaa Gln Thr Xaa Arg Xaa Xaa Gln Xaa Xaa Xaa Ala
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (7)..(7)
<223> OTHER INFORMATION: Any alpha, alpha-disubstituted amino acid
<220> FEATURE:
<221> NAME/KEY: MISC_FEATURE
<222> LOCATION: (7)..(11)
<223> OTHER INFORMATION: May or may not be a hydrocarbon crosslinker
        between residues
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MOD_RES
<222> LOCATION: (13)..(13)
<223> OTHER INFORMATION: 2-Naphthylalanine

<400> SEQUENCE: 2
```

```
Ser Leu Gln Thr Leu Arg Xaa Ile Gln Arg Xaa Leu Ala
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any alpha, alpha-disubstituted amino acid
<220> FEATURE:
<221> NAME/KEY: MISC_FEATURE
<222> LOCATION: (7)..(11)
<223> OTHER INFORMATION: May or may not be a hydrocarbon crosslinker
      between residues
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: Beta-cyclobutyl alanine
<220> FEATURE:
<221> NAME/KEY: MOD_RES
<222> LOCATION: (13)..(13)
<223> OTHER INFORMATION: 2-Naphthylalanine

<400> SEQUENCE: 3

Ser Leu Gln Thr Leu Arg Xaa Ile Gln Arg Xaa Ala Ala
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any alpha, alpha-disubstituted amino acid
<220> FEATURE:
<221> NAME/KEY: MISC_FEATURE
<222> LOCATION: (8)..(12)
<223> OTHER INFORMATION: May or may not be a hydrocarbon crosslinker
      between residues
<220> FEATURE:
<221> NAME/KEY: MOD_RES
<222> LOCATION: (12)..(12)
<223> OTHER INFORMATION: Any alpha, alpha-disubstituted amino acid
<220> FEATURE:
<221> NAME/KEY: MOD_RES
<222> LOCATION: (14)..(14)
<223> OTHER INFORMATION: 2-Naphthylalanine

<400> SEQUENCE: 4

Arg Ser Leu Gln Thr Leu Arg Xaa Ile Gln Arg Xaa Leu Ala
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MISC_FEATURE
<222> LOCATION: (10)..(14)
<223> OTHER INFORMATION: May or may not be a hydrocarbon crosslinker
      between residues
<220> FEATURE:
<221> NAME/KEY: MOD_RES
<222> LOCATION: (14)..(14)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 2-Naphthylalanine

<400> SEQUENCE: 5

Arg Glu Arg Ser Leu Gln Thr Leu Arg Xaa Ile Gln Arg Xaa Leu Ala
1               5                   10                  15

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (17)..(17)
<223> OTHER INFORMATION: 2-Naphthylalanine

<400> SEQUENCE: 6

His Arg Glu Arg Ser Leu Gln Thr Leu Arg Xaa Ile Gln Arg Xaa Leu
1               5                   10                  15

Ala

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any alpha, alpha-disubstituted amino acid
<220> FEATURE:
<221> NAME/KEY: MISC_FEATURE
<222> LOCATION: (12)..(16)
<223> OTHER INFORMATION: May or may not be a hydrocarbon crosslinker
      between residues
<220> FEATURE:
<221> NAME/KEY: MOD_RES
<222> LOCATION: (16)..(16)
<223> OTHER INFORMATION: Any alpha, alpha-disubstituted amino acid
<220> FEATURE:
<221> NAME/KEY: MOD_RES
<222> LOCATION: (18)..(18)
```

```
<223> OTHER INFORMATION: 2-Naphthylalanine

<400> SEQUENCE: 7

Glu His Arg Glu Arg Ser Leu Gln Thr Leu Arg Xaa Ile Gln Arg Xaa
1               5                   10                  15

Leu Ala

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any alpha, alpha-disubstituted amino acid
<220> FEATURE:
<221> NAME/KEY: MISC_FEATURE
<222> LOCATION: (14)..(18)
<223> OTHER INFORMATION: May or may not be a hydrocarbon crosslinker
      between residues
<220> FEATURE:
<221> NAME/KEY: MOD_RES
<222> LOCATION: (18)..(18)
<223> OTHER INFORMATION: Any alpha, alpha-disubstituted amino acid
<220> FEATURE:
<221> NAME/KEY: MOD_RES
<222> LOCATION: (20)..(20)
<223> OTHER INFORMATION: 2-Naphthylalanine

<400> SEQUENCE: 8

Gln Leu Glu His Arg Glu Arg Ser Leu Gln Thr Leu Arg Xaa Ile Gln
1               5                   10                  15

Arg Xaa Leu Ala
            20

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any alpha, alpha-disubstituted amino acid
<220> FEATURE:
<221> NAME/KEY: MISC_FEATURE
<222> LOCATION: (12)..(16)
<223> OTHER INFORMATION: May or may not be a hydrocarbon crosslinker
      between residues
<220> FEATURE:
<221> NAME/KEY: MOD_RES
<222> LOCATION: (16)..(16)
<223> OTHER INFORMATION: Any alpha, alpha-disubstituted amino acid
<220> FEATURE:
<221> NAME/KEY: MOD_RES
<222> LOCATION: (17)..(17)
<223> OTHER INFORMATION: Beta-cyclobutyl alanine
<220> FEATURE:
<221> NAME/KEY: MOD_RES
<222> LOCATION: (18)..(18)
<223> OTHER INFORMATION: 2-Naphthylalanine

<400> SEQUENCE: 9

Glu His Arg Glu Arg Ser Leu Gln Thr Leu Arg Xaa Ile Gln Arg Xaa
1               5                   10                  15

Ala Ala
```

```
<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MISC_FEATURE
<222> LOCATION: (10)..(14)
<223> OTHER INFORMATION: May or may not be a hydrocarbon crosslinker
      between residues
<220> FEATURE:
<221> NAME/KEY: MOD_RES
<222> LOCATION: (14)..(14)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 2-Naphthylalanine

<400> SEQUENCE: 10

Gln Glu Arg Ser Leu Gln Thr Leu Arg Xaa Ile Gln Arg Xaa Leu Ala
1               5                   10                  15

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (17)..(17)
<223> OTHER INFORMATION: 2-Naphthylalanine

<400> SEQUENCE: 11

His Gln Glu Arg Ser Leu Gln Thr Leu Arg Xaa Ile Gln Arg Xaa Leu
1               5                   10                  15

Ala

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any alpha, alpha-disubstituted amino acid
<220> FEATURE:
<221> NAME/KEY: MISC_FEATURE
```

-continued

```
<222> LOCATION: (12)..(16)
<223> OTHER INFORMATION: May or may not be a hydrocarbon crosslinker
      between residues
<220> FEATURE:
<221> NAME/KEY: MOD_RES
<222> LOCATION: (16)..(16)
<223> OTHER INFORMATION: Any alpha, alpha-disubstituted amino acid
<220> FEATURE:
<221> NAME/KEY: MOD_RES
<222> LOCATION: (18)..(18)
<223> OTHER INFORMATION: 2-Naphthylalanine

<400> SEQUENCE: 12

Glu His Gln Glu Arg Ser Leu Gln Thr Leu Arg Xaa Ile Gln Arg Xaa
1               5                   10                  15

Leu Ala

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MISC_FEATURE
<222> LOCATION: (10)..(14)
<223> OTHER INFORMATION: May or may not be a hydrocarbon crosslinker
      between residues
<220> FEATURE:
<221> NAME/KEY: MOD_RES
<222> LOCATION: (14)..(14)
<223> OTHER INFORMATION: Any alpha, alpha-disubstituted amino acid
<220> FEATURE:
<221> NAME/KEY: MOD_RES
<222> LOCATION: (15)..(15)
<223> OTHER INFORMATION: Beta-cyclobutyl alanine
<220> FEATURE:
<221> NAME/KEY: MOD_RES
<222> LOCATION: (16)..(16)
<223> OTHER INFORMATION: 2-Naphthylalanine

<400> SEQUENCE: 13

Arg Glu Arg Ser Leu Gln Thr Leu Arg Xaa Ile Gln Arg Xaa Ala Ala
1               5                   10                  15

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
```

```
<220> FEATURE:
<221> NAME/KEY: MOD_RES
<222> LOCATION: (17)..(17)
<223> OTHER INFORMATION: 2-Naphthylalanine

<400> SEQUENCE: 14

His Arg Glu Arg Ser Leu Gln Thr Leu Arg Xaa Ile Gln Arg Xaa Ala
1               5                   10                  15

Ala

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Ala, Cyclohexyl L-alanine, Cyclopropyl-L-
      alanine, Beta-cyclobutyl alanine, D-Leucine, N-methyl leucine,
      N-methyl cyclohexyl alanine, Cyclohexyl D-alanine or
      L-alpha-neopentylglycine
<220> FEATURE:
<221> NAME/KEY: MOD_RES
<222> LOCATION: (4)..(4)
<223> OTHER INFORMATION: Leu, Ala, Cyclohexyl L-alanine, Cyclopropyl-L-
      alanine, Beta-cyclobutyl alanine, D-Leucine, N-methyl leucine,
      N-methyl cyclohexyl alanine, Cyclohexyl D-alanine or L-alpha-
      neopentylglycine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MOD_RES
<222> LOCATION: (7)..(7)
<223> OTHER INFORMATION: Ile, Ala, Norleucine, N-methyl-L-isoleucine,
      Beta-cyclobutylalanine or D-Isoleucine
<220> FEATURE:
<221> NAME/KEY: MOD_RES
<222> LOCATION: (9)..(9)
<223> OTHER INFORMATION: Arg, Ala, Gln, Glu, Lys, His, N-methylarginine,
      Homoarginine, N-methylarginine, Norarginine or Citrulline
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Leu, Ala, Beta-cyclobutyl alanine, Cyclohexyl
      L-alanine, Cyclopropyl-L-alanine, 4-Chlorophenyl alanine,
      D-Leucine, Alpha methylleucine, Cyclohexyl D-alanine, N-methyl
      cyclohexyl alanine, Allyl glycine, 1-aminocyclobutane-1
<220> FEATURE:
<221> NAME/KEY: MOD_RES
<222> LOCATION: (11)..(11)
<223> OTHER INFORMATION: CONT. FROM ABOVE: -carboxylic acid,
      1-aminocyclohexane-1-carboxylic acid, Azetidine-3-carboxylic acid,
      N-methyl cyclohexyl alanine, Beta-tBu-Ala, Tertleucine,
      4-fluorophenyl alanine, or 3,4-Chlorophenyl alanine
<220> FEATURE:
<221> NAME/KEY: MOD_RES
<222> LOCATION: (12)..(12)
<223> OTHER INFORMATION: 2-Naphthylalanine

<400> SEQUENCE: 15

Xaa Gln Thr Xaa Arg Xaa Xaa Gln Xaa Xaa Xaa Ala
1               5                   10

<210> SEQ ID NO 16
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 16

Ala Gln Thr Ala Arg Xaa Ile Gln Arg Xaa Leu Ala
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 17

Leu Gln Thr Ala Arg Xaa Ala Gln Arg Xaa Leu Ala
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
```

```
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 18

Leu Gln Thr Leu Arg Xaa Ala Gln Arg Xaa Ala Ala
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 19

Leu Gln Thr Leu Arg Xaa Ile Gln Ala Xaa Leu Ala
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 20

Leu Gln Thr Leu Arg Xaa Ile Gln Ala Xaa Ala Ala
1               5                   10

<210> SEQ ID NO 21
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 21

Ala Gln Thr Ala Arg Xaa Ile Gln Arg Xaa Leu Ala
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 22

Leu Gln Thr Ala Arg Xaa Ala Gln Arg Xaa Leu Ala
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
```

```
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 23

Leu Gln Thr Leu Arg Xaa Ala Gln Arg Xaa Ala Ala
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 24

Leu Gln Thr Leu Arg Xaa Ile Gln Ala Xaa Leu Ala
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 25

Leu Gln Thr Leu Arg Xaa Ile Gln Ala Xaa Ala Ala
1               5                   10
```

-continued

```
<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine
<220> FEATURE:
<221> NAME/KEY: MOD_RES
<222> LOCATION: (13)..(13)
<223> OTHER INFORMATION: Beta-alanine
<220> FEATURE:
<221> NAME/KEY: MOD_RES
<222> LOCATION: (14)..(14)
<223> OTHER INFORMATION: Beta-alanine

<400> SEQUENCE: 26

Leu Gln Thr Leu Arg Xaa Ile Gln Ala Xaa Leu Ala Ala Ala
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 27

Leu Gln Thr Leu Arg Xaa Ile Gln Ala Xaa Leu Ala Ala Ala
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (17)..(17)
<223> OTHER INFORMATION: 2-Naphthylalanine

<400> SEQUENCE: 28

His Arg Glu Arg Ser Leu Gln Thr Leu Arg Xaa Ile Gln Ala Xaa Leu
1               5                   10                  15

Ala

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 29

His Arg Glu Arg Ser Leu Gln Thr Leu Arg Xaa Ile Gln Ala Xaa Ala
1               5                   10                  15

Ala

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Ala, Cyclohexyl L-alanine, Cyclopropyl-L-
      alanine, Beta-cyclobutyl alanine, D-Leucine, N-methyl leucine,
      N-methyl cyclohexyl alanine, Cyclohexyl D-alanine or
      L-alpha-neopentylglycine
<220> FEATURE:
<221> NAME/KEY: MOD_RES
<222> LOCATION: (4)..(4)
<223> OTHER INFORMATION: Leu, Ala, Cyclohexyl L-alanine, Cyclopropyl-L-
```

```
       alanine, Beta-cyclobutyl alanine, D-Leucine, N-methyl leucine,
       N-methyl cyclohexyl alanine, Cyclohexyl D-alanine or L-alpha-
       neopentylglycine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MOD_RES
<222> LOCATION: (7)..(7)
<223> OTHER INFORMATION: Ile, Ala, Norleucine, N-methyl-L-isoleucine,
       Beta-cyclobutylalanine or D-Isoleucine
<220> FEATURE:
<221> NAME/KEY: MOD_RES
<222> LOCATION: (9)..(9)
<223> OTHER INFORMATION: Arg, Ala, Gln, Glu, Lys, His, N-methylarginine,
       Homoarginine, N-methylarginine, Norarginine or Citrulline
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Leu, Ala, Beta-cyclobutyl alanine, Cyclohexyl
       L-alanine, Cyclopropyl-L-alanine, 4-Chlorophenyl alanine,
       D-Leucine, Alpha methylleucine, Cyclohexyl D-alanine, N-methyl
       cyclohexyl alanine, Allyl glycine, 1-aminocyclobutane-1
<220> FEATURE:
<221> NAME/KEY: MOD_RES
<222> LOCATION: (11)..(11)
<223> OTHER INFORMATION: CONT. FROM ABOVE: -carboxylic acid,
       1-aminocyclohexane-1-carboxylic acid, Azetidine-3-carboxylic acid,
       N-methyl cyclohexyl alanine, Beta-tBu-Ala, Tertleucine,
       4-fluorophenyl alanine, or 3,4-Chlorophenyl alanine
<220> FEATURE:
<221> NAME/KEY: MOD_RES
<222> LOCATION: (12)..(12)
<223> OTHER INFORMATION: 2-Naphthylalanine

<400> SEQUENCE: 30

Xaa Gln Thr Xaa Arg Xaa Xaa Gln Xaa Xaa Xaa Ala
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
       between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 31

Leu Gln Thr Leu Arg Xaa Ile Gln Arg Xaa Leu Ala
1               5                   10

<210> SEQ ID NO 32
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 32

Leu Gln Thr Leu Arg Xaa Ile Gln Arg Xaa Leu Ala Pro Asp
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 33

Leu Gln Thr Leu Arg Xaa Ile Gln Arg Xaa Leu Ala Pro
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
```

```
-continued

<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine
<220> FEATURE:
<221> NAME/KEY: MOD_RES
<222> LOCATION: (13)..(13)
<223> OTHER INFORMATION: Beta-alanine
<220> FEATURE:
<221> NAME/KEY: MOD_RES
<222> LOCATION: (14)..(14)
<223> OTHER INFORMATION: Beta-alanine

<400> SEQUENCE: 34

Leu Gln Thr Leu Arg Xaa Ile Gln Arg Xaa Leu Ala Ala Ala
1               5                   10

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any alpha, alpha-disubstituted amino acid
<220> FEATURE:
<221> NAME/KEY: MOD_RES
<222> LOCATION: (3)..(3)
<223> OTHER INFORMATION: Leu, Ala, Cyclohexyl L-alanine, Cyclopropyl-L-
      alanine, D-Leucine, Beta-cyclobutyl alanine, N-methyl leucine,
      N-methyl cyclohexyl alanine, Cyclohexyl D-alanine,
      or L-alpha-neopentylglycine
<220> FEATURE:
<221> NAME/KEY: MOD_RES
<222> LOCATION: (5)..(5)
<223> OTHER INFORMATION: Any alpha, alpha-disubstituted amino acid

<400> SEQUENCE: 35

Xaa Thr Xaa Arg Xaa
1               5

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MISC_FEATURE
<222> LOCATION: (10)..(14)
<223> OTHER INFORMATION: May or may not be a hydrocarbon crosslinker
      between residues
<220> FEATURE:
<221> NAME/KEY: MOD_RES
<222> LOCATION: (14)..(14)
<223> OTHER INFORMATION: Any alpha, alpha-disubstituted amino acid
<220> FEATURE:
<221> NAME/KEY: MOD_RES
<222> LOCATION: (20)..(20)
<223> OTHER INFORMATION: 2-Naphthylalanine

<400> SEQUENCE: 36

Gln Leu Glu His Arg Glu Arg Ser Leu Xaa Thr Leu Arg Xaa Ile Gln
1               5                   10                  15
```

Arg Met Leu Ala
            20

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any alpha, alpha-disubstituted amino acid
<220> FEATURE:
<221> NAME/KEY: MOD_RES
<222> LOCATION: (5)..(5)
<223> OTHER INFORMATION: Any alpha, alpha-disubstituted amino acid

<400> SEQUENCE: 37

Xaa Ser Leu Gln Xaa
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any alpha, alpha-disubstituted amino acid
<220> FEATURE:
<221> NAME/KEY: MOD_RES
<222> LOCATION: (5)..(5)
<223> OTHER INFORMATION: Any alpha, alpha-disubstituted amino acid

<400> SEQUENCE: 38

Xaa Ile Gln Arg Xaa
1               5

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any alpha, alpha-disubstituted amino acid
<220> FEATURE:
<221> NAME/KEY: MISC_FEATURE
<222> LOCATION: (3)..(7)
<223> OTHER INFORMATION: May or may not be a hydrocarbon crosslinker
      between residues
<220> FEATURE:
<221> NAME/KEY: MOD_RES
<222> LOCATION: (7)..(7)
<223> OTHER INFORMATION: Any alpha, alpha-disubstituted amino acid
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MISC_FEATURE
<222> LOCATION: (10)..(14)
<223> OTHER INFORMATION: May or may not be a hydrocarbon crosslinker
      between residues
<220> FEATURE:
<221> NAME/KEY: MOD_RES

```
<222> LOCATION: (14)..(14)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 2-Naphthylalanine

<400> SEQUENCE: 39

Arg Glu Xaa Ser Leu Gln Xaa Leu Arg Xaa Ile Gln Arg Xaa Leu Ala
1               5                   10                  15

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any alpha, alpha-disubstituted amino acid
<220> FEATURE:
<221> NAME/KEY: MISC_FEATURE
<222> LOCATION: (3)..(7)
<223> OTHER INFORMATION: May or may not be a hydrocarbon crosslinker
      between residues
<220> FEATURE:
<221> NAME/KEY: MOD_RES
<222> LOCATION: (7)..(7)
<223> OTHER INFORMATION: Any alpha, alpha-disubstituted amino acid
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MISC_FEATURE
<222> LOCATION: (10)..(14)
<223> OTHER INFORMATION: May or may not be a hydrocarbon crosslinker
      between residues
<220> FEATURE:
<221> NAME/KEY: MOD_RES
<222> LOCATION: (14)..(14)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 2-Naphthylalanine
<220> FEATURE:
<221> NAME/KEY: MOD_RES
<222> LOCATION: (17)..(17)
<223> OTHER INFORMATION: Beta-alanine
<220> FEATURE:
<221> NAME/KEY: MOD_RES
<222> LOCATION: (18)..(18)
<223> OTHER INFORMATION: Beta-alanine

<400> SEQUENCE: 40

Arg Glu Xaa Ser Leu Gln Xaa Leu Arg Xaa Ile Gln Arg Xaa Leu Ala
1               5                   10                  15

Ala Ala

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 2-Naphthylalanine
```

```
<400> SEQUENCE: 41

Asp Ile Gln Arg Met Leu Ala
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (7)..(7)
<223> OTHER INFORMATION: 2-Naphthylalanine

<400> SEQUENCE: 42

Leu Ile Gln Arg Leu Leu Ala
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (6)..(6)
<223> OTHER INFORMATION: Beta-cyclobutyl alanine
<220> FEATURE:
<221> NAME/KEY: MOD_RES
<222> LOCATION: (7)..(7)
<223> OTHER INFORMATION: 2-Naphthylalanine

<400> SEQUENCE: 43

Leu Ile Gln Arg Leu Ala Ala
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
```

```
<222> LOCATION: (7)..(7)
<223> OTHER INFORMATION: 2-Naphthylalanine

<400> SEQUENCE: 44

Leu Ile Gln Ala Leu Leu Ala
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (6)..(6)
<223> OTHER INFORMATION: Beta-cyclobutyl alanine
<220> FEATURE:
<221> NAME/KEY: MOD_RES
<222> LOCATION: (7)..(7)
<223> OTHER INFORMATION: 2-Naphthylalanine

<400> SEQUENCE: 45

Leu Ile Gln Ala Leu Ala Ala
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Norleucine

<400> SEQUENCE: 46

Leu Thr Leu Arg Leu
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Norleucine

<400> SEQUENCE: 47

Gln Thr Leu Arg Leu
1               5
```

```
<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Beta-Leucine
<220> FEATURE:
<221> NAME/KEY: MOD_RES
<222> LOCATION: (5)..(5)
<223> OTHER INFORMATION: Norleucine

<400> SEQUENCE: 48

Gln Thr Leu Arg Leu
1               5

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: 2-Naphthylalanine
<220> FEATURE:
<221> NAME/KEY: MOD_RES
<222> LOCATION: (10)..(10)
<223> OTHER INFORMATION: Beta-alanine
<220> FEATURE:
<221> NAME/KEY: MOD_RES
<222> LOCATION: (11)..(11)
<223> OTHER INFORMATION: Beta-alanine

<400> SEQUENCE: 49

Leu Arg Leu Ile Gln Arg Leu Leu Ala Ala Ala
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: 2-Naphthylalanine

<400> SEQUENCE: 50

Leu Arg Leu Ile Gln Arg Leu Leu Ala
```

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: 2-Naphthylalanine

<400> SEQUENCE: 51

Leu Gln Thr Leu Arg Asp Ile Gln Arg Met Leu Ala
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (10)..(10)
<223> OTHER INFORMATION: Norleucine
<220> FEATURE:
<221> NAME/KEY: MOD_RES
<222> LOCATION: (12)..(12)
<223> OTHER INFORMATION: 2-Naphthylalanine

<400> SEQUENCE: 52

Leu Gln Thr Leu Arg Leu Ile Gln Arg Leu Leu Ala
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: 2-Naphthylalanine

<400> SEQUENCE: 53

Leu Gln Thr Leu Arg Asp Ile Gln Arg Met Leu Ala Pro Asp
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (10)..(10)

```
<223> OTHER INFORMATION: Norleucine
<220> FEATURE:
<221> NAME/KEY: MOD_RES
<222> LOCATION: (12)..(12)
<223> OTHER INFORMATION: 2-Naphthylalanine

<400> SEQUENCE: 54

Leu Gln Thr Leu Arg Leu Ile Gln Arg Leu Leu Ala Pro Asp
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: 2-Naphthylalanine

<400> SEQUENCE: 55

Leu Gln Thr Leu Arg Asp Ile Gln Arg Met Leu Ala Pro
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Norleucine
<220> FEATURE:
<221> NAME/KEY: MOD_RES
<222> LOCATION: (10)..(10)
<223> OTHER INFORMATION: Norleucine
<220> FEATURE:
<221> NAME/KEY: MOD_RES
<222> LOCATION: (12)..(12)
<223> OTHER INFORMATION: 2-Naphthylalanine

<400> SEQUENCE: 56

Leu Gln Thr Leu Arg Leu Ile Gln Arg Leu Leu Ala Pro
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: 2-Naphthylalanine

<400> SEQUENCE: 57

Arg Ser Leu Gln Thr Leu Arg Asp Ile Gln Arg Met Leu Ala
1               5                   10

<210> SEQ ID NO 58
<211> LENGTH: 14
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (12)..(12)
<223> OTHER INFORMATION: Norleucine
<220> FEATURE:
<221> NAME/KEY: MOD_RES
<222> LOCATION: (14)..(14)
<223> OTHER INFORMATION: 2-Naphthylalanine

<400> SEQUENCE: 58

Arg Ser Leu Gln Thr Leu Arg Leu Ile Gln Arg Leu Leu Ala
1               5                   10

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: 2-Naphthylalanine

<400> SEQUENCE: 59

Arg Glu Arg Ser Leu Gln Thr Leu Arg Asp Ile Gln Arg Met Leu Ala
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Norleucine
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (16)..(16)
<223> OTHER INFORMATION: 2-Naphthylalanine

<400> SEQUENCE: 60

Arg Glu Arg Ser Leu Gln Thr Leu Arg Leu Ile Gln Arg Leu Leu Ala
1               5                   10                  15

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: 2-Naphthylalanine

<400> SEQUENCE: 61
```

-continued

His Arg Glu Arg Ser Leu Gln Thr Leu Arg Asp Ile Gln Arg Met Leu
1               5                   10                  15

Ala

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Norleucine
<220> FEATURE:
<221> NAME/KEY: MOD_RES
<222> LOCATION: (15)..(15)
<223> OTHER INFORMATION: Norleucine
<220> FEATURE:
<221> NAME/KEY: MOD_RES
<222> LOCATION: (17)..(17)
<223> OTHER INFORMATION: 2-Naphthylalanine

<400> SEQUENCE: 62

His Arg Glu Arg Ser Leu Gln Thr Leu Arg Leu Ile Gln Arg Leu Leu
1               5                   10                  15

Ala

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: 2-Naphthylalanine

<400> SEQUENCE: 63

Glu His Arg Glu Arg Ser Leu Gln Thr Leu Arg Asp Ile Gln Arg Met
1               5                   10                  15

Leu Ala

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Norleucine
<220> FEATURE:
<221> NAME/KEY: MOD_RES
<222> LOCATION: (16)..(16)
<223> OTHER INFORMATION: Norleucine
<220> FEATURE:
<221> NAME/KEY: MOD_RES
<222> LOCATION: (18)..(18)
<223> OTHER INFORMATION: 2-Naphthylalanine

<400> SEQUENCE: 64

Glu His Arg Glu Arg Ser Leu Gln Thr Leu Arg Leu Ile Gln Arg Leu
1               5                   10                  15

Leu Ala

<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: 2-Naphthylalanine

<400> SEQUENCE: 65

Gln Leu Glu His Arg Glu Arg Ser Leu Gln Thr Leu Arg Asp Ile Gln
1               5                   10                  15

Arg Met Leu Ala
            20

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (18)..(18)
<223> OTHER INFORMATION: Norleucine
<220> FEATURE:
<221> NAME/KEY: MOD_RES
<222> LOCATION: (20)..(20)
<223> OTHER INFORMATION: 2-Naphthylalanine

<400> SEQUENCE: 66

Gln Leu Glu His Arg Glu Arg Ser Leu Gln Thr Leu Arg Leu Ile Gln
1               5                   10                  15

Arg Leu Leu Ala
            20

<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Norleucine
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (20)..(20)
<223> OTHER INFORMATION: 2-Naphthylalanine

<400> SEQUENCE: 67

Gln Leu Glu His Arg Glu Arg Ser Leu Leu Thr Leu Arg Leu Ile Gln
1               5                   10                  15

Arg Met Leu Ala

```
<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (12)..(12)
<223> OTHER INFORMATION: Norleucine
<220> FEATURE:
<221> NAME/KEY: MOD_RES
<222> LOCATION: (13)..(13)
<223> OTHER INFORMATION: Beta-cyclobutyl alanine
<220> FEATURE:
<221> NAME/KEY: MOD_RES
<222> LOCATION: (14)..(14)
<223> OTHER INFORMATION: 2-Naphthylalanine

<400> SEQUENCE: 68

Arg Ser Leu Gln Thr Leu Arg Leu Ile Gln Arg Leu Ala Ala
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (12)..(12)
<223> OTHER INFORMATION: Norleucine
<220> FEATURE:
<221> NAME/KEY: MOD_RES
<222> LOCATION: (13)..(13)
<223> OTHER INFORMATION: Beta-cyclobutyl alanine
<220> FEATURE:
<221> NAME/KEY: MOD_RES
<222> LOCATION: (14)..(14)
<223> OTHER INFORMATION: 2-Naphthylalanine

<400> SEQUENCE: 69

Arg Ser Leu Gln Thr Leu Arg Leu Ile Gln Ala Leu Ala Ala
1               5                   10

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Norleucine
<220> FEATURE:
<221> NAME/KEY: MOD_RES
<222> LOCATION: (15)..(15)
<223> OTHER INFORMATION: Norleucine
<220> FEATURE:
```

```
<221> NAME/KEY: MOD_RES
<222> LOCATION: (17)..(17)
<223> OTHER INFORMATION: 2-Naphthylalanine

<400> SEQUENCE: 70

His Gln Glu Arg Ser Leu Gln Thr Leu Arg Leu Ile Gln Arg Leu Leu
1               5                   10                  15
Ala

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Norleucine
<220> FEATURE:
<221> NAME/KEY: MOD_RES
<222> LOCATION: (15)..(15)
<223> OTHER INFORMATION: Norleucine
<220> FEATURE:
<221> NAME/KEY: MOD_RES
<222> LOCATION: (17)..(17)
<223> OTHER INFORMATION: 2-Naphthylalanine

<400> SEQUENCE: 71

His Arg Glu Arg Ser Leu Gln Thr Leu Arg Leu Ile Gln Ala Leu Leu
1               5                   10                  15
Ala

<210> SEQ ID NO 72
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Norleucine
<220> FEATURE:
<221> NAME/KEY: MOD_RES
<222> LOCATION: (15)..(15)
<223> OTHER INFORMATION: Norleucine
<220> FEATURE:
<221> NAME/KEY: MOD_RES
<222> LOCATION: (17)..(17)
<223> OTHER INFORMATION: 2-Naphthylalanine
<220> FEATURE:
<221> NAME/KEY: MOD_RES
<222> LOCATION: (18)..(18)
<223> OTHER INFORMATION: Beta-alanine
<220> FEATURE:
<221> NAME/KEY: MOD_RES
<222> LOCATION: (19)..(19)
<223> OTHER INFORMATION: Beta-alanine

<400> SEQUENCE: 72

His Arg Glu Arg Ser Leu Gln Thr Leu Arg Leu Ile Gln Ala Leu Leu
1               5                   10                  15
Ala Ala Ala

<210> SEQ ID NO 73
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Beta-Leucine
<220> FEATURE:
<221> NAME/KEY: MOD_RES
<222> LOCATION: (11)..(11)
<223> OTHER INFORMATION: Norleucine
<220> FEATURE:
<221> NAME/KEY: MOD_RES
<222> LOCATION: (15)..(15)
<223> OTHER INFORMATION: Norleucine
<220> FEATURE:
<221> NAME/KEY: MOD_RES
<222> LOCATION: (17)..(17)
<223> OTHER INFORMATION: 2-Naphthylalanine

<400> SEQUENCE: 73

His Arg Glu Arg Ser Leu Gln Thr Leu Arg Leu Ile Gln Arg Leu Leu
1               5                   10                  15

Ala

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Beta-Leucine
<220> FEATURE:
<221> NAME/KEY: MOD_RES
<222> LOCATION: (11)..(11)
<223> OTHER INFORMATION: Norleucine
<220> FEATURE:
<221> NAME/KEY: MOD_RES
<222> LOCATION: (15)..(15)
<223> OTHER INFORMATION: Norleucine
<220> FEATURE:
<221> NAME/KEY: MOD_RES
<222> LOCATION: (17)..(17)
<223> OTHER INFORMATION: 2-Naphthylalanine

<400> SEQUENCE: 74

His Gln Glu Arg Ser Leu Gln Thr Leu Arg Leu Ile Gln Arg Leu Leu
1               5                   10                  15

Ala

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
```

```
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 75

Leu Gln Thr Ala Arg Xaa Ile Gln Arg Xaa Leu Ala
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 76

Leu Gln Thr Leu Arg Xaa Ala Gln Arg Xaa Leu Ala
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 77

Leu Gln Thr Leu Arg Xaa Ile Gln Arg Xaa Ala Ala
1               5                   10

<210> SEQ ID NO 78
<211> LENGTH: 22
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MISC_FEATURE
<222> LOCATION: (10)..(14)
<223> OTHER INFORMATION: May or may not be a hydrocarbon crosslinker
      between residues
<220> FEATURE:
<221> NAME/KEY: MOD_RES
<222> LOCATION: (14)..(14)
<223> OTHER INFORMATION: Any alpha, alpha-disubstituted amino acid
<220> FEATURE:
<221> NAME/KEY: MOD_RES
<222> LOCATION: (18)..(18)
<223> OTHER INFORMATION: 2-aminobutyric acid
<220> FEATURE:
<221> NAME/KEY: MOD_RES
<222> LOCATION: (20)..(20)
<223> OTHER INFORMATION: 2-Naphthylalanine
<220> FEATURE:
<221> NAME/KEY: MOD_RES
<222> LOCATION: (21)..(21)
<223> OTHER INFORMATION: Beta-alanine
<220> FEATURE:
<221> NAME/KEY: MOD_RES
<222> LOCATION: (22)..(22)
<223> OTHER INFORMATION: Beta-alanine

<400> SEQUENCE: 78

Gln Leu Glu His Arg Glu Arg Ser Leu Xaa Thr Leu Arg Xaa Ile Gln
1               5                   10                  15

Arg Xaa Leu Ala Ala Ala
            20

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any alpha, alpha-disubstituted amino acid
<220> FEATURE:
<221> NAME/KEY: MISC_FEATURE
<222> LOCATION: (2)..(6)
<223> OTHER INFORMATION: May or may not be a hydrocarbon crosslinker
      between residues
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MOD_RES
<222> LOCATION: (9)..(9)
<223> OTHER INFORMATION: Any alpha, alpha-disubstituted amino acid
<220> FEATURE:
<221> NAME/KEY: MISC_FEATURE
<222> LOCATION: (9)..(13)
<223> OTHER INFORMATION: May or may not be a hydrocarbon crosslinker
      between residues
<220> FEATURE:
<221> NAME/KEY: MOD_RES
<222> LOCATION: (13)..(13)
<223> OTHER INFORMATION: Any alpha, alpha-disubstituted amino acid
<220> FEATURE:
<221> NAME/KEY: MOD_RES
<222> LOCATION: (15)..(15)
<223> OTHER INFORMATION: 2-Naphthylalanine
```

-continued

```
<220> FEATURE:
<221> NAME/KEY: MOD_RES
<222> LOCATION: (16)..(16)
<223> OTHER INFORMATION: Beta-alanine
<220> FEATURE:
<221> NAME/KEY: MOD_RES
<222> LOCATION: (17)..(17)
<223> OTHER INFORMATION: Beta-alanine

<400> SEQUENCE: 79

Glu Xaa Ser Leu Gln Xaa Leu Arg Xaa Ile Gln Arg Xaa Leu Ala Ala
1               5                   10                  15

Ala

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any alpha, alpha-disubstituted amino acid
<220> FEATURE:
<221> NAME/KEY: MISC_FEATURE
<222> LOCATION: (4)..(8)
<223> OTHER INFORMATION: May or may not be a hydrocarbon crosslinker
      between residues
<220> FEATURE:
<221> NAME/KEY: MOD_RES
<222> LOCATION: (8)..(8)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Norleucine
<220> FEATURE:
<221> NAME/KEY: MOD_RES
<222> LOCATION: (15)..(15)
<223> OTHER INFORMATION: Norleucine
<220> FEATURE:
<221> NAME/KEY: MOD_RES
<222> LOCATION: (17)..(17)
<223> OTHER INFORMATION: 2-Naphthylalanine

<400> SEQUENCE: 80

His Arg Glu Xaa Ser Leu Gln Xaa Leu Arg Leu Ile Gln Arg Leu Leu
1               5                   10                  15

Ala

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any alpha, alpha-disubstituted amino acid
<220> FEATURE:
<221> NAME/KEY: MISC_FEATURE
<222> LOCATION: (4)..(8)
<223> OTHER INFORMATION: May or may not be a hydrocarbon crosslinker
      between residues
<220> FEATURE:
<221> NAME/KEY: MOD_RES
<222> LOCATION: (8)..(8)
<223> OTHER INFORMATION: Any alpha, alpha-disubstituted amino acid
<220> FEATURE:
```

```
<221> NAME/KEY: MOD_RES
<222> LOCATION: (11)..(11)
<223> OTHER INFORMATION: Norleucine
<220> FEATURE:
<221> NAME/KEY: MOD_RES
<222> LOCATION: (15)..(15)
<223> OTHER INFORMATION: Norleucine
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 81

His Arg Glu Xaa Ser Leu Gln Xaa Leu Arg Leu Ile Gln Arg Leu Ala
1               5                   10                  15

Ala

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any alpha, alpha-disubstituted amino acid
<220> FEATURE:
<221> NAME/KEY: MISC_FEATURE
<222> LOCATION: (4)..(8)
<223> OTHER INFORMATION: May or may not be a hydrocarbon crosslinker
      between residues
<220> FEATURE:
<221> NAME/KEY: MOD_RES
<222> LOCATION: (8)..(8)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 82

His Arg Glu Xaa Ser Leu Gln Xaa Leu Arg Xaa Ile Gln Arg Xaa Ala
1               5                   10                  15

Ala

<210> SEQ ID NO 83
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any alpha, alpha-disubstituted amino acid
<220> FEATURE:
<221> NAME/KEY: MISC_FEATURE
<222> LOCATION: (4)..(8)
<223> OTHER INFORMATION: May or may not be a hydrocarbon crosslinker
      between residues
<220> FEATURE:
<221> NAME/KEY: MOD_RES
<222> LOCATION: (8)..(8)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 83

His Arg Glu Xaa Ser Leu Gln Xaa Leu Arg Xaa Ile Gln Gln Xaa Ala
1               5                   10                  15

Ala

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl L-glutamic acid
<220> FEATURE:
<221> NAME/KEY: MOD_RES
<222> LOCATION: (4)..(4)
<223> OTHER INFORMATION: Any alpha, alpha-disubstituted amino acid
<220> FEATURE:
<221> NAME/KEY: MISC_FEATURE
<222> LOCATION: (4)..(8)
<223> OTHER INFORMATION: May or may not be a hydrocarbon crosslinker
      between residues
<220> FEATURE:
<221> NAME/KEY: MOD_RES
<222> LOCATION: (8)..(8)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
```

-continued

```
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 84

His Arg Glu Xaa Ser Leu Gln Xaa Leu Arg Xaa Ile Gln Arg Xaa Ala
1               5                   10                  15

Ala

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any alpha, alpha-disubstituted amino acid
<220> FEATURE:
<221> NAME/KEY: MISC_FEATURE
<222> LOCATION: (4)..(8)
<223> OTHER INFORMATION: May or may not be a hydrocarbon crosslinker
      between residues
<220> FEATURE:
<221> NAME/KEY: MOD_RES
<222> LOCATION: (8)..(8)
<223> OTHER INFORMATION: Any alpha, alpha-disubstituted amino acid
<220> FEATURE:
<221> NAME/KEY: MOD_RES
<222> LOCATION: (10)..(10)
<223> OTHER INFORMATION: N-methylarginine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 85

His Arg Glu Xaa Ser Leu Gln Xaa Leu Arg Xaa Ile Gln Arg Xaa Ala
1               5                   10                  15

Ala

<210> SEQ ID NO 86
<211> LENGTH: 17
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (4)..(4)
<223> OTHER INFORMATION: Any alpha, alpha-disubstituted amino acid
<220> FEATURE:
<221> NAME/KEY: MISC_FEATURE
<222> LOCATION: (4)..(8)
<223> OTHER INFORMATION: May or may not be a hydrocarbon crosslinker
      between residues
<220> FEATURE:
<221> NAME/KEY: MOD_RES
<222> LOCATION: (6)..(6)
<223> OTHER INFORMATION: Cyclohexyl L-alanine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (8)..(8)
<223> OTHER INFORMATION: Any alpha, alpha-disubstituted amino acid
<220> FEATURE:
<221> NAME/KEY: MOD_RES
<222> LOCATION: (9)..(9)
<223> OTHER INFORMATION: Cyclohexyl L-alanine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 86

His Arg Gln Xaa Ser Ala Gln Xaa Ala Arg Xaa Ile Gln Arg Xaa Ala
1               5                   10                  15
Ala

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any alpha, alpha-disubstituted amino acid
<220> FEATURE:
<221> NAME/KEY: MISC_FEATURE
<222> LOCATION: (4)..(8)
<223> OTHER INFORMATION: May or may not be a hydrocarbon crosslinker
      between residues
<220> FEATURE:
<221> NAME/KEY: MOD_RES
```

```
<222> LOCATION: (8)..(8)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 87

His Arg Gln Xaa Ser Leu Gln Xaa Leu Arg Xaa Ile Gln Arg Xaa Ala
1               5                   10                  15

Ala

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any alpha, alpha-disubstituted amino acid
<220> FEATURE:
<221> NAME/KEY: MISC_FEATURE
<222> LOCATION: (2)..(5)
<223> OTHER INFORMATION: May or may not be a hydrocarbon crosslinker
      between residues
<220> FEATURE:
<221> NAME/KEY: MOD_RES
<222> LOCATION: (4)..(4)
<223> OTHER INFORMATION: N-methyl-D-glutamine
<220> FEATURE:
<221> NAME/KEY: MOD_RES
<222> LOCATION: (5)..(5)
<223> OTHER INFORMATION: Any alpha, alpha-disubstituted amino acid
<220> FEATURE:
<221> NAME/KEY: MOD_RES
<222> LOCATION: (8)..(8)
<223> OTHER INFORMATION: Any alpha, alpha-disubstituted amino acid
<220> FEATURE:
<221> NAME/KEY: MISC_FEATURE
<222> LOCATION: (8)..(12)
<223> OTHER INFORMATION: May or may not be a hydrocarbon crosslinker
      between residues
<220> FEATURE:
<221> NAME/KEY: MOD_RES
<222> LOCATION: (12)..(12)
<223> OTHER INFORMATION: Any alpha, alpha-disubstituted amino acid
<220> FEATURE:
<221> NAME/KEY: MOD_RES
<222> LOCATION: (13)..(13)
<223> OTHER INFORMATION: Beta-cyclobutyl alanine
<220> FEATURE:
<221> NAME/KEY: MOD_RES
<222> LOCATION: (14)..(14)
<223> OTHER INFORMATION: 2-Naphthylalanine
<220> FEATURE:
<221> NAME/KEY: MOD_RES
```

```
<222> LOCATION: (15)..(15)
<223> OTHER INFORMATION: Beta-alanine
<220> FEATURE:
<221> NAME/KEY: MOD_RES
<222> LOCATION: (16)..(16)
<223> OTHER INFORMATION: Beta-alanine

<400> SEQUENCE: 88

Arg Xaa Leu Gln Xaa Leu Arg Xaa Ile Gln Arg Xaa Ala Ala Ala Ala
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any alpha, alpha-disubstituted amino acid
<220> FEATURE:
<221> NAME/KEY: MISC_FEATURE
<222> LOCATION: (2)..(5)
<223> OTHER INFORMATION: May or may not be a hydrocarbon crosslinker
      between residues
<220> FEATURE:
<221> NAME/KEY: MOD_RES
<222> LOCATION: (3)..(3)
<223> OTHER INFORMATION: Cyclopropyl-L-alanine
<220> FEATURE:
<221> NAME/KEY: MOD_RES
<222> LOCATION: (4)..(4)
<223> OTHER INFORMATION: N-methyl-D-glutamine
<220> FEATURE:
<221> NAME/KEY: MOD_RES
<222> LOCATION: (5)..(5)
<223> OTHER INFORMATION: Any alpha, alpha-disubstituted amino acid
<220> FEATURE:
<221> NAME/KEY: MOD_RES
<222> LOCATION: (6)..(6)
<223> OTHER INFORMATION: Cyclopropyl-L-alanine
<220> FEATURE:
<221> NAME/KEY: MOD_RES
<222> LOCATION: (8)..(8)
<223> OTHER INFORMATION: Any alpha, alpha-disubstituted amino acid
<220> FEATURE:
<221> NAME/KEY: MISC_FEATURE
<222> LOCATION: (8)..(12)
<223> OTHER INFORMATION: May or may not be a hydrocarbon crosslinker
      between residues
<220> FEATURE:
<221> NAME/KEY: MOD_RES
<222> LOCATION: (12)..(12)
<223> OTHER INFORMATION: Any alpha, alpha-disubstituted amino acid
<220> FEATURE:
<221> NAME/KEY: MOD_RES
<222> LOCATION: (13)..(13)
<223> OTHER INFORMATION: Cyclopropyl-L-alanine
<220> FEATURE:
<221> NAME/KEY: MOD_RES
<222> LOCATION: (14)..(14)
<223> OTHER INFORMATION: 2-Naphthylalanine
<220> FEATURE:
<221> NAME/KEY: MOD_RES
<222> LOCATION: (15)..(15)
<223> OTHER INFORMATION: Beta-alanine
<220> FEATURE:
<221> NAME/KEY: MOD_RES
<222> LOCATION: (16)..(16)
<223> OTHER INFORMATION: Beta-alanine

<400> SEQUENCE: 89

Arg Xaa Ala Gln Xaa Ala Arg Xaa Ile Gln Arg Xaa Ala Ala Ala Ala
1               5                   10                  15
```

```
<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any alpha, alpha-disubstituted amino acid
<220> FEATURE:
<221> NAME/KEY: MISC_FEATURE
<222> LOCATION: (5)..(8)
<223> OTHER INFORMATION: May or may not be a hydrocarbon crosslinker
      between residues
<220> FEATURE:
<221> NAME/KEY: MOD_RES
<222> LOCATION: (8)..(8)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 90

His Arg Gln Arg Xaa Leu Gln Xaa Leu Arg Xaa Ile Gln Arg Xaa Ala
1               5                   10                  15

Ala

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any alpha, alpha-disubstituted amino acid
<220> FEATURE:
<221> NAME/KEY: MISC_FEATURE
<222> LOCATION: (5)..(8)
<223> OTHER INFORMATION: May or may not be a hydrocarbon crosslinker
      between residues
<220> FEATURE:
<221> NAME/KEY: MOD_RES
<222> LOCATION: (8)..(8)
<223> OTHER INFORMATION: Any alpha, alpha-disubstituted amino acid
<220> FEATURE:
<221> NAME/KEY: MOD_RES
<222> LOCATION: (9)..(9)
<223> OTHER INFORMATION: Cyclopropyl-L-alanine
<220> FEATURE:
<221> NAME/KEY: MOD_RES
<222> LOCATION: (11)..(11)
```

```
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclopropyl-L-alanine
<220> FEATURE:
<221> NAME/KEY: MOD_RES
<222> LOCATION: (17)..(17)
<223> OTHER INFORMATION: 2-Naphthylalanine

<400> SEQUENCE: 91

His Arg Gln Arg Xaa Leu Gln Xaa Ala Arg Xaa Ile Gln Arg Xaa Ala
1               5                   10                  15

Ala

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any alpha, alpha-disubstituted amino acid
<220> FEATURE:
<221> NAME/KEY: MISC_FEATURE
<222> LOCATION: (5)..(8)
<223> OTHER INFORMATION: May or may not be a hydrocarbon crosslinker
      between residues
<220> FEATURE:
<221> NAME/KEY: MOD_RES
<222> LOCATION: (8)..(8)
<223> OTHER INFORMATION: Any alpha, alpha-disubstituted amino acid
<220> FEATURE:
<221> NAME/KEY: MOD_RES
<222> LOCATION: (9)..(9)
<223> OTHER INFORMATION: Cyclohexyl L-alanine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 92

His Arg Gln Arg Xaa Leu Gln Xaa Ala Arg Xaa Ile Gln Arg Xaa Ala
1               5                   10                  15

Ala
```

```
<210> SEQ ID NO 93
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any alpha, alpha-disubstituted amino acid
<220> FEATURE:
<221> NAME/KEY: MISC_FEATURE
<222> LOCATION: (7)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (13)..(13)
<223> OTHER INFORMATION: Any alpha, alpha-disubstituted amino acid
<220> FEATURE:
<221> NAME/KEY: MISC_FEATURE
<222> LOCATION: (13)..(17)
<223> OTHER INFORMATION: May or may not be a hydrocarbon crosslinker
      between residues
<220> FEATURE:
<221> NAME/KEY: MOD_RES
<222> LOCATION: (17)..(17)
<223> OTHER INFORMATION: Any alpha, alpha-disubstituted amino acid

<400> SEQUENCE: 93

Leu Glu His Arg Glu Arg Xaa Leu Gln Xaa Leu Arg Xaa Ile Gln Arg
1               5                   10                  15

Xaa Leu

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any alpha, alpha-disubstituted amino acid
<220> FEATURE:
<221> NAME/KEY: MISC_FEATURE
<222> LOCATION: (3)..(7)
<223> OTHER INFORMATION: May or may not be a hydrocarbon crosslinker
      between residues
<220> FEATURE:
<221> NAME/KEY: MOD_RES
<222> LOCATION: (7)..(7)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
```

```
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 94

His Arg Xaa Arg Ser Leu Xaa Thr Leu Arg Xaa Ile Gln Arg Xaa Ala
1               5                   10                  15

Ala

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any alpha, alpha-disubstituted amino acid
<220> FEATURE:
<221> NAME/KEY: MISC_FEATURE
<222> LOCATION: (3)..(7)
<223> OTHER INFORMATION: May or may not be a hydrocarbon crosslinker
      between residues
<220> FEATURE:
<221> NAME/KEY: MOD_RES
<222> LOCATION: (7)..(7)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 95

His Arg Xaa Arg Ser Leu Xaa Thr Leu Arg Xaa Ile Gln Arg Xaa Ala
1               5                   10                  15

Ala

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any alpha, alpha-disubstituted amino acid
<220> FEATURE:
<221> NAME/KEY: MISC_FEATURE
<222> LOCATION: (3)..(7)
```

```
<223> OTHER INFORMATION: May or may not be a hydrocarbon crosslinker
      between residues
<220> FEATURE:
<221> NAME/KEY: MOD_RES
<222> LOCATION: (7)..(7)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 4-Chlorophenyl alanine
<220> FEATURE:
<221> NAME/KEY: MOD_RES
<222> LOCATION: (17)..(17)
<223> OTHER INFORMATION: 2-Naphthylalanine

<400> SEQUENCE: 96

His Arg Xaa Arg Ser Leu Xaa Thr Leu Arg Xaa Ile Gln Arg Xaa Phe
1               5                   10                  15

Ala

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any alpha, alpha-disubstituted amino acid
<220> FEATURE:
<221> NAME/KEY: MISC_FEATURE
<222> LOCATION: (3)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine
<220> FEATURE:
<221> NAME/KEY: MOD_RES
<222> LOCATION: (13)..(13)
<223> OTHER INFORMATION: Beta-alanine
<220> FEATURE:
<221> NAME/KEY: MOD_RES
<222> LOCATION: (14)..(14)
<223> OTHER INFORMATION: Beta-alanine

<400> SEQUENCE: 97

Leu Gln Xaa Leu Arg Asp Ile Gln Arg Xaa Leu Ala Ala Ala
1               5                   10

<210> SEQ ID NO 98
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 98

Leu Gln Thr Leu Glu Xaa Ile Gln Arg Xaa Leu Ala
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 99

Leu Gln Thr Leu Arg Xaa Ile Gln Glu Xaa Leu Ala
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
```

```
<221> NAME/KEY: MOD_RES
<222> LOCATION: (12)..(12)
<223> OTHER INFORMATION: 2-Naphthylalanine

<400> SEQUENCE: 100

Leu Gln Thr Leu Lys Xaa Ile Gln Arg Xaa Leu Ala
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 101

Leu Gln Thr Leu Arg Xaa Ile Gln Lys Xaa Leu Ala
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 102

Leu Gln Thr Ile Arg Xaa Ile Gln Arg Xaa Leu Ala
1               5                   10

<210> SEQ ID NO 103
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 103

Leu Gln Thr Leu Arg Xaa Ile Gln Arg Xaa Leu Ala
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (7)..(7)
<223> OTHER INFORMATION: D-amino acid
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine

<400> SEQUENCE: 104

Leu Gln Thr Leu Arg Xaa Ile Gln Arg Xaa Leu Ala
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
```

```
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: D-amino acid
<220> FEATURE:
<221> NAME/KEY: MOD_RES
<222> LOCATION: (12)..(12)
<223> OTHER INFORMATION: 2-Naphthylalanine

<400> SEQUENCE: 105

Leu Gln Thr Leu Arg Xaa Ile Gln Arg Xaa Leu Ala
1               5                   10

<210> SEQ ID NO 106

<400> SEQUENCE: 106

000

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 107

Leu Gln Thr Leu Arg Xaa Ile Gln Arg Xaa Ala Ala
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
```

```
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 108

Leu Gln Thr Leu Arg Xaa Ile Gln Arg Xaa Ala Ala
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 109

Leu Glu Thr Leu Arg Xaa Ile Gln Arg Xaa Ala Ala
1               5                   10

<210> SEQ ID NO 110
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
```

```
         between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine
<220> FEATURE:
<221> NAME/KEY: MOD_RES
<222> LOCATION: (13)..(13)
<223> OTHER INFORMATION: Beta-alanine
<220> FEATURE:
<221> NAME/KEY: MOD_RES
<222> LOCATION: (14)..(14)
<223> OTHER INFORMATION: Beta-alanine

<400> SEQUENCE: 110

Leu Gln Thr Leu Arg Xaa Ile Gln Arg Xaa Ala Ala Ala Ala
1               5                   10

<210> SEQ ID NO 111
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine
<220> FEATURE:
<221> NAME/KEY: MOD_RES
<222> LOCATION: (13)..(13)
<223> OTHER INFORMATION: Beta-alanine
<220> FEATURE:
<221> NAME/KEY: MOD_RES
<222> LOCATION: (14)..(14)
<223> OTHER INFORMATION: Beta-alanine

<400> SEQUENCE: 111

Leu Gln Thr Leu Arg Xaa Ile Gln Arg Xaa Ala Ala Ala Ala
1               5                   10

<210> SEQ ID NO 112
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 112

Leu Gln Thr Leu Arg Xaa Ile Gln His Xaa Ala Ala
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-cyclobutyl alanine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 113

Ala Gln Thr Leu Arg Xaa Ile Gln Arg Xaa Ala Ala
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Beta-cyclobutyl alanine
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 114

Ala Gln Thr Leu Arg Xaa Ile Gln Arg Xaa Ala Ala
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Beta-cyclobutyl alanine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 115

Leu Gln Thr Ala Arg Xaa Ile Gln Arg Xaa Ala Ala
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (8)..(8)
<223> OTHER INFORMATION: N-methyl-D-glutamine
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 116

Leu Gln Thr Leu Arg Xaa Ile Gln Arg Xaa Ala Ala
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (5)..(5)
<223> OTHER INFORMATION: N-methylarginine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 117

Leu Gln Thr Leu Arg Xaa Ile Gln Arg Xaa Ala Ala
1               5                   10
```

```
<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl leucine
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 118

Leu Gln Thr Leu Arg Xaa Ile Gln Arg Xaa Ala Ala
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Cyclopropyl-L-alanine
<220> FEATURE:
<221> NAME/KEY: MOD_RES
<222> LOCATION: (12)..(12)
<223> OTHER INFORMATION: 2-Naphthylalanine

<400> SEQUENCE: 119
```

Leu Gln Thr Leu Arg Xaa Ile Gln Arg Xaa Ala Ala
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 120

Leu Gln Thr Leu Arg Xaa Ile Gln Arg Xaa Ala Ala
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (3)..(3)
<223> OTHER INFORMATION: N-methyl L-threonine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine -continued

<400> SEQUENCE: 121

Leu Gln Thr Leu Arg Xaa Ile Gln Arg Xaa Ala Ala
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Cyclohexyl L-alanine
<220> FEATURE:
<221> NAME/KEY: MOD_RES
<222> LOCATION: (12)..(12)
<223> OTHER INFORMATION: 2-Naphthylalanine

<400> SEQUENCE: 122

Leu Gln Thr Leu Arg Xaa Ile Gln Arg Xaa Ala Ala
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (4)..(4)
<223> OTHER INFORMATION: Cyclohexyl L-alanine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:

```
<221> NAME/KEY: MOD_RES
<222> LOCATION: (12)..(12)
<223> OTHER INFORMATION: 2-Naphthylalanine

<400> SEQUENCE: 123

Leu Gln Thr Ala Arg Xaa Ile Gln Arg Xaa Ala Ala
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (5)..(5)
<223> OTHER INFORMATION: N-methylarginine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 124

Leu Gln Thr Leu Arg Xaa Ile Gln Arg Xaa Ala Ala
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (9)..(9)
<223> OTHER INFORMATION: N-methylarginine
<220> FEATURE:
<221> NAME/KEY: MOD_RES
```

```
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 125

Leu Gln Thr Leu Arg Xaa Ile Gln Arg Xaa Ala Ala
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (4)..(4)
<223> OTHER INFORMATION: Alpha-methylleucine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 126

Leu Gln Thr Leu Arg Xaa Ile Gln Arg Xaa Ala Ala
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
```

-continued

```
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Cyclohexyl L-alanine
<220> FEATURE:
<221> NAME/KEY: MOD_RES
<222> LOCATION: (12)..(12)
<223> OTHER INFORMATION: 2-Naphthylalanine

<400> SEQUENCE: 127

Leu Gln Thr Leu Arg Xaa Ile Gln Arg Xaa Ala Ala
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (5)..(5)
<223> OTHER INFORMATION: N-methylarginine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (9)..(9)
<223> OTHER INFORMATION: N-methylarginine
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 128

Leu Gln Thr Leu Arg Xaa Ile Gln Arg Xaa Ala Ala
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
```

```
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (7)..(7)
<223> OTHER INFORMATION: Beta-cyclobutyl alanine
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 129

Leu Gln Thr Leu Arg Xaa Ala Gln Arg Xaa Ala Ala
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 130

Leu Gln Thr Leu Arg Xaa Ile Gln Arg Xaa Ala Ala
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: N-methyl-D-glutamine
<220> FEATURE:
<221> NAME/KEY: MOD_RES
<222> LOCATION: (4)..(4)
<223> OTHER INFORMATION: N-methyl leucine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 131

Leu Gln Thr Leu Arg Xaa Ile Gln Arg Xaa Ala Ala
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (5)..(5)
<223> OTHER INFORMATION: Homoarginine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 132

Leu Gln Thr Leu Arg Xaa Ile Gln Arg Xaa Ala Ala
1               5                   10

<210> SEQ ID NO 133
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (9)..(9)
<223> OTHER INFORMATION: Homoarginine
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 133

Leu Gln Thr Leu Arg Xaa Ile Gln Arg Xaa Ala Ala
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (7)..(7)
<223> OTHER INFORMATION: N-methyl-L-isoleucine
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 134
```

```
Leu Gln Thr Leu Arg Xaa Ile Gln Arg Xaa Ala Ala
1               5                   10
```

```
<210> SEQ ID NO 135
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 135

Leu Gln Thr Leu Arg Xaa Ile Gln Arg Xaa Ala Ala
1               5                   10
```

```
<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 136
```

Leu Gln Thr Leu Arg Xaa Ile Gln Arg Xaa Ala Ala
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 137

Leu Gln Thr Leu Arg Xaa Ile Gln Arg Xaa Ala Ala
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 138

Leu Gln Thr Leu Arg Xaa Ile Gln Arg Xaa Ala Ala

```
1               5                   10
```

<210> SEQ ID NO 139
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 139

```
Leu Gln Thr Leu Arg Xaa Ile Gln Arg Xaa Ala Ala
1               5                   10
```

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 140

```
Leu Gln Thr Leu Arg Xaa Ile Gln Arg Xaa Ala Ala
1               5                   10
```

```
<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 141

Leu Gln Thr Leu Arg Xaa Ile Gln Arg Xaa Ala Ala
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 142

Leu Gln Thr Leu Arg Xaa Ile Gln Arg Xaa Ala Ala
1               5                   10
```

```
<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 143

Leu Gln Thr Leu Arg Xaa Ile Gln Arg Xaa Ala Ala
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 144

Leu Gln Thr Leu Arg Xaa Ile Gln Arg Xaa Ala Ala
1               5                   10
```

```
<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 145

His Arg Glu Arg Ser Leu Gln Thr Leu Arg Xaa Ile Gln Gln Xaa Ala
1               5                   10                  15

Ala

<210> SEQ ID NO 146
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 146

His Arg Glu Arg Ser Leu Gln Thr Leu Arg Xaa Ile Gln Glu Xaa Ala
1               5                   10                  15

Ala

<210> SEQ ID NO 147
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 147

His Arg Gln Arg Ser Leu Gln Thr Leu Arg Xaa Ile Gln Arg Xaa Ala
1               5                   10                  15

Ala

<210> SEQ ID NO 148
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine
<220> FEATURE:
<221> NAME/KEY: MOD_RES
<222> LOCATION: (18)..(18)
<223> OTHER INFORMATION: Beta-alanine
<220> FEATURE:
<221> NAME/KEY: MOD_RES
<222> LOCATION: (19)..(19)
<223> OTHER INFORMATION: Beta-alanine

<400> SEQUENCE: 148

His Arg Gln Arg Ser Leu Gln Thr Leu Arg Xaa Ile Gln Arg Xaa Ala
1               5                   10                  15

Ala Ala Ala

<210> SEQ ID NO 149
<211> LENGTH: 31
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine
<220> FEATURE:
<221> NAME/KEY: MOD_RES
<222> LOCATION: (18)..(18)
<223> OTHER INFORMATION: Beta-alanine
<220> FEATURE:
<221> NAME/KEY: MOD_RES
<222> LOCATION: (19)..(19)
<223> OTHER INFORMATION: Beta-alanine

<400> SEQUENCE: 149

His Arg Gln Arg Ser Leu Gln Thr Leu Arg Xaa Ile Gln Arg Xaa Ala
1               5                   10                  15

Ala Ala Ala Gly Arg Lys Lys Arg Arg Gln Arg Arg Arg Pro Gln
            20                  25                  30

<210> SEQ ID NO 150
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine
<220> FEATURE:
<221> NAME/KEY: MOD_RES
<222> LOCATION: (18)..(18)
<223> OTHER INFORMATION: Beta-alanine
<220> FEATURE:
<221> NAME/KEY: MOD_RES
<222> LOCATION: (19)..(19)
```

```
<223> OTHER INFORMATION: Beta-alanine

<400> SEQUENCE: 150

His Arg Gln Arg Ser Leu Gln Thr Leu Arg Xaa Ile Gln Arg Xaa Ala
1               5                   10                  15

Ala Ala Ala

<210> SEQ ID NO 151
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl L-glutamic acid
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 151

His Arg Glu Arg Ser Leu Gln Thr Leu Arg Xaa Ile Gln Arg Xaa Ala
1               5                   10                  15

Ala

<210> SEQ ID NO 152
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: N-methylarginine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
```

```
<220> FEATURE:
<221> NAME/KEY: MOD_RES
<222> LOCATION: (17)..(17)
<223> OTHER INFORMATION: 2-Naphthylalanine

<400> SEQUENCE: 152

His Arg Glu Arg Ser Leu Gln Thr Leu Arg Xaa Ile Gln Arg Xaa Ala
1               5                   10                  15

Ala

<210> SEQ ID NO 153
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 153

His Arg Gln Arg Ser Leu Gln Thr Leu Arg Xaa Ile Gln Arg Xaa Ala
1               5                   10                  15

Ala

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl L-glutamic acid
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
```

```
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 154

His Arg Glu Arg Ser Leu Gln Thr Leu Arg Xaa Ile Gln Arg Xaa Ala
1               5                   10                  15

Ala

<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 155

His Arg Gln Arg Ser Leu Gln Thr Leu Arg Xaa Ile Gln Arg Xaa Ala
1               5                   10                  15

Ala

<210> SEQ ID NO 156
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Beta-cyclobutyl alanine
<220> FEATURE:
<221> NAME/KEY: MOD_RES
<222> LOCATION: (11)..(11)
```

```
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 156

His Arg Gln Arg Ser Ala Gln Thr Leu Arg Xaa Ile Gln Arg Xaa Ala
1               5                   10                  15

Ala

<210> SEQ ID NO 157
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl aspartic acid
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 157

His Arg Asp Arg Ser Leu Gln Thr Leu Arg Xaa Ile Gln Arg Xaa Ala
1               5                   10                  15

Ala

<210> SEQ ID NO 158
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methylarginine
```

```
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 158

His Arg Gln Arg Ser Leu Gln Thr Leu Arg Xaa Ile Gln Arg Xaa Ala
1               5                   10                  15

Ala

<210> SEQ ID NO 159
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 159

His Arg Gln Arg Thr Leu Gln Thr Leu Arg Xaa Ile Gln Arg Xaa Ala
1               5                   10                  15

Ala

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
```

```
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 160

His Arg Gln Arg Ser Leu Gln Thr Leu Arg Xaa Ile Gln Arg Xaa Ala
1               5                   10                  15

Ala

<210> SEQ ID NO 161
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine
<220> FEATURE:
<221> NAME/KEY: MOD_RES
<222> LOCATION: (18)..(18)
<223> OTHER INFORMATION: Lys-PEG4-palmitoyl

<400> SEQUENCE: 161

His Arg Gln Arg Ser Leu Gln Thr Leu Arg Xaa Ile Gln Arg Xaa Ala
1               5                   10                  15

Ala Lys

<210> SEQ ID NO 162
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
```

```
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclopropyl-L-alanine
<220> FEATURE:
<221> NAME/KEY: MOD_RES
<222> LOCATION: (17)..(17)
<223> OTHER INFORMATION: 2-Naphthylalanine

<400> SEQUENCE: 162

His Arg Gln Arg Ser Leu Gln Thr Leu Arg Xaa Ile Gln Arg Xaa Ala
1               5                   10                  15

Ala

<210> SEQ ID NO 163
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (9)..(9)
<223> OTHER INFORMATION: Cyclohexyl L-alanine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 163

His Arg Gln Arg Ser Leu Gln Thr Ala Arg Xaa Ile Gln Arg Xaa Ala
1               5                   10                  15

Ala

<210> SEQ ID NO 164
<211> LENGTH: 17
<212> TYPE: PRT
<213> ORGANISM: Artificial Sequence
<220> FEATURE:
<223> OTHER INFORMATION: Description of Artificial Sequence: Synthetic
```

```
              peptide
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (14)..(14)
<223> OTHER INFORMATION: N-methylarginine
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 164

His Arg Gln Arg Ser Leu Gln Thr Leu Arg Xaa Ile Gln Arg Xaa Ala
1               5                   10                  15

Ala

<210> SEQ ID NO 165
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (8)..(8)
<223> OTHER INFORMATION: N-methyl L-threonine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
```

```
<220> FEATURE:
<221> NAME/KEY: MOD_RES
<222> LOCATION: (17)..(17)
<223> OTHER INFORMATION: 2-Naphthylalanine

<400> SEQUENCE: 165

His Arg Gln Arg Ser Leu Gln Thr Leu Arg Xaa Ile Gln Arg Xaa Ala
1               5                   10                  15
Ala

<210> SEQ ID NO 166
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methylarginine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 166

His Arg Gln Arg Ser Leu Gln Thr Leu Arg Xaa Ile Gln Arg Xaa Ala
1               5                   10                  15
Ala

<210> SEQ ID NO 167
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Homoarginine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
```

```
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 167

His Arg Gln Arg Ser Leu Gln Thr Leu Arg Xaa Ile Gln Arg Xaa Ala
1               5                   10                  15

Ala

<210> SEQ ID NO 168
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: N-methylarginine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 168

His Arg Gln Arg Ser Leu Gln Thr Leu Arg Xaa Ile Gln Arg Xaa Ala
1               5                   10                  15

Ala

<210> SEQ ID NO 169
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: (5-amino-5-oxopentyl)glycine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
```

```
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 169

His Arg Gln Arg Ser Leu Xaa Thr Leu Arg Xaa Ile Gln Arg Xaa Ala
1               5                   10                  15

Ala

<210> SEQ ID NO 170
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Homoarginine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 170

His Arg Gln Arg Ser Leu Gln Thr Leu Arg Xaa Ile Gln Arg Xaa Ala
1               5                   10                  15

Ala

<210> SEQ ID NO 171
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (14)..(14)
```

```
<223> OTHER INFORMATION: Homoarginine
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-cyclobutyl alanine
<220> FEATURE:
<221> NAME/KEY: MOD_RES
<222> LOCATION: (17)..(17)
<223> OTHER INFORMATION: 2-Naphthylalanine

<400> SEQUENCE: 171

His Arg Gln Arg Ser Leu Gln Thr Leu Arg Xaa Ile Gln Arg Xaa Ala
1               5                   10                  15

Ala

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Alpha-methylleucine
<220> FEATURE:
<221> NAME/KEY: MOD_RES
<222> LOCATION: (12)..(12)
<223> OTHER INFORMATION: 2-Naphthylalanine

<400> SEQUENCE: 172

Leu Gln Thr Leu Arg Xaa Ile Gln Arg Xaa Leu Ala
1               5                   10

<210> SEQ ID NO 173
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
```

<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: Cyclohexyl L-alanine
<220> FEATURE:
<221> NAME/KEY: MOD_RES
<222> LOCATION: (13)..(13)
<223> OTHER INFORMATION: 2-Naphthylalanine

<400> SEQUENCE: 173

Leu Gln Thr Leu Arg Xaa Ile Gln Arg Xaa Asp Ala Ala
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: N-methyl cyclohexyl alanine
<220> FEATURE:
<221> NAME/KEY: MOD_RES
<222> LOCATION: (12)..(12)
<223> OTHER INFORMATION: 2-Naphthylalanine

<400> SEQUENCE: 174

Leu Gln Thr Leu Arg Xaa Ile Gln Arg Xaa Ala Ala
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)

```
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Allyl glycine
<220> FEATURE:
<221> NAME/KEY: MOD_RES
<222> LOCATION: (12)..(12)
<223> OTHER INFORMATION: 2-Naphthylalanine

<400> SEQUENCE: 175

Leu Gln Thr Leu Arg Xaa Ile Gln Arg Xaa Gly Ala
1               5                   10

<210> SEQ ID NO 176
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 1-aminocyclobutane-1-carboxylic acid
<220> FEATURE:
<221> NAME/KEY: MOD_RES
<222> LOCATION: (17)..(17)
<223> OTHER INFORMATION: 2-Naphthylalanine

<400> SEQUENCE: 176

His Arg Gln Arg Ser Leu Gln Thr Leu Arg Xaa Ile Gln Arg Xaa Xaa
1               5                   10                  15

Ala

<210> SEQ ID NO 177
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 1-aminocyclohexane-1-carboxylic acid
<220> FEATURE:
<221> NAME/KEY: MOD_RES
```

```
<222> LOCATION: (17)..(17)
<223> OTHER INFORMATION: 2-Naphthylalanine

<400> SEQUENCE: 177

His Arg Gln Arg Ser Leu Gln Thr Leu Arg Xaa Ile Gln Arg Xaa Xaa
1               5                   10                  15

Ala

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Azetidine-3-carboxylic acid
<220> FEATURE:
<221> NAME/KEY: MOD_RES
<222> LOCATION: (17)..(17)
<223> OTHER INFORMATION: 2-Naphthylalanine

<400> SEQUENCE: 178

His Arg Gln Arg Ser Leu Gln Thr Leu Arg Xaa Ile Gln Arg Xaa Xaa
1               5                   10                  15

Ala

<210> SEQ ID NO 179
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 4-Chlorophenyl alanine
<220> FEATURE:
<221> NAME/KEY: MOD_RES
<222> LOCATION: (17)..(17)
<223> OTHER INFORMATION: 2-Naphthylalanine

<400> SEQUENCE: 179
```

His Arg Gln Arg Ser Leu Gln Thr Leu Arg Xaa Ile Gln Arg Xaa Phe
1               5                   10                  15

Ala

<210> SEQ ID NO 180
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 180

His Arg Gln Arg Ser Leu Gln Thr Leu Arg Xaa Ile Gln Arg Xaa Ala
1               5                   10                  15

Ala

<210> SEQ ID NO 181
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 181

His Arg Gln Arg Ser Leu Gln Thr Leu Arg Xaa Ile Gln Arg Xaa Ala
1               5                   10                  15

Ala

<210> SEQ ID NO 182
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: N-methyl cyclohexyl alanine
<220> FEATURE:
<221> NAME/KEY: MOD_RES
<222> LOCATION: (17)..(17)
<223> OTHER INFORMATION: 2-Naphthylalanine

<400> SEQUENCE: 182

His Arg Gln Arg Ser Leu Gln Thr Leu Arg Xaa Ile Gln Arg Xaa Ala
1               5                   10                  15

Ala

<210> SEQ ID NO 183
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Homoarginine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine -continued

```
<400> SEQUENCE: 183

His Arg Gln Arg Ser Leu Gln Thr Leu Arg Xaa Ile Gln Arg Xaa Ala
1               5                   10                  15

Ala

<210> SEQ ID NO 184
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: N-methylarginine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 184

His Arg Gln Arg Ser Leu Gln Thr Leu Arg Xaa Ile Gln Arg Xaa Ala
1               5                   10                  15

Ala

<210> SEQ ID NO 185
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Cyclohexyl L-alanine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
```

```
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 185

His Arg Gln Arg Ser Ala Gln Thr Leu Arg Xaa Ile Gln Arg Xaa Ala
1               5                   10                  15
Ala

<210> SEQ ID NO 186
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: N-methyl cyclohexyl alanine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 186

His Arg Gln Arg Ser Ala Gln Thr Leu Arg Xaa Ile Gln Arg Xaa Ala
1               5                   10                  15
Ala

<210> SEQ ID NO 187
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Cyclohexyl L-alanine
<220> FEATURE:
<221> NAME/KEY: MOD_RES
<222> LOCATION: (8)..(8)
<223> OTHER INFORMATION: N-methyl-D-glutamine
<220> FEATURE:
<221> NAME/KEY: MOD_RES
<222> LOCATION: (12)..(12)
<223> OTHER INFORMATION: Any alpha, alpha-disubstituted amino acid
```

```
<220> FEATURE:
<221> NAME/KEY: MISC_FEATURE
<222> LOCATION: (12)..(16)
<223> OTHER INFORMATION: May or may not be a hydrocarbon crosslinker
      between residues
<220> FEATURE:
<221> NAME/KEY: MOD_RES
<222> LOCATION: (16)..(16)
<223> OTHER INFORMATION: Any alpha, alpha-disubstituted amino acid
<220> FEATURE:
<221> NAME/KEY: MOD_RES
<222> LOCATION: (17)..(17)
<223> OTHER INFORMATION: Cyclohexyl L-alanine
<220> FEATURE:
<221> NAME/KEY: MOD_RES
<222> LOCATION: (18)..(18)
<223> OTHER INFORMATION: 2-Naphthylalanine

<400> SEQUENCE: 187

His Arg Gln Arg Ser Asp Ala Gln Thr Leu Arg Xaa Ile Gln Arg Xaa
1               5                   10                  15

Ala Ala

<210> SEQ ID NO 188
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: D-2-Naphthylalanine

<400> SEQUENCE: 188

His Arg Gln Arg Ser Leu Gln Thr Leu Arg Xaa Ile Gln Arg Xaa Ala
1               5                   10                  15

Ala

<210> SEQ ID NO 189
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: N-methylarginine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
```

-continued

```
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 189

His Arg Gln Arg Ser Leu Gln Thr Leu Arg Xaa Ile Gln Arg Xaa Ala
1               5                   10                  15

Ala

<210> SEQ ID NO 190
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (14)..(14)
<223> OTHER INFORMATION: N-methylarginine
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 190

His Arg Gln Arg Ser Leu Gln Thr Leu Arg Xaa Ile Gln Arg Xaa Ala
1               5                   10                  15

Ala

<210> SEQ ID NO 191
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
```

```
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-tBu-Ala
<220> FEATURE:
<221> NAME/KEY: MOD_RES
<222> LOCATION: (17)..(17)
<223> OTHER INFORMATION: 2-Naphthylalanine

<400> SEQUENCE: 191

His Arg Gln Arg Ser Leu Gln Thr Leu Arg Xaa Ile Gln Arg Xaa Ala
1               5                   10                  15

Ala

<210> SEQ ID NO 192
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Tertleucine
<220> FEATURE:
<221> NAME/KEY: MOD_RES
<222> LOCATION: (17)..(17)
<223> OTHER INFORMATION: 2-Naphthylalanine

<400> SEQUENCE: 192

His Arg Gln Arg Ser Leu Gln Thr Leu Arg Xaa Ile Gln Arg Xaa Leu
1               5                   10                  15

Ala

<210> SEQ ID NO 193
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
```

```
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Beta-tBu-Ala
<220> FEATURE:
<221> NAME/KEY: MOD_RES
<222> LOCATION: (17)..(17)
<223> OTHER INFORMATION: 2-Naphthylalanine

<400> SEQUENCE: 193

His Arg Gln Arg Ser Leu Gln Thr Leu Arg Xaa Ile Gln Arg Xaa Ala
1               5                   10                  15

Ala

<210> SEQ ID NO 194
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Tertleucine
<220> FEATURE:
<221> NAME/KEY: MOD_RES
<222> LOCATION: (17)..(17)
<223> OTHER INFORMATION: 2-Naphthylalanine

<400> SEQUENCE: 194

His Arg Gln Arg Ser Leu Gln Thr Leu Arg Xaa Ile Gln Arg Xaa Leu
1               5                   10                  15

Ala

<210> SEQ ID NO 195
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
```

```
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: 4-Chlorophenyl alanine
<220> FEATURE:
<221> NAME/KEY: MOD_RES
<222> LOCATION: (12)..(12)
<223> OTHER INFORMATION: 2-Naphthylalanine

<400> SEQUENCE: 195

Leu Gln Thr Leu Arg Xaa Ile Gln Arg Xaa Phe Ala
1               5                   10

<210> SEQ ID NO 196
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 4-Chlorophenyl alanine
<220> FEATURE:
<221> NAME/KEY: MOD_RES
<222> LOCATION: (17)..(17)
<223> OTHER INFORMATION: 2-Naphthylalanine

<400> SEQUENCE: 196

His Arg Gln Arg Ser Leu Gln Thr Leu Arg Xaa Ile Gln Arg Xaa Phe
1               5                   10                  15

Ala

<210> SEQ ID NO 197
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
```

```
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 4-Chlorophenyl alanine
<220> FEATURE:
<221> NAME/KEY: MOD_RES
<222> LOCATION: (17)..(17)
<223> OTHER INFORMATION: 2-Naphthylalanine

<400> SEQUENCE: 197

His Arg Gln Arg Ser Leu Gln Thr Leu Arg Xaa Ile Gln Arg Xaa Phe
1               5                   10                  15

Ala

<210> SEQ ID NO 198
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any alpha, alpha-disubstituted amino acid
<220> FEATURE:
<221> NAME/KEY: MISC_FEATURE
<222> LOCATION: (3)..(7)
<223> OTHER INFORMATION: May or may not be a hydrocarbon crosslinker
      between residues
<220> FEATURE:
<221> NAME/KEY: MOD_RES
<222> LOCATION: (7)..(7)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 4-Chlorophenyl alanine
<220> FEATURE:
<221> NAME/KEY: MOD_RES
<222> LOCATION: (17)..(17)
<223> OTHER INFORMATION: 2-Naphthylalanine

<400> SEQUENCE: 198

His Arg Xaa Arg Ser Leu Xaa Thr Leu Arg Xaa Ile Gln Arg Xaa Phe
1               5                   10                  15

Ala

<210> SEQ ID NO 199
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Cyclohexyl L-alanine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 4-Chlorophenyl alanine
<220> FEATURE:
<221> NAME/KEY: MOD_RES
<222> LOCATION: (17)..(17)
<223> OTHER INFORMATION: 2-Naphthylalanine

<400> SEQUENCE: 199

His Arg Gln Arg Ser Ala Gln Thr Leu Arg Xaa Ile Gln Arg Xaa Phe
1               5                   10                  15

Ala

<210> SEQ ID NO 200
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Cyclohexyl L-alanine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 4-fluorophenyl alanine
<220> FEATURE:
<221> NAME/KEY: MOD_RES
<222> LOCATION: (17)..(17)
<223> OTHER INFORMATION: 2-Naphthylalanine
```

<400> SEQUENCE: 200

His Arg Gln Arg Ser Ala Gln Thr Leu Arg Xaa Ile Gln Arg Xaa Phe
1               5                   10                  15

Ala

<210> SEQ ID NO 201
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: L-alpha-neopentylglycine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 4-Chlorophenyl alanine
<220> FEATURE:
<221> NAME/KEY: MOD_RES
<222> LOCATION: (17)..(17)
<223> OTHER INFORMATION: 2-Naphthylalanine

<400> SEQUENCE: 201

His Arg Gln Arg Ser Gly Gln Thr Leu Arg Xaa Ile Gln Arg Xaa Phe
1               5                   10                  15

Ala

<210> SEQ ID NO 202
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:

```
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 4-fluorophenyl alanine
<220> FEATURE:
<221> NAME/KEY: MOD_RES
<222> LOCATION: (17)..(17)
<223> OTHER INFORMATION: 2-Naphthylalanine

<400> SEQUENCE: 202

His Arg Gln Arg Ser Leu Gln Thr Leu Arg Xaa Ile Gln Arg Xaa Phe
1               5                   10                  15
Ala

<210> SEQ ID NO 203
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 3,4-Chlorophenyl alanine
<220> FEATURE:
<221> NAME/KEY: MOD_RES
<222> LOCATION: (17)..(17)
<223> OTHER INFORMATION: 2-Naphthylalanine

<400> SEQUENCE: 203

His Arg Gln Arg Ser Leu Gln Thr Leu Arg Xaa Ile Gln Arg Xaa Phe
1               5                   10                  15
Ala

<210> SEQ ID NO 204
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (7)..(7)
```

```
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (12)..(12)
<223> OTHER INFORMATION: Norleucine
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 204

His Arg Gln Arg Ser Leu Gln Thr Leu Arg Xaa Leu Gln Arg Xaa Ala
1               5                   10                  15

Ala

<210> SEQ ID NO 205
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 205

His Arg Gln Arg Ser Leu Gln Thr Leu Arg Xaa Ile Gln Arg Xaa Ala
1               5                   10                  15

Ala

<210> SEQ ID NO 206
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 4-Chlorophenyl alanine
<220> FEATURE:
<221> NAME/KEY: MOD_RES
<222> LOCATION: (17)..(17)
<223> OTHER INFORMATION: 2-Naphthylalanine

<400> SEQUENCE: 206

His Arg Gln Arg Ser Leu Gln Thr Leu Arg Xaa Ile Gln Arg Xaa Phe
1               5                   10                  15

Ala

<210> SEQ ID NO 207
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 207

His Arg Gln Arg Ser Leu Gln Thr Leu Arg Xaa Ile Gln Arg Xaa Ala
1               5                   10                  15

Ala

<210> SEQ ID NO 208
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 4-Chlorophenyl alanine
<220> FEATURE:
<221> NAME/KEY: MOD_RES
<222> LOCATION: (17)..(17)
<223> OTHER INFORMATION: 2-Naphthylalanine

<400> SEQUENCE: 208

His Arg Gln Arg Ser Leu Gln Thr Leu Arg Xaa Ile Gln Arg Xaa Phe
1               5                   10                  15

Ala

<210> SEQ ID NO 209
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Homoarginine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 209

His Arg Gln Arg Ser Leu Gln Thr Leu Arg Xaa Ile Gln Arg Xaa Ala
1               5                   10                  15
```

Ala

```
<210> SEQ ID NO 210
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Homoarginine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 4-Chlorophenyl alanine
<220> FEATURE:
<221> NAME/KEY: MOD_RES
<222> LOCATION: (17)..(17)
<223> OTHER INFORMATION: 2-Naphthylalanine

<400> SEQUENCE: 210

His Arg Gln Arg Ser Leu Gln Thr Leu Arg Xaa Ile Gln Arg Xaa Phe
1               5                   10                  15
Ala

<210> SEQ ID NO 211
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Cyclohexyl L-alanine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
```

<223> OTHER INFORMATION: 2-Naphthylalanine

<400> SEQUENCE: 211

His Arg Gln Arg Ser Ala Gln Thr Leu Arg Xaa Ile Gln Arg Xaa Ala
1               5                   10                  15

Ala

<210> SEQ ID NO 212
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Cyclohexyl L-alanine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: 4-Chlorophenyl alanine
<220> FEATURE:
<221> NAME/KEY: MOD_RES
<222> LOCATION: (17)..(17)
<223> OTHER INFORMATION: 2-Naphthylalanine

<400> SEQUENCE: 212

His Arg Gln Arg Ser Ala Gln Thr Leu Arg Xaa Ile Gln Arg Xaa Phe
1               5                   10                  15

Ala

<210> SEQ ID NO 213
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid

```
<220> FEATURE:
<221> NAME/KEY: MOD_RES
<222> LOCATION: (11)..(11)
<223> OTHER INFORMATION: Beta-cyclobutyl alanine
<220> FEATURE:
<221> NAME/KEY: MOD_RES
<222> LOCATION: (12)..(12)
<223> OTHER INFORMATION: 2-Naphthylalanine

<400> SEQUENCE: 213

Leu Gln Thr Leu Arg Xaa Ile Gln Arg Xaa Ala Ala
1               5                   10

<210> SEQ ID NO 214
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (11)..(11)
<223> OTHER INFORMATION: 4-Chlorophenyl alanine
<220> FEATURE:
<221> NAME/KEY: MOD_RES
<222> LOCATION: (12)..(12)
<223> OTHER INFORMATION: 2-Naphthylalanine

<400> SEQUENCE: 214

Leu Gln Thr Leu Arg Xaa Ile Gln Arg Xaa Phe Ala
1               5                   10

<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl histidine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
```

```
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 215

His Arg Gln Arg Ser Leu Gln Thr Leu Arg Xaa Ile Gln Arg Xaa Ala
1               5                   10                  15

Ala

<210> SEQ ID NO 216
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 216

Cys Arg Gln Arg Ser Leu Gln Thr Leu Arg Xaa Ile Gln Arg Xaa Ala
1               5                   10                  15

Ala

<210> SEQ ID NO 217
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl-L-cysteine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
```

```
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 217

Cys Arg Gln Arg Ser Leu Gln Thr Leu Arg Xaa Ile Gln Arg Xaa Ala
1               5                   10                  15
Ala

<210> SEQ ID NO 218
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Homohistidine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 218

His Arg Gln Arg Ser Leu Gln Thr Leu Arg Xaa Ile Gln Arg Xaa Ala
1               5                   10                  15
Ala

<210> SEQ ID NO 219
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: His peptoid
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
```

```
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 219

Xaa Arg Gln Arg Ser Leu Gln Thr Leu Arg Xaa Ile Gln Arg Xaa Ala
1               5                   10                  15

Ala

<210> SEQ ID NO 220
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Homoarginine
<220> FEATURE:
<221> NAME/KEY: MOD_RES
<222> LOCATION: (10)..(10)
<223> OTHER INFORMATION: Norarginine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 220

His Arg Gln Arg Ser Leu Gln Thr Leu Arg Xaa Ile Gln Arg Xaa Ala
1               5                   10                  15

Ala

<210> SEQ ID NO 221
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Homoarginine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
```

```
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (14)..(14)
<223> OTHER INFORMATION: Norarginine
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 221

His Arg Gln Arg Ser Leu Gln Thr Leu Arg Xaa Ile Gln Arg Xaa Ala
1               5                   10                  15

Ala

<210> SEQ ID NO 222
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Homoarginine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (14)..(14)
<223> OTHER INFORMATION: Citrulline
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 222

His Arg Gln Arg Ser Leu Gln Thr Leu Arg Xaa Ile Gln Xaa Xaa Ala
1               5                   10                  15

Ala

<210> SEQ ID NO 223
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Homoarginine
<220> FEATURE:
<221> NAME/KEY: MOD_RES
<222> LOCATION: (10)..(10)
<223> OTHER INFORMATION: Citrulline
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 223

His Arg Gln Arg Ser Leu Gln Thr Leu Xaa Xaa Ile Gln Arg Xaa Ala
1               5                   10                  15

Ala

<210> SEQ ID NO 224
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Citrulline
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
```

<223> OTHER INFORMATION: 2-Naphthylalanine

<400> SEQUENCE: 224

His Xaa Gln Arg Ser Leu Gln Thr Leu Arg Xaa Ile Gln Arg Xaa Ala
1               5                   10                  15
Ala

<210> SEQ ID NO 225
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norarginine
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (7)..(7)
<223> OTHER INFORMATION: N-methyl-D-glutamine
<220> FEATURE:
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 225

His Arg Gln Arg Ser Leu Gln Thr Leu Arg Xaa Ile Gln Arg Xaa Ala
1               5                   10                  15
Ala

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Guanidino-L-phenylalanine
<220> FEATURE:
<221> NAME/KEY: MOD_RES
<222> LOCATION: (3)..(3)
<223> OTHER INFORMATION: N-methyl-D-glutamine
<220> FEATURE:
<221> NAME/KEY: MOD_RES
<222> LOCATION: (7)..(7)
<223> OTHER INFORMATION: N-methyl-D-glutamine
<220> FEATURE:

```
<221> NAME/KEY: MOD_RES
<222> LOCATION: (11)..(11)
<223> OTHER INFORMATION: Any alpha, alpha-disubstituted amino acid
<220> FEATURE:
<221> NAME/KEY: MISC_FEATURE
<222> LOCATION: (11)..(15)
<223> OTHER INFORMATION: May or may not be a hydrocarbon crosslinker
      between residues
<220> FEATURE:
<221> NAME/KEY: MOD_RES
<222> LOCATION: (15)..(15)
<223> OTHER INFORMATION: Any alpha, alpha-disubstituted amino acid
<220> FEATURE:
<221> NAME/KEY: MOD_RES
<222> LOCATION: (16)..(16)
<223> OTHER INFORMATION: Cyclohexyl L-alanine
<220> FEATURE:
<221> NAME/KEY: MOD_RES
<222> LOCATION: (17)..(17)
<223> OTHER INFORMATION: 2-Naphthylalanine

<400> SEQUENCE: 226

His Phe Gln Arg Ser Leu Gln Thr Leu Arg Xaa Ile Gln Arg Xaa Ala
1               5                   10                  15

Ala

<210> SEQ ID NO 227
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any alpha, alpha-disubstituted amino acid
<220> FEATURE:
<221> NAME/KEY: MISC_FEATURE
<222> LOCATION: (6)..(10)
<223> OTHER INFORMATION: May or may not be a hydrocarbon crosslinker
      between residues
<220> FEATURE:
<221> NAME/KEY: MOD_RES
<222> LOCATION: (10)..(10)
<223> OTHER INFORMATION: Any alpha, alpha-disubstituted amino acid
<220> FEATURE:
<221> NAME/KEY: MOD_RES
<222> LOCATION: (12)..(12)
<223> OTHER INFORMATION: 2-Naphthylalanine
<220> FEATURE:
<221> NAME/KEY: MOD_RES
<222> LOCATION: (13)..(13)
<223> OTHER INFORMATION: Beta-alanine
<220> FEATURE:
<221> NAME/KEY: MOD_RES
<222> LOCATION: (14)..(14)
<223> OTHER INFORMATION: Beta-alanine

<400> SEQUENCE: 227

Leu Gln Thr Leu Arg Xaa Ile Gln Arg Xaa Leu Ala Ala Ala Gly Arg
1               5                   10                  15

Lys Lys Arg Arg Gln Arg Arg Arg Pro Gln Lys
                20                  25

<210> SEQ ID NO 228
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Any alpha, alpha-disubstituted amino acid
<220> FEATURE:
<221> NAME/KEY: MOD_RES
<222> LOCATION: (5)..(5)
<223> OTHER INFORMATION: Any alpha, alpha-disubstituted amino acid

<400> SEQUENCE: 228

Xaa Ser Leu Gln Xaa
1               5

<210> SEQ ID NO 229
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any alpha, alpha-disubstituted amino acid
<220> FEATURE:
<221> NAME/KEY: MOD_RES
<222> LOCATION: (3)..(3)
<223> OTHER INFORMATION: Cyclohexyl L-alanine
<220> FEATURE:
<221> NAME/KEY: MOD_RES
<222> LOCATION: (4)..(4)
<223> OTHER INFORMATION: N-methyl-D-glutamine
<220> FEATURE:
<221> NAME/KEY: MOD_RES
<222> LOCATION: (5)..(5)
<223> OTHER INFORMATION: Any alpha, alpha-disubstituted amino acid

<400> SEQUENCE: 229

Xaa Ser Ala Gln Xaa
1               5

<210> SEQ ID NO 230
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any alpha, alpha-disubstituted amino acid
<220> FEATURE:
<221> NAME/KEY: MOD_RES
<222> LOCATION: (5)..(5)
<223> OTHER INFORMATION: Any alpha, alpha-disubstituted amino acid

<400> SEQUENCE: 230

Xaa Ile Gln Arg Xaa
1               5

<210> SEQ ID NO 231
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any alpha, alpha-disubstituted amino acid
<220> FEATURE:
<221> NAME/KEY: MOD_RES
```

<222> LOCATION: (5)..(5)
<223> OTHER INFORMATION: Any alpha, alpha-disubstituted amino acid

<400> SEQUENCE: 231

Xaa Ile Gln Gln Xaa
1               5

<210> SEQ ID NO 232
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Leu Gln Thr Leu Arg
1               5

<210> SEQ ID NO 233
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine

<400> SEQUENCE: 233

Leu Gln Thr Leu Arg
1               5

<210> SEQ ID NO 234
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (5)..(5)
<223> OTHER INFORMATION: Homoarginine

<400> SEQUENCE: 234

Leu Gln Thr Leu Arg
1               5

<210> SEQ ID NO 235
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (4)..(4)
<223> OTHER INFORMATION: N-methyl leucine

<400> SEQUENCE: 235

Leu Gln Thr Leu Arg
1               5

<210> SEQ ID NO 236
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (5)..(5)
<223> OTHER INFORMATION: N-methylarginine

<400> SEQUENCE: 236

Leu Gln Thr Leu Arg
1               5

<210> SEQ ID NO 237
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine

<400> SEQUENCE: 237

Leu Gln Thr Leu Arg
1               5

<210> SEQ ID NO 238
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Leu Glu Thr Leu Arg
1               5

<210> SEQ ID NO 239
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-cyclobutyl alanine

<400> SEQUENCE: 239

Ala Gln Thr Leu Arg
1               5

<210> SEQ ID NO 240

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-cyclobutyl alanine
<220> FEATURE:
<221> NAME/KEY: MOD_RES
<222> LOCATION: (2)..(2)
<223> OTHER INFORMATION: N-methyl-D-glutamine

<400> SEQUENCE: 240

Ala Gln Thr Leu Arg
1               5

<210> SEQ ID NO 241
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Beta-cyclobutyl alanine

<400> SEQUENCE: 241

Leu Gln Thr Ala Arg
1               5

<210> SEQ ID NO 242
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (3)..(3)
<223> OTHER INFORMATION: N-methyl L-threonine

<400> SEQUENCE: 242

Leu Gln Thr Leu Arg
1               5

<210> SEQ ID NO 243
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (4)..(4)
<223> OTHER INFORMATION: Cyclohexyl L-alanine

<400> SEQUENCE: 243
```

Leu Gln Thr Ala Arg
1               5

<210> SEQ ID NO 244
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-D-glutamine
<220> FEATURE:
<221> NAME/KEY: MOD_RES
<222> LOCATION: (4)..(4)
<223> OTHER INFORMATION: Alpha-methylleucine

<400> SEQUENCE: 244

Leu Gln Thr Leu Arg
1               5

<210> SEQ ID NO 245
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

His Arg Glu Arg
1

<210> SEQ ID NO 246
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

His Arg Gln Arg
1

<210> SEQ ID NO 247
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl L-glutamic acid

<400> SEQUENCE: 247

His Arg Glu Arg
1

<210> SEQ ID NO 248
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (3)..(3)
<223> OTHER INFORMATION: N-methyl-D-glutamine

<400> SEQUENCE: 248

His Arg Gln Arg
1

<210> SEQ ID NO 249
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl aspartic acid

<400> SEQUENCE: 249

His Arg Asp Arg
1

<210> SEQ ID NO 250
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methylarginine

<400> SEQUENCE: 250

His Arg Gln Arg
1

<210> SEQ ID NO 251
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Homoarginine

<400> SEQUENCE: 251

His Arg Gln Arg
1

<210> SEQ ID NO 252
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: N-methylarginine

<400> SEQUENCE: 252
```

His Arg Gln Arg
1

<210> SEQ ID NO 253
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Homoarginine

<400> SEQUENCE: 253

His Arg Gln Arg
1

<210> SEQ ID NO 254
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: N-methylarginine

<400> SEQUENCE: 254

His Arg Gln Arg
1

<210> SEQ ID NO 255
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl-D-glutamine

<400> SEQUENCE: 255

His Arg Gln Arg
1

<210> SEQ ID NO 256
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl histidine

<400> SEQUENCE: 256

His Arg Gln Arg
1

<210> SEQ ID NO 257
<211> LENGTH: 4
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 257

Cys Arg Gln Arg
1

<210> SEQ ID NO 258
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl-L-cysteine

<400> SEQUENCE: 258

Cys Arg Gln Arg
1

<210> SEQ ID NO 259
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Homohistidine

<400> SEQUENCE: 259

His Arg Gln Arg
1

<210> SEQ ID NO 260
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: His peptoid

<400> SEQUENCE: 260

His Arg Gln Arg
1

<210> SEQ ID NO 261
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Citrulline
<220> FEATURE:
<221> NAME/KEY: MOD_RES
<222> LOCATION: (3)..(3)
```

```
<223> OTHER INFORMATION: N-methyl-D-glutamine

<400> SEQUENCE: 261

His Xaa Gln Arg
1

<210> SEQ ID NO 262
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norarginine
<220> FEATURE:
<221> NAME/KEY: MOD_RES
<222> LOCATION: (3)..(3)
<223> OTHER INFORMATION: N-methyl-D-glutamine

<400> SEQUENCE: 262

His Arg Gln Arg
1

<210> SEQ ID NO 263
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Guanidino-L-phenylalanine
<220> FEATURE:
<221> NAME/KEY: MOD_RES
<222> LOCATION: (3)..(3)
<223> OTHER INFORMATION: N-methyl-D-glutamine

<400> SEQUENCE: 263

His Phe Gln Arg
1

<210> SEQ ID NO 264
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Lys-PEG4-palmitoyl

<400> SEQUENCE: 264

Gly Arg Lys Lys Arg Arg Gln Arg Arg Arg Pro Gln Lys
1               5                   10

<210> SEQ ID NO 265
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265
```

```
Leu Arg Asp Ile Gln Arg
1               5

<210> SEQ ID NO 266
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

His Arg Glu Arg Ser
1               5

<210> SEQ ID NO 267
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

His Arg Gln Arg Ser
1               5

<210> SEQ ID NO 268
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-aminobutyric acid
<220> FEATURE:
<221> NAME/KEY: MOD_RES
<222> LOCATION: (3)..(3)
<223> OTHER INFORMATION: 2-Naphthylalanine
<220> FEATURE:
<221> NAME/KEY: MOD_RES
<222> LOCATION: (4)..(4)
<223> OTHER INFORMATION: Beta-alanine
<220> FEATURE:
<221> NAME/KEY: MOD_RES
<222> LOCATION: (5)..(5)
<223> OTHER INFORMATION: Beta-alanine

<400> SEQUENCE: 268

Xaa Leu Ala Ala Ala
1               5

<210> SEQ ID NO 269
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Arg Glu Arg Ser Leu
1               5

<210> SEQ ID NO 270
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gln Leu Glu His
1

<210> SEQ ID NO 271
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (5)..(5)
<223> OTHER INFORMATION: Norleucine

<400> SEQUENCE: 271

Leu Ile Gln Arg Leu
1               5

<210> SEQ ID NO 272
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Leu Gln Thr Leu Glu
1               5

<210> SEQ ID NO 273
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Leu Gln Arg Leu Lys
1               5

<210> SEQ ID NO 274
<211> LENGTH: 30
<212> TYPE: PRT
<213> ORGANISM: Homo sapiens

<400> SEQUENCE: 274

Pro Asp Gly Leu Ser Gln Glu Gln Leu Glu His Arg Glu Arg Ser Leu
1               5                   10                  15

Gln Thr Leu Arg Asp Ile Gln Arg Met Leu Phe Pro Asp Glu
            20                  25                  30

<210> SEQ ID NO 275
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 275

Arg Glu Arg Ser
1

<210> SEQ ID NO 276
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

His Gln Glu Arg Ser
1               5

<210> SEQ ID NO 277
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Arg Ser Leu Gln Thr Leu Arg
1               5

<210> SEQ ID NO 278
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Glu His Arg Glu Arg Ser
1               5

<210> SEQ ID NO 279
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gly Arg Lys Lys Arg Arg Gln Arg Arg Arg Pro Gln
1               5                   10
```